United States Patent
Schmitt et al.

(10) Patent No.: US 11,026,969 B2
(45) Date of Patent: Jun. 8, 2021

(54) HIGH AFFINITY T CELL RECEPTORS AND USES THEREOF

(71) Applicants: Fred Hutchinson Cancer Research Center, Seattle, WA (US); Adaptive Biotechnologies Corporation, Seattle, WA (US)

(72) Inventors: Thomas M. Schmitt, Seattle, WA (US); Philip D. Greenberg, Seattle, WA (US); Aude G. Chapuis, Seattle, WA (US); Harlan S. Robins, Seattle, WA (US); Anna M. Sherwood, Seattle, WA (US)

(73) Assignees: Fred Hutchinson Cancer Research Center, Seattle, WA (US); Adaptive Biotechnologies Corporation, Seattle, WA (US)

( * ) Notice: Subject to any disclaimer, the term of this patent is extended or adjusted under 35 U.S.C. 154(b) by 530 days.

(21) Appl. No.: 16/064,161

(22) PCT Filed: Dec. 23, 2016

(86) PCT No.: PCT/US2016/068556
§ 371 (c)(1),
(2) Date: Jun. 20, 2018

(87) PCT Pub. No.: WO2017/112944
PCT Pub. Date: Jun. 29, 2017

(65) Prior Publication Data
US 2018/0369280 A1 Dec. 27, 2018

Related U.S. Application Data

(60) Provisional application No. 62/387,546, filed on Dec. 23, 2015.

(51) Int. Cl.
| | | |
|---|---|---|
| A61K 35/12 | (2015.01) |
| A61P 35/00 | (2006.01) |
| C07K 14/435 | (2006.01) |
| C07K 14/705 | (2006.01) |
| A61K 35/17 | (2015.01) |
| A61P 35/02 | (2006.01) |
| A61K 9/00 | (2006.01) |
| C07K 14/725 | (2006.01) |
| A61K 45/06 | (2006.01) |
| A61K 38/20 | (2006.01) |
| C07K 14/54 | (2006.01) |
| C07K 14/55 | (2006.01) |

(52) U.S. Cl.
CPC .......... *A61K 35/12* (2013.01); *A61K 9/0019* (2013.01); *A61K 35/17* (2013.01); *A61K 38/20* (2013.01); *A61P 35/00* (2018.01); *A61P 35/02* (2018.01); *C07K 14/435* (2013.01); *C07K 14/5443* (2013.01); *C07K 14/55* (2013.01); *C07K 14/705* (2013.01); *C07K 14/7051* (2013.01); *A61K 45/06* (2013.01); *A61K 2300/00* (2013.01)

(58) Field of Classification Search
CPC ...... A61K 35/12; A61K 9/0019; A61K 35/17; A61K 38/20; A61K 45/06; A61K 2300/00; A61P 35/02; A61P 35/00; C07K 14/435; C07K 14/5443; C07K 14/55; C07K 14/705; C07K 14/7051
See application file for complete search history.

(56) References Cited

U.S. PATENT DOCUMENTS

| | | | | |
|---|---|---|---|---|
| 2009/0312403 | A1* | 12/2009 | Gaiger | A61K 39/0011 514/44 R |
| 2016/0289760 | A1* | 10/2016 | Suzuki | C12Q 1/6886 |
| 2017/0174764 | A1* | 6/2017 | Cohen | A61K 39/0008 |

FOREIGN PATENT DOCUMENTS

| | | |
|---|---|---|
| WO | 2012/038055 A1 | 3/2012 |
| WO | 2013/166321 A1 | 11/2013 |
| WO | 2015/077615 A1 | 5/2015 |

OTHER PUBLICATIONS

Han A, Glanville J, Hansmann L, Davis MM. Nat Biotechnol. Jul. 2014; 32(7):684-92 (Year: 2014).*
Sequence alignment of Suzuki Seq 1857 and instant Seq 99; Jan. 13, 2021 (Year: 2021).*
Sequence alignment of Cohen Seq 134 and instant Seq 105; Jan. 13, 2021 (Year: 2021).*
Aggen et al., "Single-chain VαVβ T-cell receptors function without mispairing with endogenous TCR chains," *Gene Therapy* 19:365-374, 2012.
Howie et al., "High-throughput pairing of T-cell receptor alpha and beta sequences," *A Nature Conference: Immune Profiling in Health and Disease*, Seattle, Washington, Sep. 9-11, 2015, Sep. 2015. (11 pages).
International Search Report and Written Opinion, dated May 31, 2017, for International Application No. PCT/US2016/068556, 21 pages.

(Continued)

*Primary Examiner* — Scott Long
*Assistant Examiner* — Anjeanette Roberts
(74) *Attorney, Agent, or Firm* — Seed IP Law Group LLP

(57) ABSTRACT

The present disclosure provides TCRs with high or enhanced affinity against various tumor associated antigens (including human Wilms tumor protein 1 (WT 1) epitopes and mesothelin epitopes), T cells expressing such high affinity antigen specific TCRs, nucleic acids encoding the same, and compositions for use in treating diseases or disorders in which cells overexpress one or more of these antigens, such as in cancer.

17 Claims, 4 Drawing Sheets
Specification includes a Sequence Listing.

(56) References Cited

OTHER PUBLICATIONS

Kirsch et al., "T-cell receptor profiling in cancer," *Molecular Oncology* 9:2063-2070, 2015.
Office Action, dated Sep. 2, 2019, for European Application No. 16 826 275.6, 7 pages.
Office Action, dated Sep. 11, 2020, for European Application No. 16 826 275.6, 6 pages.

* cited by examiner

SEQUENCE LISTING

<160> NUMBER OF SEQ ID NOS: 258

<210> SEQ ID NO 1

```
<211> LENGTH: 123
<212> TYPE: PRT
<213> ORGANISM: Artificial Sequence
<220> FEATURE:
<223> OTHER INFORMATION: ME201alpha chain variable domain

<400> SEQUENCE: 1

Met Asn Ser Ser Leu Asp Phe Leu Ile Leu Ile Leu Met Phe Gly Gly
1               5                   10                  15

Thr Ser Ser Asn Ser Val Lys Gln Thr Gly Gln Ile Thr Val Ser Glu
            20                  25                  30

Gly Ala Ser Val Thr Met Asn Cys Thr Tyr Thr Ser Thr Gly Tyr Pro
        35                  40                  45

Thr Leu Phe Trp Tyr Val Glu Tyr Pro Ser Lys Pro Leu Gln Leu Leu
    50                  55                  60

Gln Arg Glu Thr Met Glu Asn Ser Lys Asn Phe Gly Gly Gly Asn Ile
65                  70                  75                  80

Lys Asp Lys Asn Ser Pro Ile Val Lys Tyr Ser Val Gln Val Ser Asp
                85                  90                  95

Ser Ala Val Tyr Tyr Cys Leu Leu Arg Asn His Asp Lys Leu Ile Phe
            100                 105                 110

Gly Thr Gly Thr Arg Leu Gln Val Phe Pro Asn
        115                 120

<210> SEQ ID NO 2
<211> LENGTH: 140
<212> TYPE: PRT
<213> ORGANISM: Artificial Sequence
<220> FEATURE:
<223> OTHER INFORMATION: ME201alpha  chain constant domain

<400> SEQUENCE: 2

Ile Gln Asn Pro Asp Pro Ala Val Tyr Gln Leu Arg Asp Ser Lys Ser
1               5                   10                  15

Ser Asp Lys Ser Val Cys Leu Phe Thr Asp Phe Asp Ser Gln Thr Asn
            20                  25                  30

Val Ser Gln Ser Lys Asp Ser Asp Val Tyr Ile Thr Asp Lys Thr Val
        35                  40                  45

Leu Asp Met Arg Ser Met Asp Phe Lys Ser Asn Ser Ala Val Ala Trp
    50                  55                  60

Ser Asn Lys Ser Asp Phe Ala Cys Ala Asn Ala Phe Asn Asn Ser Ile
65                  70                  75                  80

Ile Pro Glu Asp Thr Phe Phe Pro Ser Pro Glu Ser Ser Cys Asp Val
                85                  90                  95

Lys Leu Val Glu Lys Ser Phe Glu Thr Asp Thr Asn Leu Asn Phe Gln
            100                 105                 110

Asn Leu Ser Val Ile Gly Phe Arg Ile Leu Leu Leu Lys Val Ala Gly
        115                 120                 125

Phe Asn Leu Leu Met Thr Leu Arg Leu Trp Ser Ser
    130                 135                 140

<210> SEQ ID NO 3
<211> LENGTH: 140
<212> TYPE: PRT
<213> ORGANISM: Artificial Sequence
<220> FEATURE:
<223> OTHER INFORMATION: ME201alpha (T170C) chain constant domain

<400> SEQUENCE: 3
```

Ile Gln Asn Pro Asp Pro Ala Val Tyr Gln Leu Arg Asp Ser Lys Ser
1               5                   10                  15

Ser Asp Lys Ser Val Cys Leu Phe Thr Asp Phe Asp Ser Gln Thr Asn
                20                  25                  30

Val Ser Gln Ser Lys Asp Ser Asp Val Tyr Ile Thr Asp Lys Cys Val
            35                  40                  45

Leu Asp Met Arg Ser Met Asp Phe Lys Ser Asn Ser Ala Val Ala Trp
        50                  55                  60

Ser Asn Lys Ser Asp Phe Ala Cys Ala Asn Ala Phe Asn Asn Ser Ile
65                  70                  75                  80

Ile Pro Glu Asp Thr Phe Phe Pro Ser Pro Glu Ser Ser Cys Asp Val
                85                  90                  95

Lys Leu Val Glu Lys Ser Phe Glu Thr Asp Thr Asn Leu Asn Phe Gln
            100                 105                 110

Asn Leu Ser Val Ile Gly Phe Arg Ile Leu Leu Leu Lys Val Ala Gly
        115                 120                 125

Phe Asn Leu Leu Met Thr Leu Arg Leu Trp Ser Ser
    130                 135                 140

<210> SEQ ID NO 4
<211> LENGTH: 263
<212> TYPE: PRT
<213> ORGANISM: Artificial Sequence
<220> FEATURE:
<223> OTHER INFORMATION: ME201alpha chain

<400> SEQUENCE: 4

Met Asn Ser Ser Leu Asp Phe Leu Ile Leu Ile Leu Met Phe Gly Gly
1               5                   10                  15

Thr Ser Ser Asn Ser Val Lys Gln Thr Gly Gln Ile Thr Val Ser Glu
                20                  25                  30

Gly Ala Ser Val Thr Met Asn Cys Thr Tyr Thr Ser Thr Gly Tyr Pro
            35                  40                  45

Thr Leu Phe Trp Tyr Val Glu Tyr Pro Ser Lys Pro Leu Gln Leu Leu
        50                  55                  60

Gln Arg Glu Thr Met Glu Asn Ser Lys Asn Phe Gly Gly Gly Asn Ile
65                  70                  75                  80

Lys Asp Lys Asn Ser Pro Ile Val Lys Tyr Ser Val Gln Val Ser Asp
                85                  90                  95

Ser Ala Val Tyr Tyr Cys Leu Leu Arg Asn His Asp Lys Leu Ile Phe
            100                 105                 110

Gly Thr Gly Thr Arg Leu Gln Val Phe Pro Asn Ile Gln Asn Pro Asp
        115                 120                 125

Pro Ala Val Tyr Gln Leu Arg Asp Ser Lys Ser Ser Lys Ser Val
130                 135                 140

Cys Leu Phe Thr Asp Phe Asp Ser Gln Thr Asn Val Ser Gln Ser Lys
145                 150                 155                 160

Asp Ser Asp Val Tyr Ile Thr Asp Lys Thr Val Leu Asp Met Arg Ser
                165                 170                 175

Met Asp Phe Lys Ser Asn Ser Ala Val Ala Trp Ser Asn Lys Ser Asp
            180                 185                 190

Phe Ala Cys Ala Asn Ala Phe Asn Asn Ser Ile Ile Pro Glu Asp Thr
        195                 200                 205

Phe Phe Pro Ser Pro Glu Ser Ser Cys Asp Val Lys Leu Val Glu Lys
    210                 215                 220

```
Ser Phe Glu Thr Asp Thr Asn Leu Asn Phe Gln Asn Leu Ser Val Ile
225                 230                 235                 240

Gly Phe Arg Ile Leu Leu Leu Lys Val Ala Gly Phe Asn Leu Leu Met
            245                 250                 255

Thr Leu Arg Leu Trp Ser Ser
            260
```

<210> SEQ ID NO 5
<211> LENGTH: 263
<212> TYPE: PRT
<213> ORGANISM: Artificial Sequence
<220> FEATURE:
<223> OTHER INFORMATION: ME201alpha (T170C) chain

<400> SEQUENCE: 5

```
Met Asn Ser Ser Leu Asp Phe Leu Ile Leu Ile Leu Met Phe Gly Gly
1               5                   10                  15

Thr Ser Ser Asn Ser Val Lys Gln Thr Gly Gln Ile Thr Val Ser Glu
            20                  25                  30

Gly Ala Ser Val Thr Met Asn Cys Thr Tyr Thr Ser Thr Gly Tyr Pro
        35                  40                  45

Thr Leu Phe Trp Tyr Val Glu Tyr Pro Ser Lys Pro Leu Gln Leu Leu
    50                  55                  60

Gln Arg Glu Thr Met Glu Asn Ser Lys Asn Phe Gly Gly Gly Asn Ile
65                  70                  75                  80

Lys Asp Lys Asn Ser Pro Ile Val Lys Tyr Ser Val Gln Val Ser Asp
                85                  90                  95

Ser Ala Val Tyr Tyr Cys Leu Leu Arg Asn His Asp Lys Leu Ile Phe
            100                 105                 110

Gly Thr Gly Thr Arg Leu Gln Val Phe Pro Asn Ile Gln Asn Pro Asp
        115                 120                 125

Pro Ala Val Tyr Gln Leu Arg Asp Ser Lys Ser Ser Asp Lys Ser Val
    130                 135                 140

Cys Leu Phe Thr Asp Phe Asp Ser Gln Thr Asn Val Ser Gln Ser Lys
145                 150                 155                 160

Asp Ser Asp Val Tyr Ile Thr Asp Lys Cys Val Leu Asp Met Arg Ser
                165                 170                 175

Met Asp Phe Lys Ser Asn Ser Ala Val Ala Trp Ser Asn Lys Ser Asp
            180                 185                 190

Phe Ala Cys Ala Asn Ala Phe Asn Asn Ser Ile Ile Pro Glu Asp Thr
        195                 200                 205

Phe Phe Pro Ser Pro Glu Ser Ser Cys Asp Val Lys Leu Val Glu Lys
    210                 215                 220

Ser Phe Glu Thr Asp Thr Asn Leu Asn Phe Gln Asn Leu Ser Val Ile
225                 230                 235                 240

Gly Phe Arg Ile Leu Leu Leu Lys Val Ala Gly Phe Asn Leu Leu Met
                245                 250                 255

Thr Leu Arg Leu Trp Ser Ser
            260
```

<210> SEQ ID NO 6
<211> LENGTH: 132
<212> TYPE: PRT
<213> ORGANISM: Artificial Sequence
<220> FEATURE:
<223> OTHER INFORMATION: ME201beta chain variable domain

<400> SEQUENCE: 6

```
Met Gly Pro Gly Leu Leu Cys Trp Val Leu Leu Cys Leu Leu Gly Ala
1               5                   10                  15

Gly Ser Val Glu Thr Gly Val Thr Gln Ser Pro Thr His Leu Ile Lys
            20                  25                  30

Thr Arg Gly Gln Gln Val Thr Leu Arg Cys Ser Ser Gln Ser Gly His
        35                  40                  45

Asn Thr Val Ser Trp Tyr Gln Gln Ala Leu Gly Gln Gly Pro Gln Phe
    50                  55                  60

Ile Phe Gln Tyr Tyr Arg Glu Glu Asn Gly Arg Gly Asn Phe Pro
65                  70                  75                  80

Pro Arg Phe Ser Gly Leu Gln Phe Pro Asn Tyr Ser Ser Glu Leu Asn
                85                  90                  95

Val Asn Ala Leu Glu Leu Asp Asp Ser Ala Leu Tyr Leu Cys Ala Ser
            100                 105                 110

Ser Gln Asp Ser Tyr Asn Glu Gln Phe Phe Gly Pro Gly Thr Arg Leu
            115                 120                 125

Thr Val Leu Glu
    130
```

<210> SEQ ID NO 7
<211> LENGTH: 178
<212> TYPE: PRT
<213> ORGANISM: Artificial Sequence
<220> FEATURE:
<223> OTHER INFORMATION: ME201beta chain constant domain

<400> SEQUENCE: 7

```
Asp Leu Lys Asn Val Phe Pro Pro Glu Val Ala Val Phe Glu Pro Ser
1               5                   10                  15

Glu Ala Glu Ile Ser His Thr Gln Lys Ala Thr Leu Val Cys Leu Ala
            20                  25                  30

Thr Gly Phe Tyr Pro Asp His Val Glu Leu Ser Trp Trp Val Asn Gly
        35                  40                  45

Lys Glu Val His Ser Gly Val Ser Thr Asp Pro Gln Pro Leu Lys Glu
    50                  55                  60

Gln Pro Ala Leu Asn Asp Ser Arg Tyr Cys Leu Ser Ser Arg Leu Arg
65                  70                  75                  80

Val Ser Ala Thr Phe Trp Gln Asn Pro Arg Asn His Phe Arg Cys Gln
                85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
            115                 120                 125

Asp Cys Gly Phe Thr Ser Glu Ser Tyr Gln Gln Gly Val Leu Ser Ala
    130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Ser
                165                 170                 175

Arg Gly
```

<210> SEQ ID NO 8
<211> LENGTH: 178
<212> TYPE: PRT
<213> ORGANISM: Artificial Sequence
<220> FEATURE:

<223> OTHER INFORMATION: ME201beta (S188C) chain constant domain

<400> SEQUENCE: 8

```
Asp Leu Lys Asn Val Phe Pro Pro Glu Val Ala Val Phe Glu Pro Ser
1               5                   10                  15
Glu Ala Glu Ile Ser His Thr Gln Lys Ala Thr Leu Val Cys Leu Ala
            20                  25                  30
Thr Gly Phe Tyr Pro Asp His Val Glu Leu Ser Trp Trp Val Asn Gly
        35                  40                  45
Lys Glu Val His Ser Gly Val Cys Thr Asp Pro Gln Pro Leu Lys Glu
    50                  55                  60
Gln Pro Ala Leu Asn Asp Ser Arg Tyr Cys Leu Ser Arg Leu Arg
65                  70                  75                  80
Val Ser Ala Thr Phe Trp Gln Asn Pro Arg Asn His Phe Arg Cys Gln
                85                  90                  95
Val Gln Phe Tyr Gly Leu Ser Glu Asn Asp Glu Trp Thr Gln Asp Arg
            100                 105                 110
Ala Lys Pro Val Thr Gln Ile Val Ser Ala Glu Ala Trp Gly Arg Ala
        115                 120                 125
Asp Cys Gly Phe Thr Ser Glu Ser Tyr Gln Gln Gly Val Leu Ser Ala
    130                 135                 140
Thr Ile Leu Tyr Glu Ile Leu Leu Gly Lys Ala Thr Leu Tyr Ala Val
145                 150                 155                 160
Leu Val Ser Ala Leu Val Leu Met Ala Met Val Lys Arg Lys Asp Ser
                165                 170                 175
Arg Gly
```

<210> SEQ ID NO 9
<211> LENGTH: 310
<212> TYPE: PRT
<213> ORGANISM: Artificial Sequence
<220> FEATURE:
<223> OTHER INFORMATION: ME201beta chain

<400> SEQUENCE: 9

```
Met Gly Pro Gly Leu Leu Cys Trp Val Leu Leu Cys Leu Leu Gly Ala
1               5                   10                  15
Gly Ser Val Glu Thr Gly Val Thr Gln Ser Pro Thr His Leu Ile Lys
            20                  25                  30
Thr Arg Gly Gln Gln Val Thr Leu Arg Cys Ser Ser Gln Ser Gly His
        35                  40                  45
Asn Thr Val Ser Trp Tyr Gln Gln Ala Leu Gly Gln Gly Pro Gln Phe
    50                  55                  60
Ile Phe Gln Tyr Tyr Arg Glu Glu Glu Asn Gly Arg Gly Asn Phe Pro
65                  70                  75                  80
Pro Arg Phe Ser Gly Leu Gln Phe Pro Asn Tyr Ser Ser Glu Leu Asn
                85                  90                  95
Val Asn Ala Leu Glu Leu Asp Asp Ser Ala Leu Tyr Leu Cys Ala Ser
            100                 105                 110
Ser Gln Asp Ser Tyr Asn Glu Gln Phe Phe Gly Pro Gly Thr Arg Leu
        115                 120                 125
Thr Val Leu Glu Asp Leu Lys Asn Val Phe Pro Pro Glu Val Ala Val
    130                 135                 140
Phe Glu Pro Ser Glu Ala Glu Ile Ser His Thr Gln Lys Ala Thr Leu
145                 150                 155                 160
```

Val Cys Leu Ala Thr Gly Phe Tyr Pro Asp His Val Glu Leu Ser Trp
            165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
            195                 200                 205

Ser Arg Leu Arg Val Ser Ala Thr Phe Trp Gln Asn Pro Arg Asn His
            210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
            245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
            290                 295                 300

Arg Lys Asp Ser Arg Gly
305                 310

<210> SEQ ID NO 10
<211> LENGTH: 310
<212> TYPE: PRT
<213> ORGANISM: Artificial Sequence
<220> FEATURE:
<223> OTHER INFORMATION: ME201 beta (S188C) chain

<400> SEQUENCE: 10

Met Gly Pro Gly Leu Leu Cys Trp Val Leu Leu Cys Leu Leu Gly Ala
1               5                   10                  15

Gly Ser Val Glu Thr Gly Val Thr Gln Ser Pro Thr His Leu Ile Lys
            20                  25                  30

Thr Arg Gly Gln Gln Val Thr Leu Arg Cys Ser Ser Gln Ser Gly His
            35                  40                  45

Asn Thr Val Ser Trp Tyr Gln Gln Ala Leu Gly Gln Gly Pro Gln Phe
        50                  55                  60

Ile Phe Gln Tyr Tyr Arg Glu Glu Glu Asn Gly Arg Gly Asn Phe Pro
65                  70                  75                  80

Pro Arg Phe Ser Gly Leu Gln Phe Pro Asn Tyr Ser Ser Glu Leu Asn
            85                  90                  95

Val Asn Ala Leu Glu Leu Asp Asp Ser Ala Leu Tyr Leu Cys Ala Ser
            100                 105                 110

Ser Gln Asp Ser Tyr Asn Glu Gln Phe Phe Gly Pro Gly Thr Arg Leu
            115                 120                 125

Thr Val Leu Glu Asp Leu Lys Asn Val Phe Pro Pro Glu Val Ala Val
            130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
            165                 170                 175

Trp Val Asn Gly Lys Glu Val His Ser Gly Val Cys Thr Asp Pro Gln
            180                 185                 190

Pro Leu Lys Glu Gln Pro Ala Leu Asn Asp Ser Arg Tyr Cys Leu Ser
            195                 200                 205

```
Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly
305                 310

<210> SEQ ID NO 11
<211> LENGTH: 595
<212> TYPE: PRT
<213> ORGANISM: Artificial Sequence
<220> FEATURE:
<223> OTHER INFORMATION: ME201beta (S188C)-P2A-ME201alpha (T170C)

<400> SEQUENCE: 11

Met Gly Pro Gly Leu Leu Cys Trp Val Leu Leu Cys Leu Leu Gly Ala
1               5                   10                  15

Gly Ser Val Glu Thr Gly Val Thr Gln Ser Pro Thr His Leu Ile Lys
            20                  25                  30

Thr Arg Gly Gln Gln Val Thr Leu Arg Cys Ser Ser Gln Ser Gly His
        35                  40                  45

Asn Thr Val Ser Trp Tyr Gln Gln Ala Leu Gly Gln Gly Pro Gln Phe
    50                  55                  60

Ile Phe Gln Tyr Tyr Arg Glu Glu Asn Gly Arg Gly Asn Phe Pro
65                  70                  75                  80

Pro Arg Phe Ser Gly Leu Gln Phe Pro Asn Tyr Ser Ser Glu Leu Asn
                85                  90                  95

Val Asn Ala Leu Glu Leu Asp Asp Ser Ala Leu Tyr Leu Cys Ala Ser
            100                 105                 110

Ser Gln Asp Ser Tyr Asn Glu Gln Phe Phe Gly Pro Gly Thr Arg Leu
        115                 120                 125

Thr Val Leu Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Cys Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255
```

```
Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly Gly Ser Gly Ala Thr Asn Phe Ser Leu Leu
305                 310                 315                 320

Lys Gln Ala Gly Asp Val Glu Glu Asn Pro Gly Pro Met Asn Ser Ser
            325                 330                 335

Leu Asp Phe Leu Ile Leu Ile Leu Met Phe Gly Gly Thr Ser Ser Asn
        340                 345                 350

Ser Val Lys Gln Thr Gly Gln Ile Thr Val Ser Glu Gly Ala Ser Val
    355                 360                 365

Thr Met Asn Cys Thr Tyr Thr Ser Thr Gly Tyr Pro Thr Leu Phe Trp
370                 375                 380

Tyr Val Glu Tyr Pro Ser Lys Pro Leu Gln Leu Leu Gln Arg Glu Thr
385                 390                 395                 400

Met Glu Asn Ser Lys Asn Phe Gly Gly Gly Asn Ile Lys Asp Lys Asn
            405                 410                 415

Ser Pro Ile Val Lys Tyr Ser Val Gln Val Ser Asp Ser Ala Val Tyr
        420                 425                 430

Tyr Cys Leu Leu Arg Asn His Asp Lys Leu Ile Phe Gly Thr Gly Thr
    435                 440                 445

Arg Leu Gln Val Phe Pro Asn Ile Gln Asn Pro Asp Pro Ala Val Tyr
450                 455                 460

Gln Leu Arg Asp Ser Lys Ser Ser Asp Lys Ser Val Cys Leu Phe Thr
465                 470                 475                 480

Asp Phe Asp Ser Gln Thr Asn Val Ser Gln Ser Lys Asp Ser Asp Val
            485                 490                 495

Tyr Ile Thr Asp Lys Cys Val Leu Asp Met Arg Ser Met Asp Phe Lys
        500                 505                 510

Ser Asn Ser Ala Val Ala Trp Ser Asn Lys Ser Asp Phe Ala Cys Ala
    515                 520                 525

Asn Ala Phe Asn Asn Ser Ile Ile Pro Glu Asp Thr Phe Phe Pro Ser
530                 535                 540

Pro Glu Ser Ser Cys Asp Val Lys Leu Val Glu Lys Ser Phe Glu Thr
545                 550                 555                 560

Asp Thr Asn Leu Asn Phe Gln Asn Leu Ser Val Ile Gly Phe Arg Ile
            565                 570                 575

Leu Leu Leu Lys Val Ala Gly Phe Asn Leu Leu Met Thr Leu Arg Leu
        580                 585                 590

Trp Ser Ser
        595

<210> SEQ ID NO 12
<211> LENGTH: 132
<212> TYPE: PRT
<213> ORGANISM: Artificial Sequence
<220> FEATURE:
<223> OTHER INFORMATION: ME5301alpha chain variable domain

<400> SEQUENCE: 12

Met Lys Lys Leu Leu Ala Met Ile Leu Trp Leu Gln Leu Asp Arg Leu
1               5                   10                  15
```

```
Ser Gly Glu Leu Lys Val Glu Gln Asn Pro Leu Phe Leu Ser Met Gln
            20                  25                  30

Glu Gly Lys Asn Tyr Thr Ile Tyr Cys Asn Tyr Ser Thr Thr Ser Asp
        35                  40                  45

Arg Leu Tyr Trp Tyr Arg Gln Asp Pro Gly Lys Ser Leu Glu Ser Leu
    50                  55                  60

Phe Val Leu Leu Ser Asn Gly Ala Val Lys Gln Glu Gly Arg Leu Met
65                  70                  75                  80

Ala Ser Leu Asp Thr Lys Ala Arg Leu Ser Thr Leu His Ile Thr Ala
                85                  90                  95

Ala Val His Asp Leu Ser Ala Thr Tyr Phe Cys Ala Val Gly Asn Tyr
            100                 105                 110

Gly Gly Ser Gln Gly Asn Leu Ile Phe Gly Lys Gly Thr Lys Leu Ser
        115                 120                 125

Val Lys Pro Asn
        130

<210> SEQ ID NO 13
<211> LENGTH: 272
<212> TYPE: PRT
<213> ORGANISM: Artificial Sequence
<220> FEATURE:
<223> OTHER INFORMATION: ME5301alpha chain

<400> SEQUENCE: 13

Met Lys Lys Leu Leu Ala Met Ile Leu Trp Leu Gln Leu Asp Arg Leu
1               5                   10                  15

Ser Gly Glu Leu Lys Val Glu Gln Asn Pro Leu Phe Leu Ser Met Gln
            20                  25                  30

Glu Gly Lys Asn Tyr Thr Ile Tyr Cys Asn Tyr Ser Thr Thr Ser Asp
        35                  40                  45

Arg Leu Tyr Trp Tyr Arg Gln Asp Pro Gly Lys Ser Leu Glu Ser Leu
    50                  55                  60

Phe Val Leu Leu Ser Asn Gly Ala Val Lys Gln Glu Gly Arg Leu Met
65                  70                  75                  80

Ala Ser Leu Asp Thr Lys Ala Arg Leu Ser Thr Leu His Ile Thr Ala
                85                  90                  95

Ala Val His Asp Leu Ser Ala Thr Tyr Phe Cys Ala Val Gly Asn Tyr
            100                 105                 110

Gly Gly Ser Gln Gly Asn Leu Ile Phe Gly Lys Gly Thr Lys Leu Ser
        115                 120                 125

Val Lys Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240
```

Leu Asn Phe Gln Asn Leu Ser Val Ile Gly Phe Arg Ile Leu Leu Leu
            245                 250                 255

Lys Val Ala Gly Phe Asn Leu Leu Met Thr Leu Arg Leu Trp Ser Ser
        260                 265                 270

<210> SEQ ID NO 14
<211> LENGTH: 272
<212> TYPE: PRT
<213> ORGANISM: Artificial Sequence
<220> FEATURE:
<223> OTHER INFORMATION: ME5301alpha (T179C) chain

<400> SEQUENCE: 14

Met Lys Lys Leu Leu Ala Met Ile Leu Trp Leu Gln Leu Asp Arg Leu
1               5                   10                  15

Ser Gly Glu Leu Lys Val Glu Gln Asn Pro Leu Phe Leu Ser Met Gln
            20                  25                  30

Glu Gly Lys Asn Tyr Thr Ile Tyr Cys Asn Tyr Ser Thr Thr Ser Asp
        35                  40                  45

Arg Leu Tyr Trp Tyr Arg Gln Asp Pro Gly Lys Ser Leu Glu Ser Leu
    50                  55                  60

Phe Val Leu Leu Ser Asn Gly Ala Val Lys Gln Glu Gly Arg Leu Met
65                  70                  75                  80

Ala Ser Leu Asp Thr Lys Ala Arg Leu Ser Thr Leu His Ile Thr Ala
                85                  90                  95

Ala Val His Asp Leu Ser Ala Thr Tyr Phe Cys Ala Val Gly Asn Tyr
            100                 105                 110

Gly Gly Ser Gln Gly Asn Leu Ile Phe Gly Lys Gly Thr Lys Leu Ser
        115                 120                 125

Val Lys Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Cys Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 15
<211> LENGTH: 134
<212> TYPE: PRT
<213> ORGANISM: Artificial Sequence
<220> FEATURE:
<223> OTHER INFORMATION: ME5301beta chain variable domain

<400> SEQUENCE: 15

Met Gly Pro Gly Leu Leu Cys Trp Val Leu Leu Cys Leu Leu Gly Ala
1               5                   10                  15

Gly Ser Val Glu Thr Gly Val Thr Gln Ser Pro Thr His Leu Ile Lys
              20                  25                  30

Thr Arg Gly Gln Gln Val Thr Leu Arg Cys Ser Ser Gln Ser Gly His
          35                  40                  45

Asn Thr Val Ser Trp Tyr Gln Gln Ala Leu Gly Gln Gly Pro Gln Phe
     50                  55                  60

Ile Phe Gln Tyr Tyr Arg Glu Glu Asn Gly Arg Gly Asn Phe Pro
65                  70                  75                  80

Pro Arg Phe Ser Gly Leu Gln Phe Pro Asn Tyr Ser Ser Glu Leu Asn
                 85                  90                  95

Val Asn Ala Leu Glu Leu Asp Asp Ser Ala Leu Tyr Leu Cys Ala Ser
            100                 105                 110

Ser Leu Ala Gly Gly Tyr Gly Asp Thr Gln Tyr Phe Gly Pro Gly Thr
        115                 120                 125

Arg Leu Thr Val Leu Glu
        130

<210> SEQ ID NO 16
<211> LENGTH: 312
<212> TYPE: PRT
<213> ORGANISM: Artificial Sequence
<220> FEATURE:
<223> OTHER INFORMATION: ME5301beta chain

<400> SEQUENCE: 16

Met Gly Pro Gly Leu Leu Cys Trp Val Leu Leu Cys Leu Leu Gly Ala
1               5                   10                  15

Gly Ser Val Glu Thr Gly Val Thr Gln Ser Pro Thr His Leu Ile Lys
              20                  25                  30

Thr Arg Gly Gln Gln Val Thr Leu Arg Cys Ser Ser Gln Ser Gly His
          35                  40                  45

Asn Thr Val Ser Trp Tyr Gln Gln Ala Leu Gly Gln Gly Pro Gln Phe
     50                  55                  60

Ile Phe Gln Tyr Tyr Arg Glu Glu Asn Gly Arg Gly Asn Phe Pro
65                  70                  75                  80

Pro Arg Phe Ser Gly Leu Gln Phe Pro Asn Tyr Ser Ser Glu Leu Asn
                 85                  90                  95

Val Asn Ala Leu Glu Leu Asp Asp Ser Ala Leu Tyr Leu Cys Ala Ser
            100                 105                 110

Ser Leu Ala Gly Gly Tyr Gly Asp Thr Gln Tyr Phe Gly Pro Gly Thr
        115                 120                 125

Arg Leu Thr Val Leu Glu Asp Leu Lys Asn Val Phe Pro Pro Glu Val
        130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310

<210> SEQ ID NO 17
<211> LENGTH: 312
<212> TYPE: PRT
<213> ORGANISM: Artificial Sequence
<220> FEATURE:
<223> OTHER INFORMATION: ME5301 beta (S190C) chain

<400> SEQUENCE: 17

Met Gly Pro Gly Leu Leu Cys Trp Val Leu Leu Cys Leu Leu Gly Ala
1               5                   10                  15

Gly Ser Val Glu Thr Gly Val Thr Gln Ser Pro Thr His Leu Ile Lys
            20                  25                  30

Thr Arg Gly Gln Gln Val Thr Leu Arg Cys Ser Ser Gln Ser Gly His
        35                  40                  45

Asn Thr Val Ser Trp Tyr Gln Gln Ala Leu Gly Gln Gly Pro Gln Phe
    50                  55                  60

Ile Phe Gln Tyr Tyr Arg Glu Glu Asn Gly Arg Gly Asn Phe Pro
65                  70                  75                  80

Pro Arg Phe Ser Gly Leu Gln Phe Pro Asn Tyr Ser Ser Glu Leu Asn
                85                  90                  95

Val Asn Ala Leu Glu Leu Asp Asp Ser Ala Leu Tyr Leu Cys Ala Ser
            100                 105                 110

Ser Leu Ala Gly Gly Tyr Gly Asp Thr Gln Tyr Phe Gly Pro Gly Thr
        115                 120                 125

Arg Leu Thr Val Leu Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Cys Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
            290                 295                 300

Val Lys Arg Lys Asp Ser Arg Gly
305                 310

<210> SEQ ID NO 18
<211> LENGTH: 606
<212> TYPE: PRT
<213> ORGANISM: Artificial Sequence
<220> FEATURE:
<223> OTHER INFORMATION: ME5301 beta (S190C)-P2A-ME5301 alpha (T179C)

<400> SEQUENCE: 18

Met Gly Pro Gly Leu Leu Cys Trp Val Leu Leu Cys Leu Leu Gly Ala
1               5                   10                  15

Gly Ser Val Glu Thr Gly Val Thr Gln Ser Pro Thr His Leu Ile Lys
            20                  25                  30

Thr Arg Gly Gln Gln Val Thr Leu Arg Cys Ser Ser Gln Ser Gly His
        35                  40                  45

Asn Thr Val Ser Trp Tyr Gln Gln Ala Leu Gly Gln Gly Pro Gln Phe
    50                  55                  60

Ile Phe Gln Tyr Tyr Arg Glu Glu Asn Gly Arg Gly Asn Phe Pro
65                  70                  75                  80

Pro Arg Phe Ser Gly Leu Gln Phe Pro Asn Tyr Ser Ser Glu Leu Asn
                85                  90                  95

Val Asn Ala Leu Glu Leu Asp Asp Ser Ala Leu Tyr Leu Cys Ala Ser
            100                 105                 110

Ser Leu Ala Gly Gly Tyr Gly Asp Thr Gln Tyr Phe Gly Pro Gly Thr
        115                 120                 125

Arg Leu Thr Val Leu Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Cys Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly Gly Ser Gly Ala Thr Asn Phe Ser
305                 310                 315                 320

Leu Leu Lys Gln Ala Gly Asp Val Glu Glu Asn Pro Gly Pro Met Lys
                325                 330                 335

Lys Leu Leu Ala Met Ile Leu Trp Leu Gln Leu Asp Arg Leu Ser Gly
                340                 345                 350

Glu Leu Lys Val Glu Gln Asn Pro Leu Phe Leu Ser Met Gln Glu Gly
                355                 360                 365

Lys Asn Tyr Thr Ile Tyr Cys Asn Tyr Ser Thr Thr Ser Asp Arg Leu
            370                 375                 380

Tyr Trp Tyr Arg Gln Asp Pro Gly Lys Ser Leu Glu Ser Leu Phe Val
385                 390                 395                 400

Leu Leu Ser Asn Gly Ala Val Lys Gln Glu Gly Arg Leu Met Ala Ser
                405                 410                 415

Leu Asp Thr Lys Ala Arg Leu Ser Thr Leu His Ile Thr Ala Ala Val
                420                 425                 430

His Asp Leu Ser Ala Thr Tyr Phe Cys Ala Val Gly Asn Tyr Gly Gly
            435                 440                 445

Ser Gln Gly Asn Leu Ile Phe Gly Lys Gly Thr Lys Leu Ser Val Lys
            450                 455                 460

Pro Asn Ile Gln Asn Pro Asp Pro Ala Val Tyr Gln Leu Arg Asp Ser
465                 470                 475                 480

Lys Ser Ser Asp Lys Ser Val Cys Leu Phe Thr Asp Phe Asp Ser Gln
                485                 490                 495

Thr Asn Val Ser Gln Ser Lys Asp Ser Asp Val Tyr Ile Thr Asp Lys
            500                 505                 510

Cys Val Leu Asp Met Arg Ser Met Asp Phe Lys Ser Asn Ser Ala Val
            515                 520                 525

Ala Trp Ser Asn Lys Ser Asp Phe Ala Cys Ala Asn Ala Phe Asn Asn
            530                 535                 540

Ser Ile Ile Pro Glu Asp Thr Phe Phe Pro Ser Pro Glu Ser Ser Cys
545                 550                 555                 560

Asp Val Lys Leu Val Glu Lys Ser Phe Glu Thr Asp Thr Asn Leu Asn
                565                 570                 575

Phe Gln Asn Leu Ser Val Ile Gly Phe Arg Ile Leu Leu Leu Lys Val
            580                 585                 590

Ala Gly Phe Asn Leu Leu Met Thr Leu Arg Leu Trp Ser Ser
            595                 600                 605

<210> SEQ ID NO 19
<211> LENGTH: 137
<212> TYPE: PRT
<213> ORGANISM: Artificial Sequence
<220> FEATURE:
<223> OTHER INFORMATION: WT374 alpha chain variable domain

<400> SEQUENCE: 19

Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
                20                  25                  30

Asn Ser Pro Ser Leu Ser Val Gln Glu Gly Arg Ile Ser Ile Leu Asn
            35                  40                  45

Cys Asp Tyr Thr Asn Ser Met Phe Asp Tyr Phe Leu Trp Tyr Lys Lys
        50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

```
Lys His Leu Ser Leu His Ile Val Pro Ser Gln Pro Gly Asp Ser Ala
            100                 105                 110

Val Tyr Phe Cys Ala Ala Arg Gly Gln Gly Asn Leu Ile Phe Gly Lys
            115                 120                 125

Gly Thr Lys Leu Ser Val Lys Pro Asn
            130                 135

<210> SEQ ID NO 20
<211> LENGTH: 277
<212> TYPE: PRT
<213> ORGANISM: Artificial Sequence
<220> FEATURE:
<223> OTHER INFORMATION: WT374 alpha chain

<400> SEQUENCE: 20

Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Arg Gly Gln Gly Asn Leu Ile Phe Gly Lys
            115                 120                 125

Gly Thr Lys Leu Ser Val Lys Pro Asn Ile Gln Asn Pro Asp Pro Ala
            130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
            195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
            275

<210> SEQ ID NO 21
<211> LENGTH: 277
<212> TYPE: PRT
<213> ORGANISM: Artificial Sequence
```

<220> FEATURE:
<223> OTHER INFORMATION: WT374 alpha (T184C) chain

<400> SEQUENCE: 21

Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Arg Gly Gln Gly Asn Leu Ile Phe Gly Lys
        115                 120                 125

Gly Thr Lys Leu Ser Val Lys Pro Asn Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Cys Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
        275

<210> SEQ ID NO 22
<211> LENGTH: 132
<212> TYPE: PRT
<213> ORGANISM: Artificial Sequence
<220> FEATURE:
<223> OTHER INFORMATION: WT374 beta chain variable domain

<400> SEQUENCE: 22

Met Gly Thr Arg Leu Leu Cys Trp Ala Ala Leu Cys Leu Leu Gly Ala
1               5                   10                  15

Glu Leu Thr Glu Ala Gly Val Ala Gln Ser Pro Arg Tyr Lys Ile Ile
            20                  25                  30

Glu Lys Arg Gln Ser Val Ala Phe Trp Cys Asn Pro Ile Ser Gly His
        35                  40                  45

Ala Thr Leu Tyr Trp Tyr Gln Gln Ile Leu Gly Gln Gly Pro Lys Leu

```
            50                  55                  60
Leu Ile Gln Phe Gln Asn Asn Gly Val Val Asp Asp Ser Gln Leu Pro
 65                  70                  75                  80

Lys Asp Arg Phe Ser Ala Glu Arg Leu Lys Gly Val Asp Ser Thr Leu
                 85                  90                  95

Lys Ile Gln Pro Ala Lys Leu Glu Asp Ser Ala Val Tyr Leu Cys Ala
                100                 105                 110

Ser Ser Leu Tyr Arg Gly Glu Gln Tyr Phe Gly Pro Gly Thr Arg Leu
            115                 120                 125

Thr Val Thr Glu
        130

<210> SEQ ID NO 23
<211> LENGTH: 310
<212> TYPE: PRT
<213> ORGANISM: Artificial Sequence
<220> FEATURE:
<223> OTHER INFORMATION: WT374 beta chain

<400> SEQUENCE: 23

Met Gly Thr Arg Leu Leu Cys Trp Ala Ala Leu Cys Leu Leu Gly Ala
 1               5                  10                  15

Glu Leu Thr Glu Ala Gly Val Ala Gln Ser Pro Arg Tyr Lys Ile Ile
                 20                  25                  30

Glu Lys Arg Gln Ser Val Ala Phe Trp Cys Asn Pro Ile Ser Gly His
             35                  40                  45

Ala Thr Leu Tyr Trp Tyr Gln Gln Ile Leu Gly Gln Gly Pro Lys Leu
         50                  55                  60

Leu Ile Gln Phe Gln Asn Asn Gly Val Val Asp Asp Ser Gln Leu Pro
 65                  70                  75                  80

Lys Asp Arg Phe Ser Ala Glu Arg Leu Lys Gly Val Asp Ser Thr Leu
                 85                  90                  95

Lys Ile Gln Pro Ala Lys Leu Glu Asp Ser Ala Val Tyr Leu Cys Ala
                100                 105                 110

Ser Ser Leu Tyr Arg Gly Glu Gln Tyr Phe Gly Pro Gly Thr Arg Leu
            115                 120                 125

Thr Val Thr Glu Asp Leu Lys Asn Val Phe Pro Pro Glu Val Ala Val
        130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
```

```
            275                 280                 285
Leu Tyr Ala Val Leu Val Ser Ala Leu Val Leu Met Ala Met Val Lys
    290                 295                 300

Arg Lys Asp Ser Arg Gly
305                 310

<210> SEQ ID NO 24
<211> LENGTH: 310
<212> TYPE: PRT
<213> ORGANISM: Artificial Sequence
<220> FEATURE:
<223> OTHER INFORMATION: WT374 beta (S188C) chain

<400> SEQUENCE: 24

Met Gly Thr Arg Leu Leu Cys Trp Ala Ala Leu Cys Leu Leu Gly Ala
1               5                   10                  15

Glu Leu Thr Glu Ala Gly Val Ala Gln Ser Pro Arg Tyr Lys Ile Ile
            20                  25                  30

Glu Lys Arg Gln Ser Val Ala Phe Trp Cys Asn Pro Ile Ser Gly His
        35                  40                  45

Ala Thr Leu Tyr Trp Tyr Gln Gln Ile Leu Gly Gln Gly Pro Lys Leu
    50                  55                  60

Leu Ile Gln Phe Gln Asn Asn Gly Val Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Lys Leu Glu Asp Ser Ala Val Tyr Leu Cys Ala
            100                 105                 110

Ser Ser Leu Tyr Arg Gly Glu Gln Tyr Phe Gly Pro Gly Thr Arg Leu
        115                 120                 125

Thr Val Thr Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Cys Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly
305                 310
```

```
<210> SEQ ID NO 25
<211> LENGTH: 609
<212> TYPE: PRT
<213> ORGANISM: Artificial Sequence
<220> FEATURE:
<223> OTHER INFORMATION: WT374 beta (S188C)-P2A-WT374 alpha (T184C)

<400> SEQUENCE: 25

Met Gly Thr Arg Leu Leu Cys Trp Ala Ala Leu Cys Leu Leu Gly Ala
1               5                   10                  15

Glu Leu Thr Glu Ala Gly Val Ala Gln Ser Pro Arg Tyr Lys Ile Ile
            20                  25                  30

Glu Lys Arg Gln Ser Val Ala Phe Trp Cys Asn Pro Ile Ser Gly His
        35                  40                  45

Ala Thr Leu Tyr Trp Tyr Gln Gln Ile Leu Gly Gln Gly Pro Lys Leu
    50                  55                  60

Leu Ile Gln Phe Gln Asn Asn Gly Val Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Lys Leu Glu Asp Ser Ala Val Tyr Leu Cys Ala
            100                 105                 110

Ser Ser Leu Tyr Arg Gly Glu Gln Tyr Phe Gly Pro Gly Thr Arg Leu
        115                 120                 125

Thr Val Thr Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Cys Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly Gly Ser Gly Ala Thr Asn Phe Ser Leu Leu
305                 310                 315                 320

Lys Gln Ala Gly Asp Val Glu Glu Asn Pro Gly Pro Met Ala Met Leu
                325                 330                 335

Leu Gly Ala Ser Val Leu Ile Leu Trp Leu Gln Pro Asp Trp Val Asn
            340                 345                 350

Ser Gln Gln Lys Asn Asp Asp Gln Gln Val Lys Gln Asn Ser Pro Ser
        355                 360                 365

Leu Ser Val Gln Glu Gly Arg Ile Ser Ile Leu Asn Cys Asp Tyr Thr
```

```
            370                 375                 380
Asn Ser Met Phe Asp Tyr Phe Leu Trp Tyr Lys Lys Tyr Pro Ala Glu
385                 390                 395                 400

Gly Pro Thr Phe Leu Ile Ser Ile Ser Ser Ile Lys Asp Lys Asn Glu
                405                 410                 415

Asp Gly Arg Phe Thr Val Phe Leu Asn Lys Ser Ala Lys His Leu Ser
                420                 425                 430

Leu His Ile Val Pro Ser Gln Pro Gly Asp Ser Ala Val Tyr Phe Cys
            435                 440                 445

Ala Ala Arg Gly Gln Gly Asn Leu Ile Phe Gly Lys Gly Thr Lys Leu
        450                 455                 460

Ser Val Lys Pro Asn Ile Gln Asn Pro Asp Pro Ala Val Tyr Gln Leu
465                 470                 475                 480

Arg Asp Ser Lys Ser Ser Asp Lys Ser Val Cys Leu Phe Thr Asp Phe
                485                 490                 495

Asp Ser Gln Thr Asn Val Ser Gln Ser Lys Asp Ser Asp Val Tyr Ile
                500                 505                 510

Thr Asp Lys Cys Val Leu Asp Met Arg Ser Met Asp Phe Lys Ser Asn
            515                 520                 525

Ser Ala Val Ala Trp Ser Asn Lys Ser Asp Phe Ala Cys Ala Asn Ala
        530                 535                 540

Phe Asn Asn Ser Ile Ile Pro Glu Asp Thr Phe Phe Pro Ser Pro Glu
545                 550                 555                 560

Ser Ser Cys Asp Val Lys Leu Val Glu Lys Ser Phe Glu Thr Asp Thr
                565                 570                 575

Asn Leu Asn Phe Gln Asn Leu Ser Val Ile Gly Phe Arg Ile Leu Leu
                580                 585                 590

Leu Lys Val Ala Gly Phe Asn Leu Leu Met Thr Leu Arg Leu Trp Ser
            595                 600                 605

Ser

<210> SEQ ID NO 26
<211> LENGTH: 138
<212> TYPE: PRT
<213> ORGANISM: Artificial Sequence
<220> FEATURE:
<223> OTHER INFORMATION: WT375 alpha chain variable domain

<400> SEQUENCE: 26

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
                20                  25                  30

Ala Glu Gly Asn Pro Leu Thr Val Lys Cys Thr Tyr Ser Val Ser Gly
            35                  40                  45

Asn Pro Tyr Leu Phe Trp Tyr Val Gln Tyr Pro Asn Arg Gly Leu Gln
        50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
                100                 105                 110

Arg Asp Ile Arg Tyr Tyr Gly Gly Ser Gln Gly Asn Leu Ile Phe Gly
            115                 120                 125
```

Lys Gly Thr Lys Leu Ser Val Lys Pro Asn
    130                 135

<210> SEQ ID NO 27
<211> LENGTH: 278
<212> TYPE: PRT
<213> ORGANISM: Artificial Sequence
<220> FEATURE:
<223> OTHER INFORMATION: WT375 alpha chain

<400> SEQUENCE: 27

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Ile Arg Tyr Tyr Gly Gly Ser Gln Gly Asn Leu Ile Phe Gly
        115                 120                 125

Lys Gly Thr Lys Leu Ser Val Lys Pro Asn Ile Gln Asn Pro Asp Pro
    130                 135                 140

Ala Val Tyr Gln Leu Arg Asp Ser Lys Ser Ser Asp Lys Ser Val Cys
145                 150                 155                 160

Leu Phe Thr Asp Phe Asp Ser Gln Thr Asn Val Ser Gln Ser Lys Asp
                165                 170                 175

Ser Asp Val Tyr Ile Thr Asp Lys Thr Val Leu Asp Met Arg Ser Met
            180                 185                 190

Asp Phe Lys Ser Asn Ser Ala Val Ala Trp Ser Asn Lys Ser Asp Phe
        195                 200                 205

Ala Cys Ala Asn Ala Phe Asn Asn Ser Ile Ile Pro Glu Asp Thr Phe
    210                 215                 220

Phe Pro Ser Pro Glu Ser Ser Cys Asp Val Lys Leu Val Glu Lys Ser
225                 230                 235                 240

Phe Glu Thr Asp Thr Asn Leu Asn Phe Gln Asn Leu Ser Val Ile Gly
                245                 250                 255

Phe Arg Ile Leu Leu Leu Lys Val Ala Gly Phe Asn Leu Leu Met Thr
            260                 265                 270

Leu Arg Leu Trp Ser Ser
        275

<210> SEQ ID NO 28
<211> LENGTH: 278
<212> TYPE: PRT
<213> ORGANISM: Artificial Sequence
<220> FEATURE:
<223> OTHER INFORMATION: WT375 alpha (T185C) chain

<400> SEQUENCE: 28

Met Ala Ser Ala Pro Ile Ser Met Leu Ala Met Leu Phe Thr Leu Ser

```
   1               5                  10                 15
Gly Leu Arg Ala Gln Ser Val Ala Gln Pro Glu Asp Gln Val Asn Val
             20                 25                 30

Ala Glu Gly Asn Pro Leu Thr Val Lys Cys Thr Tyr Ser Val Ser Gly
             35                 40                 45

Asn Pro Tyr Leu Phe Trp Tyr Val Gln Tyr Pro Asn Arg Gly Leu Gln
 50                 55                 60

Phe Leu Leu Lys Tyr Ile Thr Gly Asp Asn Leu Val Lys Gly Ser Tyr
 65                 70                 75                 80

Gly Phe Glu Ala Glu Phe Asn Lys Ser Gln Thr Ser Phe His Leu Lys
             85                 90                 95

Lys Pro Ser Ala Leu Val Ser Asp Ser Ala Leu Tyr Phe Cys Ala Val
            100                105                110

Arg Asp Ile Arg Tyr Tyr Gly Gly Ser Gln Gly Asn Leu Ile Phe Gly
            115                120                125

Lys Gly Thr Lys Leu Ser Val Lys Pro Asn Ile Gln Asn Pro Asp Pro
        130                135                140

Ala Val Tyr Gln Leu Arg Asp Ser Lys Ser Ser Asp Lys Ser Val Cys
145                150                155                160

Leu Phe Thr Asp Phe Asp Ser Gln Thr Asn Val Ser Gln Ser Lys Asp
                165                170                175

Ser Asp Val Tyr Ile Thr Asp Lys Cys Val Leu Asp Met Arg Ser Met
            180                185                190

Asp Phe Lys Ser Asn Ser Ala Val Ala Trp Ser Asn Lys Ser Asp Phe
            195                200                205

Ala Cys Ala Asn Ala Phe Asn Asn Ser Ile Ile Pro Glu Asp Thr Phe
210                215                220

Phe Pro Ser Pro Glu Ser Ser Cys Asp Val Lys Leu Val Glu Lys Ser
225                230                235                240

Phe Glu Thr Asp Thr Asn Leu Asn Phe Gln Asn Leu Ser Val Ile Gly
                245                250                255

Phe Arg Ile Leu Leu Leu Lys Val Ala Gly Phe Asn Leu Leu Met Thr
            260                265                270

Leu Arg Leu Trp Ser Ser
            275

<210> SEQ ID NO 29
<211> LENGTH: 133
<212> TYPE: PRT
<213> ORGANISM: Artificial Sequence
<220> FEATURE:
<223> OTHER INFORMATION: WT375 beta chain variable domain

<400> SEQUENCE: 29

Met Gly Cys Arg Leu Leu Cys Cys Val Val Phe Cys Leu Leu Gln Ala
 1               5                  10                 15

Gly Pro Leu Asp Thr Ala Val Ser Gln Thr Pro Lys Tyr Leu Val Thr
             20                 25                 30

Gln Met Gly Asn Asp Lys Ser Ile Lys Cys Glu Gln Asn Leu Gly His
             35                 40                 45

Asp Thr Met Tyr Trp Tyr Lys Gln Asp Ser Lys Lys Phe Leu Lys Ile
 50                 55                 60

Met Phe Ser Tyr Asn Asn Lys Glu Leu Ile Ile Asn Glu Thr Val Pro
 65                 70                 75                 80

Asn Arg Phe Ser Pro Lys Ser Pro Asp Lys Ala His Leu Asn Leu His
```

```
                    85                  90                  95
Ile Asn Ser Leu Glu Leu Gly Asp Ser Ala Val Tyr Phe Cys Ala Ser
            100                 105                 110

Ser Pro Gly Pro Ser Asn Asn Glu Gln Phe Phe Gly Pro Gly Thr Arg
            115                 120                 125

Leu Thr Val Leu Glu
            130

<210> SEQ ID NO 30
<211> LENGTH: 311
<212> TYPE: PRT
<213> ORGANISM: Artificial Sequence
<220> FEATURE:
<223> OTHER INFORMATION: WT375 beta chain

<400> SEQUENCE: 30

Met Gly Cys Arg Leu Leu Cys Cys Val Val Phe Cys Leu Leu Gln Ala
1               5                   10                  15

Gly Pro Leu Asp Thr Ala Val Ser Gln Thr Pro Lys Tyr Leu Val Thr
            20                  25                  30

Gln Met Gly Asn Asp Lys Ser Ile Lys Cys Glu Gln Asn Leu Gly His
        35                  40                  45

Asp Thr Met Tyr Trp Tyr Lys Gln Asp Ser Lys Lys Phe Leu Lys Ile
    50                  55                  60

Met Phe Ser Tyr Asn Asn Lys Glu Leu Ile Ile Asn Glu Thr Val Pro
65                  70                  75                  80

Asn Arg Phe Ser Pro Lys Ser Pro Asp Lys Ala His Leu Asn Leu His
                85                  90                  95

Ile Asn Ser Leu Glu Leu Gly Asp Ser Ala Val Tyr Phe Cys Ala Ser
            100                 105                 110

Ser Pro Gly Pro Ser Asn Asn Glu Gln Phe Phe Gly Pro Gly Thr Arg
            115                 120                 125

Leu Thr Val Leu Glu Asp Leu Lys Asn Val Phe Pro Pro Glu Val Ala
            130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
```

<210> SEQ ID NO 31
<211> LENGTH: 311
<212> TYPE: PRT
<213> ORGANISM: Artificial Sequence
<220> FEATURE:
<223> OTHER INFORMATION: WT375 beta (S189C) chain

<400> SEQUENCE: 31

Met Gly Cys Arg Leu Leu Cys Cys Val Val Phe Cys Leu Leu Gln Ala
1               5                   10                  15

Gly Pro Leu Asp Thr Ala Val Ser Gln Thr Pro Lys Tyr Leu Val Thr
            20                  25                  30

Gln Met Gly Asn Asp Lys Ser Ile Lys Cys Glu Gln Asn Leu Gly His
        35                  40                  45

Asp Thr Met Tyr Trp Tyr Lys Gln Asp Ser Lys Lys Phe Leu Lys Ile
    50                  55                  60

Met Phe Ser Tyr Asn Asn Lys Glu Leu Ile Ile Asn Glu Thr Val Pro
65                  70                  75                  80

Asn Arg Phe Ser Pro Lys Ser Pro Asp Lys Ala His Leu Asn Leu His
                85                  90                  95

Ile Asn Ser Leu Glu Leu Gly Asp Ser Ala Val Tyr Phe Cys Ala Ser
            100                 105                 110

Ser Pro Gly Pro Ser Asn Asn Glu Gln Phe Phe Gly Pro Gly Thr Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 32
<211> LENGTH: 611
<212> TYPE: PRT
<213> ORGANISM: Artificial Sequence
<220> FEATURE:
<223> OTHER INFORMATION: WT375 beta (S189C)-P2A-WT375 alpha (T185C)

<400> SEQUENCE: 32

Met Gly Cys Arg Leu Leu Cys Cys Val Val Phe Cys Leu Leu Gln Ala
1               5                   10                  15

Gly Pro Leu Asp Thr Ala Val Ser Gln Thr Pro Lys Tyr Leu Val Thr
            20                  25                  30

Gln Met Gly Asn Asp Lys Ser Ile Lys Cys Glu Gln Asn Leu Gly His
        35                  40                  45

Asp Thr Met Tyr Trp Tyr Lys Gln Asp Ser Lys Lys Phe Leu Lys Ile
    50                  55                  60

Met Phe Ser Tyr Asn Asn Lys Glu Leu Ile Ile Asn Glu Thr Val Pro
65                  70                  75                  80

Asn Arg Phe Ser Pro Lys Ser Pro Asp Lys Ala His Leu Asn Leu His
                85                  90                  95

Ile Asn Ser Leu Glu Leu Gly Asp Ser Ala Val Tyr Phe Cys Ala Ser
            100                 105                 110

Ser Pro Gly Pro Ser Asn Asn Glu Gln Phe Phe Gly Pro Gly Thr Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly Gly Ser Gly Ala Thr Asn Phe Ser Leu
305                 310                 315                 320

Leu Lys Gln Ala Gly Asp Val Glu Glu Asn Pro Gly Pro Met Ala Ser
                325                 330                 335

Ala Pro Ile Ser Met Leu Ala Met Leu Phe Thr Leu Ser Gly Leu Arg
            340                 345                 350

Ala Gln Ser Val Ala Gln Pro Glu Asp Gln Val Asn Val Ala Glu Gly
        355                 360                 365

Asn Pro Leu Thr Val Lys Cys Thr Tyr Ser Val Ser Gly Asn Pro Tyr
    370                 375                 380

Leu Phe Trp Tyr Val Gln Tyr Pro Asn Arg Gly Leu Gln Phe Leu Leu
385                 390                 395                 400

Lys Tyr Ile Thr Gly Asp Asn Leu Val Lys Gly Ser Tyr Gly Phe Glu

```
                 405                 410                 415

Ala Glu Phe Asn Lys Ser Gln Thr Ser Phe His Leu Lys Lys Pro Ser
                420                 425                 430

Ala Leu Val Ser Asp Ser Ala Leu Tyr Phe Cys Ala Val Arg Asp Ile
                435                 440                 445

Arg Tyr Tyr Gly Gly Ser Gln Gly Asn Leu Ile Phe Gly Lys Gly Thr
                450                 455                 460

Lys Leu Ser Val Lys Pro Asn Ile Gln Asn Pro Asp Pro Ala Val Tyr
465                 470                 475                 480

Gln Leu Arg Asp Ser Lys Ser Ser Asp Lys Ser Val Cys Leu Phe Thr
                485                 490                 495

Asp Phe Asp Ser Gln Thr Asn Val Ser Gln Ser Lys Asp Ser Asp Val
                500                 505                 510

Tyr Ile Thr Asp Lys Cys Val Leu Asp Met Arg Ser Met Asp Phe Lys
                515                 520                 525

Ser Asn Ser Ala Val Ala Trp Ser Asn Lys Ser Asp Phe Ala Cys Ala
                530                 535                 540

Asn Ala Phe Asn Asn Ser Ile Ile Pro Glu Asp Thr Phe Phe Pro Ser
545                 550                 555                 560

Pro Glu Ser Ser Cys Asp Val Lys Leu Val Glu Lys Ser Phe Glu Thr
                565                 570                 575

Asp Thr Asn Leu Asn Phe Gln Asn Leu Ser Val Ile Gly Phe Arg Ile
                580                 585                 590

Leu Leu Leu Lys Val Ala Gly Phe Asn Leu Leu Met Thr Leu Arg Leu
                595                 600                 605

Trp Ser Ser
    610

<210> SEQ ID NO 33
<211> LENGTH: 137
<212> TYPE: PRT
<213> ORGANISM: Artificial Sequence
<220> FEATURE:
<223> OTHER INFORMATION: WT378 alpha chain variable domain

<400> SEQUENCE: 33

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
                20                  25                  30

Leu Ser Val Pro Glu Gly Ala Ile Val Ser Leu Asn Cys Thr Tyr Ser
                35                  40                  45

Asn Ser Ala Phe Gln Tyr Phe Met Trp Tyr Arg Gln Tyr Ser Arg Lys
                50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
                100                 105                 110

Ile Tyr Gly Trp Gly Gly Ala Thr Asn Lys Leu Ile Phe Gly Thr
                115                 120                 125

Gly Thr Leu Leu Ala Val Gln Pro Asn
    130                 135
```

<210> SEQ ID NO 34
<211> LENGTH: 277
<212> TYPE: PRT
<213> ORGANISM: Artificial Sequence
<220> FEATURE:
<223> OTHER INFORMATION: WT378 alpha chain

<400> SEQUENCE: 34

```
Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Ile Tyr Gly Trp Gly Gly Ala Thr Asn Lys Leu Ile Phe Gly Thr
        115                 120                 125

Gly Thr Leu Leu Ala Val Gln Pro Asn Ile Gln Asn Pro Asp Pro Ala
130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
        275
```

<210> SEQ ID NO 35
<211> LENGTH: 277
<212> TYPE: PRT
<213> ORGANISM: Artificial Sequence
<220> FEATURE:
<223> OTHER INFORMATION: WT378 alpha (T184C) chain

<400> SEQUENCE: 35

```
Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30
```

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
 50                  55                  60

Gly Pro Glu Leu Leu Met Tyr Thr Tyr Ser Ser Gly Asn Lys Glu Asp
 65                  70                  75                  80

Gly Arg Phe Thr Ala Gln Val Asp Lys Ser Ser Lys Tyr Ile Ser Leu
                 85                  90                  95

Phe Ile Arg Asp Ser Gln Pro Ser Asp Ser Ala Thr Tyr Leu Cys Ala
            100                 105                 110

Ile Tyr Gly Trp Gly Gly Ala Thr Asn Lys Leu Ile Phe Gly Thr
        115                 120                 125

Gly Thr Leu Leu Ala Val Gln Pro Asn Ile Gln Asn Pro Asp Pro Ala
130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Cys Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
        275

<210> SEQ ID NO 36
<211> LENGTH: 135
<212> TYPE: PRT
<213> ORGANISM: Artificial Sequence
<220> FEATURE:
<223> OTHER INFORMATION: WT378 beta chain variable domain

<400> SEQUENCE: 36

Met Gly Thr Ser Leu Leu Cys Trp Val Val Leu Gly Phe Leu Gly Thr
 1               5                  10                  15

Asp His Thr Gly Ala Gly Val Ser Gln Ser Pro Arg Tyr Lys Val Thr
             20                  25                  30

Lys Arg Gly Gln Asp Val Ala Leu Arg Cys Asp Pro Ile Ser Gly His
         35                  40                  45

Val Ser Leu Tyr Trp Tyr Arg Gln Ala Leu Gly Gln Gly Pro Glu Phe
     50                  55                  60

Leu Thr Tyr Phe Asn Tyr Glu Ala Gln Gln Asp Lys Ser Gly Leu Pro
 65                  70                  75                  80

Asn Asp Arg Phe Ser Ala Glu Arg Pro Glu Gly Ser Ile Ser Thr Leu
                 85                  90                  95

Thr Ile Gln Arg Thr Glu Gln Arg Asp Ser Ala Met Tyr Arg Cys Ala
            100                 105                 110

Ser Ser Leu Tyr Gly Gly Ser Ser Tyr Glu Gln Tyr Phe Gly Pro Gly
            115                 120                 125

Thr Arg Leu Thr Val Thr Glu
            130             135

<210> SEQ ID NO 37
<211> LENGTH: 313
<212> TYPE: PRT
<213> ORGANISM: Artificial Sequence
<220> FEATURE:
<223> OTHER INFORMATION: WT378 beta chain

<400> SEQUENCE: 37

Met Gly Thr Ser Leu Leu Cys Trp Val Val Leu Gly Phe Leu Gly Thr
1               5                   10                  15

Asp His Thr Gly Ala Gly Val Ser Gln Ser Pro Arg Tyr Lys Val Thr
            20                  25                  30

Lys Arg Gly Gln Asp Val Ala Leu Arg Cys Asp Pro Ile Ser Gly His
            35                  40                  45

Val Ser Leu Tyr Trp Tyr Arg Gln Ala Leu Gly Gln Gly Pro Glu Phe
        50                  55                  60

Leu Thr Tyr Phe Asn Tyr Glu Ala Gln Gln Asp Lys Ser Gly Leu Pro
65                  70                  75                  80

Asn Asp Arg Phe Ser Ala Glu Arg Pro Glu Gly Ser Ile Ser Thr Leu
                85                  90                  95

Thr Ile Gln Arg Thr Glu Gln Arg Asp Ser Ala Met Tyr Arg Cys Ala
            100                 105                 110

Ser Ser Leu Tyr Gly Gly Ser Ser Tyr Glu Gln Tyr Phe Gly Pro Gly
            115                 120                 125

Thr Arg Leu Thr Val Thr Glu Asp Leu Lys Asn Val Phe Pro Pro Glu
            130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
            195                 200                 205

Cys Leu Ser Ser Arg Leu Arg Val Ser Ala Thr Phe Trp Gln Asn Pro
        210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Glu Ser Tyr
            260                 265                 270

Gln Gln Gly Val Leu Ser Ala Thr Ile Leu Tyr Glu Ile Leu Leu Gly
            275                 280                 285

Lys Ala Thr Leu Tyr Ala Val Leu Val Ser Ala Leu Val Leu Met Ala
        290                 295                 300

Met Val Lys Arg Lys Asp Ser Arg Gly
305                 310

<210> SEQ ID NO 38
<211> LENGTH: 313

<212> TYPE: PRT
<213> ORGANISM: Artificial Sequence
<220> FEATURE:
<223> OTHER INFORMATION: WT378 beta (S191C) chain

<400> SEQUENCE: 38

```
Met Gly Thr Ser Leu Leu Cys Trp Val Val Leu Gly Phe Leu Gly Thr
1               5                   10                  15

Asp His Thr Gly Ala Gly Val Ser Gln Ser Pro Arg Tyr Lys Val Thr
            20                  25                  30

Lys Arg Gly Gln Asp Val Ala Leu Arg Cys Asp Pro Ile Ser Gly His
        35                  40                  45

Val Ser Leu Tyr Trp Tyr Arg Gln Ala Leu Gly Gln Gly Pro Glu Phe
    50                  55                  60

Leu Thr Tyr Phe Asn Tyr Glu Ala Gln Gln Asp Lys Ser Gly Leu Pro
65                  70                  75                  80

Asn Asp Arg Phe Ser Ala Glu Arg Pro Glu Gly Ser Ile Ser Thr Leu
                85                  90                  95

Thr Ile Gln Arg Thr Glu Gln Arg Asp Ser Ala Met Tyr Arg Cys Ala
            100                 105                 110

Ser Ser Leu Tyr Gly Gly Ser Ser Tyr Glu Gln Tyr Phe Gly Pro Gly
        115                 120                 125

Thr Arg Leu Thr Val Thr Glu Asp Leu Lys Asn Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Cys Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Glu Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
    290                 295                 300

Met Val Lys Arg Lys Asp Ser Arg Gly
305                 310
```

<210> SEQ ID NO 39
<211> LENGTH: 612
<212> TYPE: PRT
<213> ORGANISM: Artificial Sequence
<220> FEATURE:
<223> OTHER INFORMATION: WT378 beta (S191C)-P2A-WT378 alpha (T184C)

<400> SEQUENCE: 39

```
Met Gly Thr Ser Leu Leu Cys Trp Val Val Leu Gly Phe Leu Gly Thr
1               5                   10                  15
```

```
Asp His Thr Gly Ala Gly Val Ser Gln Ser Pro Arg Tyr Lys Val Thr
             20                  25                  30

Lys Arg Gly Gln Asp Val Ala Leu Arg Cys Asp Pro Ile Ser Gly His
         35                  40                  45

Val Ser Leu Tyr Trp Tyr Arg Gln Ala Leu Gly Gln Gly Pro Glu Phe
 50                  55                  60

Leu Thr Tyr Phe Asn Tyr Glu Ala Gln Gln Asp Lys Ser Gly Leu Pro
 65                  70                  75                  80

Asn Asp Arg Phe Ser Ala Glu Arg Pro Glu Gly Ser Ile Ser Thr Leu
                 85                  90                  95

Thr Ile Gln Arg Thr Glu Gln Arg Asp Ser Ala Met Tyr Arg Cys Ala
             100                 105                 110

Ser Ser Leu Tyr Gly Gly Ser Ser Tyr Glu Gln Tyr Phe Gly Pro Gly
         115                 120                 125

Thr Arg Leu Thr Val Thr Glu Asp Leu Lys Asn Val Phe Pro Pro Glu
130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                 165                 170                 175

Leu Ser Trp Trp Val Asn Gly Lys Glu Val His Ser Gly Val Cys Thr
             180                 185                 190

Asp Pro Gln Pro Leu Lys Glu Gln Pro Ala Leu Asn Asp Ser Arg Tyr
         195                 200                 205

Cys Leu Ser Ser Arg Leu Arg Val Ser Ala Thr Phe Trp Gln Asn Pro
 210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                 245                 250                 255

Ala Glu Ala Trp Gly Arg Ala Asp Cys Gly Phe Thr Ser Glu Ser Tyr
             260                 265                 270

Gln Gln Gly Val Leu Ser Ala Thr Ile Leu Tyr Glu Ile Leu Leu Gly
         275                 280                 285

Lys Ala Thr Leu Tyr Ala Val Leu Val Ser Ala Leu Val Leu Met Ala
290                 295                 300

Met Val Lys Arg Lys Asp Ser Arg Gly Gly Ser Gly Ala Thr Asn Phe
305                 310                 315                 320

Ser Leu Leu Lys Gln Ala Gly Asp Val Glu Glu Asn Pro Gly Pro Met
                 325                 330                 335

Met Lys Ser Leu Arg Val Leu Leu Val Ile Leu Trp Leu Gln Leu Ser
             340                 345                 350

Trp Val Trp Ser Gln Gln Lys Glu Val Glu Gln Asp Pro Gly Pro Leu
         355                 360                 365

Ser Val Pro Glu Gly Ala Ile Val Ser Leu Asn Cys Thr Tyr Ser Asn
370                 375                 380

Ser Ala Phe Gln Tyr Phe Met Trp Tyr Arg Gln Tyr Ser Arg Lys Gly
385                 390                 395                 400

Pro Glu Leu Leu Met Tyr Thr Tyr Ser Ser Gly Asn Lys Glu Asp Gly
                 405                 410                 415

Arg Phe Thr Ala Gln Val Asp Lys Ser Ser Lys Tyr Ile Ser Leu Phe
             420                 425                 430
```

-continued

```
Ile Arg Asp Ser Gln Pro Ser Asp Ser Ala Thr Tyr Leu Cys Ala Ile
        435                 440                 445

Tyr Gly Trp Gly Gly Gly Ala Thr Asn Lys Leu Ile Phe Gly Thr Gly
450                 455                 460

Thr Leu Leu Ala Val Gln Pro Asn Ile Gln Asn Pro Asp Pro Ala Val
465                 470                 475                 480

Tyr Gln Leu Arg Asp Ser Lys Ser Ser Asp Lys Ser Val Cys Leu Phe
                485                 490                 495

Thr Asp Phe Asp Ser Gln Thr Asn Val Ser Gln Ser Lys Asp Ser Asp
            500                 505                 510

Val Tyr Ile Thr Asp Lys Cys Val Leu Asp Met Arg Ser Met Asp Phe
        515                 520                 525

Lys Ser Asn Ser Ala Val Ala Trp Ser Asn Lys Ser Asp Phe Ala Cys
530                 535                 540

Ala Asn Ala Phe Asn Asn Ser Ile Ile Pro Glu Asp Thr Phe Phe Pro
545                 550                 555                 560

Ser Pro Glu Ser Ser Cys Asp Val Lys Leu Val Glu Lys Ser Phe Glu
                565                 570                 575

Thr Asp Thr Asn Leu Asn Phe Gln Asn Leu Ser Val Ile Gly Phe Arg
            580                 585                 590

Ile Leu Leu Leu Lys Val Ala Gly Phe Asn Leu Leu Met Thr Leu Arg
        595                 600                 605

Leu Trp Ser Ser
    610

<210> SEQ ID NO 40
<211> LENGTH: 134
<212> TYPE: PRT
<213> ORGANISM: Artificial Sequence
<220> FEATURE:
<223> OTHER INFORMATION: WT379 alpha chain variable domain

<400> SEQUENCE: 40

Met Lys Ser Leu Arg Val Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Gly Gly Ser Gly Gly Tyr Gln Lys Val Thr Phe Gly Ile Gly Thr Lys
        115                 120                 125

Leu Gln Val Ile Pro Asn
    130

<210> SEQ ID NO 41
<211> LENGTH: 274
<212> TYPE: PRT
<213> ORGANISM: Artificial Sequence
<220> FEATURE:
```

<223> OTHER INFORMATION: WT379 alpha chain

<400> SEQUENCE: 41

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
            85                  90                  95

Ile Arg Asp Ser Gln Pro Ser Asp Ser Ala Thr Tyr Leu Cys Ala Val
        100                 105                 110

Gly Gly Ser Gly Gly Tyr Gln Lys Val Thr Phe Gly Ile Gly Thr Lys
    115                 120                 125

Leu Gln Val Ile Pro Asn Ile Gln Asn Pro Asp Pro Ala Val Tyr Gln
130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 42
<211> LENGTH: 274
<212> TYPE: PRT
<213> ORGANISM: Artificial Sequence
<220> FEATURE:
<223> OTHER INFORMATION: WT379 alpha (T181C) chain

<400> SEQUENCE: 42

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

```
Pro Glu Leu Ile Met Phe Ile Tyr Ser Asn Gly Asp Lys Glu Asp Gly
 65                  70                  75                  80

Arg Phe Thr Ala Gln Leu Asn Lys Ala Ser Gln Tyr Val Ser Leu Leu
                 85                  90                  95

Ile Arg Asp Ser Gln Pro Ser Asp Ser Ala Thr Tyr Leu Cys Ala Val
                100                 105                 110

Gly Gly Ser Gly Gly Tyr Gln Lys Val Thr Phe Gly Ile Gly Thr Lys
                115                 120                 125

Leu Gln Val Ile Pro Asn Ile Gln Asn Pro Asp Pro Ala Val Tyr Gln
        130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Cys Val Leu Asp Met Arg Ser Met Asp Phe Lys Ser
                180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
        210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
        260                 265                 270

Ser Ser
```

<210> SEQ ID NO 43
<211> LENGTH: 133
<212> TYPE: PRT
<213> ORGANISM: Artificial Sequence
<220> FEATURE:
<223> OTHER INFORMATION: WT379 beta chain variable domain

<400> SEQUENCE: 43

```
Met Ser Asn Gln Val Leu Cys Cys Val Val Leu Cys Phe Leu Gly Ala
 1               5                  10                  15

Asn Thr Val Asp Gly Gly Ile Thr Gln Ser Pro Lys Tyr Leu Phe Arg
                 20                  25                  30

Lys Glu Gly Gln Asn Val Thr Leu Ser Cys Glu Gln Asn Leu Asn His
             35                  40                  45

Asp Ala Met Tyr Trp Tyr Arg Gln Asp Pro Gly Gln Gly Leu Arg Leu
         50                  55                  60

Ile Tyr Tyr Ser Gln Ile Val Asn Asp Phe Gln Lys Gly Asp Ile Ala
 65                  70                  75                  80

Glu Gly Tyr Ser Val Ser Arg Glu Lys Lys Glu Ser Phe Pro Leu Thr
                 85                  90                  95

Val Thr Ser Ala Gln Lys Asn Pro Thr Ala Phe Tyr Leu Cys Ala Ser
                100                 105                 110

Ser Gly Arg Ala Gly Val Gly Leu Phe Phe Gly Gly Gly Ser Arg
                115                 120                 125

Leu Thr Val Leu Glu
        130
```

<210> SEQ ID NO 44
<211> LENGTH: 311
<212> TYPE: PRT
<213> ORGANISM: Artificial Sequence
<220> FEATURE:
<223> OTHER INFORMATION: WT379 beta chain

<400> SEQUENCE: 44

```
Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Gly Arg Ala Gly Val Gly Glu Leu Phe Phe Gly Glu Gly Ser Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310
```

<210> SEQ ID NO 45
<211> LENGTH: 311
<212> TYPE: PRT
<213> ORGANISM: Artificial Sequence
<220> FEATURE:
<223> OTHER INFORMATION: WT379 beta (S189C) chain

<400> SEQUENCE: 45

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Gly Arg Ala Gly Val Gly Glu Leu Phe Phe Gly Glu Gly Ser Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 46
<211> LENGTH: 607
<212> TYPE: PRT
<213> ORGANISM: Artificial Sequence
<220> FEATURE:
<223> OTHER INFORMATION: WT379 beta (S189C)-P2A-WT379 alpha (T181C)

<400> SEQUENCE: 46

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

```
Asp Ala Met Tyr Trp Tyr Arg Gln Asp Pro Gly Gln Gly Leu Arg Leu
             50                  55                  60

Ile Tyr Tyr Ser Gln Ile Val Asn Asp Phe Gln Lys Gly Asp Ile Ala
 65                  70                  75                  80

Glu Gly Tyr Ser Val Ser Arg Glu Lys Lys Glu Ser Phe Pro Leu Thr
                 85                  90                  95

Val Thr Ser Ala Gln Lys Asn Pro Thr Ala Phe Tyr Leu Cys Ala Ser
                100                 105                 110

Ser Gly Arg Ala Gly Val Gly Leu Phe Phe Gly Glu Gly Ser Arg
            115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly Gly Ser Gly Ala Thr Asn Phe Ser Leu
305                 310                 315                 320

Leu Lys Gln Ala Gly Asp Val Glu Glu Asn Pro Gly Pro Met Lys Ser
                325                 330                 335

Leu Arg Val Leu Leu Val Ile Leu Trp Leu Gln Leu Ser Trp Val Trp
            340                 345                 350

Ser Gln Gln Lys Glu Val Glu Gln Asn Ser Gly Pro Leu Ser Val Pro
        355                 360                 365

Glu Gly Ala Ile Ala Ser Leu Asn Cys Thr Tyr Ser Asp Arg Gly Ser
    370                 375                 380

Gln Ser Phe Phe Trp Tyr Arg Gln Tyr Ser Gly Lys Ser Pro Glu Leu
385                 390                 395                 400

Ile Met Phe Ile Tyr Ser Asn Gly Asp Lys Glu Asp Gly Arg Phe Thr
                405                 410                 415

Ala Gln Leu Asn Lys Ala Ser Gln Tyr Val Ser Leu Leu Ile Arg Asp
            420                 425                 430

Ser Gln Pro Ser Asp Ser Ala Thr Tyr Leu Cys Ala Val Gly Gly Ser
        435                 440                 445

Gly Gly Tyr Gln Lys Val Thr Phe Gly Ile Gly Thr Lys Leu Gln Val
    450                 455                 460

Ile Pro Asn Ile Gln Asn Pro Asp Pro Ala Val Tyr Gln Leu Arg Asp
```

```
                465                 470                 475                 480
Ser Lys Ser Ser Asp Lys Ser Val Cys Leu Phe Thr Asp Phe Asp Ser
                    485                 490                 495

Gln Thr Asn Val Ser Gln Ser Lys Asp Ser Asp Val Tyr Ile Thr Asp
                500                 505                 510

Lys Cys Val Leu Asp Met Arg Ser Met Asp Phe Lys Ser Asn Ser Ala
                515                 520                 525

Val Ala Trp Ser Asn Lys Ser Asp Phe Ala Cys Ala Asn Ala Phe Asn
            530                 535                 540

Asn Ser Ile Ile Pro Glu Asp Thr Phe Phe Pro Ser Pro Glu Ser Ser
545                 550                 555                 560

Cys Asp Val Lys Leu Val Glu Lys Ser Phe Glu Thr Asp Thr Asn Leu
                565                 570                 575

Asn Phe Gln Asn Leu Ser Val Ile Gly Phe Arg Ile Leu Leu Leu Lys
                580                 585                 590

Val Ala Gly Phe Asn Leu Leu Met Thr Leu Arg Leu Trp Ser Ser
                595                 600                 605

<210> SEQ ID NO 47
<211> LENGTH: 135
<212> TYPE: PRT
<213> ORGANISM: Artificial Sequence
<220> FEATURE:
<223> OTHER INFORMATION: WT3710 alpha chain variable domain

<400> SEQUENCE: 47

Met Ile Ser Leu Arg Val Leu Leu Val Ile Leu Trp Leu Gln Leu Ser
1               5                   10                  15

Trp Val Trp Ser Gln Arg Lys Glu Val Glu Gln Asp Pro Gly Pro Phe
                20                  25                  30

Asn Val Pro Glu Gly Ala Thr Val Ala Phe Asn Cys Thr Tyr Ser Asn
                35                  40                  45

Ser Ala Ser Gln Ser Phe Phe Trp Tyr Arg Gln Asp Cys Arg Lys Glu
        50                  55                  60

Pro Lys Leu Leu Met Ser Val Tyr Ser Ser Gly Asn Glu Asp Gly Arg
65                  70                  75                  80

Phe Thr Ala Gln Leu Asn Arg Ala Ser Gln Tyr Ile Ser Leu Leu Ile
                85                  90                  95

Arg Asp Ser Lys Leu Ser Asp Ser Ala Thr Tyr Leu Cys Val Val Lys
                100                 105                 110

Pro Asp Pro Gly Ala Gly Ser Tyr Gln Leu Thr Phe Gly Lys Gly Thr
            115                 120                 125

Lys Leu Ser Val Ile Pro Asn
    130                 135

<210> SEQ ID NO 48
<211> LENGTH: 275
<212> TYPE: PRT
<213> ORGANISM: Artificial Sequence
<220> FEATURE:
<223> OTHER INFORMATION: WT3710 alpha chain

<400> SEQUENCE: 48

Met Ile Ser Leu Arg Val Leu Leu Val Ile Leu Trp Leu Gln Leu Ser
1               5                   10                  15

Trp Val Trp Ser Gln Arg Lys Glu Val Glu Gln Asp Pro Gly Pro Phe
                20                  25                  30
```

Asn Val Pro Glu Gly Ala Thr Val Ala Phe Asn Cys Thr Tyr Ser Asn
            35                  40                  45

Ser Ala Ser Gln Ser Phe Phe Trp Tyr Arg Gln Asp Cys Arg Lys Glu
 50                  55                  60

Pro Lys Leu Leu Met Ser Val Tyr Ser Ser Gly Asn Glu Asp Gly Arg
 65                  70                  75                  80

Phe Thr Ala Gln Leu Asn Arg Ala Ser Gln Tyr Ile Ser Leu Leu Ile
                85                  90                  95

Arg Asp Ser Lys Leu Ser Asp Ser Ala Thr Tyr Leu Cys Val Val Lys
            100                 105                 110

Pro Asp Pro Gly Ala Gly Ser Tyr Gln Leu Thr Phe Gly Lys Gly Thr
            115                 120                 125

Lys Leu Ser Val Ile Pro Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
            195                 200                 205

Asn Ala Phe Asn Asn Ser Ile Ile Pro Glu Asp Thr Phe Phe Pro Ser
        210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275

<210> SEQ ID NO 49
<211> LENGTH: 275
<212> TYPE: PRT
<213> ORGANISM: Artificial Sequence
<220> FEATURE:
<223> OTHER INFORMATION: WT3710 alpha (T182C) chain

<400> SEQUENCE: 49

Met Ile Ser Leu Arg Val Leu Val Ile Leu Trp Leu Gln Leu Ser
1               5                   10                  15

Trp Val Trp Ser Gln Arg Lys Glu Val Glu Gln Asp Pro Gly Pro Phe
            20                  25                  30

Asn Val Pro Glu Gly Ala Thr Val Ala Phe Asn Cys Thr Tyr Ser Asn
            35                  40                  45

Ser Ala Ser Gln Ser Phe Phe Trp Tyr Arg Gln Asp Cys Arg Lys Glu
 50                  55                  60

Pro Lys Leu Leu Met Ser Val Tyr Ser Ser Gly Asn Glu Asp Gly Arg
 65                  70                  75                  80

Phe Thr Ala Gln Leu Asn Arg Ala Ser Gln Tyr Ile Ser Leu Leu Ile
                85                  90                  95

Arg Asp Ser Lys Leu Ser Asp Ser Ala Thr Tyr Leu Cys Val Val Lys
            100                 105                 110

Pro Asp Pro Gly Ala Gly Ser Tyr Gln Leu Thr Phe Gly Lys Gly Thr
            115                 120                 125

Lys Leu Ser Val Ile Pro Asn Ile Gln Asn Pro Asp Pro Ala Val Tyr
130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Cys Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275

<210> SEQ ID NO 50
<211> LENGTH: 134
<212> TYPE: PRT
<213> ORGANISM: Artificial Sequence
<220> FEATURE:
<223> OTHER INFORMATION: WT3710 beta chain variable domain

<400> SEQUENCE: 50

Met Ser Leu Gly Leu Leu Cys Cys Gly Ala Phe Ser Leu Leu Trp Ala
1               5                   10                  15

Gly Pro Val Asn Ala Gly Val Thr Gln Thr Pro Lys Phe Arg Val Leu
            20                  25                  30

Lys Thr Gly Gln Ser Met Thr Leu Leu Cys Ala Gln Asp Met Asn His
        35                  40                  45

Glu Tyr Met Tyr Trp Tyr Arg Gln Asp Pro Gly Met Gly Leu Arg Leu
    50                  55                  60

Ile His Tyr Ser Val Gly Glu Gly Thr Thr Ala Lys Gly Glu Val Pro
65                  70                  75                  80

Asp Gly Tyr Asn Val Ser Arg Leu Lys Lys Gln Asn Phe Leu Leu Gly
                85                  90                  95

Leu Glu Ser Ala Ala Pro Ser Gln Thr Ser Val Tyr Phe Cys Ala Ser
            100                 105                 110

Arg Gly Tyr His Arg Leu Asn Asn Glu Gln Phe Phe Gly Pro Gly Thr
        115                 120                 125

Arg Leu Thr Val Leu Glu
    130

<210> SEQ ID NO 51
<211> LENGTH: 312
<212> TYPE: PRT
<213> ORGANISM: Artificial Sequence
<220> FEATURE:
<223> OTHER INFORMATION: WT3710 beta chain

<400> SEQUENCE: 51

Met Ser Leu Gly Leu Leu Cys Cys Gly Ala Phe Ser Leu Leu Trp Ala
1               5                   10                  15

Gly Pro Val Asn Ala Gly Val Thr Gln Thr Pro Lys Phe Arg Val Leu
            20                  25                  30

Lys Thr Gly Gln Ser Met Thr Leu Leu Cys Ala Gln Asp Met Asn His
        35                  40                  45

Glu Tyr Met Tyr Trp Tyr Arg Gln Asp Pro Gly Met Gly Leu Arg Leu
50                  55                  60

Ile His Tyr Ser Val Gly Glu Gly Thr Thr Ala Lys Gly Glu Val Pro
65                  70                  75                  80

Asp Gly Tyr Asn Val Ser Arg Leu Lys Lys Gln Asn Phe Leu Leu Gly
            85                  90                  95

Leu Glu Ser Ala Ala Pro Ser Gln Thr Ser Val Tyr Phe Cys Ala Ser
        100                 105                 110

Arg Gly Tyr His Arg Leu Asn Asn Glu Gln Phe Phe Gly Pro Gly Thr
    115                 120                 125

Arg Leu Thr Val Leu Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310

<210> SEQ ID NO 52
<211> LENGTH: 312
<212> TYPE: PRT
<213> ORGANISM: Artificial Sequence
<220> FEATURE:
<223> OTHER INFORMATION: WT3710 beta (S190C) chain

<400> SEQUENCE: 52

Met Ser Leu Gly Leu Leu Cys Cys Gly Ala Phe Ser Leu Leu Trp Ala
1               5                   10                  15

Gly Pro Val Asn Ala Gly Val Thr Gln Thr Pro Lys Phe Arg Val Leu
            20                  25                  30

Lys Thr Gly Gln Ser Met Thr Leu Leu Cys Ala Gln Asp Met Asn His
        35                  40                  45

```
Glu Tyr Met Tyr Trp Tyr Arg Gln Asp Pro Gly Met Gly Leu Arg Leu
 50                  55                  60

Ile His Tyr Ser Val Gly Glu Gly Thr Thr Ala Lys Gly Glu Val Pro
 65                  70                  75                  80

Asp Gly Tyr Asn Val Ser Arg Leu Lys Lys Gln Asn Phe Leu Leu Gly
                 85                  90                  95

Leu Glu Ser Ala Ala Pro Ser Gln Thr Ser Val Tyr Phe Cys Ala Ser
                100                 105                 110

Arg Gly Tyr His Arg Leu Asn Asn Glu Gln Phe Phe Gly Pro Gly Thr
            115                 120                 125

Arg Leu Thr Val Leu Glu Asp Leu Lys Asn Val Phe Pro Pro Glu Val
        130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Cys Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
290                 295                 300

Val Lys Arg Lys Asp Ser Arg Gly
305                 310

<210> SEQ ID NO 53
<211> LENGTH: 609
<212> TYPE: PRT
<213> ORGANISM: Artificial Sequence
<220> FEATURE:
<223> OTHER INFORMATION: WT3710 beta (S190C)-P2A-WT3710 alpha (T182C)

<400> SEQUENCE: 53

Met Ser Leu Gly Leu Cys Cys Gly Ala Phe Ser Leu Leu Trp Ala
 1               5                  10                  15

Gly Pro Val Asn Ala Gly Val Thr Gln Thr Pro Lys Phe Arg Val Leu
                 20                  25                  30

Lys Thr Gly Gln Ser Met Thr Leu Leu Cys Ala Gln Asp Met Asn His
             35                  40                  45

Glu Tyr Met Tyr Trp Tyr Arg Gln Asp Pro Gly Met Gly Leu Arg Leu
 50                  55                  60

Ile His Tyr Ser Val Gly Glu Gly Thr Thr Ala Lys Gly Glu Val Pro
 65                  70                  75                  80

Asp Gly Tyr Asn Val Ser Arg Leu Lys Lys Gln Asn Phe Leu Leu Gly
                 85                  90                  95
```

```
Leu Glu Ser Ala Ala Pro Ser Gln Thr Ser Val Tyr Phe Cys Ala Ser
                100                 105                 110

Arg Gly Tyr His Arg Leu Asn Glu Gln Phe Phe Gly Pro Gly Thr
            115                 120                 125

Arg Leu Thr Val Leu Glu Asp Leu Lys Asn Val Phe Pro Pro Glu Val
130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Cys Thr Asp
                180                 185                 190

Pro Gln Pro Leu Lys Glu Gln Pro Ala Leu Asn Asp Ser Arg Tyr Cys
                195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
                260                 265                 270

Gln Gly Val Leu Ser Ala Thr Ile Leu Tyr Glu Ile Leu Leu Gly Lys
            275                 280                 285

Ala Thr Leu Tyr Ala Val Leu Val Ser Ala Leu Val Leu Met Ala Met
    290                 295                 300

Val Lys Arg Lys Asp Ser Arg Gly Gly Ser Gly Ala Thr Asn Phe Ser
305                 310                 315                 320

Leu Leu Lys Gln Ala Gly Asp Val Glu Glu Asn Pro Gly Pro Met Ile
                325                 330                 335

Ser Leu Arg Val Leu Leu Val Ile Leu Trp Leu Gln Leu Ser Trp Val
            340                 345                 350

Trp Ser Gln Arg Lys Glu Val Glu Gln Asp Pro Gly Pro Phe Asn Val
    355                 360                 365

Pro Glu Gly Ala Thr Val Ala Phe Asn Cys Thr Tyr Ser Asn Ser Ala
370                 375                 380

Ser Gln Ser Phe Phe Trp Tyr Arg Gln Asp Cys Arg Lys Glu Pro Lys
385                 390                 395                 400

Leu Leu Met Ser Val Tyr Ser Ser Gly Asn Glu Asp Gly Arg Phe Thr
                405                 410                 415

Ala Gln Leu Asn Arg Ala Ser Gln Tyr Ile Ser Leu Leu Ile Arg Asp
            420                 425                 430

Ser Lys Leu Ser Asp Ser Ala Thr Tyr Leu Cys Val Val Lys Pro Asp
    435                 440                 445

Pro Gly Ala Gly Ser Tyr Gln Leu Thr Phe Gly Lys Gly Thr Lys Leu
450                 455                 460

Ser Val Ile Pro Asn Ile Gln Asn Pro Asp Pro Ala Val Tyr Gln Leu
465                 470                 475                 480

Arg Asp Ser Lys Ser Ser Asp Lys Ser Val Cys Leu Phe Thr Asp Phe
                485                 490                 495

Asp Ser Gln Thr Asn Val Ser Gln Ser Lys Asp Ser Asp Val Tyr Ile
                500                 505                 510
```

```
Thr Asp Lys Cys Val Leu Asp Met Arg Ser Met Asp Phe Lys Ser Asn
            515                 520                 525

Ser Ala Val Ala Trp Ser Asn Lys Ser Asp Phe Ala Cys Ala Asn Ala
        530                 535                 540

Phe Asn Asn Ser Ile Ile Pro Glu Asp Thr Phe Phe Pro Ser Pro Glu
545                 550                 555                 560

Ser Ser Cys Asp Val Lys Leu Val Glu Lys Ser Phe Glu Thr Asp Thr
                565                 570                 575

Asn Leu Asn Phe Gln Asn Leu Ser Val Ile Gly Phe Arg Ile Leu Leu
                580                 585                 590

Leu Lys Val Ala Gly Phe Asn Leu Leu Met Thr Leu Arg Leu Trp Ser
            595                 600                 605

Ser
```

<210> SEQ ID NO 54
<211> LENGTH: 138
<212> TYPE: PRT
<213> ORGANISM: Artificial Sequence
<220> FEATURE:
<223> OTHER INFORMATION: WT371 alpha chain variable domain

<400> SEQUENCE: 54

```
Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
                20                  25                  30

Val Gln Glu Lys Glu Ala Val Thr Leu Asp Cys Thr Tyr Asp Thr Ser
            35                  40                  45

Asp Pro Ser Tyr Gly Leu Phe Trp Tyr Lys Gln Pro Ser Ser Gly Glu
        50                  55                  60

Met Ile Phe Leu Ile Tyr Gln Gly Ser Tyr Asp Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Ala Arg Glu Glu Thr Ser Gly Ser Arg Leu Thr Phe Gly
        115                 120                 125

Glu Gly Thr Gln Leu Thr Val Asn Pro Asp
    130                 135
```

<210> SEQ ID NO 55
<211> LENGTH: 278
<212> TYPE: PRT
<213> ORGANISM: Artificial Sequence
<220> FEATURE:
<223> OTHER INFORMATION: WT371 alpha chain

<400> SEQUENCE: 55

```
Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
                20                  25                  30

Val Gln Glu Lys Glu Ala Val Thr Leu Asp Cys Thr Tyr Asp Thr Ser
            35                  40                  45

Asp Pro Ser Tyr Gly Leu Phe Trp Tyr Lys Gln Pro Ser Ser Gly Glu
        50                  55                  60
```

```
Met Ile Phe Leu Ile Tyr Gln Gly Ser Tyr Asp Gln Gln Asn Ala Thr
 65                  70                  75                  80

Glu Gly Arg Tyr Ser Leu Asn Phe Gln Lys Ala Arg Lys Ser Ala Asn
                 85                  90                  95

Leu Val Ile Ser Ala Ser Gln Leu Gly Asp Ser Ala Met Tyr Phe Cys
            100                 105                 110

Ala Met Arg Ala Arg Glu Glu Thr Ser Gly Ser Arg Leu Thr Phe Gly
            115                 120                 125

Glu Gly Thr Gln Leu Thr Val Asn Pro Asp Ile Gln Asn Pro Asp Pro
        130                 135                 140

Ala Val Tyr Gln Leu Arg Asp Ser Lys Ser Ser Asp Lys Ser Val Cys
145                 150                 155                 160

Leu Phe Thr Asp Phe Asp Ser Gln Thr Asn Val Ser Gln Ser Lys Asp
                165                 170                 175

Ser Asp Val Tyr Ile Thr Asp Lys Thr Val Leu Asp Met Arg Ser Met
            180                 185                 190

Asp Phe Lys Ser Asn Ser Ala Val Ala Trp Ser Asn Lys Ser Asp Phe
            195                 200                 205

Ala Cys Ala Asn Ala Phe Asn Asn Ser Ile Ile Pro Glu Asp Thr Phe
210                 215                 220

Phe Pro Ser Pro Glu Ser Ser Cys Asp Val Lys Leu Val Glu Lys Ser
225                 230                 235                 240

Phe Glu Thr Asp Thr Asn Leu Asn Phe Gln Asn Leu Ser Val Ile Gly
                245                 250                 255

Phe Arg Ile Leu Leu Leu Lys Val Ala Gly Phe Asn Leu Leu Met Thr
            260                 265                 270

Leu Arg Leu Trp Ser Ser
            275

<210> SEQ ID NO 56
<211> LENGTH: 278
<212> TYPE: PRT
<213> ORGANISM: Artificial Sequence
<220> FEATURE:
<223> OTHER INFORMATION: WT371 alpha (T185C) chain

<400> SEQUENCE: 56

Met Ser Leu Ser Ser Leu Leu Lys Val Val Thr Ala Ser Leu Trp Leu
 1               5                  10                  15

Gly Pro Gly Ile Ala Gln Lys Ile Thr Gln Thr Gln Pro Gly Met Phe
                20                  25                  30

Val Gln Glu Lys Glu Ala Val Thr Leu Asp Cys Thr Tyr Asp Thr Ser
            35                  40                  45

Asp Pro Ser Tyr Gly Leu Phe Trp Tyr Lys Gln Pro Ser Ser Gly Glu
        50                  55                  60

Met Ile Phe Leu Ile Tyr Gln Gly Ser Tyr Asp Gln Gln Asn Ala Thr
 65                  70                  75                  80

Glu Gly Arg Tyr Ser Leu Asn Phe Gln Lys Ala Arg Lys Ser Ala Asn
                 85                  90                  95

Leu Val Ile Ser Ala Ser Gln Leu Gly Asp Ser Ala Met Tyr Phe Cys
            100                 105                 110

Ala Met Arg Ala Arg Glu Glu Thr Ser Gly Ser Arg Leu Thr Phe Gly
            115                 120                 125

Glu Gly Thr Gln Leu Thr Val Asn Pro Asp Ile Gln Asn Pro Asp Pro
        130                 135                 140
```

Ala Val Tyr Gln Leu Arg Asp Ser Lys Ser Ser Asp Lys Ser Val Cys
145                 150                 155                 160

Leu Phe Thr Asp Phe Asp Ser Gln Thr Asn Val Ser Gln Ser Lys Asp
            165                 170                 175

Ser Asp Val Tyr Ile Thr Asp Lys Cys Val Leu Asp Met Arg Ser Met
            180                 185                 190

Asp Phe Lys Ser Asn Ser Ala Val Ala Trp Ser Asn Lys Ser Asp Phe
            195                 200                 205

Ala Cys Ala Asn Ala Phe Asn Asn Ser Ile Ile Pro Glu Asp Thr Phe
210                 215                 220

Phe Pro Ser Pro Glu Ser Ser Cys Asp Val Lys Leu Val Glu Lys Ser
225                 230                 235                 240

Phe Glu Thr Asp Thr Asn Leu Asn Phe Gln Asn Leu Ser Val Ile Gly
            245                 250                 255

Phe Arg Ile Leu Leu Leu Lys Val Ala Gly Phe Asn Leu Leu Met Thr
            260                 265                 270

Leu Arg Leu Trp Ser Ser
            275

<210> SEQ ID NO 57
<211> LENGTH: 133
<212> TYPE: PRT
<213> ORGANISM: Artificial Sequence
<220> FEATURE:
<223> OTHER INFORMATION: WT371 beta chain variable domain

<400> SEQUENCE: 57

Met Gly Cys Arg Leu Leu Cys Cys Val Val Phe Cys Leu Leu Gln Ala
1               5                   10                  15

Gly Pro Leu Asp Thr Ala Val Ser Gln Thr Pro Lys Tyr Leu Val Thr
            20                  25                  30

Gln Met Gly Asn Asp Lys Ser Ile Lys Cys Glu Gln Asn Leu Gly His
            35                  40                  45

Asp Thr Met Tyr Trp Tyr Lys Gln Asp Ser Lys Lys Phe Leu Lys Ile
50                  55                  60

Met Phe Ser Tyr Asn Asn Lys Glu Leu Ile Ile Asn Glu Thr Val Pro
65                  70                  75                  80

Asn Arg Phe Ser Pro Lys Ser Pro Asp Lys Ala His Leu Asn Leu His
            85                  90                  95

Ile Asn Ser Leu Glu Leu Gly Asp Ser Ala Val Tyr Phe Cys Ala Ser
            100                 105                 110

Ser Gln Asp Gly Arg Ser Arg Pro Gln His Phe Gly Asp Gly Thr Arg
            115                 120                 125

Leu Ser Ile Leu Glu
    130

<210> SEQ ID NO 58
<211> LENGTH: 176
<212> TYPE: PRT
<213> ORGANISM: Artificial Sequence
<220> FEATURE:
<223> OTHER INFORMATION: WT371 beta chain constant domain

<400> SEQUENCE: 58

Asp Leu Asn Lys Val Phe Pro Pro Glu Val Ala Val Phe Glu Pro Ser
1               5                   10                  15

Glu Ala Glu Ile Ser His Thr Gln Lys Ala Thr Leu Val Cys Leu Ala
            20                  25                  30

Thr Gly Phe Phe Pro Asp His Val Glu Leu Ser Trp Trp Val Asn Gly
        35                  40                  45

Lys Glu Val His Ser Gly Val Ser Thr Asp Pro Gln Pro Leu Lys Glu
 50                  55                  60

Gln Pro Ala Leu Asn Asp Ser Arg Tyr Cys Leu Ser Ser Arg Leu Arg
 65                  70                  75                  80

Val Ser Ala Thr Phe Trp Gln Asn Pro Arg Asn His Phe Arg Cys Gln
                 85                  90                  95

Val Gln Phe Tyr Gly Leu Ser Glu Asn Asp Glu Trp Thr Gln Asp Arg
                100                 105                 110

Ala Lys Pro Val Thr Gln Ile Val Ser Ala Glu Ala Trp Gly Arg Ala
                115                 120                 125

Asp Cys Gly Phe Thr Ser Val Ser Tyr Gln Gln Gly Val Leu Ser Ala
                130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Phe
                165                 170                 175

<210> SEQ ID NO 59
<211> LENGTH: 176
<212> TYPE: PRT
<213> ORGANISM: Artificial Sequence
<220> FEATURE:
<223> OTHER INFORMATION: WT371 beta (S189C) chain constant domain

<400> SEQUENCE: 59

Asp Leu Asn Lys Val Phe Pro Pro Glu Val Ala Val Phe Glu Pro Ser
1                5                  10                  15

Glu Ala Glu Ile Ser His Thr Gln Lys Ala Thr Leu Val Cys Leu Ala
                 20                  25                  30

Thr Gly Phe Phe Pro Asp His Val Glu Leu Ser Trp Trp Val Asn Gly
        35                  40                  45

Lys Glu Val His Ser Gly Val Cys Thr Asp Pro Gln Pro Leu Lys Glu
 50                  55                  60

Gln Pro Ala Leu Asn Asp Ser Arg Tyr Cys Leu Ser Ser Arg Leu Arg
 65                  70                  75                  80

Val Ser Ala Thr Phe Trp Gln Asn Pro Arg Asn His Phe Arg Cys Gln
                 85                  90                  95

Val Gln Phe Tyr Gly Leu Ser Glu Asn Asp Glu Trp Thr Gln Asp Arg
                100                 105                 110

Ala Lys Pro Val Thr Gln Ile Val Ser Ala Glu Ala Trp Gly Arg Ala
                115                 120                 125

Asp Cys Gly Phe Thr Ser Val Ser Tyr Gln Gln Gly Val Leu Ser Ala
                130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Phe
                165                 170                 175

<210> SEQ ID NO 60
<211> LENGTH: 309
<212> TYPE: PRT
<213> ORGANISM: Artificial Sequence
<220> FEATURE:
<223> OTHER INFORMATION: WT371 beta chain

<400> SEQUENCE: 60

```
Met Gly Cys Arg Leu Leu Cys Cys Val Val Phe Cys Leu Leu Gln Ala
1               5                   10                  15

Gly Pro Leu Asp Thr Ala Val Ser Gln Thr Pro Lys Tyr Leu Val Thr
                20                  25                  30

Gln Met Gly Asn Asp Lys Ser Ile Lys Cys Glu Gln Asn Leu Gly His
            35                  40                  45

Asp Thr Met Tyr Trp Tyr Lys Gln Asp Ser Lys Lys Phe Leu Lys Ile
        50                  55                  60

Met Phe Ser Tyr Asn Asn Lys Glu Leu Ile Ile Asn Glu Thr Val Pro
65                  70                  75                  80

Asn Arg Phe Ser Pro Lys Ser Pro Asp Lys Ala His Leu Asn Leu His
                85                  90                  95

Ile Asn Ser Leu Glu Leu Gly Asp Ser Ala Val Tyr Phe Cys Ala Ser
            100                 105                 110

Ser Gln Asp Gly Arg Ser Arg Pro Gln His Phe Gly Asp Gly Thr Arg
        115                 120                 125

Leu Ser Ile Leu Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe
305
```

<210> SEQ ID NO 61
<211> LENGTH: 311
<212> TYPE: PRT
<213> ORGANISM: Artificial Sequence
<220> FEATURE:
<223> OTHER INFORMATION: WT371 beta (S189C) chain

<400> SEQUENCE: 61

```
Met Gly Cys Arg Leu Leu Cys Cys Val Val Phe Cys Leu Leu Gln Ala
1               5                   10                  15

Gly Pro Leu Asp Thr Ala Val Ser Gln Thr Pro Lys Tyr Leu Val Thr
                20                  25                  30

Gln Met Gly Asn Asp Lys Ser Ile Lys Cys Glu Gln Asn Leu Gly His
```

```
                35                  40                  45
Asp Thr Met Tyr Trp Tyr Lys Gln Asp Ser Lys Lys Phe Leu Lys Ile
    50                  55                  60
Met Phe Ser Tyr Asn Asn Lys Glu Leu Ile Ile Asn Glu Thr Val Pro
 65                 70                  75                  80
Asn Arg Phe Ser Pro Lys Ser Pro Asp Lys Ala His Leu Asn Leu His
                85                  90                  95
Ile Asn Ser Leu Glu Leu Gly Asp Ser Ala Val Tyr Phe Cys Ala Ser
            100                 105                 110
Ser Gln Asp Gly Arg Ser Arg Pro Gln His Phe Gly Asp Gly Thr Arg
        115                 120                 125
Leu Ser Ile Leu Glu Asp Leu Lys Asn Val Phe Pro Pro Glu Val Ala
    130                 135                 140
Val Phe Glu Pro Ser Glu Ala Glu Ile Ser His Thr Gln Lys Ala Thr
145                 150                 155                 160
Leu Val Cys Leu Ala Thr Gly Phe Tyr Pro Asp His Val Glu Leu Ser
                165                 170                 175
Trp Trp Val Asn Gly Lys Glu Val His Ser Gly Val Cys Thr Asp Pro
            180                 185                 190
Gln Pro Leu Lys Glu Gln Pro Ala Leu Asn Asp Ser Arg Tyr Cys Leu
        195                 200                 205
Ser Ser Arg Leu Arg Val Ser Ala Thr Phe Trp Gln Asn Pro Arg Asn
    210                 215                 220
His Phe Arg Cys Gln Val Gln Phe Tyr Gly Leu Ser Glu Asn Asp Glu
225                 230                 235                 240
Trp Thr Gln Asp Arg Ala Lys Pro Val Thr Gln Ile Val Ser Ala Glu
                245                 250                 255
Ala Trp Gly Arg Ala Asp Cys Gly Phe Thr Ser Glu Ser Tyr Gln Gln
            260                 265                 270
Gly Val Leu Ser Ala Thr Ile Leu Tyr Glu Ile Leu Leu Gly Lys Ala
        275                 280                 285
Thr Leu Tyr Ala Val Leu Val Ser Ala Leu Val Leu Met Ala Met Val
    290                 295                 300
Lys Arg Lys Asp Ser Arg Gly
305                 310

<210> SEQ ID NO 62
<211> LENGTH: 609
<212> TYPE: PRT
<213> ORGANISM: Artificial Sequence
<220> FEATURE:
<223> OTHER INFORMATION: WT371 beta (S189C)-P2A-WT371 alpha (T185C)

<400> SEQUENCE: 62

Met Gly Cys Arg Leu Leu Cys Cys Val Val Phe Cys Leu Leu Gln Ala
  1               5                  10                  15
Gly Pro Leu Asp Thr Ala Val Ser Gln Thr Pro Lys Tyr Leu Val Thr
                20                  25                  30
Gln Met Gly Asn Asp Lys Ser Ile Lys Cys Glu Gln Asn Leu Gly His
            35                  40                  45
Asp Thr Met Tyr Trp Tyr Lys Gln Asp Ser Lys Lys Phe Leu Lys Ile
        50                  55                  60
Met Phe Ser Tyr Asn Asn Lys Glu Leu Ile Ile Asn Glu Thr Val Pro
 65                 70                  75                  80
Asn Arg Phe Ser Pro Lys Ser Pro Asp Lys Ala His Leu Asn Leu His
```

```
                85                  90                  95
Ile Asn Ser Leu Glu Leu Gly Asp Ser Ala Val Tyr Phe Cys Ala Ser
            100                 105                 110

Ser Gln Asp Gly Arg Ser Arg Pro Gln His Phe Gly Asp Gly Thr Arg
            115                 120                 125

Leu Ser Ile Leu Glu Asp Leu Asn Lys Val Phe Pro Pro Glu Val Ala
            130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
            165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
            210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
            245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
290                 295                 300

Lys Arg Lys Asp Phe Gly Ser Gly Ala Thr Asn Phe Ser Leu Leu Lys
305                 310                 315                 320

Gln Ala Gly Asp Val Glu Glu Asn Pro Gly Pro Met Ser Leu Ser Ser
            325                 330                 335

Leu Leu Lys Val Val Thr Ala Ser Leu Trp Leu Gly Pro Gly Ile Ala
            340                 345                 350

Gln Lys Ile Thr Gln Thr Gln Pro Gly Met Phe Val Gln Glu Lys Glu
            355                 360                 365

Ala Val Thr Leu Asp Cys Thr Tyr Asp Thr Ser Asp Pro Ser Tyr Gly
            370                 375                 380

Leu Phe Trp Tyr Lys Gln Pro Ser Ser Gly Glu Met Ile Phe Leu Ile
385                 390                 395                 400

Tyr Gln Gly Ser Tyr Asp Gln Gln Asn Ala Thr Glu Gly Arg Tyr Ser
            405                 410                 415

Leu Asn Phe Gln Lys Ala Arg Lys Ser Ala Asn Leu Val Ile Ser Ala
            420                 425                 430

Ser Gln Leu Gly Asp Ser Ala Met Tyr Phe Cys Ala Met Arg Ala Arg
            435                 440                 445

Glu Glu Thr Ser Gly Ser Arg Leu Thr Phe Gly Glu Gly Thr Gln Leu
            450                 455                 460

Thr Val Asn Pro Asp Ile Gln Asn Pro Asp Pro Ala Val Tyr Gln Leu
465                 470                 475                 480

Arg Asp Ser Lys Ser Ser Asp Lys Ser Val Cys Leu Phe Thr Asp Phe
            485                 490                 495

Asp Ser Gln Thr Asn Val Ser Gln Ser Lys Asp Ser Asp Val Tyr Ile
            500                 505                 510
```

```
Thr Asp Lys Cys Val Leu Asp Met Arg Ser Met Asp Phe Lys Ser Asn
        515                 520                 525

Ser Ala Val Ala Trp Ser Asn Lys Ser Asp Phe Ala Cys Ala Asn Ala
        530                 535                 540

Phe Asn Asn Ser Ile Ile Pro Glu Asp Thr Phe Phe Pro Ser Pro Glu
545                 550                 555                 560

Ser Ser Cys Asp Val Lys Leu Val Glu Lys Ser Phe Glu Thr Asp Thr
            565                 570                 575

Asn Leu Asn Phe Gln Asn Leu Ser Val Ile Gly Phe Arg Ile Leu Leu
            580                 585                 590

Leu Lys Val Ala Gly Phe Asn Leu Met Thr Leu Arg Leu Trp Ser
        595                 600                 605

Ser

<210> SEQ ID NO 63
<211> LENGTH: 133
<212> TYPE: PRT
<213> ORGANISM: Artificial Sequence
<220> FEATURE:
<223> OTHER INFORMATION: WT372 alpha chain variable domain

<400> SEQUENCE: 63

Met Lys Ser Leu Arg Val Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Pro Thr Ser Gly Thr Tyr Lys Tyr Ile Phe Gly Thr Gly Thr Arg Leu
        115                 120                 125

Lys Val Leu Ala Asn
    130

<210> SEQ ID NO 64
<211> LENGTH: 273
<212> TYPE: PRT
<213> ORGANISM: Artificial Sequence
<220> FEATURE:
<223> OTHER INFORMATION: WT372 alpha chain

<400> SEQUENCE: 64

Met Lys Ser Leu Arg Val Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60
```

```
Pro Glu Leu Ile Met Phe Ile Tyr Ser Asn Gly Asp Lys Glu Asp Gly
 65                  70                  75                  80

Arg Phe Thr Ala Gln Leu Asn Lys Ala Ser Gln Tyr Val Ser Leu Leu
                 85                  90                  95

Ile Arg Asp Ser Gln Pro Ser Asp Ser Ala Thr Tyr Leu Cys Ala Val
                100                 105                 110

Pro Thr Ser Gly Thr Tyr Lys Tyr Ile Phe Gly Thr Gly Thr Arg Leu
                115                 120                 125

Lys Val Leu Ala Asn Ile Gln Asn Pro Asp Pro Ala Val Tyr Gln Leu
            130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
            195                 200                 205

Phe Asn Asn Ser Ile Ile Pro Glu Asp Thr Phe Phe Pro Ser Pro Glu
            210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 65
<211> LENGTH: 273
<212> TYPE: PRT
<213> ORGANISM: Artificial Sequence
<220> FEATURE:
<223> OTHER INFORMATION: WT372 alpha (T180C) chain

<400> SEQUENCE: 65

Met Lys Ser Leu Arg Val Leu Val Ile Leu Trp Leu Gln Leu Ser
1                5                  10                  15

Trp Val Trp Ser Gln Gln Lys Glu Val Glu Gln Asn Ser Gly Pro Leu
                20                  25                  30

Ser Val Pro Glu Gly Ala Ile Ala Ser Leu Asn Cys Thr Tyr Ser Asp
                35                  40                  45

Arg Gly Ser Gln Ser Phe Phe Trp Tyr Arg Gln Tyr Ser Gly Lys Ser
            50                  55                  60

Pro Glu Leu Ile Met Phe Ile Tyr Ser Asn Gly Asp Lys Glu Asp Gly
 65                  70                  75                  80

Arg Phe Thr Ala Gln Leu Asn Lys Ala Ser Gln Tyr Val Ser Leu Leu
                 85                  90                  95

Ile Arg Asp Ser Gln Pro Ser Asp Ser Ala Thr Tyr Leu Cys Ala Val
                100                 105                 110

Pro Thr Ser Gly Thr Tyr Lys Tyr Ile Phe Gly Thr Gly Thr Arg Leu
                115                 120                 125

Lys Val Leu Ala Asn Ile Gln Asn Pro Asp Pro Ala Val Tyr Gln Leu
            130                 135                 140
```

```
Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Val Tyr Ile
            165                 170                 175

Thr Asp Lys Cys Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
            195                 200                 205

Phe Asn Asn Ser Ile Ile Pro Glu Asp Thr Phe Phe Pro Ser Pro Glu
            210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
            245                 250                 255

Leu Lys Val Ala Gly Phe Asn Leu Leu Met Thr Leu Arg Leu Trp Ser
            260                 265                 270

Ser
```

<210> SEQ ID NO 66
<211> LENGTH: 134
<212> TYPE: PRT
<213> ORGANISM: Artificial Sequence
<220> FEATURE:
<223> OTHER INFORMATION: WT372 beta chain variable domain

<400> SEQUENCE: 66

```
Met Ser Asn Gln Val Leu Cys Cys Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
            35                  40                  45

Asp Ala Met Tyr Trp Tyr Arg Gln Asp Pro Gly Gln Gly Leu Arg Leu
50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
            85                  90                  95

Val Thr Ser Ala Gln Lys Asn Pro Thr Ala Phe Tyr Leu Cys Ala Ser
            100                 105                 110

Ser Ile Arg Asp Ser Ser Asn Gln Pro Gln His Phe Gly Asp Gly Thr
            115                 120                 125

Arg Leu Ser Ile Leu Glu
    130
```

<210> SEQ ID NO 67
<211> LENGTH: 310
<212> TYPE: PRT
<213> ORGANISM: Artificial Sequence
<220> FEATURE:
<223> OTHER INFORMATION: WT372 beta chain

<400> SEQUENCE: 67

```
Met Ser Asn Gln Val Leu Cys Cys Val Leu Cys Phe Leu Gly Ala
1               5                   10                  15

Asn Thr Val Asp Gly Gly Ile Thr Gln Ser Pro Lys Tyr Leu Phe Arg
            20                  25                  30
```

```
Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
 50                  55                  60

Ile Tyr Tyr Ser Gln Ile Val Asn Asp Phe Gln Lys Gly Asp Ile Ala
 65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Ile Arg Asp Ser Ser Asn Gln Pro Gln His Phe Gly Asp Gly Thr
        115                 120                 125

Arg Leu Ser Ile Leu Glu Asp Leu Asn Lys Val Phe Pro Pro Glu Val
130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Phe
305                 310

<210> SEQ ID NO 68
<211> LENGTH: 312
<212> TYPE: PRT
<213> ORGANISM: Artificial Sequence
<220> FEATURE:
<223> OTHER INFORMATION: WT372 beta (S190C) chain

<400> SEQUENCE: 68

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
                20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
 50                  55                  60

Ile Tyr Tyr Ser Gln Ile Val Asn Asp Phe Gln Lys Gly Asp Ile Ala
 65                  70                  75                  80
```

-continued

```
Glu Gly Tyr Ser Val Ser Arg Glu Lys Lys Glu Ser Phe Pro Leu Thr
            85                  90                  95

Val Thr Ser Ala Gln Lys Asn Pro Thr Ala Phe Tyr Leu Cys Ala Ser
            100                 105                 110

Ser Ile Arg Asp Ser Ser Asn Gln Pro Gln His Phe Gly Asp Gly Thr
            115                 120                 125

Arg Leu Ser Ile Leu Glu Asp Leu Lys Asn Val Phe Pro Pro Glu Val
130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Cys Thr Asp
                180                 185                 190

Pro Gln Pro Leu Lys Glu Gln Pro Ala Leu Asn Asp Ser Arg Tyr Cys
                195                 200                 205

Leu Ser Ser Arg Leu Arg Val Ser Ala Thr Phe Trp Gln Asn Pro Arg
            210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
                260                 265                 270

Gln Gly Val Leu Ser Ala Thr Ile Leu Tyr Glu Ile Leu Leu Gly Lys
            275                 280                 285

Ala Thr Leu Tyr Ala Val Leu Val Ser Ala Leu Val Leu Met Ala Met
290                 295                 300

Val Lys Arg Lys Asp Ser Arg Gly
305                 310

<210> SEQ ID NO 69
<211> LENGTH: 605
<212> TYPE: PRT
<213> ORGANISM: Artificial Sequence
<220> FEATURE:
<223> OTHER INFORMATION: WT372 beta (S190C)-P2A-WT372 alpha (T180C)

<400> SEQUENCE: 69

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
                100                 105                 110

Ser Ile Arg Asp Ser Ser Asn Gln Pro Gln His Phe Gly Asp Gly Thr
            115                 120                 125
```

```
Arg Leu Ser Ile Leu Glu Asp Leu Asn Lys Val Phe Pro Pro Glu Val
    130                 135                 140
Ala Val Phe Glu Pro Ser Glu Ala Glu Ile Ser His Thr Gln Lys Ala
145                 150                 155                 160
Thr Leu Val Cys Leu Ala Thr Gly Phe Phe Pro Asp His Val Glu Leu
                165                 170                 175
Ser Trp Trp Val Asn Gly Lys Glu Val His Ser Gly Val Cys Thr Asp
            180                 185                 190
Pro Gln Pro Leu Lys Glu Gln Pro Ala Leu Asn Asp Ser Arg Tyr Cys
        195                 200                 205
Leu Ser Ser Arg Leu Arg Val Ser Ala Thr Phe Trp Gln Asn Pro Arg
210                 215                 220
Asn His Phe Arg Cys Gln Val Gln Phe Tyr Gly Leu Ser Glu Asn Asp
225                 230                 235                 240
Glu Trp Thr Gln Asp Arg Ala Lys Pro Val Thr Gln Ile Val Ser Ala
                245                 250                 255
Glu Ala Trp Gly Arg Ala Asp Cys Gly Phe Thr Ser Val Ser Tyr Gln
            260                 265                 270
Gln Gly Val Leu Ser Ala Thr Ile Leu Tyr Glu Ile Leu Leu Gly Lys
        275                 280                 285
Ala Thr Leu Tyr Ala Val Leu Val Ser Ala Leu Val Leu Met Ala Met
290                 295                 300
Val Lys Arg Lys Asp Phe Gly Ser Gly Ala Thr Asn Phe Ser Leu Leu
305                 310                 315                 320
Lys Gln Ala Gly Asp Val Glu Glu Asn Pro Gly Pro Met Lys Ser Leu
                325                 330                 335
Arg Val Leu Leu Val Ile Leu Trp Leu Gln Leu Ser Trp Val Trp Ser
            340                 345                 350
Gln Gln Lys Glu Val Glu Gln Asn Ser Gly Pro Leu Ser Val Pro Glu
        355                 360                 365
Gly Ala Ile Ala Ser Leu Asn Cys Thr Tyr Ser Asp Arg Gly Ser Gln
370                 375                 380
Ser Phe Phe Trp Tyr Arg Gln Tyr Ser Gly Lys Ser Pro Glu Leu Ile
385                 390                 395                 400
Met Phe Ile Tyr Ser Asn Gly Asp Lys Glu Asp Gly Arg Phe Thr Ala
                405                 410                 415
Gln Leu Asn Lys Ala Ser Gln Tyr Val Ser Leu Leu Ile Arg Asp Ser
            420                 425                 430
Gln Pro Ser Asp Ser Ala Thr Tyr Leu Cys Ala Val Pro Thr Ser Gly
        435                 440                 445
Thr Tyr Lys Tyr Ile Phe Gly Thr Gly Thr Arg Leu Lys Val Leu Ala
450                 455                 460
Asn Ile Gln Asn Pro Asp Pro Ala Val Tyr Gln Leu Arg Asp Ser Lys
465                 470                 475                 480
Ser Ser Asp Lys Ser Val Cys Leu Phe Thr Asp Phe Asp Ser Gln Thr
                485                 490                 495
Asn Val Ser Gln Ser Lys Asp Ser Asp Val Tyr Ile Thr Asp Lys Cys
            500                 505                 510
Val Leu Asp Met Arg Ser Met Asp Phe Lys Ser Asn Ser Ala Val Ala
        515                 520                 525
Trp Ser Asn Lys Ser Asp Phe Ala Cys Ala Asn Ala Phe Asn Asn Ser
530                 535                 540
Ile Ile Pro Glu Asp Thr Phe Phe Pro Ser Pro Glu Ser Ser Cys Asp
```

```
                  545                 550                 555                 560
Val Lys Leu Val Glu Lys Ser Phe Glu Thr Asp Thr Asn Leu Asn Phe
                  565                 570                 575

Gln Asn Leu Ser Val Ile Gly Phe Arg Ile Leu Leu Lys Val Ala
                  580                 585                 590

Gly Phe Asn Leu Leu Met Thr Leu Arg Leu Trp Ser Ser
                  595                 600                 605
```

```
<210> SEQ ID NO 70
<211> LENGTH: 142
<212> TYPE: PRT
<213> ORGANISM: Artificial Sequence
<220> FEATURE:
<223> OTHER INFORMATION: WT373 alpha chain variable domain

<400> SEQUENCE: 70

Met Ala Met Leu Leu Gly Ala Ser Val Leu Ile Leu Trp Leu Gln Pro
1               5                   10                  15

Asp Trp Val Asn Ser Gln Gln Lys Asn Asp Gln Gln Val Lys Gln
            20                  25                  30

Asn Ser Pro Ser Leu Ser Val Gln Glu Gly Arg Ile Ser Ile Leu Asn
            35                  40                  45

Cys Asp Tyr Thr Asn Ser Met Phe Asp Tyr Phe Leu Trp Tyr Lys Lys
        50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Gly Ala Arg Gly Gly Thr Ser Tyr Gly Lys
        115                 120                 125

Leu Thr Phe Gly Gln Gly Thr Ile Leu Thr Val His Pro Asn
    130                 135                 140
```

```
<210> SEQ ID NO 71
<211> LENGTH: 282
<212> TYPE: PRT
<213> ORGANISM: Artificial Sequence
<220> FEATURE:
<223> OTHER INFORMATION: WT373 alpha chain

<400> SEQUENCE: 71

Met Ala Met Leu Leu Gly Ala Ser Val Leu Ile Leu Trp Leu Gln Pro
1               5                   10                  15

Asp Trp Val Asn Ser Gln Gln Lys Asn Asp Gln Gln Val Lys Gln
            20                  25                  30

Asn Ser Pro Ser Leu Ser Val Gln Glu Gly Arg Ile Ser Ile Leu Asn
            35                  40                  45

Cys Asp Tyr Thr Asn Ser Met Phe Asp Tyr Phe Leu Trp Tyr Lys Lys
        50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110
```

Val Tyr Phe Cys Ala Ala Gly Ala Arg Gly Gly Thr Ser Tyr Gly Lys
            115                 120                 125

Leu Thr Phe Gly Gln Gly Thr Ile Leu Thr Val His Pro Asn Ile Gln
            130                 135                 140

Asn Pro Asp Pro Ala Val Tyr Gln Leu Arg Asp Ser Lys Ser Ser Asp
145                 150                 155                 160

Lys Ser Val Cys Leu Phe Thr Asp Phe Asp Ser Gln Thr Asn Val Ser
                165                 170                 175

Gln Ser Lys Asp Ser Asp Val Tyr Ile Thr Asp Lys Thr Val Leu Asp
            180                 185                 190

Met Arg Ser Met Asp Phe Lys Ser Asn Ser Ala Val Ala Trp Ser Asn
            195                 200                 205

Lys Ser Asp Phe Ala Cys Ala Asn Ala Phe Asn Asn Ser Ile Ile Pro
            210                 215                 220

Glu Asp Thr Phe Phe Pro Ser Pro Glu Ser Ser Cys Asp Val Lys Leu
225                 230                 235                 240

Val Glu Lys Ser Phe Glu Thr Asp Thr Asn Leu Asn Phe Gln Asn Leu
                245                 250                 255

Ser Val Ile Gly Phe Arg Ile Leu Leu Leu Lys Val Ala Gly Phe Asn
            260                 265                 270

Leu Leu Met Thr Leu Arg Leu Trp Ser Ser
            275                 280

<210> SEQ ID NO 72
<211> LENGTH: 282
<212> TYPE: PRT
<213> ORGANISM: Artificial Sequence
<220> FEATURE:
<223> OTHER INFORMATION: WT373 alpha (T189C) chain

<400> SEQUENCE: 72

Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
            35                  40                  45

Cys Asp Tyr Thr Asn Ser Met Phe Asp Tyr Phe Leu Trp Tyr Lys Lys
50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Gly Ala Arg Gly Gly Thr Ser Tyr Gly Lys
            115                 120                 125

Leu Thr Phe Gly Gln Gly Thr Ile Leu Thr Val His Pro Asn Ile Gln
            130                 135                 140

Asn Pro Asp Pro Ala Val Tyr Gln Leu Arg Asp Ser Lys Ser Ser Asp
145                 150                 155                 160

Lys Ser Val Cys Leu Phe Thr Asp Phe Asp Ser Gln Thr Asn Val Ser
                165                 170                 175

Gln Ser Lys Asp Ser Asp Val Tyr Ile Thr Asp Lys Cys Val Leu Asp
            180                 185                 190

```
Met Arg Ser Met Asp Phe Lys Ser Asn Ser Ala Val Ala Trp Ser Asn
            195                 200                 205

Lys Ser Asp Phe Ala Cys Ala Asn Ala Phe Asn Asn Ser Ile Ile Pro
    210                 215                 220

Glu Asp Thr Phe Phe Pro Ser Pro Glu Ser Ser Cys Asp Val Lys Leu
225                 230                 235                 240

Val Glu Lys Ser Phe Glu Thr Asp Thr Asn Leu Asn Phe Gln Asn Leu
            245                 250                 255

Ser Val Ile Gly Phe Arg Ile Leu Leu Lys Val Ala Gly Phe Asn
            260                 265                 270

Leu Leu Met Thr Leu Arg Leu Trp Ser Ser
            275                 280

<210> SEQ ID NO 73
<211> LENGTH: 135
<212> TYPE: PRT
<213> ORGANISM: Artificial Sequence
<220> FEATURE:
<223> OTHER INFORMATION: WT373 beta chain variable domain

<400> SEQUENCE: 73

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Ala Gln Gly Ala Tyr Gly Asn Gln Pro Gln His Phe Gly Asp Gly
        115                 120                 125

Thr Arg Leu Ser Ile Leu Glu
    130                 135

<210> SEQ ID NO 74
<211> LENGTH: 311
<212> TYPE: PRT
<213> ORGANISM: Artificial Sequence
<220> FEATURE:
<223> OTHER INFORMATION: WT373 beta chain

<400> SEQUENCE: 74

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80
```

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Ala Gln Gly Ala Tyr Gly Asn Gln Pro Gln His Phe Gly Asp Gly
        115                 120                 125

Thr Arg Leu Ser Ile Leu Glu Asp Leu Asn Lys Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Val Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
    290                 295                 300

Met Val Lys Arg Lys Asp Phe
305                 310

<210> SEQ ID NO 75
<211> LENGTH: 313
<212> TYPE: PRT
<213> ORGANISM: Artificial Sequence
<220> FEATURE:
<223> OTHER INFORMATION: WT373 beta (S191C) chain

<400> SEQUENCE: 75

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Ala Gln Gly Ala Tyr Gly Asn Gln Pro Gln His Phe Gly Asp Gly
        115                 120                 125

```
Thr Arg Leu Ser Ile Leu Glu Asp Leu Lys Asn Val Phe Pro Pro Glu
            130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Cys Thr
            180                 185                 190

Asp Pro Gln Pro Leu Lys Glu Gln Pro Ala Leu Asn Asp Ser Arg Tyr
            195                 200                 205

Cys Leu Ser Ser Arg Leu Arg Val Ser Ala Thr Phe Trp Gln Asn Pro
210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Glu Ser Tyr
            260                 265                 270

Gln Gln Gly Val Leu Ser Ala Thr Ile Leu Tyr Glu Ile Leu Leu Gly
            275                 280                 285

Lys Ala Thr Leu Tyr Ala Val Leu Val Ser Ala Leu Val Leu Met Ala
290                 295                 300

Met Val Lys Arg Lys Asp Ser Arg Gly
305                 310

<210> SEQ ID NO 76
<211> LENGTH: 615
<212> TYPE: PRT
<213> ORGANISM: Artificial Sequence
<220> FEATURE:
<223> OTHER INFORMATION: WT373 beta (S191C)-P2A-WT373 alpha (T189C)

<400> SEQUENCE: 76

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
                20                  25                  30

Lys Glu Gly Gln Asn Val Thr Leu Ser Cys Glu Gln Asn Leu Asn His
            35                  40                  45

Asp Ala Met Tyr Trp Tyr Arg Gln Asp Pro Gly Gln Gly Leu Arg Leu
        50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Ala Gln Gly Ala Tyr Gly Asn Gln Pro Gln His Phe Gly Asp Gly
        115                 120                 125

Thr Arg Leu Ser Ile Leu Glu Asp Leu Asn Lys Val Phe Pro Pro Glu
            130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Phe Pro Asp His Val Glu
                165                 170                 175
```

```
Leu Ser Trp Trp Val Asn Gly Lys Glu Val His Ser Gly Val Cys Thr
            180                 185                 190

Asp Pro Gln Pro Leu Lys Glu Gln Pro Ala Leu Asn Asp Ser Arg Tyr
            195                 200                 205

Cys Leu Ser Ser Arg Leu Arg Val Ser Ala Thr Phe Trp Gln Asn Pro
210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
            245                 250                 255

Ala Glu Ala Trp Gly Arg Ala Asp Cys Gly Phe Thr Ser Val Ser Tyr
            260                 265                 270

Gln Gln Gly Val Leu Ser Ala Thr Ile Leu Tyr Glu Ile Leu Leu Gly
            275                 280                 285

Lys Ala Thr Leu Tyr Ala Val Leu Val Ser Ala Leu Val Leu Met Ala
            290                 295                 300

Met Val Lys Arg Lys Asp Phe Gly Ser Gly Ala Thr Asn Phe Ser Leu
305                 310                 315                 320

Leu Lys Gln Ala Gly Asp Val Glu Glu Asn Pro Gly Pro Met Ala Met
            325                 330                 335

Leu Leu Gly Ala Ser Val Leu Ile Leu Trp Leu Gln Pro Asp Trp Val
            340                 345                 350

Asn Ser Gln Gln Lys Asn Asp Asp Gln Gln Val Lys Gln Asn Ser Pro
            355                 360                 365

Ser Leu Ser Val Gln Glu Gly Arg Ile Ser Ile Leu Asn Cys Asp Tyr
            370                 375                 380

Thr Asn Ser Met Phe Asp Tyr Phe Leu Trp Tyr Lys Lys Tyr Pro Ala
385                 390                 395                 400

Glu Gly Pro Thr Phe Leu Ile Ser Ile Ser Ser Ile Lys Asp Lys Asn
            405                 410                 415

Glu Asp Gly Arg Phe Thr Val Phe Leu Asn Lys Ser Ala Lys His Leu
            420                 425                 430

Ser Leu His Ile Val Pro Ser Gln Pro Gly Asp Ser Ala Val Tyr Phe
            435                 440                 445

Cys Ala Ala Gly Ala Arg Gly Gly Thr Ser Tyr Gly Lys Leu Thr Phe
450                 455                 460

Gly Gln Gly Thr Ile Leu Thr Val His Pro Asn Ile Gln Asn Pro Asp
465                 470                 475                 480

Pro Ala Val Tyr Gln Leu Arg Asp Ser Lys Ser Ser Asp Lys Ser Val
            485                 490                 495

Cys Leu Phe Thr Asp Phe Asp Ser Gln Thr Asn Val Ser Gln Ser Lys
            500                 505                 510

Asp Ser Asp Val Tyr Ile Thr Asp Lys Cys Val Leu Asp Met Arg Ser
            515                 520                 525

Met Asp Phe Lys Ser Asn Ser Ala Val Ala Trp Ser Asn Lys Ser Asp
            530                 535                 540

Phe Ala Cys Ala Asn Ala Phe Asn Asn Ser Ile Ile Pro Glu Asp Thr
545                 550                 555                 560

Phe Phe Pro Ser Pro Glu Ser Ser Cys Asp Val Lys Leu Val Glu Lys
            565                 570                 575

Ser Phe Glu Thr Asp Thr Asn Leu Asn Phe Gln Asn Leu Ser Val Ile
            580                 585                 590
```

Gly Phe Arg Ile Leu Leu Leu Lys Val Ala Gly Phe Asn Leu Leu Met
            595                 600                 605

Thr Leu Arg Leu Trp Ser Ser
            610                 615

<210> SEQ ID NO 77
<211> LENGTH: 129
<212> TYPE: PRT
<213> ORGANISM: Artificial Sequence
<220> FEATURE:
<223> OTHER INFORMATION: WT376 alpha chain variable domain

<400> SEQUENCE: 77

Met Leu Leu Ile Thr Ser Met Leu Val Leu Trp Met Gln Leu Ser Gln
1               5                   10                  15

Val Asn Gly Gln Gln Val Met Gln Ile Pro Gln Tyr Gln His Val Gln
            20                  25                  30

Glu Gly Glu Asp Phe Thr Thr Tyr Cys Asn Ser Ser Thr Thr Leu Ser
        35                  40                  45

Asn Ile Gln Trp Tyr Lys Gln Arg Pro Gly Gly His Pro Val Phe Leu
    50                  55                  60

Ile Gln Leu Val Lys Ser Gly Glu Val Lys Lys Gln Lys Arg Leu Thr
65                  70                  75                  80

Phe Gln Phe Gly Glu Ala Lys Lys Asn Ser Ser Leu His Ile Thr Ala
                85                  90                  95

Thr Gln Thr Thr Asp Val Gly Thr Tyr Phe Cys Ala Gly Arg Thr Ser
            100                 105                 110

Tyr Asp Lys Val Ile Phe Gly Pro Gly Thr Ser Leu Ser Val Ile Pro
        115                 120                 125

Asn

<210> SEQ ID NO 78
<211> LENGTH: 269
<212> TYPE: PRT
<213> ORGANISM: Artificial Sequence
<220> FEATURE:
<223> OTHER INFORMATION: WT376 alpha chain

<400> SEQUENCE: 78

Met Leu Leu Ile Thr Ser Met Leu Val Leu Trp Met Gln Leu Ser Gln
1               5                   10                  15

Val Asn Gly Gln Gln Val Met Gln Ile Pro Gln Tyr Gln His Val Gln
            20                  25                  30

Glu Gly Glu Asp Phe Thr Thr Tyr Cys Asn Ser Ser Thr Thr Leu Ser
        35                  40                  45

Asn Ile Gln Trp Tyr Lys Gln Arg Pro Gly Gly His Pro Val Phe Leu
    50                  55                  60

Ile Gln Leu Val Lys Ser Gly Glu Val Lys Lys Gln Lys Arg Leu Thr
65                  70                  75                  80

Phe Gln Phe Gly Glu Ala Lys Lys Asn Ser Ser Leu His Ile Thr Ala
                85                  90                  95

Thr Gln Thr Thr Asp Val Gly Thr Tyr Phe Cys Ala Gly Arg Thr Ser
            100                 105                 110

Tyr Asp Lys Val Ile Phe Gly Pro Gly Thr Ser Leu Ser Val Ile Pro
        115                 120                 125

Asn Ile Gln Asn Pro Asp Pro Ala Val Tyr Gln Leu Arg Asp Ser Lys
    130                 135                 140

```
Ser Ser Asp Lys Ser Val Cys Leu Phe Thr Asp Phe Asp Ser Gln Thr
145                 150                 155                 160

Asn Val Ser Gln Ser Lys Asp Ser Asp Val Tyr Ile Thr Asp Lys Thr
            165                 170                 175

Val Leu Asp Met Arg Ser Met Asp Phe Lys Ser Asn Ser Ala Val Ala
        180                 185                 190

Trp Ser Asn Lys Ser Asp Phe Ala Cys Ala Asn Ala Phe Asn Asn Ser
            195                 200                 205

Ile Ile Pro Glu Asp Thr Phe Phe Pro Ser Pro Glu Ser Ser Cys Asp
        210                 215                 220

Val Lys Leu Val Glu Lys Ser Phe Glu Thr Asp Thr Asn Leu Asn Phe
225                 230                 235                 240

Gln Asn Leu Ser Val Ile Gly Phe Arg Ile Leu Leu Leu Lys Val Ala
            245                 250                 255

Gly Phe Asn Leu Leu Met Thr Leu Arg Leu Trp Ser Ser
            260                 265
```

<210> SEQ ID NO 79
<211> LENGTH: 269
<212> TYPE: PRT
<213> ORGANISM: Artificial Sequence
<220> FEATURE:
<223> OTHER INFORMATION: WT376 alpha (T176C) chain

<400> SEQUENCE: 79

```
Met Leu Leu Ile Thr Ser Met Leu Val Leu Trp Met Gln Leu Ser Gln
1               5                   10                  15

Val Asn Gly Gln Gln Val Met Gln Ile Pro Gln Tyr Gln His Val Gln
            20                  25                  30

Glu Gly Glu Asp Phe Thr Thr Tyr Cys Asn Ser Ser Thr Thr Leu Ser
        35                  40                  45

Asn Ile Gln Trp Tyr Lys Gln Arg Pro Gly Gly His Pro Val Phe Leu
    50                  55                  60

Ile Gln Leu Val Lys Ser Gly Glu Val Lys Lys Gln Lys Arg Leu Thr
65                  70                  75                  80

Phe Gln Phe Gly Glu Ala Lys Lys Asn Ser Ser Leu His Ile Thr Ala
            85                  90                  95

Thr Gln Thr Thr Asp Val Gly Thr Tyr Phe Cys Ala Gly Arg Thr Ser
        100                 105                 110

Tyr Asp Lys Val Ile Phe Gly Pro Gly Thr Ser Leu Ser Val Ile Pro
        115                 120                 125

Asn Ile Gln Asn Pro Asp Pro Ala Val Tyr Gln Leu Arg Asp Ser Lys
    130                 135                 140

Ser Ser Asp Lys Ser Val Cys Leu Phe Thr Asp Phe Asp Ser Gln Thr
145                 150                 155                 160

Asn Val Ser Gln Ser Lys Asp Ser Asp Val Tyr Ile Thr Asp Lys Cys
            165                 170                 175

Val Leu Asp Met Arg Ser Met Asp Phe Lys Ser Asn Ser Ala Val Ala
        180                 185                 190

Trp Ser Asn Lys Ser Asp Phe Ala Cys Ala Asn Ala Phe Asn Asn Ser
            195                 200                 205

Ile Ile Pro Glu Asp Thr Phe Phe Pro Ser Pro Glu Ser Ser Cys Asp
        210                 215                 220

Val Lys Leu Val Glu Lys Ser Phe Glu Thr Asp Thr Asn Leu Asn Phe
225                 230                 235                 240
```

```
Gln Asn Leu Ser Val Ile Gly Phe Arg Ile Leu Leu Lys Val Ala
                245                 250                 255

Gly Phe Asn Leu Leu Met Thr Leu Arg Leu Trp Ser Ser
            260                 265

<210> SEQ ID NO 80
<211> LENGTH: 133
<212> TYPE: PRT
<213> ORGANISM: Artificial Sequence
<220> FEATURE:
<223> OTHER INFORMATION: WT376 beta chain variable domain

<400> SEQUENCE: 80

Met Ala Ser Leu Leu Phe Phe Cys Gly Ala Phe Tyr Leu Leu Gly Thr
 1               5                  10                  15

Gly Ser Met Asp Ala Asp Val Thr Gln Thr Pro Arg Asn Arg Ile Thr
            20                  25                  30

Lys Thr Gly Lys Arg Ile Met Leu Glu Cys Ser Gln Thr Lys Gly His
        35                  40                  45

Asp Arg Met Tyr Trp Tyr Arg Gln Asp Pro Gly Leu Gly Leu Arg Leu
    50                  55                  60

Ile Tyr Tyr Ser Phe Asp Val Lys Asp Ile Asn Lys Gly Glu Ile Ser
65                  70                  75                  80

Asp Gly Tyr Ser Val Ser Arg Gln Ala Gln Ala Lys Phe Ser Leu Ser
                85                  90                  95

Leu Glu Ser Ala Ile Pro Asn Gln Thr Ala Leu Tyr Phe Cys Ala Thr
            100                 105                 110

Ser Ala Gly Thr Val Gly Asn Thr Ile Tyr Phe Gly Glu Gly Ser Trp
        115                 120                 125

Leu Thr Val Val Glu
    130

<210> SEQ ID NO 81
<211> LENGTH: 309
<212> TYPE: PRT
<213> ORGANISM: Artificial Sequence
<220> FEATURE:
<223> OTHER INFORMATION: WT376 beta chain

<400> SEQUENCE: 81

Met Ala Ser Leu Leu Phe Phe Cys Gly Ala Phe Tyr Leu Leu Gly Thr
 1               5                  10                  15

Gly Ser Met Asp Ala Asp Val Thr Gln Thr Pro Arg Asn Arg Ile Thr
            20                  25                  30

Lys Thr Gly Lys Arg Ile Met Leu Glu Cys Ser Gln Thr Lys Gly His
        35                  40                  45

Asp Arg Met Tyr Trp Tyr Arg Gln Asp Pro Gly Leu Gly Leu Arg Leu
    50                  55                  60

Ile Tyr Tyr Ser Phe Asp Val Lys Asp Ile Asn Lys Gly Glu Ile Ser
65                  70                  75                  80

Asp Gly Tyr Ser Val Ser Arg Gln Ala Gln Ala Lys Phe Ser Leu Ser
                85                  90                  95

Leu Glu Ser Ala Ile Pro Asn Gln Thr Ala Leu Tyr Phe Cys Ala Thr
            100                 105                 110

Ser Ala Gly Thr Val Gly Asn Thr Ile Tyr Phe Gly Glu Gly Ser Trp
        115                 120                 125

Leu Thr Val Val Glu Asp Leu Asn Lys Val Phe Pro Pro Glu Val Ala
    130                 135                 140
```

-continued

```
Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
            165                 170                 175

Trp Trp Val Asn Gly Lys Glu Val His Ser Gly Val Ser Thr Asp Pro
        180                 185                 190

Gln Pro Leu Lys Glu Gln Pro Ala Leu Asn Asp Ser Arg Tyr Cys Leu
    195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
            245                 250                 255

Ala Trp Gly Arg Ala Asp Cys Gly Phe Thr Ser Val Ser Tyr Gln Gln
        260                 265                 270

Gly Val Leu Ser Ala Thr Ile Leu Tyr Glu Ile Leu Leu Gly Lys Ala
    275                 280                 285

Thr Leu Tyr Ala Val Leu Val Ser Ala Leu Val Leu Met Ala Met Val
    290                 295                 300

Lys Arg Lys Asp Phe
305
```

<210> SEQ ID NO 82
<211> LENGTH: 311
<212> TYPE: PRT
<213> ORGANISM: Artificial Sequence
<220> FEATURE:
<223> OTHER INFORMATION: WT376 beta (S189C) chain

<400> SEQUENCE: 82

```
Met Ala Ser Leu Leu Phe Phe Cys Gly Ala Phe Tyr Leu Leu Gly Thr
1               5                   10                  15

Gly Ser Met Asp Ala Asp Val Thr Gln Thr Pro Arg Asn Arg Ile Thr
            20                  25                  30

Lys Thr Gly Lys Arg Ile Met Leu Glu Cys Ser Gln Thr Lys Gly His
        35                  40                  45

Asp Arg Met Tyr Trp Tyr Arg Gln Asp Pro Gly Leu Gly Leu Arg Leu
    50                  55                  60

Ile Tyr Tyr Ser Phe Asp Val Lys Asp Ile Asn Lys Gly Glu Ile Ser
65                  70                  75                  80

Asp Gly Tyr Ser Val Ser Arg Gln Ala Gln Ala Lys Phe Ser Leu Ser
                85                  90                  95

Leu Glu Ser Ala Ile Pro Asn Gln Thr Ala Leu Tyr Phe Cys Ala Thr
            100                 105                 110

Ser Ala Gly Thr Val Gly Asn Thr Ile Tyr Phe Gly Glu Gly Ser Trp
        115                 120                 125

Leu Thr Val Val Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
            165                 170                 175

Trp Trp Val Asn Gly Lys Glu Val His Ser Gly Val Cys Thr Asp Pro
        180                 185                 190
```

```
Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
        210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
        290                 295                 300

Lys Arg Lys Asp Ser Arg Gly
305                 310

<210> SEQ ID NO 83
<211> LENGTH: 600
<212> TYPE: PRT
<213> ORGANISM: Artificial Sequence
<220> FEATURE:
<223> OTHER INFORMATION: WT376 beta (S189C)-P2A-WT376 alpha (T176C)

<400> SEQUENCE: 83

Met Ala Ser Leu Leu Phe Phe Cys Gly Ala Phe Tyr Leu Leu Gly Thr
1               5                   10                  15

Gly Ser Met Asp Ala Asp Val Thr Gln Thr Pro Arg Asn Arg Ile Thr
            20                  25                  30

Lys Thr Gly Lys Arg Ile Met Leu Glu Cys Ser Gln Thr Lys Gly His
        35                  40                  45

Asp Arg Met Tyr Trp Tyr Arg Gln Asp Pro Gly Leu Gly Leu Arg Leu
    50                  55                  60

Ile Tyr Tyr Ser Phe Asp Val Lys Asp Ile Asn Lys Gly Glu Ile Ser
65              70                  75                  80

Asp Gly Tyr Ser Val Ser Arg Gln Ala Gln Ala Lys Phe Ser Leu Ser
                85                  90                  95

Leu Glu Ser Ala Ile Pro Asn Gln Thr Ala Leu Tyr Phe Cys Ala Thr
            100                 105                 110

Ser Ala Gly Thr Val Gly Asn Thr Ile Tyr Phe Gly Glu Gly Ser Trp
        115                 120                 125

Leu Thr Val Val Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240
```

-continued

Trp Thr Gln Asp Arg Ala Lys Pro Val Thr Gln Ile Val Ser Ala Glu
            245                 250                 255

Ala Trp Gly Arg Ala Asp Cys Gly Phe Thr Ser Val Ser Tyr Gln Gln
        260                 265                 270

Gly Val Leu Ser Ala Thr Ile Leu Tyr Glu Ile Leu Leu Gly Lys Ala
    275                 280                 285

Thr Leu Tyr Ala Val Leu Val Ser Ala Leu Val Leu Met Ala Met Val
290                 295                 300

Lys Arg Lys Asp Phe Gly Ser Gly Ala Thr Asn Phe Ser Leu Leu Lys
305                 310                 315                 320

Gln Ala Gly Asp Val Glu Glu Asn Pro Gly Pro Met Leu Leu Ile Thr
                325                 330                 335

Ser Met Leu Val Leu Trp Met Gln Leu Ser Gln Val Asn Gly Gln Gln
            340                 345                 350

Val Met Gln Ile Pro Gln Tyr Gln His Val Gln Glu Gly Glu Asp Phe
        355                 360                 365

Thr Thr Tyr Cys Asn Ser Ser Thr Thr Leu Ser Asn Ile Gln Trp Tyr
    370                 375                 380

Lys Gln Arg Pro Gly Gly His Pro Val Phe Leu Ile Gln Leu Val Lys
385                 390                 395                 400

Ser Gly Glu Val Lys Lys Gln Lys Arg Leu Thr Phe Gln Phe Gly Glu
                405                 410                 415

Ala Lys Lys Asn Ser Ser Leu His Ile Thr Ala Thr Gln Thr Thr Asp
            420                 425                 430

Val Gly Thr Tyr Phe Cys Ala Gly Arg Thr Ser Tyr Asp Lys Val Ile
        435                 440                 445

Phe Gly Pro Gly Thr Ser Leu Ser Val Ile Pro Asn Ile Gln Asn Pro
    450                 455                 460

Asp Pro Ala Val Tyr Gln Leu Arg Asp Ser Lys Ser Ser Asp Lys Ser
465                 470                 475                 480

Val Cys Leu Phe Thr Asp Phe Asp Ser Gln Thr Asn Val Ser Gln Ser
                485                 490                 495

Lys Asp Ser Asp Val Tyr Ile Thr Asp Lys Cys Val Leu Asp Met Arg
            500                 505                 510

Ser Met Asp Phe Lys Ser Asn Ser Ala Val Ala Trp Ser Asn Lys Ser
        515                 520                 525

Asp Phe Ala Cys Ala Asn Ala Phe Asn Asn Ser Ile Ile Pro Glu Asp
    530                 535                 540

Thr Phe Phe Pro Ser Pro Glu Ser Ser Cys Asp Val Lys Leu Val Glu
545                 550                 555                 560

Lys Ser Phe Glu Thr Asp Thr Asn Leu Asn Phe Gln Asn Leu Ser Val
                565                 570                 575

Ile Gly Phe Arg Ile Leu Leu Leu Lys Val Ala Gly Phe Asn Leu Leu
            580                 585                 590

Met Thr Leu Arg Leu Trp Ser Ser
        595                 600

<210> SEQ ID NO 84
<211> LENGTH: 133
<212> TYPE: PRT
<213> ORGANISM: Artificial Sequence
<220> FEATURE:
<223> OTHER INFORMATION: WT377 alpha chain variable domain

<400> SEQUENCE: 84

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Pro Ser Tyr Gly Leu Phe Trp Tyr Lys Gln Pro Ser Ser Gly Glu
    50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
            85                  90                  95

Leu Val Ile Ser Ala Ser Gln Leu Gly Asp Ser Ala Met Tyr Phe Cys
            100                 105                 110

Ala Ile Ser Gly Asn Thr Pro Leu Val Phe Gly Lys Gly Thr Arg Leu
            115                 120                 125

Ser Val Ile Ala Asn
        130

<210> SEQ ID NO 85
<211> LENGTH: 273
<212> TYPE: PRT
<213> ORGANISM: Artificial Sequence
<220> FEATURE:
<223> OTHER INFORMATION: WT377 alpha chain

<400> SEQUENCE: 85

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Pro Ser Tyr Gly Leu Phe Trp Tyr Lys Gln Pro Ser Ser Gly Glu
    50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
            85                  90                  95

Leu Val Ile Ser Ala Ser Gln Leu Gly Asp Ser Ala Met Tyr Phe Cys
            100                 105                 110

Ala Ile Ser Gly Asn Thr Pro Leu Val Phe Gly Lys Gly Thr Arg Leu
            115                 120                 125

Ser Val Ile Ala Asn Ile Gln Asn Pro Asp Pro Ala Val Tyr Gln Leu
        130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
            165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
        210                 215                 220

-continued

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
            245                 250                 255

Leu Lys Val Ala Gly Phe Asn Leu Leu Met Thr Leu Arg Leu Trp Ser
        260                 265                 270

Ser

<210> SEQ ID NO 86
<211> LENGTH: 273
<212> TYPE: PRT
<213> ORGANISM: Artificial Sequence
<220> FEATURE:
<223> OTHER INFORMATION: WT377 alpha (T180C) chain

<400> SEQUENCE: 86

Met Ser Leu Ser Ser Leu Leu Lys Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Pro Ser Tyr Gly Leu Phe Trp Tyr Lys Gln Pro Ser Ser Gly Glu
    50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Ile Ser Gly Asn Thr Pro Leu Val Phe Gly Lys Gly Thr Arg Leu
        115                 120                 125

Ser Val Ile Ala Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Cys Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
            245                 250                 255

Leu Lys Val Ala Gly Phe Asn Leu Leu Met Thr Leu Arg Leu Trp Ser
        260                 265                 270

Ser

<210> SEQ ID NO 87
<211> LENGTH: 143
<212> TYPE: PRT

<213> ORGANISM: Artificial Sequence
<220> FEATURE:
<223> OTHER INFORMATION: WT377 beta chain variable domain

<400> SEQUENCE: 87

```
Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
            20                  25                  30

Val Ile Gln Ser Pro Arg His Leu Ile Lys Glu Lys Arg Glu Thr Ala
        35                  40                  45

Thr Leu Lys Cys Tyr Pro Ile Pro Arg His Asp Thr Val Tyr Trp Tyr
    50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Leu Arg Gly Gly Leu
        115                 120                 125

Glu Lys Leu Phe Phe Gly Ser Gly Thr Gln Leu Ser Val Leu Glu
    130                 135                 140
```

<210> SEQ ID NO 88
<211> LENGTH: 319
<212> TYPE: PRT
<213> ORGANISM: Artificial Sequence
<220> FEATURE:
<223> OTHER INFORMATION: WT377 beta chain

<400> SEQUENCE: 88

```
Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
            20                  25                  30

Val Ile Gln Ser Pro Arg His Leu Ile Lys Glu Lys Arg Glu Thr Ala
        35                  40                  45

Thr Leu Lys Cys Tyr Pro Ile Pro Arg His Asp Thr Val Tyr Trp Tyr
    50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Leu Arg Gly Gly Leu
        115                 120                 125

Glu Lys Leu Phe Phe Gly Ser Gly Thr Gln Leu Ser Val Leu Glu Asp
    130                 135                 140

Leu Asn Lys Val Phe Pro Pro Glu Val Ala Val Phe Glu Pro Ser Glu
145                 150                 155                 160

Ala Glu Ile Ser His Thr Gln Lys Ala Thr Leu Val Cys Leu Ala Thr
                165                 170                 175

Gly Phe Phe Pro Asp His Val Glu Leu Ser Trp Trp Val Asn Gly Lys
            180                 185                 190
```

```
Glu Val His Ser Gly Val Ser Thr Asp Pro Gln Pro Leu Lys Glu Gln
            195                 200                 205

Pro Ala Leu Asn Asp Ser Arg Tyr Cys Leu Ser Ser Arg Leu Arg Val
    210                 215                 220

Ser Ala Thr Phe Trp Gln Asn Pro Arg Asn His Phe Arg Cys Gln Val
225                 230                 235                 240

Gln Phe Tyr Gly Leu Ser Glu Asn Asp Glu Trp Thr Gln Asp Arg Ala
            245                 250                 255

Lys Pro Val Thr Gln Ile Val Ser Glu Ala Trp Gly Arg Ala Asp
    260                 265                 270

Cys Gly Phe Thr Ser Val Ser Tyr Gln Gln Gly Val Leu Ser Ala Thr
            275                 280                 285

Ile Leu Tyr Glu Ile Leu Leu Gly Lys Ala Thr Leu Tyr Ala Val Leu
    290                 295                 300

Val Ser Ala Leu Val Leu Met Ala Met Val Lys Arg Lys Asp Phe
305                 310                 315
```

<210> SEQ ID NO 89
<211> LENGTH: 321
<212> TYPE: PRT
<213> ORGANISM: Artificial Sequence
<220> FEATURE:
<223> OTHER INFORMATION: WT377 beta (S199C) chain

<400> SEQUENCE: 89

```
Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
            20                  25                  30

Val Ile Gln Ser Pro Arg His Leu Ile Lys Glu Lys Arg Glu Thr Ala
        35                  40                  45

Thr Leu Lys Cys Tyr Pro Ile Pro Arg His Asp Thr Val Tyr Trp Tyr
    50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
            85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Leu Arg Gly Gly Leu
        115                 120                 125

Glu Lys Leu Phe Phe Gly Ser Gly Thr Gln Leu Ser Val Leu Glu Asp
    130                 135                 140

Leu Lys Asn Val Phe Pro Pro Glu Val Ala Val Phe Glu Pro Ser Glu
145                 150                 155                 160

Ala Glu Ile Ser His Thr Gln Lys Ala Thr Leu Val Cys Leu Ala Thr
            165                 170                 175

Gly Phe Tyr Pro Asp His Val Glu Leu Ser Trp Trp Val Asn Gly Lys
        180                 185                 190

Glu Val His Ser Gly Val Cys Thr Asp Pro Gln Pro Leu Lys Glu Gln
    195                 200                 205

Pro Ala Leu Asn Asp Ser Arg Tyr Cys Leu Ser Ser Arg Leu Arg Val
    210                 215                 220

Ser Ala Thr Phe Trp Gln Asn Pro Arg Asn His Phe Arg Cys Gln Val
225                 230                 235                 240
```

```
Gln Phe Tyr Gly Leu Ser Glu Asn Asp Glu Trp Thr Gln Asp Arg Ala
                245                 250                 255

Lys Pro Val Thr Gln Ile Val Ser Ala Glu Ala Trp Gly Arg Ala Asp
            260                 265                 270

Cys Gly Phe Thr Ser Glu Ser Tyr Gln Gln Gly Val Leu Ser Ala Thr
        275                 280                 285

Ile Leu Tyr Glu Ile Leu Leu Gly Lys Ala Thr Leu Tyr Ala Val Leu
    290                 295                 300

Val Ser Ala Leu Val Leu Met Ala Met Val Lys Arg Lys Asp Ser Arg
305                 310                 315                 320

Gly

<210> SEQ ID NO 90
<211> LENGTH: 614
<212> TYPE: PRT
<213> ORGANISM: Artificial Sequence
<220> FEATURE:
<223> OTHER INFORMATION: WT377 beta (S199C)-P2A-WT377 alpha (T180C)

<400> SEQUENCE: 90

Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
            20                  25                  30

Val Ile Gln Ser Pro Arg His Leu Ile Lys Glu Lys Arg Glu Thr Ala
        35                  40                  45

Thr Leu Lys Cys Tyr Pro Ile Pro Arg His Asp Thr Val Tyr Trp Tyr
    50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Leu Arg Gly Gly Leu
        115                 120                 125

Glu Lys Leu Phe Phe Gly Ser Gly Thr Gln Leu Ser Val Leu Glu Asp
130                 135                 140

Leu Asn Lys Val Phe Pro Pro Glu Val Ala Val Phe Glu Pro Ser Glu
145                 150                 155                 160

Ala Glu Ile Ser His Thr Gln Lys Ala Thr Leu Val Cys Leu Ala Thr
                165                 170                 175

Gly Phe Phe Pro Asp His Val Glu Leu Ser Trp Trp Val Asn Gly Lys
            180                 185                 190

Glu Val His Ser Gly Val Cys Thr Asp Pro Gln Pro Leu Lys Glu Gln
        195                 200                 205

Pro Ala Leu Asn Asp Ser Arg Tyr Cys Leu Ser Ser Arg Leu Arg Val
    210                 215                 220

Ser Ala Thr Phe Trp Gln Asn Pro Arg Asn His Phe Arg Cys Gln Val
225                 230                 235                 240

Gln Phe Tyr Gly Leu Ser Glu Asn Asp Glu Trp Thr Gln Asp Arg Ala
                245                 250                 255

Lys Pro Val Thr Gln Ile Val Ser Ala Glu Ala Trp Gly Arg Ala Asp
            260                 265                 270

Cys Gly Phe Thr Ser Val Ser Tyr Gln Gln Gly Val Leu Ser Ala Thr
```

```
            275                 280                 285
Ile Leu Tyr Glu Ile Leu Leu Gly Lys Ala Thr Leu Tyr Ala Val Leu
290                 295                 300
Val Ser Ala Leu Val Leu Met Ala Met Val Lys Arg Lys Asp Phe Gly
305                 310                 315                 320
Ser Gly Ala Thr Asn Phe Ser Leu Leu Lys Gln Ala Gly Asp Val Glu
                325                 330                 335
Glu Asn Pro Gly Pro Met Ser Leu Ser Ser Leu Leu Lys Val Val Thr
            340                 345                 350
Ala Ser Leu Trp Leu Gly Pro Gly Ile Ala Gln Lys Ile Thr Gln Thr
        355                 360                 365
Gln Pro Gly Met Phe Val Gln Glu Lys Glu Ala Val Thr Leu Asp Cys
    370                 375                 380
Thr Tyr Asp Thr Ser Asp Pro Ser Tyr Gly Leu Phe Trp Tyr Lys Gln
385                 390                 395                 400
Pro Ser Ser Gly Glu Met Ile Phe Leu Ile Tyr Gln Gly Ser Tyr Asp
                405                 410                 415
Gln Gln Asn Ala Thr Glu Gly Arg Tyr Ser Leu Asn Phe Gln Lys Ala
            420                 425                 430
Arg Lys Ser Ala Asn Leu Val Ile Ser Ala Ser Gln Leu Gly Asp Ser
        435                 440                 445
Ala Met Tyr Phe Cys Ala Ile Ser Gly Asn Thr Pro Leu Val Phe Gly
    450                 455                 460
Lys Gly Thr Arg Leu Ser Val Ile Ala Asn Ile Gln Asn Pro Asp Pro
465                 470                 475                 480
Ala Val Tyr Gln Leu Arg Asp Ser Lys Ser Ser Asp Lys Ser Val Cys
                485                 490                 495
Leu Phe Thr Asp Phe Asp Ser Gln Thr Asn Val Ser Gln Ser Lys Asp
            500                 505                 510
Ser Asp Val Tyr Ile Thr Asp Lys Cys Val Leu Asp Met Arg Ser Met
        515                 520                 525
Asp Phe Lys Ser Asn Ser Ala Val Ala Trp Ser Asn Lys Ser Asp Phe
    530                 535                 540
Ala Cys Ala Asn Ala Phe Asn Asn Ser Ile Ile Pro Glu Asp Thr Phe
545                 550                 555                 560
Phe Pro Ser Pro Glu Ser Ser Cys Asp Val Lys Leu Val Glu Lys Ser
                565                 570                 575
Phe Glu Thr Asp Thr Asn Leu Asn Phe Gln Asn Leu Ser Val Ile Gly
            580                 585                 590
Phe Arg Ile Leu Leu Leu Lys Val Ala Gly Phe Asn Leu Leu Met Thr
        595                 600                 605
Leu Arg Leu Trp Ser Ser
    610

<210> SEQ ID NO 91
<211> LENGTH: 11
<212> TYPE: PRT
<213> ORGANISM: Artificial Sequence
<220> FEATURE:
<223> OTHER INFORMATION: ME201 alpha CDR3

<400> SEQUENCE: 91

Cys Leu Leu Arg Asn His Asp Lys Leu Ile Phe
1               5                   10
```

```
<210> SEQ ID NO 92
<211> LENGTH: 15
<212> TYPE: PRT
<213> ORGANISM: Artificial Sequence
<220> FEATURE:
<223> OTHER INFORMATION: ME5301 alpha CDR3

<400> SEQUENCE: 92

Cys Ala Val Gly Asn Tyr Gly Gly Ser Gln Gly Asn Leu Ile Phe
1               5                   10                  15

<210> SEQ ID NO 93
<211> LENGTH: 11
<212> TYPE: PRT
<213> ORGANISM: Artificial Sequence
<220> FEATURE:
<223> OTHER INFORMATION: WT374 alpha CDR3

<400> SEQUENCE: 93

Cys Ala Ala Arg Gly Gln Gly Asn Leu Ile Phe
1               5                   10

<210> SEQ ID NO 94
<211> LENGTH: 18
<212> TYPE: PRT
<213> ORGANISM: Artificial Sequence
<220> FEATURE:
<223> OTHER INFORMATION: WT375 alpha CDR3

<400> SEQUENCE: 94

Cys Ala Val Arg Asp Ile Arg Tyr Tyr Gly Gly Ser Gln Gly Asn Leu
1               5                   10                  15

Ile Phe

<210> SEQ ID NO 95
<211> LENGTH: 16
<212> TYPE: PRT
<213> ORGANISM: Artificial Sequence
<220> FEATURE:
<223> OTHER INFORMATION: WT378 alpha CDR3

<400> SEQUENCE: 95

Cys Ala Ile Tyr Gly Trp Gly Gly Gly Ala Thr Asn Lys Leu Ile Phe
1               5                   10                  15

<210> SEQ ID NO 96
<211> LENGTH: 14
<212> TYPE: PRT
<213> ORGANISM: Artificial Sequence
<220> FEATURE:
<223> OTHER INFORMATION: WT379 alpha CDR3

<400> SEQUENCE: 96

Cys Ala Val Gly Gly Ser Gly Gly Tyr Gln Lys Val Thr Phe
1               5                   10

<210> SEQ ID NO 97
<211> LENGTH: 16
<212> TYPE: PRT
<213> ORGANISM: Artificial Sequence
<220> FEATURE:
<223> OTHER INFORMATION: WT3710 alpha CDR3

<400> SEQUENCE: 97

Cys Val Val Lys Pro Asp Pro Gly Ala Gly Ser Tyr Gln Leu Thr Phe
1               5                   10                  15
```

<210> SEQ ID NO 98
<211> LENGTH: 16
<212> TYPE: PRT
<213> ORGANISM: Artificial Sequence
<220> FEATURE:
<223> OTHER INFORMATION: WT371 alpha CDR3

<400> SEQUENCE: 98

Cys Ala Met Arg Ala Arg Glu Glu Thr Ser Gly Ser Arg Leu Thr Phe
1               5                   10                  15

<210> SEQ ID NO 99
<211> LENGTH: 13
<212> TYPE: PRT
<213> ORGANISM: Artificial Sequence
<220> FEATURE:
<223> OTHER INFORMATION: WT372 alpha CDR3

<400> SEQUENCE: 99

Cys Ala Val Pro Thr Ser Gly Thr Tyr Lys Tyr Ile Phe
1               5                   10

<210> SEQ ID NO 100
<211> LENGTH: 16
<212> TYPE: PRT
<213> ORGANISM: Artificial Sequence
<220> FEATURE:
<223> OTHER INFORMATION: WT373 alpha CDR3

<400> SEQUENCE: 100

Cys Ala Ala Gly Ala Arg Gly Gly Thr Ser Tyr Gly Lys Leu Thr Phe
1               5                   10                  15

<210> SEQ ID NO 101
<211> LENGTH: 12
<212> TYPE: PRT
<213> ORGANISM: Artificial Sequence
<220> FEATURE:
<223> OTHER INFORMATION: WT376 alpha CDR3

<400> SEQUENCE: 101

Cys Ala Gly Arg Thr Ser Tyr Asp Lys Val Ile Phe
1               5                   10

<210> SEQ ID NO 102
<211> LENGTH: 11
<212> TYPE: PRT
<213> ORGANISM: Artificial Sequence
<220> FEATURE:
<223> OTHER INFORMATION: WT377 alpha CDR3

<400> SEQUENCE: 102

Cys Ala Ile Ser Gly Asn Thr Pro Leu Val Phe
1               5                   10

<210> SEQ ID NO 103
<211> LENGTH: 13
<212> TYPE: PRT
<213> ORGANISM: Artificial Sequence
<220> FEATURE:
<223> OTHER INFORMATION: ME201 beta CDR3

<400> SEQUENCE: 103

Cys Ala Ser Ser Gln Asp Ser Tyr Asn Glu Gln Phe Phe
1               5                   10

```
<210> SEQ ID NO 104
<211> LENGTH: 15
<212> TYPE: PRT
<213> ORGANISM: Artificial Sequence
<220> FEATURE:
<223> OTHER INFORMATION: ME5301 beta CDR3

<400> SEQUENCE: 104

Cys Ala Ser Ser Leu Ala Gly Gly Tyr Gly Asp Thr Gln Tyr Phe
1               5                   10                  15

<210> SEQ ID NO 105
<211> LENGTH: 12
<212> TYPE: PRT
<213> ORGANISM: Artificial Sequence
<220> FEATURE:
<223> OTHER INFORMATION: WT374 beta CDR3

<400> SEQUENCE: 105

Cys Ala Ser Ser Leu Tyr Arg Gly Glu Gln Tyr Phe
1               5                   10

<210> SEQ ID NO 106
<211> LENGTH: 14
<212> TYPE: PRT
<213> ORGANISM: Artificial Sequence
<220> FEATURE:
<223> OTHER INFORMATION: WT375 beta CDR3

<400> SEQUENCE: 106

Cys Ala Ser Ser Pro Gly Pro Ser Asn Asn Glu Gln Phe Phe
1               5                   10

<210> SEQ ID NO 107
<211> LENGTH: 15
<212> TYPE: PRT
<213> ORGANISM: Artificial Sequence
<220> FEATURE:
<223> OTHER INFORMATION: WT378 beta CDR3

<400> SEQUENCE: 107

Cys Ala Ser Ser Leu Tyr Gly Gly Ser Ser Tyr Glu Gln Tyr Phe
1               5                   10                  15

<210> SEQ ID NO 108
<211> LENGTH: 14
<212> TYPE: PRT
<213> ORGANISM: Artificial Sequence
<220> FEATURE:
<223> OTHER INFORMATION: WT379 beta CDR3

<400> SEQUENCE: 108

Cys Ala Ser Ser Gly Arg Ala Gly Val Gly Glu Leu Phe Phe
1               5                   10

<210> SEQ ID NO 109
<211> LENGTH: 15
<212> TYPE: PRT
<213> ORGANISM: Artificial Sequence
<220> FEATURE:
<223> OTHER INFORMATION: WT3710 beta CDR3

<400> SEQUENCE: 109

Cys Ala Ser Arg Gly Tyr His Arg Leu Asn Asn Glu Gln Phe Phe
1               5                   10                  15

<210> SEQ ID NO 110
```

```
<211> LENGTH: 14
<212> TYPE: PRT
<213> ORGANISM: Artificial Sequence
<220> FEATURE:
<223> OTHER INFORMATION: WT371 beta CDR3

<400> SEQUENCE: 110

Cys Ala Ser Ser Gln Asp Gly Arg Ser Arg Pro Gln His Phe
1               5                   10

<210> SEQ ID NO 111
<211> LENGTH: 15
<212> TYPE: PRT
<213> ORGANISM: Artificial Sequence
<220> FEATURE:
<223> OTHER INFORMATION: WT372 beta CDR3

<400> SEQUENCE: 111

Cys Ala Ser Ser Ile Arg Asp Ser Ser Asn Gln Pro Gln His Phe
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: WT373 beta CDR3

<400> SEQUENCE: 112

Cys Ala Ser Ser Ala Gln Gly Ala Tyr Gly Asn Gln Pro Gln His Phe
1               5                   10                  15

<210> SEQ ID NO 113
<211> LENGTH: 14
<212> TYPE: PRT
<213> ORGANISM: Artificial Sequence
<220> FEATURE:
<223> OTHER INFORMATION: WT376 beta CDR3

<400> SEQUENCE: 113

Cys Ala Thr Ser Ala Gly Thr Val Gly Asn Thr Ile Tyr Phe
1               5                   10

<210> SEQ ID NO 114
<211> LENGTH: 14
<212> TYPE: PRT
<213> ORGANISM: Artificial Sequence
<220> FEATURE:
<223> OTHER INFORMATION: WT377 beta CDR3

<400> SEQUENCE: 114

Cys Ala Ser Ser Leu Arg Gly Gly Leu Glu Lys Leu Phe Phe
1               5                   10

<210> SEQ ID NO 115
<211> LENGTH: 9
<212> TYPE: PRT
<213> ORGANISM: Artificial Sequence
<220> FEATURE:
<223> OTHER INFORMATION: Mesothelin (20-28) Peptide Antigen

<400> SEQUENCE: 115

Ser Leu Leu Phe Leu Leu Phe Ser Leu
1               5

<210> SEQ ID NO 116
<211> LENGTH: 9
```

```
<212> TYPE: PRT
<213> ORGANISM: Artificial Sequence
<220> FEATURE:
<223> OTHER INFORMATION: Mesothelin (530-538) Peptide Antigen

<400> SEQUENCE: 116

Val Leu Pro Leu Thr Val Ala Glu Val
1               5

<210> SEQ ID NO 117
<211> LENGTH: 9
<212> TYPE: PRT
<213> ORGANISM: Artificial Sequence
<220> FEATURE:
<223> OTHER INFORMATION: WT-1 Peptide Antigen

<400> SEQUENCE: 117

Val Leu Asp Phe Ala Pro Pro Gly Ala
1               5

<210> SEQ ID NO 118
<211> LENGTH: 22
<212> TYPE: PRT
<213> ORGANISM: Artificial Sequence
<220> FEATURE:
<223> OTHER INFORMATION: Porcine teschovirus-1 2A (P2A) peptide

<400> SEQUENCE: 118

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 119
<211> LENGTH: 21
<212> TYPE: PRT
<213> ORGANISM: Artificial Sequence
<220> FEATURE:
<223> OTHER INFORMATION: Thoseaasigna virus 2A (T2A) peptide

<400> SEQUENCE: 119

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 120
<211> LENGTH: 23
<212> TYPE: PRT
<213> ORGANISM: Artificial Sequence
<220> FEATURE:
<223> OTHER INFORMATION: Equine rhinitis A virus (ERAV) 2A (E2A) peptide

<400> SEQUENCE: 120

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 121
<211> LENGTH: 25
<212> TYPE: PRT
<213> ORGANISM: Artificial Sequence
<220> FEATURE:
<223> OTHER INFORMATION: Foot-and-Mouth disease virus 2A (F2A) peptide
```

```
<400> SEQUENCE: 121

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 122
<211> LENGTH: 369
<212> TYPE: DNA
<213> ORGANISM: Artificial Sequence
<220> FEATURE:
<223> OTHER INFORMATION: ME201 alpha chain variable domain WT

<400> SEQUENCE: 122
atgaactcct ctctggactt tctaattctg atcttaatgt ttggaggaac cagcagcaat      60
tcagtcaagc agacgggcca ataaccgtc tcggagggag catctgtgac tatgaactgc     120
acatacacat ccacggggta ccctacccctt ttctggtatg tggaataccc cagcaaacct    180
ctgcagcttc ttcagagaga gacaatggaa acagcaaaa acttcggagg cggaaatatt     240
aaagacaaaa actcccccat tgtgaaatat tcagtccagg tatcagactc agccgtgtac    300
tactgtcttc tgaggaatca cgacaagctc atctttggga ctgggaccag attacaagtc    360
tttccaaat                                                              369

<210> SEQ ID NO 123
<211> LENGTH: 369
<212> TYPE: DNA
<213> ORGANISM: Artificial Sequence
<220> FEATURE:
<223> OTHER INFORMATION: ME201 alpha chain variable domain - Codon
      Optimized

<400> SEQUENCE: 123
atgaacagca gcctggactt cctgatcctg attctgatgt tcggcggcac cagcagcaac      60
agcgtgaagc agacaggcca gatcaccgtg tctgagggcg ccagcgtgac catgaactgc     120
acctacacca gcaccggcta ccccaccctg ttttggtacg tggaataccc cagcaagccc    180
ctccagctgc tccagcggga aaccatggaa acagcaaga acttcggcgg aggcaacatc     240
aaggacaaga acagcccat cgtgaagtac agcgtgcagg tgtccgacag cgccgtgtac    300
tactgcctgc tgcggaacca cgacaagctg atcttcggca ccggcacccg gctccaggtg    360
ttccccaac                                                              369

<210> SEQ ID NO 124
<211> LENGTH: 423
<212> TYPE: DNA
<213> ORGANISM: Artificial Sequence
<220> FEATURE:
<223> OTHER INFORMATION: ME201 alpha chain constant domain WT

<400> SEQUENCE: 124
atccagaacc ctgaccctgc cgtgtaccag ctgagagact ctaaatccag tgacaagtct      60
gtctgcctat tcaccgattt tgattctcaa acaaatgtgt cacaaagtaa ggattctgat    120
gtgtatatca cagacaaaac tgtgctagac atgaggtcta tggacttcaa gagcaacagt    180
gctgtggcct ggagcaacaa atctgacttt gcatgtgcaa acgccttcaa caacagcatt    240
attccagaag acaccttctt ccccagccca gaaagttcct gtgatgtcaa gctggtcgag    300
aaaagctttg aaacagatac gaacctaaac tttcaaaacc tgtcagtgat tgggttccga    360
```

```
atcctcctcc tgaaagtggc cgggtttaat ctgctcatga cgctgcggct gtggtccagc    420
tga                                                                  423
```

<210> SEQ ID NO 125
<211> LENGTH: 423
<212> TYPE: DNA
<213> ORGANISM: Artificial Sequence
<220> FEATURE:
<223> OTHER INFORMATION: ME201 alpha chain constant domain - Codon-Optimized

<400> SEQUENCE: 125

```
atccagaacc ccgaccccgc agtgtaccag ctgcgggaca gcaagagcag cgacaagagc     60
gtgtgcctgt tcaccgactt cgacagccag accaacgtgt cccagagcaa ggacagcgac    120
gtgtacatca ccgataagac cgtgctggac atgcggagca tggacttcaa gagcaacagc    180
gccgtggcct ggtccaacaa gagcgacttc gcctgcgcca acgccttcaa caacagcatt    240
atccccgagg acacattctt cccaagcccc gagagcagct cgacgtgaa gctggtggaa    300 aagagcttcg agacagacac caacctgaac ttccagaacc tcagcgtgat cggcttccgg    360
atcctgctgc tgaaggtggc cggcttcaac ctgctgatga ccctgcggct gtggtccagc    420
tga                                                                  423
```

<210> SEQ ID NO 126
<211> LENGTH: 423
<212> TYPE: DNA
<213> ORGANISM: Artificial Sequence
<220> FEATURE:
<223> OTHER INFORMATION: ME201 alpha chain constant domain - Cys Modified

<400> SEQUENCE: 126

```
atccagaacc ctgaccctgc cgtgtaccag ctgagagact ctaaatccag tgacaagtct     60
gtctgcctat tcaccgattt tgattctcaa acaaatgtgt cacaaagtaa ggattctgat    120
gtgtatatca cagacaaatg cgtgctagac atgaggtcta tggacttcaa gagcaacagt    180
gctgtggcct ggagcaacaa atctgacttt gcatgtgcaa acgccttcaa caacagcatt    240
attccagaag acaccttctt ccccagccca gaaagttcct gtgatgtcaa gctggtcgag    300
aaaagctttg aaacagatac gaacctaaac tttcaaaacc tgtcagtgat tgggttccga    360
atcctcctcc tgaaagtggc cgggtttaat ctgctcatga cgctgcggct gtggtccagc    420
tga                                                                  423
```

<210> SEQ ID NO 127
<211> LENGTH: 423
<212> TYPE: DNA
<213> ORGANISM: Artificial Sequence
<220> FEATURE:
<223> OTHER INFORMATION: ME201 alpha chain constant domain - Codon-Optimized, Cys Modified

<400> SEQUENCE: 127

```
atccagaacc ccgaccccgc agtgtaccag ctgcgggaca gcaagagcag cgacaagagc     60
gtgtgcctgt tcaccgactt cgacagccag accaacgtgt cccagagcaa ggacagcgac    120
gtgtacatca ccgataagtg cgtgctggac atgcggagca tggacttcaa gagcaacagc    180
gccgtggcct ggtccaacaa gagcgacttc gcctgcgcca acgccttcaa caacagcatt    240
atccccgagg acacattctt cccaagcccc gagagcagct gcgacgtgaa gctggtggaa    300
```

| | |
|---|---|
| aagagcttcg agacagacac caacctgaac ttccagaacc tcagcgtgat cggcttccgg | 360 |
| atcctgctgc tgaaggtggc cggcttcaac ctgctgatga ccctgcggct gtggtccagc | 420 |
| tga | 423 |

<210> SEQ ID NO 128
<211> LENGTH: 792
<212> TYPE: DNA
<213> ORGANISM: Artificial Sequence
<220> FEATURE:
<223> OTHER INFORMATION: ME201 alpha chain WT

<400> SEQUENCE: 128

| | |
|---|---|
| atgaactcct ctctggactt tctaattctg atcttaatgt ttggaggaac cagcagcaat | 60 |
| tcagtcaagc agacgggcca ataaccgtc tcggagggag catctgtgac tatgaactgc | 120 |
| acatacacat ccacggggta ccctaccctt ttctggtatg tggaatacccc cagcaaacct | 180 |
| ctgcagcttc ttcagagaga gacaatggaa aacagcaaaa acttcggagg cggaaatatt | 240 |
| aaagacaaaa actcccccat tgtgaaatat tcagtccagg tatcagactc agccgtgtac | 300 |
| tactgtcttc tgaggaatca cgacaagctc atctttggga ctgggaccag attacaagtc | 360 |
| tttccaaata tccagaaccc tgaccctgcc gtgtaccagc tgagagactc taaatccagt | 420 |
| gacaagtctg tctgcctatt caccgatttt gattctcaaa caaatgtgtc acaaagtaag | 480 |
| gattctgatg tgtatatcac agacaaaact gtgctagaca tgaggtctat ggacttcaag | 540 |
| agcaacagtg ctgtggcctg agcaacaaa tctgactttg catgtgcaaa cgccttcaac | 600 |
| aacagcatta ttccagaaga caccttcttc cccagcccag aaagttcctg tgatgtcaag | 660 |
| ctggtcgaga aaagctttga aacagatacg aacctaaact tcaaaacct gtcagtgatt | 720 |
| gggttccgaa tcctcctcct gaaagtggcc gggtttaatc tgctcatgac gctgcggctg | 780 |
| tggtccagct ga | 792 |

<210> SEQ ID NO 129
<211> LENGTH: 792
<212> TYPE: DNA
<213> ORGANISM: Artificial Sequence
<220> FEATURE:
<223> OTHER INFORMATION: ME201 alpha chain - Codon-Optimized, Cys Modified

<400> SEQUENCE: 129

| | |
|---|---|
| atgaacagca gcctggactt cctgatcctg attctgatgt tcggcggcac cagcagcaac | 60 |
| agcgtgaagc agacaggcca gatcaccgtg tctgagggcg ccagcgtgac catgaactgc | 120 |
| acctacacca gcaccggcta ccccaccctg ttttggtacg tggaataccc cagcaagccc | 180 |
| ctccagctgc tccagcggga aaccatggaa aacagcaaga acttcggcgg aggcaacatc | 240 |
| aaggacaaga acagccccat cgtgaagtac agcgtgcagg tgtccgacag cgccgtgtac | 300 |
| tactgcctgc tgcggaacca cgacaagctg atcttcggca ccggcacccg gctccaggtg | 360 |
| ttccccaaca tccagaaccc cgaccccgca gtgtaccagc tgcgggacag caagagcagc | 420 |
| gacaagagcg tgtgcctgtt caccgacttc gacagccaga ccaacgtgtc ccagagcaag | 480 |
| gacagcgacg tgtacatcac cgataagtgc gtgctggaca tgcggagcat ggacttcaag | 540 |
| agcaacagcg ccgtggcctg gtccaacaag agcgacttcg cctgcgccaa cgccttcaac | 600 |
| aacagcatta tccccgagga cacattcttc ccaagcccg agagcagctg cgacgtgaag | 660 |
| ctggtggaaa agagcttcga gacagacacc aacctgaact tccagaacct cagcgtgatc | 720 |

```
ggcttccgga tcctgctgct gaaggtggcc ggcttcaacc tgctgatgac cctgcggctg      780
tggtccagct ga                                                          792
```

<210> SEQ ID NO 130
<211> LENGTH: 396
<212> TYPE: DNA
<213> ORGANISM: Artificial Sequence
<220> FEATURE:
<223> OTHER INFORMATION: ME201 beta chain variable domain WT

<400> SEQUENCE: 130

```
atgggccctg ggctcctctg ctgggtgctg ctttgtctcc tgggagcagg ctcagtggag       60
actggagtca cccaaagtcc cacacacctg atcaaaacga ggacagca agtgactctg       120 agatgctctt ctcagtctgg gcacaacact gtgtcctggt accaacaggc cctgggtcag      180
gggccccagt ttatctttca gtattatagg gaggaagaga atggcagagg aaacttccct      240
cctagattct caggtctcca gttccctaat tatagctctg agctgaatgt gaacgccttg      300
gagctggacg actcggccct gtatctctgt gccagcagcc aagactcgta caatgagcag      360
ttcttcgggc cagggacacg gctcaccgtg ctagag                                396
```

<210> SEQ ID NO 131
<211> LENGTH: 396
<212> TYPE: DNA
<213> ORGANISM: Artificial Sequence
<220> FEATURE:
<223> OTHER INFORMATION: ME201 beta chain variable domain - Codon Optimized

<400> SEQUENCE: 131

```
atgggacctg gcctgctgtg ttgggtgctg ctgtgtctgc tgggagccgg cagtgtggaa       60
accggcgtga cacagagccc cacccacctg atcaagacca gaggccagca agtgaccctg      120
cggtgcagct ctcagagcgg ccacaatacc gtgtcctggt atcagcaggc cctgggccag      180
ggaccccagt tcatcttcca gtactacaga gaggaagaga acggcagagg caacttccca      240
ccccggttta gcggcctgca gttccccaac tacagctccg agctgaacgt gaacgccctg      300
gaactggacg acagcgccct gtacctgtgt gccagcagcc aggacagcta caacgagcag      360
ttcttcggcc ctggcacccg gctgaccgtg ctggaa                                396
```

<210> SEQ ID NO 132
<211> LENGTH: 534
<212> TYPE: DNA
<213> ORGANISM: Artificial Sequence
<220> FEATURE:
<223> OTHER INFORMATION: ME201 beta chain constant domain WT

<400> SEQUENCE: 132

```
gacctgaaaa acgtgttccc acccgaggtc gctgtgtttg agccatcaga agcagagatc       60
tcccacaccc aaaaggccac actggtgtgc ctggccacag gcttctaccc cgaccacgtg      120
gagctgagct ggtgggtgaa tgggaaggag gtgcacagtg gggtcagcac agacccgcag      180
cccctcaagg agcagcccgc cctcaatgac tccagatact gcctgagcag ccgcctgagg      240
gtctcggcca ccttctggca gaaccccgcg aaccacttcc gctgtcaagt ccagttctac      300
gggctctcgg agaatgacga gtggaccag gataggccaa acctgtcac ccagatcgtc       360 agcgccgagg cctgggtag agcagactgt ggcttcacct ccgagtctta ccagcaaggg      420
gtcctgtctg ccaccatcct ctatgagatc ttgctaggga aggccacctt gtatgccgtg      480
```

```
ctggtcagtg ccctcgtgct gatggccatg gtcaagagaa aggattccag aggc       534
```

<210> SEQ ID NO 133
<211> LENGTH: 534
<212> TYPE: DNA
<213> ORGANISM: Artificial Sequence
<220> FEATURE:
<223> OTHER INFORMATION: ME201 beta chain constant domain - Cys Modified

<400> SEQUENCE: 133

```
gacctgaaaa acgtgttccc acccgaggtc gctgtgtttg agccatcaga agcagagatc    60
tcccacaccc aaaaggccac actggtgtgc ctggccacag gcttctaccc cgaccacgtg   120
gagctgagct ggtgggtgaa tgggaaggag gtgcacagtg gggtctgcac agacccgcag   180
cccctcaagg agcagcccgc cctcaatgac tccagatact gcctgagcag ccgcctgagg   240
gtctcggcca ccttctggca gaaccccgc aaccacttcc gctgtcaagt ccagttctac    300
gggctctcgg agaatgacga gtggacccag gatagggcca aacctgtcac ccagatcgtc   360
agcgccgagg cctggggtag agcagactgt ggcttcacct ccgagtctta ccagcaaggg   420
gtcctgtctg ccaccatcct ctatgagatc ttgctaggga aggccacctt gtatgccgtg   480
ctggtcagtg ccctcgtgct gatggccatg gtcaagagaa aggattccag aggc          534
```

<210> SEQ ID NO 134
<211> LENGTH: 534
<212> TYPE: DNA
<213> ORGANISM: Artificial Sequence
<220> FEATURE:
<223> OTHER INFORMATION: ME201 beta chain constant domain - Codon
     Optimized

<400> SEQUENCE: 134

```
gatctgaaga acgtgttccc cccagaggtg gccgtgttcg agcctagcga ggccgagatc    60
agccacaccc agaaagccac cctcgtgtgc ctggccaccg gcttttaccc cgaccacgtg   120
gaactgtctt ggtgggtcaa cggcaaagag gtgcacagcg gcgtcagcac cgaccccag    180
cccctgaaag agcagcccgc cctgaacgac agccggtact gtctgagcag cagactgaga   240
gtgtccgcca ccttctggca gaaccccgg aaccacttca gatgccaggt gcagttctac    300
ggcctgagcg agaacgacga gtggacccag gaccgggcca agcccgtgac ccagatcgtg   360
tctgctgagg cctggggcag agccgattgc ggcttcacca gcgagagcta ccagcagggc   420
gtgctgagcg ccaccatcct gtacgagatc ctgctgggca aggccaccct gtacgccgtg   480
ctggtgtccg ccctggtgct gatggccatg gtcaagcgga aggacagccg gggc          534
```

<210> SEQ ID NO 135
<211> LENGTH: 534
<212> TYPE: DNA
<213> ORGANISM: Artificial Sequence
<220> FEATURE:
<223> OTHER INFORMATION: ME201 beta chain constant domain -
     Codon-Optimized, Cys Modified

<400> SEQUENCE: 135

```
gatctgaaga acgtgttccc cccagaggtg gccgtgttcg agcctagcga ggccgagatc    60
agccacaccc agaaagccac cctcgtgtgc ctggccaccg gcttttaccc cgaccacgtg   120
gaactgtctt ggtgggtcaa cggcaaagag gtgcacagcg gcgtctgcac cgaccccag    180
cccctgaaag agcagcccgc cctgaacgac agccggtact gtctgagcag cagactgaga   240
gtgtccgcca ccttctggca gaaccccgg aaccacttca gatgccaggt gcagttctac    300
```

```
ggcctgagcg agaacgacga gtggacccag gaccgggcca agcccgtgac ccagatcgtg      360
tctgctgagg cctggggcag agccgattgc ggcttcacca gcgagagcta ccagcagggc      420
gtgctgagcg ccaccatcct gtacgagatc ctgctgggca aggccaccct gtacgccgtg      480
ctggtgtccg ccctggtgct gatggccatg gtcaagcgga aggacagccg gggc            534
```

<210> SEQ ID NO 136
<211> LENGTH: 930
<212> TYPE: DNA
<213> ORGANISM: Artificial Sequence
<220> FEATURE:
<223> OTHER INFORMATION: ME201 beta chain WT

<400> SEQUENCE: 136

```
atgggccctg ggctcctctg ctgggtgctg ctttgtctcc tgggagcagg ctcagtggag       60
actggagtca cccaaagtcc cacacacctg atcaaaacga gaggacagca agtgactctg      120
agatgctctt ccagtctgg gcacaacact gtgtcctggt accaacaggc cctgggtcag       180
ggcccccagt ttatctttca gtattatagg gaggaagaga atggcagagg aaacttccct      240
cctagattct caggtctcca gttccctaat tatagctctg agctgaatgt gaacgccttg      300
gagctggacg actcggccct gtatctctgt gccagcagcc aagactcgta caatgagcag      360
ttcttcgggc cagggacacg gctcaccgtg ctagaggacc tgaaaaacgt gttcccaccc      420
gaggtcgctg tgtttgagcc atcagaagca gagatctccc acacccaaaa ggccacactg      480
gtgtgcctgg ccacaggctt ctaccccgac cacgtggagc tgagctggtg ggtgaatggg      540
aaggaggtgc acagtggggt cagcacagac ccgcagcccc tcaaggagca gcccgccctc      600
aatgactcca gatactgcct gagcagccgc ctgagggtct cggccacctt ctggcagaac      660
ccccgcaacc acttccgctg tcaagtccag ttctacgggc tctcggagaa tgacgagtgg      720
acccaggata gggccaaacc tgtcacccag atcgtcagcg ccgaggcctg ggtagagca      780 gactgtggct tcacctccga gtcttaccag caagggtcc tgtctgccac catcctctat      840
gagatcttgc tagggaaggc caccttgtat gccgtgctgg tcagtgccct cgtgctgatg      900
gccatggtca agagaaagga ttccagaggc                                       930
```

<210> SEQ ID NO 137
<211> LENGTH: 930
<212> TYPE: DNA
<213> ORGANISM: Artificial Sequence
<220> FEATURE:
<223> OTHER INFORMATION: ME201 beta chain - Codon-Optimized, Cys
      Modified

<400> SEQUENCE: 137

```
atgggacctg gcctgctgtg ttgggtgctg ctgtgtctgc tgggagccgg cagtgtggaa       60
accggcgtga cacagagccc cacccacctg atcaagacca gaggccagca agtgaccctg      120
cggtgcagct ctcagagcgg ccacaatacc gtgtcctggt atcagcaggc cctgggccag      180
ggaccccagt tcatcttcca gtactacaga gaggaagaga acggcagagg caacttccca      240
ccccggttta gcggcctgca gttccccaac tacagctccg agctgaacgt gaacgccctg      300
gaactggacg acagcgccct gtacctgtgt gccagcagcc aggacagcta caacgagcag      360
ttcttcggcc ctggcacccg gctgaccgtg ctggaagatc tgaagaacgt gttcccccca      420
gaggtggccg tgttcgagcc tagcgaggcc gagatcagcc acacccagaa agccacccct      480
gtgtgcctgg ccaccggctt ttaccccgac cacgtggaac tgtcttggtg ggtcaacggc      540
```

```
aaagaggtgc acagcggcgt ctgcaccgac ccccagcccc tgaaagagca gcccgccctg    600
aacgacagcc ggtactgtct gagcagcaga ctgagagtgt ccgccacctt ctggcagaac    660
ccccggaacc acttcagatg ccaggtgcag ttctacggcc tgagcgagaa cgacgagtgg    720
acccaggacc gggccaagcc cgtgacccag atcgtgtctg ctgaggcctg ggcagagcc    780 gattgcggct tcaccagcga gagctaccag cagggcgtgc tgagcgccac catcctgtac    840
gagatcctgc tgggcaaggc caccctgtac gccgtgctgg tgtccgccct ggtgctgatg    900
gccatggtca agcggaagga cagccggggc                                     930
```

```
<210> SEQ ID NO 138
<211> LENGTH: 1788
<212> TYPE: DNA
<213> ORGANISM: Artificial Sequence
<220> FEATURE:
<223> OTHER INFORMATION: ME201 beta-P2A-ME201 alpha Construct - WT

<400> SEQUENCE: 138
atgggccctg ggctcctctg ctgggtgctg ctttgtctcc tgggagcagg ctcagtggag     60
actggagtca cccaaagtcc cacacacctg atcaaaacga gaggacagca agtgactctg    120
agatgctctt ctcagtctgg gcacaacact gtgtcctggt accaacaggc cctgggtcag    180 ggcccagt ttatctttca gtattatagg gaggaagaga atggcagagg aaacttccct    240
cctagattct caggtctcca gttccctaat tatagctctg agctgaatgt gaacgccttg    300
gagctggacg actcggccct gtatctctgt gccagcagcc aagactcgta caatgagcag    360
ttcttcgggc cagggacacg gctcaccgtg ctagaggacc tgaaaaacgt gttcccaccc    420
gaggtcgctg tgtttgagcc atcagaagca gagatctccc acacccaaaa ggccacactg    480
gtgtgcctgg ccacaggctt ctaccccgac cacgtggagc tgagctggtg ggtgaatggg    540
aaggaggtgc acagtggggt cagcacagac ccgcagcccc tcaaggagca gcccgccctc    600
aatgactcca gatactgcct gagcagccgc ctgagggtct cggccacctt ctggcagaac    660
ccccgcaacc acttccgctg tcaagtccag ttctacgggc tctcggagaa tgacgagtgg    720
acccaggata gggccaaacc tgtcacccag atcgtcagcg ccgaggcctg ggtagagca    780 gactgtggct tcacctccga gtcttaccag caaggggtcc tgtctgccac catcctctat    840
gagatcttgc tagggaaggc caccttgtat gccgtgctgg tcagtgccct cgtgctgatg    900
gccatggtca agagaaagga ttccagaggc ggttccggag ccacgaactt ctctctgtta    960
aagcaagcag agacgtggag gaaaaccccc ggtcccatga actcctctct ggactttcta   1020
attctgatct taatgtttgg aggaaccagc agcaattcag tcaagcagac gggccaaata   1080
accgtctcgg agggagcatc tgtgactatg aactgcacat acacatccac ggggtaccct   1140
acccttttct ggtatgtgga ataccccagc aaacctctgc agcttcttca gagagagaca   1200
atggaaaaca gcaaaaactt cggaggcgga atattaaag acaaaaactc ccccattgtg   1260
aaatattcag tccaggtatc agactcagcc gtgtactact gtcttctgag gaatcacgac   1320
aagctcatct ttgggactgg gaccagatta caagtctttc aaatatccaa gaaccctgac   1380
cctgccgtgt accagctgag agactctaaa tccagtgaca agtctgtctg cctattcacc   1440 gatttttgatt ctcaaacaaa tgtgtcacaa gtaaggatt ctgatgtgta tatcacagac   1500
aaaactgtgc tagacatgag gtctatggac ttcaagagca acagtgctgt ggcctggagc   1560
aacaaatctg actttgcatg tgcaaacgcc ttcaacaaca gcattattcc agaagacacc   1620
```

```
ttcttcccca gcccagaaag ttcctgtgat gtcaagctgg tcgagaaaag ctttgaaaca    1680
gatacgaacc taaactttca aaacctgtca gtgattgggt tccgaatcct cctcctgaaa    1740
gtggccgggt ttaatctgct catgacgctg cggctgtggt ccagctga                1788

<210> SEQ ID NO 139
<211> LENGTH: 1788
<212> TYPE: DNA
<213> ORGANISM: Artificial Sequence
<220> FEATURE:
<223> OTHER INFORMATION: ME201 beta-P2A-ME201 alpha Construct -
      Codon-Optimized, Cys Modified

<400> SEQUENCE: 139
atgggacctg gcctgctgtg ttgggtgctg ctgtgtctgc tgggagccgg cagtgtggaa      60
accggcgtga cacagagccc cacccacctg atcaagacca gaggccagca agtgaccctg     120
cggtgcagct ctcagagcgg ccacaatacc gtgtcctggt atcagcaggc cctgggccag     180
ggaccccagt tcatcttcca gtactacaga gaggaagaga cggcagagg caacttccca     240 ccccggttta gcggcctgca gttccccaac tacagctccg agctgaacgt gaacgccctg     300
gaactggacg cacagcccct gtacctgtgt gccagcagcc aggacagcta caacgagcag     360
ttcttcggcc ctggcacccg gctgaccgtg ctggaagatc tgaagaacgt gttcccccca     420
gaggtggccg tgttcgagcc tagcgaggc gagatcagcc acacccagaa agccaccctc     480
gtgtgcctgg ccaccggctt ttaccccgac cacgtggaac tgtcttggtg ggtcaacggc     540
aaagaggtgc acagcggcgt ctgcaccgac ccccagcccc tgaaagagca gcccgccctg     600
aacgacagcc ggtactgtct gagcagcaga ctgagagtgt ccgccacctt ctggcagaac     660
ccccggaacc acttcagatg ccaggtgcag ttctacggcc tgagcgagaa cgacgagtgg     720
acccaggacc gggccaagcc cgtgacccag atcgtgtctg ctgaggcctg ggcagagcc     780 gattgcggct tcaccagcga gagctaccag cagggcgtgc tgagcgccac catcctgtac     840
gagatcctgc tgggcaaggc caccctgtac gccgtgctgg tgtccgccct ggtgctgatg     900
gccatggtca gcggaagga cagccggggc ggttccggag ccacgaactt ctctctgtta     960
aagcaagcag gagacgtgga agaaaacccc ggtcccatga cagcagcct ggacttcctg    1020 atcctgattc tgatgttcgg cggcaccagc agcaacagcg tgaagcagac aggccagatc    1080
accgtgtctg agggcgccag cgtgaccatg aactgcacct acaccagcac ggctaccccc    1140
accctgtttt ggtacgtgga ataccccagc aagcccctcc agctgctcca gcgggaaacc    1200
atggaaaaca gcaagaactt cggcggaggc aacatcaagg acaagaacag ccccatcgtg    1260
aagtacagcg tgcaggtgtc cgacagcgcc gtgtactact gcctgctgcg aaccacgac    1320 aagctgatct tcggcaccgg cacccggctc caggtgttcc ccaacatcca gaaccccgac    1380
cccgcagtgt accagctgcg ggacagcaag agcagcgaca gagcgtgtg cctgttcacc    1440 gacttcgaca ccagaccaa cgtgtcccag agcaaggaca gcgacgtgta catcaccgat    1500
aagtgcgtgc tggacatgcg gagcatggac ttcaagagca cagcgccgt ggcctggtcc    1560 aacaagagcg acttcgcctg cgccaacgcc ttcaacaaca gcattatccc cgaggacaca    1620
ttcttcccaa gccccgagag cagctgcgac gtgaagctgg tggaaaagag cttcgagaca    1680
gacaccaacc tgaacttcca gaacctcagc gtgatcggct ccggatcct gctgctgaag    1740 gtggccggct tcaacctgct gatgaccctg cggctgtggt ccagctga               1788

<210> SEQ ID NO 140
```

```
<211> LENGTH: 396
<212> TYPE: DNA
<213> ORGANISM: Artificial Sequence
<220> FEATURE:
<223> OTHER INFORMATION: ME5301 alpha chain variable domain WT

<400> SEQUENCE: 140
atgaagaagc tactagcaat gattctgtgg cttcaactag accggttaag tggagagctg      60
aaagtggaac aaaaccctct gttcctgagc atgcaggagg gaaaaaacta taccatctac     120
tgcaattatt caaccacttc agacagactg tattggtaca ggcaggatcc tgggaaaagt     180
ctggaatctc tgtttgtgtt gctatcaaat ggagcagtga agcaggaggg acgattaatg     240
gcctcacttg ataccaaagc ccgtctcagc accctccaca tcacagctgc cgtgcatgac     300
ctctctgcca cctacttctg tgccgtgggc aattatggag aagccaagg aaatctcatc      360 tttggaaaag cactaaaact ctctgttaaa ccaaat                              396

<210> SEQ ID NO 141
<211> LENGTH: 396
<212> TYPE: DNA
<213> ORGANISM: Artificial Sequence
<220> FEATURE:
<223> OTHER INFORMATION: ME5301 alpha chain variable domain - Codon
      Optimized

<400> SEQUENCE: 141
atgaagaaac tgctggccat gatcctgtgg ctgcagctgg acagactgag cggcgagctg      60
aaggtggaac agaaccccct gttcctgagc atgcaggaag gcaagaacta caccatctac     120
tgcaactaca gcaccaccag cgaccggctg tactggtaca cagggaccc cggcaagagc      180 ctggaaagcc tgttcgtgct gctgagcaat ggcgccgtga agcaggaagg acggctgatg     240
gccagcctgg acaccaaggc cagactgtcc accctgcaca tcacagccgc cgtgcacgat     300
ctgagcgcca ctactttctg cgccgtgggc aattacggcg agccagggg caatctgatc      360 ttcggcaagg caccaagct gagcgtgaag cccaac                               396

<210> SEQ ID NO 142
<211> LENGTH: 819
<212> TYPE: DNA
<213> ORGANISM: Artificial Sequence
<220> FEATURE:
<223> OTHER INFORMATION: ME5301 alhpa chain WT

<400> SEQUENCE: 142
atgaagaagc tactagcaat gattctgtgg cttcaactag accggttaag tggagagctg      60
aaagtggaac aaaaccctct gttcctgagc atgcaggagg gaaaaaacta taccatctac     120
tgcaattatt caaccacttc agacagactg tattggtaca ggcaggatcc tgggaaaagt     180
ctggaatctc tgtttgtgtt gctatcaaat ggagcagtga agcaggaggg acgattaatg     240
gcctcacttg ataccaaagc ccgtctcagc accctccaca tcacagctgc cgtgcatgac     300
ctctctgcca cctacttctg tgccgtgggc aattatggag aagccaagg aaatctcatc      360 tttggaaaag cactaaaact ctctgttaaa ccaaatatcc agaaccctga ccctgccgtg     420
taccagctga gagactctaa atccagtgac aagtctgtct gcctattcac cgattttgat     480
tctcaaacaa atgtgtcaca agtaaggat tctgatgtgt atatcacaga caaaactgtg     540
ctagacatga ggtctatgga cttcaagagc aacagtgctg tggcctggag caacaaatct     600
gactttgcat gtgcaaacgc cttcaacaac agcattattc cagaagacac cttcttcccc     660
```

| | |
|---|---|
| agcccagaaa gttcctgtga tgtcaagctg gtcgagaaaa gctttgaaac agatacgaac | 720 |
| ctaaactttc aaaacctgtc agtgattggg ttccgaatcc tcctcctgaa agtggccggg | 780 |
| tttaatctgc tcatgacgct gcggctgtgg tccagctga | 819 |

<210> SEQ ID NO 143
<211> LENGTH: 819
<212> TYPE: DNA
<213> ORGANISM: Artificial Sequence
<220> FEATURE:
<223> OTHER INFORMATION: ME5301alpha chain - Codon-Optimized, Cys Modified

<400> SEQUENCE: 143

| | |
|---|---|
| atgaagaaac tgctggccat gatcctgtgg ctgcagctgg acagactgag cggcgagctg | 60 |
| aaggtggaac agaacccct gttcctgagc atgcaggaag caagaactga caccatctac | 120 |
| tgcaactaca gcaccaccag cgaccggctg tactggtaca acaggaccc cggcaagagc | 180 |
| ctggaaagcc tgttcgtgct gctgagcaat ggcgccgtga agcaggaagg acggctgatg | 240 |
| gccagcctgg acaccaaggc cagactgtcc accctgcaca tcacagccgc cgtgcacgat | 300 |
| ctgagcgcca cctactttg cgccgtgggc aattacggcg gcagccaggg caatctgatc | 360 |
| ttcggcaagg gcaccaagct gagcgtgaag cccaacatcc agaaccccga ccccgcagtg | 420 |
| taccagctgc gggacagcaa gagcagcgac aagagcgtgt gcctgttcac cgacttcgac | 480 |
| agccagacca acgtgtccca gagcaaggac agcgacgtgt acatcaccga taagtgcgtg | 540 |
| ctggacatgc ggagcatgga cttcaagagc aacagcgccg tggcctggtc caacaagagc | 600 |
| gacttcgcct gcgccaacgc cttcaacaac agcattatcc ccgaggacac attcttccca | 660 |
| agccccgaga gcagctgcga cgtgaagctg gtggaaaaga gcttcgagac agacaccaac | 720 |
| ctgaacttcc agaacctcag cgtgatcggc ttccggatcc tgctgctgaa ggtggccggc | 780 |
| ttcaacctgc tgatgaccct gcggctgtgg tccagctga | 819 |

<210> SEQ ID NO 144
<211> LENGTH: 402
<212> TYPE: DNA
<213> ORGANISM: Artificial Sequence
<220> FEATURE:
<223> OTHER INFORMATION: ME5301 beta chain variable domain WT

<400> SEQUENCE: 144

| | |
|---|---|
| atgggccctg ggctcctctg ctgggtgctg ctttgtctcc tgggagcagg ctcagtggag | 60 |
| actggagtca cccaaagtcc cacacacctg atcaaaacga gaggacagca agtgactctg | 120 |
| agatgctctt ctcagtctgg gcacaacact gtgtcctggt accaacaggc cctgggtcag | 180 |
| gggccccagt ttatctttca gtattatagg gaggaagaga tggcagagg aaacttccct | 240 |
| cctagattct caggtctcca gttccctaat tatagctctg agctgaatgt gaacgccttg | 300 |
| gagctggacg actcggccct gtatctctgt gccagcagct ggcgggagg atacggagat | 360 |
| acgcagtatt ttggcccagg cacccggctg acagtgctcg ag | 402 |

<210> SEQ ID NO 145
<211> LENGTH: 402
<212> TYPE: DNA
<213> ORGANISM: Artificial Sequence
<220> FEATURE:
<223> OTHER INFORMATION: ME5301 beta chain variable domain - Codon Optimized

<400> SEQUENCE: 145

-continued

| | |
|---|---|
| atgggacctg gcctgctgtg ttgggtgctg ctgtgtctgc tgggagccgg cagtgtggaa | 60 |
| accggcgtga cacagagccc cacccacctg atcaagacca gaggccagca agtgaccctg | 120 |
| cggtgcagct ctcagagcgg ccacaatacc gtgtcctggt atcagcaggc cctgggccag | 180 |
| ggaccccagt tcatcttcca gtactacaga gaggaagaga acggcagagg caacttccca | 240 |
| ccccggttta gcggcctgca gttccccaac tacagctccg agctgaacgt gaacgccctg | 300 |
| gaactggacg acagcgccct gtacctgtgt gcctcttctc tggctggcgg ctacggcgac | 360 |
| acccagtatt ttggccctgg caccagactg accgtgctgg aa | 402 |

<210> SEQ ID NO 146
<211> LENGTH: 936
<212> TYPE: DNA
<213> ORGANISM: Artificial Sequence
<220> FEATURE:
<223> OTHER INFORMATION: ME5301 beta chain WT

<400> SEQUENCE: 146

| | |
|---|---|
| atgggccctg ggctcctctg ctgggtgctg ctttgtctcc tgggagcagg ctcagtggag | 60 |
| actggagtca cccaaagtcc cacacacctg atcaaaacga gaggacagca agtgactctg | 120 |
| agatgctctt ctcagtctgg cacaacact gtgtcctggt accaacaggc cctgggtcag | 180 |
| gggcccagt ttatctttca gtattatagg gaggaagaga atggcagagg aaacttccct | 240 |
| cctagattct caggtctcca gttccctaat tatagctctg agctgaatgt gaacgccttg | 300 |
| gagctggacg actcggccct gtatctctgt gccagcagct ggcgggagg atacggagat | 360 |
| acgcagtatt ttggcccagg cacccggctg acagtgctcg aggacctgaa aaacgtgttc | 420 |
| ccacccgagg tcgctgtgtt tgagccatca gaagcagaga tctcccacac ccaaaaggcc | 480 |
| acactggtgt gcctggccac aggcttctac cccgaccacg tggagctgag ctggtgggtg | 540 |
| aatgggaagg aggtgcacag tggggtcagc acagacccgc agcccctcaa ggagcagccc | 600 |
| gccctcaatg actccagata ctgcctgagc agccgcctga gggtctcggc caccttctgg | 660 |
| cagaaccccc gcaaccactt ccgctgtcaa gtccagttct acgggctctc ggagaatgac | 720 |
| gagtggaccc aggataggc caaacctgtc acccagatcg tcagcgccga ggcctggggt | 780 |
| agagcagact gtggcttcac ctccgagtct taccagcaag gggtcctgtc tgccaccatc | 840 |
| ctctatgaga tcttgctagg gaaggccacc ttgtatgccg tgctggtcag tgccctcgtg | 900 |
| ctgatggcca tggtcaagag aaaggattcc agaggc | 936 |

<210> SEQ ID NO 147
<211> LENGTH: 936
<212> TYPE: DNA
<213> ORGANISM: Artificial Sequence
<220> FEATURE:
<223> OTHER INFORMATION: ME5301 beta chain - Codon-Optimized, Cys Modified

<400> SEQUENCE: 147

| | |
|---|---|
| atgggacctg gcctgctgtg ttgggtgctg ctgtgtctgc tgggagccgg cagtgtggaa | 60 |
| accggcgtga cacagagccc cacccacctg atcaagacca gaggccagca agtgaccctg | 120 |
| cggtgcagct ctcagagcgg ccacaatacc gtgtcctggt atcagcaggc cctgggccag | 180 |
| ggaccccagt tcatcttcca gtactacaga gaggaagaga acggcagagg caacttccca | 240 |
| ccccggttta gcggcctgca gttccccaac tacagctccg agctgaacgt gaacgccctg | 300 |
| gaactggacg acagcgccct gtacctgtgt gcctcttctc tggctggcgg ctacggcgac | 360 |

```
acccagtatt ttggccctgg caccagactg accgtgctgg aagatctgaa gaacgtgttc    420
cccccagagg tggccgtgtt cgagcctagc gaggccgaga tcagccacac ccagaaagcc    480
accctcgtgt gcctggccac cggcttttac cccgaccacg tggaactgtc ttggtgggtc    540
aacggcaaag aggtgcacag cggcgtctgc accgaccccc agcccctgaa agagcagccc    600
gccctgaacg acagccggta ctgtctgagc agcagactga gagtgtccgc caccttctgg    660
cagaaccccc ggaaccactt cagatgccag gtgcagttct acggcctgag cgagaacgac    720
gagtggaccc aggaccgggc caagcccgtg acccagatcg tgtctgctga ggcctggggc    780
agagccgatt gcggcttcac cagcgagagc taccagcagg gcgtgctgag cgccaccatc    840
ctgtacgaga tcctgctggg caaggccacc ctgtacgccg tgctggtgtc cgccctggtg    900
ctgatggcca tggtcaagcg aaggacagcc cggggc    936
```

<210> SEQ ID NO 148
<211> LENGTH: 1821
<212> TYPE: DNA
<213> ORGANISM: Artificial Sequence
<220> FEATURE:
<223> OTHER INFORMATION: ME5301 beta-P2A-ME5301 alpha Construct - WT

<400> SEQUENCE: 148

```
atgggccctg ggctcctctg ctgggtgctg ctttgtctcc tgggagcagg ctcagtggag     60
actggagtca cccaaagtcc cacacacctg atcaaaacga gaggacagca agtgactctg    120
agatgctctt ctcagtctgg cacaacact gtgtcctggt accaacaggc cctgggtcag    180
ggcccccagt ttatctttca gtattatagg gaggaagaga atggcagagg aaacttccct    240
cctagattct caggtctcca gttccctaat tatagctctg agctgaatgt gaacgccttg    300
gagctggacg actcggccct gtatctctgt gccagcagct tggcgggagg atacggagat    360
acgcagtatt ttggcccagg cacccggctg acagtgctcg aggacctgaa aaacgtgttc    420
ccacccgagg tcgctgtgtt tgagccatca gaagcagaga tctcccacac ccaaaaggcc    480
acactggtgt gcctggccac aggcttctac cccgaccacg tggagctgag ctggtgggtg    540
aatgggaagg aggtgcacag tggggtcagc acagacccgc agcccctcaa ggagcagccc    600
gccctcaatg actccagata ctgcctgagc agccgcctga gggtctcggc caccttctgg    660
cagaaccccc gcaaccactt ccgctgtcaa gtccagttct acgggctctc ggagaatgac    720
gagtggaccc aggataggc caaacctgtc acccagatcg tcagcgccga ggcctggggt    780
agagcagact gtggcttcac ctccgagtct taccagcaag ggtcctgtc tgccaccatc    840 ctctatgaga tcttgctagg aaggccacc ttgtatgccg tgctggtcag tgccctcgtg    900
ctgatggcca tggtcaagag aaaggattcc agaggcggtt ccggagccac gaacttctct    960
ctgttaaagc aagcaggaga cgtggaagaa accccggtc ccatgaagaa gctactagca   1020
atgattctgt ggcttcaact agaccggtta agtggagagc tgaaagtgga caaaaaccct   1080
ctgttcctga gcatgcagga gggaaaaaac tataccatct actgcaatta ttcaaccact   1140
tcagacagac tgtattggta caggcaggat cctgggaaaa gtctggaatc tctgtttgtg   1200
ttgctatcaa atggagcagt gaagcaggag ggacgattaa tggcctcact tgataccaaa   1260
gcccgtctca gcaccctcca catcacagct gccgtgcatg acctctctgc cacctacttc   1320
tgtgccgtgg gcaattatgg aggaagccaa ggaaatctca tctttggaaa aggcactaaa   1380
ctctctgtta aaccaaatat ccagaaccct gaccctgccg tgtaccagct gagagactct   1440
```

```
aaatccagtg acaagtctgt ctgcctattc accgattttg attctcaaac aaatgtgtca    1500
caaagtaagg attctgatgt gtatatcaca gacaaaactg tgctagacat gaggtctatg    1560
gacttcaaga gcaacagtgc tgtggcctgg agcaacaaat ctgactttgc atgtgcaaac    1620
gccttcaaca acagcattat tccagaagac accttcttcc ccagcccaga aagttcctgt    1680
gatgtcaagc tggtcgagaa aagctttgaa acagatacga acctaaactt tcaaaacctg    1740
tcagtgattg ggttccgaat cctcctcctg aaagtggccg ggtttaatct gctcatgacg    1800
ctgcggctgt ggtccagctg a                                              1821
```

<210> SEQ ID NO 149
<211> LENGTH: 1821
<212> TYPE: DNA
<213> ORGANISM: Artificial Sequence
<220> FEATURE:
<223> OTHER INFORMATION: ME5301 beta-P2A-ME5301 alpha Construct -
      Codon-Optimized, Cys Modified

<400> SEQUENCE: 149

```
atgggacctg gcctgctgtg ttgggtgctg ctgtgtctgc tgggagccgg cagtgtggaa      60
accggcgtga cacagagccc cacccacctg atcaagacca gaggccagca agtgaccctg     120
cggtgcagct ctcagagcgg ccacaatacc gtgtcctggt atcagcaggc cctgggccag     180
ggaccccagt tcatcttcca gtactacaga gaggaagaga cggcagagg caacttccca     240 ccccggttta gcggcctgca gttccccaac tacagctccg agctgaacgt gaacgccctg     300
gaactggaca cagcgccct gtacctgtgt gcctcttctc tggctggcgg ctacggcgac     360
acccagtatt ttggccctgg caccagactg accgtgctgg aagatctgaa gaacgtgttc     420
cccccagagg tggccgtgtt cgagcctagc gaggccgaga tcagccacac ccagaaagcc     480
accctcgtgt gcctggccac cggcttttac cccgaccacg tggaactgtc ttggtgggtc     540
aacggcaaag aggtgcacag cggcgtctgc accgaccccc agcccctgaa agagcagccc     600
gccctgaacg acagccggta ctgtctgagc agcagactga gagtgtccgc caccttctgg     660
cagaaccccc ggaaccactt cagatgccag gtgcagttct acggcctgag cgagaacgac     720
gagtggaccc aggaccgggc caagcccgtg acccagatcg tgtctgctga ggcctggggc     780
agagccgatt gcggcttcac cagcgagagc taccagcagg gcgtgctgag cgccaccatc     840
ctgtacgaga tcctgctggg caaggccacc tgtacgccg tgctggtgtc cgccctggtg     900
ctgatggcca tggtcaagcg aaggacagcc gggcggtt ccggagccac gaacttctct     960
ctgttaaagc aagcaggaga cgtggaagaa accccggtc ccatgaagaa actgctggcc    1020
atgatcctgt ggctgcagct ggacagactg agcggcgagc tgaaggtgga acagaacccc    1080
ctgttcctga gcatgcagga aggcaagaac tacaccatct actgcaacta cagcaccacc    1140
agcgaccggc tgtactggta cagacaggac cccggcaaga cctggaaag cctgttcgtg    1200 ctgctgagca tggcgccgt gaagcaggaa ggacggctga tggccagcct ggacaccaag    1260
gccagactgt ccaccctgca catcacagcc gccgtgcacg atctgagcgc cacctacttt    1320
tgcgccgtgg gcaattacgg cggcagccag ggcaatctga tcttcggcaa gggcaccaag    1380
ctgagcgtga agcccaacat ccagaacccc gaccccgcag tgtaccagct gcgggacagc    1440
aagagcagcg acaagagcgt gtgcctgttc accgacttcg acagccagac caacgtgtcc    1500
cagagcaagg acagcgacgt gtacatcacc gataagtgcg tgctggacat gcggagcatg    1560
gacttcaaga gcaacagcgc cgtggcctgg tccaacaaga gcgacttcgc ctgcgccaac    1620
```

| | |
|---|---|
| gccttcaaca acagcattat ccccgaggac acattcttcc caagccccga gagcagctgc | 1680 |
| gacgtgaagc tggtggaaaa gagcttcgag acagacacca acctgaactt ccagaacctc | 1740 |
| agcgtgatcg gcttccggat cctgctgctg aaggtggccg gcttcaacct gctgatgacc | 1800 |
| ctgcggctgt ggtccagctg a | 1821 |

<210> SEQ ID NO 150
<211> LENGTH: 411
<212> TYPE: DNA
<213> ORGANISM: Artificial Sequence
<220> FEATURE:
<223> OTHER INFORMATION: WT374 alpha chain variable domain WT

<400> SEQUENCE: 150

| | |
|---|---|
| atggccatgc tcctgggggc atcagtgctg attctgtggc ttcagccaga ctgggtaaac | 60 |
| agtcaacaga agaatgatga ccagcaagtt aagcaaaatt caccatccct gagcgtccag | 120 |
| gaaggaagaa tttctattct gaactgtgac tatactaaca gcatgtttga ttatttccta | 180 |
| tggtacaaaa ataccctgc tgaaggtcct acattcctga tatctataag ttccattaag | 240 |
| gataaaaatg aagatggaag attcactgtc ttcttaaaca aaagtgccaa gcacctctct | 300 |
| ctgcacattg tgccctccca gcctggagac tctgcagtgt acttctgtgc agcaagaggc | 360 |
| caaggaaatc tcatctttgg aaaaggcact aaactctctg ttaaaccaaa t | 411 |

<210> SEQ ID NO 151
<211> LENGTH: 411
<212> TYPE: DNA
<213> ORGANISM: Artificial Sequence
<220> FEATURE:
<223> OTHER INFORMATION: WT374 alpha chain variable domain - Codon Optimized

<400> SEQUENCE: 151

| | |
|---|---|
| atggctatgc tgctgggcgc ctctgtgctg atcctgtggc tgcagcccga ctgggtcaac | 60 |
| agccagcaga gaacgacga ccagcaagtg aagcagaaca gccccagcct gagcgtgcag | 120 |
| gaaggccgga tcagcatcct gaactgcgac tacaccaact ctatgttcga ctacttcctg | 180 |
| tggtacaaga gtaccccgc cgagggcccc accttcctga tctccatcag cagcatcaag | 240 |
| gacaagaacg aggacggccg gttcaccgtg tttctgaaca agagcgccaa gcacctgagc | 300 |
| ctgcacatcg tgcctagcca gcctggcgat agcgccgtgt acttctgtgc cgccagaggc | 360 |
| cagggcaacc tgatctttgg caagggcacc aagctgagcg tgaagcccaa c | 411 |

<210> SEQ ID NO 152
<211> LENGTH: 834
<212> TYPE: DNA
<213> ORGANISM: Artificial Sequence
<220> FEATURE:
<223> OTHER INFORMATION: WT374 alpha chain WT

<400> SEQUENCE: 152

| | |
|---|---|
| atggccatgc tcctgggggc atcagtgctg attctgtggc ttcagccaga ctgggtaaac | 60 |
| agtcaacaga agaatgatga ccagcaagtt aagcaaaatt caccatccct gagcgtccag | 120 |
| gaaggaagaa tttctattct gaactgtgac tatactaaca gcatgtttga ttatttccta | 180 |
| tggtacaaaa ataccctgc tgaaggtcct acattcctga tatctataag ttccattaag | 240 |
| gataaaaatg aagatggaag attcactgtc ttcttaaaca aaagtgccaa gcacctctct | 300 |
| ctgcacattg tgccctccca gcctggagac tctgcagtgt acttctgtgc agcaagaggc | 360 |

```
caaggaaatc tcatctttgg aaaaggcact aaactctctg ttaaaccaaa tatccagaac    420
cctgaccctg ccgtgtacca gctgagagac tctaaatcca gtgacaagtc tgtctgccta    480
ttcaccgatt ttgattctca aacaaatgtg tcacaaagta aggattctga tgtgtatatc    540
acagacaaaa ctgtgctaga catgaggtct atggacttca gagcaacag tgctgtggcc     600 tggagcaaca atctgacttt gcatgtgca aacgccttca caacagcat tattccagaa      660 gacaccttct tccccagccc agaaagttcc tgtgatgtca agctggtcga gaaaagcttt    720
gaaacagata cgaacctaaa cttcaaaac ctgtcagtga ttgggttccg aatcctcctc     780
ctgaaagtgg ccgggtttaa tctgctcatg acgctgcggc tgtggtccag ctga          834
```

<210> SEQ ID NO 153
<211> LENGTH: 834
<212> TYPE: DNA
<213> ORGANISM: Artificial Sequence
<220> FEATURE:
<223> OTHER INFORMATION: WT374 alpha chain - Codon-Optimized, Cys Modified

<400> SEQUENCE: 153

```
atggctatgc tgctgggcgc ctctgtgctg atcctgtggc tgcagcccga ctgggtcaac     60
agccagcaga agaacgacga ccagcaagtg aagcagaaca gccccagcct gagcgtgcag    120
gaaggccgga tcagcatcct gaactgcgac tacaccaact ctatgttcga ctacttcctg    180
tggtacaaga agtaccccgc cgagggcccc accttcctga tctccatcag cagcatcaag    240
gacaagaacg aggacggccg gttcaccgtg tttctgaaca agagcgccaa gcacctgagc    300
ctgcacatcg tgcctagcca gcctggcgat agcgccgtgt acttctgtgc cgccagaggc    360
cagggcaacc tgatctttgg caagggcacc aagctgagcg tgaagcccaa catccagaac    420
cccgaccccg cagtgtacca gctgcgggac agcaagagca gcgacaagag cgtgtgcctg    480
ttcaccgact cgacagcca gaccaacgtg tcccagagca aggacagcga cgtgtacatc     540
accgataagt gcgtgctgga catgcggagc atggacttca gagcaacag cgccgtggcc    600 tggtccaaca gagcgactt cgcctgcgcc aacgccttca caacagcat tatccccgag    660 gacacattct cccaagccc cgagagcagc tgcgacgtga agctggtgga aaagagcttc    720
gagacagaca ccaacctgaa cttccagaac ctcagcgtga tcggcttccg gatcctgctg    780
ctgaaggtgg ccggcttcaa cctgctgatg accctgcggc tgtggtccag ctga          834
```

<210> SEQ ID NO 154
<211> LENGTH: 396
<212> TYPE: DNA
<213> ORGANISM: Artificial Sequence
<220> FEATURE:
<223> OTHER INFORMATION: WT374 alpha chain variable domain WT

<400> SEQUENCE: 154

```
atgggcacca ggctcctctg ctgggcggcc ctctgtctcc tgggagcaga actcacagaa     60
gctggagttg cccagtctcc cagatataag attatagaga aaaggcagag tgtggctttt    120
tggtgcaatc ctatatctgg ccatgctacc ctttactggt accagcagat cctgggacag    180
ggcccaaagc ttctgattca gtttcagaat aacggtgtag tggatgattc acagttgcct    240
aaggatcgat ttctgcaga gaggctcaaa ggagtagact ccactctcaa gatccaacct    300
gcaaagcttg aggactcggc cgtgtatctc tgtgccagca gcttatatag gggggagcag    360
tacttcgggc cgggcaccag gctcacggtc acagag                              396
```

<210> SEQ ID NO 155
<211> LENGTH: 396
<212> TYPE: DNA
<213> ORGANISM: Artificial Sequence
<220> FEATURE:
<223> OTHER INFORMATION: WT374 beta chain variable domain - Codon
    Optimized

<400> SEQUENCE: 155

```
atgggcacca gactgctgtg ttgggccgct ctgtgtctgc tgggagccga actgactgaa      60
gctggcgtgg cccagagccc ccggtacaag atcatcgaga agcggcagag cgtggccttc     120
tggtgcaacc ctatcagcgg acacgccacc ctgtactggt atcagcagat cctgggccag     180
ggccccaagc tgctgattca gttccagaac aacggcgtgg tggacgacag ccagctgccc     240
aaggatagat cagcgccga gcggctgaag ggcgtggaca gcacactgaa gatccagccc     300
gccaagctgg aagatagcgc cgtgtacctg tgcgccagca gcctgtatag aggcgagcag     360
tacttcggcc ctggcacccg gctgaccgtg accgag                               396
```

<210> SEQ ID NO 156
<211> LENGTH: 930
<212> TYPE: DNA
<213> ORGANISM: Artificial Sequence
<220> FEATURE:
<223> OTHER INFORMATION: WT374 beta chain WT

<400> SEQUENCE: 156

```
atgggcacca ggctcctctg ctgggcggcc ctctgtctcc tgggagcaga actcacagaa      60
gctggagttg cccagtctcc cagatataag attatagaga aaaggcagag tgtggctttt     120
tggtgcaatc ctatatctgg ccatgctacc ctttactggt accagcagat cctgggacag     180
ggcccaaagc ttctgattca gtttcagaat aacggtgtag tggatgattc acagttgcct     240
aaggatcgat tttctgcaga gaggctcaaa ggagtagact ccactctcaa gatccaacct     300
gcaaagcttg aggactcggc cgtgtatctc tgtgccagca gcttatatag ggggagcag     360 tacttcgggc cgggcaccag gctcacggtc acagaggacc tgaaaaacgt gttcccaccc     420
gaggtcgctg tgtttgagcc atcagaagca gagatctccc acacccaaaa ggccacactg     480
gtgtgcctgg ccacaggctt ctaccccgac cacgtggagc tgagctggtg ggtgaatggg     540
aaggaggtgc acagtgggt cagcacagac ccgcagcccc tcaaggagca gcccgccctc     600
aatgactcca gatactgcct gagcagccgc ctgagggtct cggccacctt ctggcagaac     660
ccccgcaacc acttccgctg tcaagtccag ttctacgggc tctcggagaa tgacgagtgg     720
acccaggata gggccaaacc tgtcacccag atcgtcagcg ccgaggcctg ggtagagca     780 gactgtggct tcacctccga gtcttaccag aaggggtcc tgtctgccac catcctctat     840
gagatcttgc tagggaaggc caccttgtat gccgtgctgg tcagtgccct cgtgctgatg     900
gccatggtca agaaaagga ttccagaggc                                       930
```

<210> SEQ ID NO 157
<211> LENGTH: 930
<212> TYPE: DNA
<213> ORGANISM: Artificial Sequence
<220> FEATURE:
<223> OTHER INFORMATION: WT374 beta chain - Codon-Optimized, Cys
    Modified

<400> SEQUENCE: 157

```
atgggcacca gactgctgtg ttgggccgct ctgtgtctgc tgggagccga actgactgaa      60
```

```
gctggcgtgg cccagagccc ccggtacaag atcatcgaga agcggcagag cgtggccttc    120
tggtgcaacc ctatcagcgg acacgccacc ctgtactggt atcagcagat cctgggccag    180
ggccccaagc tgctgattca gttccagaac aacggcgtgg tggacgacag ccagctgccc    240
aaggatagat tcagcgccga gcggctgaag gcgtggaca gcacactgaa gatccagccc    300
gccaagctgg aagatagcgc cgtgtacctg tgcgccagca gcctgtatag aggcgagcag    360
tacttcggcc ctggcacccg gctgaccgtg accgaggatc tgaagaacgt gttcccccca    420
gaggtggccg tgttcgagcc tagcgaggcc gagatcagcc acacccagaa agccacctc    480 gtgtgcctgg ccaccggctt ttaccccgac acgtggaac tgtcttggtg gtcaacggc    540 aaagaggtgc acagcggcgt ctgcaccgac ccccagcccc tgaaagagca gcccgccctg    600
aacgacagcc ggtactgtct gagcagcaga ctgagagtgt ccgccacctt ctggcagaac    660 cccggaacc acttcagatg ccaggtgcag ttctacggcc tgagcgagaa cgacgagtgg    720
acccaggacc gggccaagcc cgtgacccag atcgtgtctg ctgaggcctg ggcagagcc    780 gattgcggct tcaccagcga gagctaccag cagggcgtgc tgagcgccac catcctgtac    840
gagatcctgc tgggcaaggc caccctgtac gccgtgctgg tgtccgccct ggtgctgatg    900
gccatggtca agcggaagga cagccggggc                                     930

<210> SEQ ID NO 158
<211> LENGTH: 1830
<212> TYPE: DNA
<213> ORGANISM: Artificial Sequence
<220> FEATURE:
<223> OTHER INFORMATION: WT374 beta-P2A-WT374 alpha Construct - WT

<400> SEQUENCE: 158
atgggcacca ggctcctctg ctgggcggcc ctctgtctcc tgggagcaga actcacagaa     60
gctggagttg cccagtctcc cagatataag attatagaga aaaggcagag tgtggctttt    120
tggtgcaatc ctatatctgg ccatgctacc ctttactggt accagcagat cctgggacag    180
ggcccaaagc ttctgattca gtttcagaat aacggtgtag tggatgattc acagttgcct    240
aaggatcgat tttctgcaga gaggctcaaa ggagtagact ccactctcaa gatccaacct    300
gcaaagcttg aggactcggc cgtgtatctc tgtgccagca gcttatatag ggggagcag    360 tacttcgggc cgggcaccag gctcacggtc acagaggacc tgaaaaacgt gttcccaccc    420
gaggtcgctg tgtttgagcc atcagaagca gagatctccc acacccaaaa ggccacactg    480
gtgtgcctgg ccacaggctt ctaccccgac acgtggagc tgagctggtg gtgaatggg    540 aaggaggtgc acagtggggt cagcacagac ccgcagcccc tcaaggagca gcccgccctc    600
aatgactcca gatactgcct gagcagccgc ctgagggtct cggccacctt ctggcagaac    660
ccccgcaacc acttccgctg tcaagtccag ttctacgggc tctcggagaa tgacgagtgg    720
acccaggata gggccaaacc tgtcacccag atcgtcagcg ccgaggcctg ggtagagca    780 gactgtggct tcacctccga gtcttaccag caagggtcc tgtctgccac catcctctat    840
gagatcttgc tagggaaggc cacctttgtat gccgtgctgg tcagtgccct cgtgctgatg    900
gccatggtca agagaaagga ttccagaggc ggttccggag ccacgaactt ctctctgtta    960 agcaagcag agacgtgga agaaaacccc ggtcccatgg ccatgctcct ggggcatca   1020 gtgctgattc tgtggcttca gccagactgg gtaaacagtc aacagaagaa tgatgaccag   1080
caagttaagc aaaattcacc atccctgagc gtccaggaag gaagaatttc tattctgaac   1140
```

```
tgtgactata ctaacagcat gtttgattat ttcctatggt acaaaaaata ccctgctgaa   1200
ggtcctacat tcctgatatc tataagttcc attaaggata aaatgaaga tggaagattc   1260 actgtcttct taaacaaaag tgccaagcac ctctctctgc acattgtgcc ctcccagcct   1320
ggagactctg cagtgtactt ctgtgcagca agaggccaag gaaatctcat ctttggaaaa   1380
ggcactaaac tctctgttaa accaaatatc cagaaccctg accctgccgt gtaccagctg   1440
agagactcta atccagtga caagtctgtc tgcctattca ccgattttga ttctcaaaca   1500
aatgtgtcac aaagtaagga ttctgatgtg tatatcacag acaaaactgt gctagacatg   1560
aggtctatgg acttcaagag caacagtgct gtggcctgga gcaacaaatc tgactttgca   1620
tgtgcaaacg ccttcaacaa cagcattatt ccagaagaca ccttcttccc cagcccagaa   1680
agttcctgtg atgtcaagct ggtcgagaaa agctttgaaa cagatacgaa cctaaacttt   1740
caaaacctgt cagtgattgg gttccgaatc ctcctcctga agtggccgg gtttaatctg    1800 ctcatgacgc tgcggctgtg gtccagctga                                   1830
```

<210> SEQ ID NO 159
<211> LENGTH: 1830
<212> TYPE: DNA
<213> ORGANISM: Artificial Sequence
<220> FEATURE:
<223> OTHER INFORMATION: WT374 beta-P2A-WT374 alpha Construct - Codon-Optimized, Cys Modified

<400> SEQUENCE: 159

```
atgggcacca gactgctgtg ttgggccgct ctgtgtctgc tgggagccga actgactgaa     60
gctggcgtgg cccagagccc ccggtacaag atcatcgaga agcggcagag cgtggccttc    120
tggtgcaacc ctatcagcgg acacgccacc ctgtactggt atcagcagat cctgggccag    180
ggccccaagc tgctgattca gttccagaac aacggcgtgg tggacgacag ccagctgccc    240
aaggatagat tcagcgccga gcggctgaag ggcgtggaca gcacactgaa gatccagccc    300
gccaagctgg aagatagcgc cgtgtacctg tgcgccagca gcctgtatag aggcgagcag    360
tacttcggcc ctggcaccc gctgaccgtg accgaggatc tgaagaacgt gttccccca    420 gaggtggccg tgttcgagcc tagcgaggcc gagatcagca cacccagaa agccaccctc    480 gtgtgcctgg ccaccggctt taccccgac cacgtggaac tgtcttggtg ggtcaacggc    540
aaagaggtgc acagcggcgt ctgcaccgac ccccagcccc tgaaagagca gcccgccctg    600
aacgacagcc ggtactgtct gagcagcaga ctgagagtgt ccgccacctt ctggcagaac    660 cccggaacc acttcagatg ccaggtgcag ttctacggcc tgagcgagaa cgacgagtgg    720
acccaggacc gggccaagcc cgtgacccag atcgtgtctg ctgaggcctg gggcagagcc    780
gattgcggct tcaccagcga gagctaccag cagggcgtgc tgagcgccac catcctgtac    840
gagatcctgc tgggcaaggc caccctgtac gccgtgctgg tgtccgccct ggtgctgatg    900
gccatggtca gcggaagga cagccggggc ggttccggag ccacgaactt ctctctgtta    960
aagcaagcag gagacgtgga agaaaacccc ggtcccatgg ctatgctgct gggcgcctct   1020
gtgctgatcc tgtggctgca gcccgactgg gtcaacagcc agcagaagaa cgacgaccag   1080
caagtgaagc agaacagccc cagcctgagc gtgcaggaag ccggatcag catcctgaac   1140 tgcgactaca caactctat gttcgactac ttcctgtggt acaagaagta cccgccgag   1200 ggccccacct tcctgatctc catcagcagc atcaaggaca gaacgagga cggccggttc    1260 accgtgtttc tgaacaagag cgccaagcac ctgagcctgc acatcgtgcc tagccagcct   1320
```

```
ggcgatagcg ccgtgtactt ctgtgccgcc agaggccagg gcaacctgat ctttggcaag     1380
ggcaccaagc tgagcgtgaa gcccaacatc cagaaccccg accccgcagt gtaccagctg     1440
cgggacagca agagcagcga caagagcgtg tgcctgttca ccgacttcga cagccagacc     1500
aacgtgtccc agagcaagga cagcgacgtg tacatcaccg ataagtgcgt gctggacatg     1560
cggagcatgg acttcaagag caacagcgcc gtggcctggt ccaacaagag cgacttcgcc     1620
tgcgccaacg ccttcaacaa cagcattatc cccgaggaca cattcttccc aagccccgag     1680
agcagctgcg acgtgaagct ggtggaaaag agcttcgaga cagacaccaa cctgaacttc     1740
cagaacctca gcgtgatcgg cttccggatc ctgctgctga aggtggccgg cttcaacctg     1800
ctgatgaccc tgcggctgtg gtccagctga                                      1830
```

<210> SEQ ID NO 160  
<211> LENGTH: 414  
<212> TYPE: DNA  
<213> ORGANISM: Artificial Sequence  
<220> FEATURE:  
<223> OTHER INFORMATION: WT375 alpha chain variable domain WT

<400> SEQUENCE: 160

```
atggcctctg cacccatctc gatgcttgcg atgctcttca cattgagtgg gctgagagct      60
cagtcagtgg ctcagccgga agatcaggtc aacgttgctg aagggaatcc tctgactgtg     120
aaatgcacct attcagtctc tggaaaccct tatcttttt ggtatgttca ataccccaac     180
cgaggcctcc agttccttct gaaatacatc acaggggata acctggttaa aggcagctat     240
ggctttgaag ctgaatttaa caagagccaa acctccttcc acctgaagaa accatctgcc     300
cttgtgagcg actccgcttt gtacttctgt gctgtgagag acattaggta ttatggagga     360
agccaaggaa atctcatctt tggaaaaggc actaaactct ctgttaaacc aaat           414
```

<210> SEQ ID NO 161  
<211> LENGTH: 414  
<212> TYPE: DNA  
<213> ORGANISM: Artificial Sequence  
<220> FEATURE:  
<223> OTHER INFORMATION: WT375 alpha chain variable domain - Codon Optimized

<400> SEQUENCE: 161

```
atggccagcg cccccattag catgctggct atgctgttca ccctgagcgg cctgagagcc      60
cagtctgtgg cccagcctga ggaccaagtg aatgtggccg agggcaaccc cctgaccgtg     120
aagtgtacct acagcgtgtc cggcaacccc tacctgtttt ggtacgtgca gtaccccaac     180
cggggcctgc agttcctgct gaagtacatc accggcgaca acctcgtgaa gggcagctac     240
ggcttcgagg ccgagttcaa caagagccag accagcttcc acctgaagaa cccagcgcc     300 ctggtgtccg actccgccct gtatttttgc gccgtgcggg acatccggta ctacggcgga     360
tctcagggca acctgatctt cggcaagggc accaagctga gcgtgaagcc caac           414
```

<210> SEQ ID NO 162  
<211> LENGTH: 837  
<212> TYPE: DNA  
<213> ORGANISM: Artificial Sequence  
<220> FEATURE:  
<223> OTHER INFORMATION: WT375 alpha chain WT

<400> SEQUENCE: 162

```
atggcctctg cacccatctc gatgcttgcg atgctcttca cattgagtgg gctgagagct      60
```

```
cagtcagtgg ctcagccgga agatcaggtc aacgttgctg aagggaatcc tctgactgtg        120
aaatgcacct attcagtctc tggaaaccct tatctttttt ggtatgttca ataccccaac        180
cgaggcctcc agttccttct gaaatacatc acaggggata acctggttaa aggcagctat        240
ggctttgaag ctgaatttaa caagagccaa acctccttcc acctgaagaa accatctgcc        300
cttgtgagcg actccgcttt gtacttctgt gctgtgagag acattaggta ttatggagga        360
agccaaggaa atctcatctt tggaaaaggc actaaactct ctgttaaacc aaatatccag        420
aaccctgacc ctgccgtgta ccagctgaga gactctaaat ccagtgacaa gtctgtctgc        480
ctattcaccg attttgattc tcaaacaaat gtgtcacaaa gtaaggattc tgatgtgtat        540
atcacagaca aaactgtgct agacatgagg tctatggact caagagcaa cagtgctgtg        600 gcctggagca caaatctga ctttgcatgt gcaaacgcct tcaacaacag cattattcca        660
gaagacacct tcttccccag cccagaaagt tcctgtgatg tcaagctggt cgagaaaagc        720
tttgaaacag atacgaacct aaactttcaa aacctgtcag tgattgggtt ccgaatcctc        780
ctcctgaaag tggccgggtt taatctgctc atgacgctgc ggctgtggtc cagctga        837
```

<210> SEQ ID NO 163
<211> LENGTH: 837
<212> TYPE: DNA
<213> ORGANISM: Artificial Sequence
<220> FEATURE:
<223> OTHER INFORMATION: WT375 alpha chain - Codon-Optimized, Cys
      Modified

<400> SEQUENCE: 163

```
atggccagcg cccccattag catgctggct atgctgttca ccctgagcgg cctgagagcc         60
cagtctgtgg cccagcctga ggaccaagtg aatgtggccg agggcaaccc cctgaccgtg        120
aagtgtacct acagcgtgtc cggcaacccc tacctgtttt ggtacgtgca gtaccccaac        180
cggggcctgc agttcctgct gaagtacatc accggcgaca acctcgtgaa gggcagctac        240
ggcttcgagg ccgagttcaa caagagccag accagcttcc acctgaagaa acccagcgcc        300
ctggtgtccg actccgccct gtattttgc gccgtgcggg acatccggta ctacggcgga        360
tctcagggca acctgatctt cggcaagggc accaagctga gcgtgaagcc aaacatccag        420
aaccccgacc ccgcagtgta ccagctgcgg gacagcaaga gcagcgacaa gagcgtgtgc        480
ctgttcaccg acttcgacag ccagaccaac gtgtcccaga gcaaggacag cgacgtgtac        540
atcaccgata gtgcgtgct ggacatgcgg agcatggact caagagcaa cagcgccgtg        600 gcctggtcca caagagcga cttcgcctgc gccaacgcct tcaacaacag cattatccc        660 gaggacacat tcttcccaag ccccgagagc agctgcgacg tgaagctggt ggaaaagagc        720
ttcgagacag acaccaacct gaacttccag aacctcagcg tgatcggctt ccggatcctg        780
ctgctgaagg tggccggctt caacctgctg atgaccctgc ggctgtggtc cagctga        837
```

<210> SEQ ID NO 164
<211> LENGTH: 399
<212> TYPE: DNA
<213> ORGANISM: Artificial Sequence
<220> FEATURE:
<223> OTHER INFORMATION: WT375 beta chain variable domain WT

<400> SEQUENCE: 164

```
atgggctgca ggctcctctg ctgtgtggtc ttctgcctcc tccaagcagg tcccttggac         60
acagctgttt cccagactcc aaaataccctg gtcacacaga tgggaaacga caagtccatt        120
```

```
aaatgtgaac aaaatctggg ccatgatact atgtattggt ataaacagga ctctaagaaa        180
tttctgaaga taatgtttag ctacaataat aaggagctca ttataaatga aacagttcca        240
aatcgcttct cacctaaatc tccagacaaa gctcacttaa atcttcacat caattccctg        300
gagcttggtg actctgctgt gtatttctgt gccagcagcc cgggtcctag taacaatgag        360
cagttcttcg ggccagggac acggctcacc gtgctagag                               399

<210> SEQ ID NO 165
<211> LENGTH: 399
<212> TYPE: DNA
<213> ORGANISM: Artificial Sequence
<220> FEATURE:
<223> OTHER INFORMATION: WT375 beta chain variable domain - Codon
      Optimized

<400> SEQUENCE: 165
atgggctgca gactgctgtg ctgcgtggtg ttctgcctgc tgcaagccgg ccctctggat         60
accgccgtgt ctcagacccc caagtacctc gtgacccaga tgggcaacga caagagcatc        120
aagtgcgagc agaacctggg ccacgacacc atgtactggt acaagcagga cagcaagaaa        180
ttcctgaaga tcatgttcag ctacaacaac aaagagctga tcatcaacga cagtgccc         240 aaccggttca gccccaagag ccccgataag gcccacctga acctgcacat caacagcctg        300
gaactgggcg acagcgccgt gtacttctgt gccagctctc ccggccctag caacaacgag        360
cagttcttcg gccctggcac ccggctgacc gtgctggaa                               399

<210> SEQ ID NO 166
<211> LENGTH: 933
<212> TYPE: DNA
<213> ORGANISM: Artificial Sequence
<220> FEATURE:
<223> OTHER INFORMATION: WT375 beta chain WT

<400> SEQUENCE: 166
atgggctgca ggctcctctg ctgtgtggtc ttctgcctcc tccaagcagg tcccttggac         60
acagctgttt cccagactcc aaaatacctg gtcacacaga tgggaaacga caagtccatt        120
aaatgtgaac aaaatctggg ccatgatact atgtattggt ataaacagga ctctaagaaa        180
tttctgaaga taatgtttag ctacaataat aaggagctca ttataaatga aacagttcca        240
aatcgcttct cacctaaatc tccagacaaa gctcacttaa atcttcacat caattccctg        300
gagcttggtg actctgctgt gtatttctgt gccagcagcc cgggtcctag taacaatgag        360
cagttcttcg ggccagggac acggctcacc gtgctagagg acctgaaaaa cgtgttccca        420
cccgaggtcg ctgtgtttga gccatcagaa gcagagatct cccacaccca aaaggccaca        480
ctggtgtgcc tggccacagg cttctacccc gaccacgtgg agctgagctg gtgggtgaat        540
gggaaggagg tgcacagtgg ggtcagcaca gacccgcagc ccctcaagga gcagcccgcc        600
ctcaatgact ccagatactg cctgagcagc cgcctgaggg tctcggccac cttctgcag         660 aaccccgca accacttccg ctgtcaagtc cagttctacg gcctctcgga gaatgacgag         720
tggacccagg atagggccaa acctgtcacc cagatcgtca gcgccgaggc ctggggtaga        780
gcagactgtg gcttccctct ccgagtcttac cagcaagggg tcctgtctgc caccatcctc        840
tatgagatct tgctagggaa ggccaccttg tatgccgtgc tggtcagtgc cctcgtgctg        900
atggccatgg tcaagagaaa ggattccaga ggc                                    933

<210> SEQ ID NO 167
```

<211> LENGTH: 933
<212> TYPE: DNA
<213> ORGANISM: Artificial Sequence
<220> FEATURE:
<223> OTHER INFORMATION: WT375 beta chain - Codon-Optimized, Cys
      Modified

<400> SEQUENCE: 167

| | | | | | |
|---|---|---|---|---|---|
| atgggctgca | gactgctgtg | ctgcgtggtg | ttctgcctgc | tgcaagccgg | ccctctggat | 60 |
| accgccgtgt | ctcagacccc | caagtacctc | gtgacccaga | tgggcaacga | caagagcatc | 120 |
| aagtgcgagc | agaacctggg | ccacgacacc | atgtactggt | acaagcagga | cagcaagaaa | 180 |
| ttcctgaaga | tcatgttcag | ctacaacaac | aaagagctga | tcatcaacga | cagtgccc | 240 |
| aaccggttca | gccccaagag | ccccgataag | gcccacctga | acctgcacat | caacagcctg | 300 |
| gaactgggcg | acagcgccgt | gtacttctgt | gccagctctc | ccggccctag | caacaacgag | 360 |
| cagttcttcg | ccctggcac | ccggctgacc | gtgctggaag | atctgaagaa | cgtgttcccc | 420 |
| ccagaggtgg | ccgtgttcga | gcctagcgag | gccgagatca | gccacaccca | gaaagccacc | 480 |
| ctcgtgtgcc | tggccaccgg | cttttacccc | gaccacgtgg | aactgtcttg | gtgggtcaac | 540 |
| ggcaaagagg | tgcacagcgg | cgtctgcacc | gaccccagc | ccctgaaaga | gcagcccgcc | 600 |
| ctgaacgaca | gccggtactg | tctgagcagc | agactgagag | tgtccgccac | cttctggcag | 660 |
| aaccccggga | accacttcag | atgccaggtg | cagttctacg | gcctgagcga | gaacgacgag | 720 |
| tggacccagg | accgggccaa | gcccgtgacc | cagatcgtgt | ctgctgaggc | ctggggcaga | 780 |
| gccgattgcg | gcttcaccag | cgagagctac | cagcagggcg | tgctgagcgc | caccatcctg | 840 |
| tacgagatcc | tgctgggcaa | ggccacctg | tacgccgtgc | tggtgtccgc | cctggtgctg | 900 |
| atggccatgg | tcaagcggaa | ggacagccgg | ggc | | | 933 |

<210> SEQ ID NO 168
<211> LENGTH: 1836
<212> TYPE: DNA
<213> ORGANISM: Artificial Sequence
<220> FEATURE:
<223> OTHER INFORMATION: WT375 beta-P2A-WT375 alpha Construct - WT

<400> SEQUENCE: 168

| | | | | | |
|---|---|---|---|---|---|
| atgggctgca | ggctcctctg | ctgtgtggtc | ttctgcctcc | tccaagcagg | tcccttggac | 60 |
| acagctgttt | cccagactcc | aaaatacctg | gtcacacaga | tgggaaacga | caagtccatt | 120 |
| aaatgtgaac | aaaatctggg | ccatgatact | atgtattggt | ataaacagga | ctctaagaaa | 180 |
| tttctgaaga | taatgtttag | ctacaataat | aaggagctca | ttataaatga | aacagttcca | 240 |
| aatcgcttct | cacctaaatc | tccagacaaa | gctcacttaa | atcttcacat | caattccctg | 300 |
| gagcttggtg | actctgctgt | gtatttctgt | gccagcagcc | cggtcctag | taacaatgag | 360 |
| cagttcttcg | ggccagggac | acggctcacc | gtgctagagg | acctgaaaaa | cgtgttccca | 420 |
| cccgaggtcg | ctgtgtttga | gccatcagaa | gcagagatct | cccacaccca | aaaggccaca | 480 |
| ctggtgtgcc | tggccacagg | cttctacccc | gaccacgtgg | agctgagctg | gtgggtgaat | 540 |
| gggaaggagg | tgcacagtgg | ggtcagcaca | gacccgcagc | ccctcaagga | gcagcccgcc | 600 |
| ctcaatgact | ccagatactg | cctgagcagc | cgcctgaggg | tctcggccac | cttctggcag | 660 |
| aaccccgca | accacttccg | ctgtcaagtc | cagttctacg | gctctcgga | gaatgacgag | 720 |
| tggacccagg | atagggccaa | acctgtcacc | cagatcgtca | gcgccgaggc | ctggggtaga | 780 |
| gcagactgtg | gcttcacctc | cgagtcttac | cagcaagggg | tcctgtctgc | caccatcctc | 840 |

```
tatgagatct tgctagggaa ggccaccttg tatgccgtgc tggtcagtgc cctcgtgctg    900
atggccatgg tcaagagaaa ggattccaga ggcggttccg gagccacgaa cttctctctg    960
ttaaagcaag caggagacgt ggaagaaaac cccggtccca tggcctctgc acccatctcg   1020
atgcttgcga tgctcttcac attgagtggg ctgagagctc agtcagtggc tcagccggaa   1080
gatcaggtca acgttgctga agggaatcct ctgactgtga aatgcaccta ttcagtctct   1140
ggaaacccct tatctttttg gtatgttcaa taccccaacc gaggcctcca gttccttctg   1200
aaatacatca caggggataa cctggttaaa ggcagctatg ctttgaagc tgaatttaac    1260
aagagccaaa cctccttcca cctgaagaaa ccatctgccc ttgtgagcga ctccgctttg   1320
tacttctgtg ctgtgagaga cattaggtat atggaggaa gccaaggaaa tctcatcttt    1380
ggaaaaggca ctaaactctc tgttaaacca aatatccaga accctgaccc tgccgtgtac   1440
cagctgagag actctaaatc cagtgacaag tctgtctgcc tattcaccga ttttgattct   1500
caaacaaatg tgtcacaaag taaggattct gatgtgtata tcacagacaa aactgtgcta   1560
gacatgaggt ctatggactt caagagcaac agtgctgtgg cctggagcaa caaatctgac   1620
tttgcatgtg caaacgcctt caacaacagc attattccag aagacacctt cttccccagc   1680
ccagaaagtt cctgtgatgt caagctggtc gagaaaagct ttgaaacaga tacgaaccta   1740
aactttcaaa acctgtcagt gattgggttc gaatcctcc tcctgaaagt ggccgggttt    1800
aatctgctca tgacgctgcg gctgtggtcc agctga                             1836
```

<210> SEQ ID NO 169  
<211> LENGTH: 1836  
<212> TYPE: DNA  
<213> ORGANISM: Artificial Sequence  
<220> FEATURE:  
<223> OTHER INFORMATION: WT375 beta-P2A-WT375 alpha Construct -  
      Codon-Optimized, Cys Modified

<400> SEQUENCE: 169

```
atgggctgca gactgctgtg ctgcgtggtg ttctgcctgc tgcaagccgg ccctctggat     60
accgccgtgt ctcagacccc caagtacctc gtgacccaga tgggcaacga caagagcatc    120
aagtgcgagc agaacctggg ccacgacacc atgtactggt acaagcagga cagcaagaaa    180
ttcctgaaga tcatgttcag ctacaacaac aaagagctga tcatcaacga cagtgccc     240
aaccggttca gccccaagag ccccgataag gcccacctga acctgcacat caacagcctg    300
gaactgggcg acagcgccgt gtacttctgt gccagctctc ccggccctag caacaacgag    360
cagttcttcg gcctggcac ccggctgacc gtgctggaag atctgaagaa cgtgttcccc     420
ccagaggtgg ccgtgttcga gcctagcgag gccgagatca gccacaccca gaaagccacc    480
ctcgtgtgcc tggccaccgg cttttacccc gaccacgtgg aactgtcttg gtgggtcaac    540
ggcaaagagg tgcacagcgg cgtctgcacc gaccccagc ccctgaaaga gcagcccgcc     600
ctgaacgaca gccggtactg tctgagcagc agactgagag tgtccgccac cttctggcag    660
aacccccgga ccacttcag atgccaggtg cagttctacg gcctgagcga aacgacgag      720
tggacccagg accgggccaa gcccgtgacc cagatcgtgt ctgctgaggc tggggcaga    780
gccgattgcg gcttcaccag cgagagctac agcaggggcg tgctgagcgc caccatcctg    840
tacgagatcc tgctgggcaa ggccaccctg tacgccgtgc tggtgtccgc cctggtgctg    900
atggccatgg tcaagcggaa ggacagccgg gcggttccg gagccacgaa cttctctctg     960
ttaaagcaag caggagacgt ggaagaaaac cccggtccca tggccagcgc ccccattagc   1020
```

-continued

| | |
|---|---|
| atgctggcta tgctgttcac cctgagcggc ctgagagccc agtctgtggc ccagcctgag | 1080 |
| gaccaagtga atgtggccga gggcaacccc ctgaccgtga agtgtaccta cagcgtgtcc | 1140 |
| ggcaacccct acctgttttg gtacgtgcag taccccaacc ggggcctgca gttcctgctg | 1200 |
| aagtacatca ccggcgacaa cctcgtgaag ggcagctacg gcttcgaggc cgagttcaac | 1260 |
| aagagccaga ccagcttcca cctgaagaaa cccagcgccc tggtgtccga ctccgccctg | 1320 |
| tattttttgcg ccgtgcggga catccggtac tacggcggat ctcagggcaa cctgatcttc | 1380 |
| ggcaagggca ccaagctgag cgtgaagccc aacatccaga ccccgaccc cgcagtgtac | 1440 |
| cagctgcggg acagcaagag cagcgacaag agcgtgtgcc tgttcaccga cttcgacagc | 1500 |
| cagaccaacg tgtcccagag caaggacagc gacgtgtaca tcaccgataa gtgcgtgctg | 1560 |
| gacatgcgga gcatggactt caagagcaac agcgccgtgg cctggtccaa caagagcgac | 1620 |
| ttcgcctgcg ccaacgcctt caacaacagc attatccccg aggacacatt cttcccaagc | 1680 |
| cccgagagca gctgcgacgt gaagctggtg gaaaagagct tcgagacaga caccaacctg | 1740 |
| aacttccaga acctcagcgt gatcggcttc cggatcctgc tgctgaaggt ggccggcttc | 1800 |
| aacctgctga tgaccctgcg gctgtggtcc agctga | 1836 |

<210> SEQ ID NO 170
<211> LENGTH: 411
<212> TYPE: DNA
<213> ORGANISM: Artificial Sequence
<220> FEATURE:
<223> OTHER INFORMATION: WT378 alpha chain variable domain WT

<400> SEQUENCE: 170

| | |
|---|---|
| atgatgaaat ccttgagagt tttactggtg atcctgtggc ttcagttaag ctgggtttgg | 60 |
| agccaacaga aggaggtgga gcaggatcct ggaccactca gtgttccaga gggagccatt | 120 |
| gtttctctca actgcactta cagcaacagt gcttttcaat acttcatgtg gtacagacag | 180 |
| tattccagaa aaggccctga gttgctgatg tacacatact ccagtggtaa caaagaagat | 240 |
| ggaaggttta cagcacaggt cgataaatcc agcaagtata tctccttgtt catcagagac | 300 |
| tcacagccca gtgattcagc cacctacctc tgtgcaattt acgggtgggg tggtggtgct | 360 |
| acaaacaagc tcatctttgg aactggcact ctgcttgctg tccagccaaa t | 411 |

<210> SEQ ID NO 171
<211> LENGTH: 411
<212> TYPE: DNA
<213> ORGANISM: Artificial Sequence
<220> FEATURE:
<223> OTHER INFORMATION: WT378 alpha chain variable domain - Codon Optimized

<400> SEQUENCE: 171

| | |
|---|---|
| atgatgaagt ccctgcgggt gctgctcgtg atcctgtggc tgcagctgag ctgggtgtgg | 60 |
| tcccagcaga aagaggtgga acaggaccct ggccctctga gcgtgccaga gggcgctatc | 120 |
| gtgtccctga actgcaccta cagcaacagc gccttccagt acttcatgtg gtacagacag | 180 |
| tacagccgga agggccccga gctgctgatg tacacctact ccagcggcaa caaagaggac | 240 |
| ggccggttca gcccaggt ggacaagagc agcaagtaca tctccctgtt catccgggac | 300 |
| agccagccca gcgattccgc cacatacctg tgcgccatct acggctgggg aggcggagcc | 360 |
| accaacaagc tgatctttgg caccggcacc ctgctggccg tgcagcccaa t | 411 |

<210> SEQ ID NO 172

<211> LENGTH: 834
<212> TYPE: DNA
<213> ORGANISM: Artificial Sequence
<220> FEATURE:
<223> OTHER INFORMATION: WT378 alpha chain WT

<400> SEQUENCE: 172

| | | |
|---|---|---|
| atgatgaaat ccttgagagt tttactggtg atcctgtggc ttcagttaag ctgggtttgg | 60 |
| agccaacaga aggaggtgga gcaggatcct ggaccactca gtgttccaga gggagccatt | 120 |
| gtttctctca actgcactta cagcaacagt gcttttcaat acttcatgtg gtacagacag | 180 |
| tattccagaa aaggccctga gttgctgatg tacacatact ccagtggtaa caaagaagat | 240 |
| ggaaggttta cagcacaggt cgataaatcc agcaagtata tctccttgtt catcagagac | 300 |
| tcacagccca gtgattcagc cacctacctc tgtgcaattt acgggtgggg tggtggtgct | 360 |
| acaaacaagc tcatctttgg aactggcact ctgcttgctg tccagccaaa tatccagaac | 420 |
| cctgaccctg ccgtgtacca gctgagagac tctaaatcca gtgacaagtc tgtctgccta | 480 |
| ttcaccgatt ttgattctca aacaaatgtg tcacaaagta aggattctga tgtgtatatc | 540 |
| acagacaaaa ctgtgctaga catgaggtct atggacttca gagcaacag tgctgtggcc | 600 |
| tggagcaaca atctgacttt gcatgtgca acgccttca acaacagcat tattccagaa | 660 |
| gacaccttct cccccagccc agaaagttcc tgtgatgtca agctggtcga gaaaagcttt | 720 |
| gaaacagata cgaacctaaa ctttcaaaac ctgtcagtga ttgggttccg aatcctcctc | 780 |
| ctgaaagtgg ccgggtttaa tctgctcatg acgctgcggc tgtggtccag ctga | 834 |

<210> SEQ ID NO 173
<211> LENGTH: 834
<212> TYPE: DNA
<213> ORGANISM: Artificial Sequence
<220> FEATURE:
<223> OTHER INFORMATION: WT378 alpha chain - Codon-Optimized, Cys Modified

<400> SEQUENCE: 173

| | | |
|---|---|---|
| atgatgaagt ccctgcgggt gctgctcgtg atcctgtggc tgcagctgag ctgggtgtgg | 60 |
| tcccagcaga agaggtgga acaggaccct ggccctctga gcgtgccaga gggcgctatc | 120 |
| gtgtccctga actgcaccta cagcaacagc gccttccagt acttcatgtg gtacagacag | 180 |
| tacagccgga agggccccga gctgctgatg tacacctact ccagcggcaa caagaggac | 240 |
| ggccggttca gcccaggt ggacaagagc agcaagtaca tctccctgtt catccgggac | 300 |
| agccagccca gcgattccgc cacatacctg tgcgccatct acggctgggg aggcggagcc | 360 |
| accaacaagc tgatctttgg caccggcacc ctgctggccg tgcagcccaa tatccagaac | 420 |
| cccgaccctg cagtgtacca gctgcgggac agcaagagca gcgacaagag cgtgtgcctg | 480 |
| ttcaccgact cgacagcca gaccaacgtg tcccagagca aggacagcga cgtgtacatc | 540 |
| accgataagt cgtgctgga catgcggagc atggacttca gagcaacag cgccgtggcc | 600 |
| tggtccaaca agagcgactt cgcctgcgcc aacgccttca caacagcat tatccccgag | 660 |
| gacacattct cccaagccc cgagagcagc tgcgacgtga agctggtgga aaagagcttc | 720 |
| gagacagaca ccaacctgaa cttccagaac ctcagcgtga tcggcttccg gatcctgctg | 780 |
| ctgaaggtgg ccggcttcaa cctgctgatg accctgcggc tgtggtccag ctga | 834 |

<210> SEQ ID NO 174
<211> LENGTH: 405
<212> TYPE: DNA

<213> ORGANISM: Artificial Sequence
<220> FEATURE:
<223> OTHER INFORMATION: WT378 beta chain variable domain WT

<400> SEQUENCE: 174

```
atgggcacca gtctcctatg ctgggtggtc ctgggtttcc tagggacaga tcacacaggt      60
gctggagtct cccagtctcc caggtacaaa gtcacaaaga ggggacagga tgtagctctc     120
aggtgtgatc caatttcggg tcatgtatcc ctttattggt accgacaggc cctggggcag     180
ggcccagagt ttctgactta cttcaattat gaagcccaac aagacaaatc agggctgccc     240
aatgatcggt tctctgcaga gaggcctgag ggatccatct ccactctgac gatccagcgc     300
acagagcagc gggactcggc catgtatcgc tgtgccagca gcctctatgg cgggtcttcc     360
tacgagcagt acttcgggcc gggcaccagg ctcacggtca cagag                     405
```

<210> SEQ ID NO 175
<211> LENGTH: 405
<212> TYPE: DNA
<213> ORGANISM: Artificial Sequence
<220> FEATURE:
<223> OTHER INFORMATION: WT378 beta chain variable domain - Codon Optimized

<400> SEQUENCE: 175

```
atgggcacaa gcctgctgtg ttgggtggtg ctgggcttcc tgggcaccga tcatacaggc      60
gctggcgtgt cccagagccc ccggtacaaa gtgaccaaga ggggccagga cgtggccctg     120
agatgcgatc ctatcagcgg ccacgtgtcc ctgtactggt acagacaggc cctgggccag     180
gacccgagt tcctgaccta cttcaactac gaggcccagc aggacaagag cggcctgccc     240
aacgatagat tcagcgccga aagacccgag ggcagcatca gcaccctgac catccagaga     300
accgagcagc gggacagcgc catgtacaga tgtgccagct ctctgtacgg cggcagcagc     360
tacgagcagt actttggccc tggcacccgg ctgaccgtga ccgag                     405
```

<210> SEQ ID NO 176
<211> LENGTH: 939
<212> TYPE: DNA
<213> ORGANISM: Artificial Sequence
<220> FEATURE:
<223> OTHER INFORMATION: WT378 beta chain WT

<400> SEQUENCE: 176

```
atgggcacca gtctcctatg ctgggtggtc ctgggtttcc tagggacaga tcacacaggt      60
gctggagtct cccagtctcc caggtacaaa gtcacaaaga ggggacagga tgtagctctc     120
aggtgtgatc caatttcggg tcatgtatcc ctttattggt accgacaggc cctggggcag     180
ggcccagagt ttctgactta cttcaattat gaagcccaac aagacaaatc agggctgccc     240
aatgatcggt tctctgcaga gaggcctgag ggatccatct ccactctgac gatccagcgc     300
acagagcagc gggactcggc catgtatcgc tgtgccagca gcctctatgg cgggtcttcc     360
tacgagcagt acttcgggcc gggcaccagg ctcacggtca cagaggacct gaaaaacgtg     420
ttcccacccg aggtcgctgt gtttgagcca tcagaagcag atctcccca cccaaaag       480
gccacactgg tgtgcctggc acaggcttc taccccgacc acgtggagct gagctggtgg     540
gtgaatggga aggaggtgca cagtggggtc agcacagacc cgcagcccct caaggagcag     600
cccgccctca tgactccag atactgcctg agcagccgcc tgagggtctc ggccaccttc     660
tggcagaacc ccgcaacca cttccgctgt caagtccagt tctacgggct ctcggagaat     720
```

```
gacgagtgga cccaggatag ggccaaacct gtcacccaga tcgtcagcgc cgaggcctgg    780
ggtagagcag actgtggctt cacctccgag tcttaccagc aagggtcct gtctgccacc    840 atcctctatg agatcttgct agggaaggcc accttgtatg ccgtgctggt cagtgccctc    900
gtgctgatgg ccatggtcaa gagaaaggat tccagaggc                          939
```

<210> SEQ ID NO 177
<211> LENGTH: 939
<212> TYPE: DNA
<213> ORGANISM: Artificial Sequence
<220> FEATURE:
<223> OTHER INFORMATION: WT378 beta chain - Codon-Optimized, Cys Modified

<400> SEQUENCE: 177

```
atgggcacaa gcctgctgtg ttgggtggtg ctgggcttcc tgggcaccga tcatacaggc     60
gctggcgtgt cccagagccc ccggtacaaa gtgaccaaga ggggccagga cgtggccctg    120
agatgcgatc ctatcagcgg ccacgtgtcc ctgtactggt acagacaggc cctgggccag    180
ggacccgagt tcctgaccta cttcaactac gaggcccagc aggacaagag cggcctgccc    240
aacgatagat tcagcgccga aagacccgag ggcagcatca gcaccctgac catccagaga    300
accgagcagc gggacagcgc catgtacaga tgtgccagct ctctgtacgg cggcagcagc    360
tacgagcagt actttggccc tggcacccgg ctgaccgtga ccgaggatct gaagaacgtg    420
ttccccccag aggtggccgt gttcgagcct agcgaggccg agatcagcca cacccagaaa    480
gccaccctcg tgtgcctggc caccggcttt taccccgacc acgtggaact gtcttggtgg    540
gtcaacggca agaggtgca gcgcggcgtc tgcaccgacc ccagcccct gaaagagcag    600 cccgccctga cgacagccg gtactgtctg agcagcagac tgagagtgtc cgccaccttc    660
tggcagaacc cccggaacca cttcagatgc caggtgcagt tctacggcct gagcgagaac    720
gacgagtgga cccaggaccg ggccaagccc gtgacccaga tcgtgtctgc tgaggcctgg    780
ggcagagccg attgcggctt caccagcgag agctaccagc agggcgtgct gagcgccacc    840
atcctgtacg agatcctgct gggcaaggcc accctgtacg ccgtgctggt gtccgccctg    900
gtgctgatgg ccatggtcaa gcggaaggac agccggggc                          939
```

<210> SEQ ID NO 178
<211> LENGTH: 1839
<212> TYPE: DNA
<213> ORGANISM: Artificial Sequence
<220> FEATURE:
<223> OTHER INFORMATION: WT378 beta-P2A-WT378 alpha Construct - WT

<400> SEQUENCE: 178

```
atgggcacca gtctcctatg ctgggtggtc ctgggtttcc tagggacaga tcacacaggt     60
gctggagtct cccagtctcc caggtacaaa gtcacaaaga ggggacagga tgtagctctc    120
aggtgtgatc caatttcggg tcatgtatcc ctttattggt accgacaggc cctggggcag    180
ggcccagagt ttctgactta cttcaattat gaagcccaac aagacaaatc agggctgccc    240
aatgatcggt tctctgcaga gaggcctgag ggatccatct ccactctgac gatccagcgc    300
acagagcagc gggactcggc catgtatcgc tgtgccagca gcctctatgg cgggtcttcc    360
tacgagcagt acttcgggcc gggcaccagg ctcacggtca cagaggacct gaaaaacgtg    420
ttcccacccg aggtcgctgt gtttgagcca tcagaagcag agatctccca cacccaaaag    480
gccacactgg tgtgcctggc cacaggcttc taccccgacc acgtggagct gagctggtgg    540
```

```
gtgaatggga aggaggtgca cagtggggtc agcacagacc cgcagcccct caaggagcag    600
cccgccctca atgactccag atactgcctg agcagccgcc tgagggtctc ggccaccttc    660
tggcagaacc cccgcaacca cttccgctgt caagtccagt tctacgggct ctcggagaat    720
gacgagtgga cccaggatag ggccaaacct gtcacccaga tcgtcagcgc cgaggcctgg    780
ggtagagcag actgtggctt cacctccgag tcttaccagc aagggtcct  gtctgccacc    840 atcctctatg agatcttgct agggaaggcc accttgtatg ccgtgctggt cagtgccctc    900
gtgctgatgg ccatggtcaa gagaaaggat tccagaggcg gttccggagc cacgaacttc    960
tctctgttaa gcaagcagg  agacgtgaa  gaaaccccg  gtcccatgat gaaatccttg    1020
agagttttac tggtgatcct gtggcttcag ttaagctggg tttggagcca acagaaggag    1080
gtggagcagg atcctggacc actcagtgtt ccagagggag ccattgtttc tctcaactgc    1140
acttacagca acagtgcttt tcaatacttc atgtggtaca gacagtattc cagaaaaggc    1200
cctgagttgc tgatgtacac atactccagt ggtaacaaag aagatggaag gtttacagca    1260
caggtcgata atccagcaa  gtatatctcc ttgttcatca gagactcaca gcccagtgat    1320
tcagccacct acctctgtgc aatttacggg tggggtggtg gtgctacaaa caagctcatc    1380
tttggaactg gcactctgct tgctgtccag ccaaatatcc agaaccctga ccctgccgtg    1440
taccagctga gagactctaa atccagtgac aagtctgtct gcctattcac cgattttgat    1500
tctcaaacaa atgtgtcaca agtaaggat  tctgatgtgt atatcacaga caaaactgtg    1560
ctagacatga ggtctatgga cttcaagagc aacagtgctg tggcctggag caacaaatct    1620
gactttgcat gtgcaaacgc cttcaacaac agcattattc cagaagacac cttcttcccc    1680
agcccagaaa gttcctgtga tgtcaagctg gtcgagaaaa gctttgaaac agatacgaac    1740
ctaaactttc aaaacctgtc agtgattggg ttccgaatcc tcctcctgaa agtggccggg    1800
tttaatctgc tcatgacgct gcggctgtgg tccagctga                           1839
```

<210> SEQ ID NO 179
<211> LENGTH: 1839
<212> TYPE: DNA
<213> ORGANISM: Artificial Sequence
<220> FEATURE:
<223> OTHER INFORMATION: WT378 beta-P2A-WT378 alpha Construct - Codon-Optimized, Cys Modified

<400> SEQUENCE: 179

```
atgggcacaa gcctgctgtg ttgggtggtg ctgggcttcc tgggcaccga tcatacaggc     60
gctggcgtgt cccagagccc ccggtacaaa gtgaccaaga ggggccagga cgtggccctg    120
agatgcgatc ctatcagcgg ccacgtgtcc ctgtactggt acagacaggc cctgggccag    180
ggacccgagt tcctgaccta cttcaactac gaggcccagc aggacaagag cggcctgccc    240
aacgatagat tcagcgccga aagacccgag ggcagcatca gcaccctgac catccagaga    300
accgagcagc gggacagcgc catgtacaga tgtgccagct ctctgtacgg cggcagcagc    360
tacgagcagt actttggccc tggcacccgg ctgaccgtga ccgaggatct gaagaacgtg    420 ttcccccccag aggtggccgt gttcgagcct agcgaggccg agatcagcca cacccagaaa    480 gccacccteg tgtgcctgge caccggcttt taccccgace acgtgaaact gtcttggtgg    540
gtcaacggca agaggtgca  cagcggcgtc tgcaccgacc ccagcccct gaaagagcag    600 cccgccctga cgacagccg gtactgtctg agcagcagac tgagagtgtc cgccaccttc    660
tggcagaacc cccggaacca cttcagatgc caggtgcagt tctacggcct gagcgagaac    720
```

```
gacgagtgga cccaggaccg ggccaagccc gtgacccaga tcgtgtctgc tgaggcctgg    780
ggcagagccg attgcggctt caccagcgag agctaccagc agggcgtgct gagcgccacc    840
atcctgtacg agatcctgct gggcaaggcc accctgtacg ccgtgctggt gtccgccctg    900
gtgctgatgg ccatggtcaa gcggaaggac agcggggcg gttccggagc cacgaacttc    960
tctctgttaa gcaagcagg agacgtggaa gaaaacccg gtcccatgat gaagtccctg    1020
cgggtgctgc tcgtgatcct gtggctgcag ctgagctggg tgtggtccca gcagaaagag   1080
gtggaacagg accctggccc tctgagcgtg ccagagggcg ctatcgtgtc cctgaactgc   1140
acctacagca cagcgccctt ccagtacttc atgtggtaca gacagtacag ccggaagggc   1200
cccgagctgc tgatgtacac ctactccagc ggcaacaaag aggacggccg gttcacagcc   1260
caggtggaca gagcagcaa gtacatctcc ctgttcatcc gggacagcca gcccagcgat   1320
tccgccacat acctgtgcgc catctacggc tggggaggcg gagccaccaa caagctgatc   1380
tttggcaccg gcaccctgct ggccgtgcag cccaatatcc agaacccga ccctgcagtg    1440 taccagctgc gggacagcaa gagcagcgac aagagcgtgt gcctgttcac cgacttcgac   1500
agccagacca acgtgtccca gagcaaggac agcgacgtgt acatcaccga taagtgcgtg   1560
ctggacatgc ggagcatgga cttcaagagc aacagcgccg tggcctggtc caacaagagc   1620
gacttcgcct gcgccaacgc cttcaacaac agcattatcc ccgaggacac attcttccca   1680
agccccgaga gcagctgcga cgtgaagctg gtggaaaaga gcttcgagac agacaccaac   1740
ctgaacttcc agaacctcag cgtgatcggc ttccggatcc tgctgctgaa ggtggccggc   1800
ttcaacctgc tgatgaccct gcggctgtgg tccagctga                           1839

<210> SEQ ID NO 180
<211> LENGTH: 402
<212> TYPE: DNA
<213> ORGANISM: Artificial Sequence
<220> FEATURE:
<223> OTHER INFORMATION: WT379 alpha chain variable domain WT

<400> SEQUENCE: 180
atgaaatcct tgagagtttt actagtgatc ctgtggcttc agttgagctg ggtttggagc     60
caacagaagg aggtggagca gaattctgga cccctcagtg ttccagaggg agccattgcc    120
tctctcaact gcacttacag tgaccgaggt tcccagtcct tcttctggta cagacaatat    180
tctgggaaaa gccctgagtt gataatgttc atatactcca atggtgacaa agaagatgga    240
aggtttacag cacagctcaa taagccagc cagtatgttt ctctgctcat cagagactcc    300
cagcccagtg attcagccac ctacctctgt gccgtgggcg gatctggggg ttaccagaaa    360
gttacctttg gaattggaac aaagctccaa gtcatcccaa at                       402

<210> SEQ ID NO 181
<211> LENGTH: 402
<212> TYPE: DNA
<213> ORGANISM: Artificial Sequence
<220> FEATURE:
<223> OTHER INFORMATION: WT379 alpha chain variable domain - Codon
      Optimized

<400> SEQUENCE: 181
atgaagtccc tgcgggtgct gctcgtgatc ctgtggctgc agctgagctg ggtgtggtcc     60
cagcagaaag aggtggaaca gaacagcggg ccctctgagcg tgccagaagg cgctatcgcc   120
agcctgaact gcacctacag cgacagaggc agccagagct tcttctggta cagacagtac    180
```

| | |
|---|---|
| agcggcaaga gccccgagct gatcatgttc atctacagca acggcgacaa agaggacggc | 240 |
| cggttcaccg cccagctgaa caaggccagc cagtacgtgt ccctgctgat cagagacagc | 300 |
| cagcccagcg acagcgccac ctatctgtgt gccgtgggag gctctggcgg ctaccagaaa | 360 |
| gtgaccttcg gcatcggcac caagctgcaa gtgatcccca ac | 402 |

<210> SEQ ID NO 182
<211> LENGTH: 825
<212> TYPE: DNA
<213> ORGANISM: Artificial Sequence
<220> FEATURE:
<223> OTHER INFORMATION: WT379 alpha chain WT

<400> SEQUENCE: 182

| | |
|---|---|
| atgaaatcct tgagagtttt actagtgatc ctgtggcttc agttgagctg ggtttggagc | 60 |
| caacagaagg aggtggagca gaattctgga cccctcagtg ttccagaggg agccattgcc | 120 |
| tctctcaact gcacttacag tgaccgaggt tcccagtcct tcttctggta cagacaatat | 180 |
| tctgggaaaa gccctgagtt gataatgttc atatactcca atggtgacaa agaagatgga | 240 |
| aggtttacag cacagctcaa taaagccagc cagtatgttt ctctgctcat cagagactcc | 300 |
| cagcccagtg attcagccac ctacctctgt gccgtgggcg atctggggg ttaccagaaa | 360 |
| gttacctttg gaattggaac aaagctccaa gtcatcccaa atatccagaa ccctgaccct | 420 |
| gccgtgtacc agctgagaga ctctaaatcc agtgacaagt ctgtctgcct attcaccgat | 480 |
| tttgattctc aaacaaatgt gtcacaaagt aaggattctg atgtgtatat cacagacaaa | 540 |
| actgtgctag acatgaggtc tatggacttc aagagcaaca gtgctgtggc ctggagcaac | 600 |
| aaatctgact ttgcatgtgc aaacgccttc aacaacagca ttattccaga agacaccttc | 660 |
| ttccccagcc cagaaagttc ctgtgatgtc aagctggtcg agaaaagctt tgaaacagat | 720 |
| acgaacctaa actttcaaaa cctgtcagtg attgggttcc gaatcctcct cctgaaagtg | 780 |
| gccgggttta atctgctcat gacgctgcgg ctgtggtcca gctga | 825 |

<210> SEQ ID NO 183
<211> LENGTH: 825
<212> TYPE: DNA
<213> ORGANISM: Artificial Sequence
<220> FEATURE:
<223> OTHER INFORMATION: WT379 alpha chain - Codon-Optimized, Cys
    Modified

<400> SEQUENCE: 183

| | |
|---|---|
| atgaagtccc tgcgggtgct gctcgtgatc ctgtggctgc agctgagctg ggtgtggtcc | 60 |
| cagcagaaag aggtggaaca gaacagcggc cctctgagcg tgccagaagg cgctatcgcc | 120 |
| agcctgaact gcacctacag cgacagaggc agccagagct tcttctggta cagacagtac | 180 |
| agcggcaaga gccccgagct gatcatgttc atctacagca acggcgacaa agaggacggc | 240 |
| cggttcaccg cccagctgaa caaggccagc cagtacgtgt ccctgctgat cagagacagc | 300 |
| cagcccagcg acagcgccac ctatctgtgt gccgtgggag gctctggcgg ctaccagaaa | 360 |
| gtgaccttcg gcatcggcac caagctgcaa gtgatcccca acatccagaa ccccgacccc | 420 |
| gcagtgtacc agctgcggga cagcaagagc agcgacaaga gcgtgtgcct gttcaccgac | 480 |
| ttcgacagcc agaccaacgt gtcccagagc aaggacagcg acgtgtacat caccgataag | 540 |
| tgcgtgctgg acatgcggag catggacttc aagagcaaca gcgccgtggc ctggtccaac | 600 |
| aagagcgact tcgcctgcgc caacgccttc aacaacagca ttatccccga ggacacattc | 660 |

```
ttcccaagcc ccgagagcag ctgcgacgtg aagctggtgg aaaagagctt cgagacagac      720
accaacctga acttccagaa cctcagcgtg atcggcttcc ggatcctgct gctgaaggtg      780
gccggcttca acctgctgat gaccctgcgg ctgtggtcca gctga                     825
```

```
<210> SEQ ID NO 184
<211> LENGTH: 399
<212> TYPE: DNA
<213> ORGANISM: Artificial Sequence
<220> FEATURE:
<223> OTHER INFORMATION: WT379 beta chain variable domain WT

<400> SEQUENCE: 184
atgagcaacc aggtgctctg ctgtgtggtc ctttgtttcc tgggagcaaa caccgtggat       60
ggtggaatca ctcagtcccc aaagtacctg ttcagaaagg aaggacagaa tgtgaccctg      120
agttgtgaac agaatttgaa ccacgatgcc atgtactggt accgacagga cccagggcaa      180
gggctgagat tgatctacta ctcacagata gtaaatgact tcagaaagg agatatagct       240 gaagggtaca cgtctctcg ggagaagaag gaatcctttc ctctcactgt gacatcggcc       300
caaaagaacc cgacagcttt ctatctctgt gccagtagcg ggagggccgg ggttggggag      360
ctgttttttg gagaaggctc taggctgacc gtactggag                             399
```

```
<210> SEQ ID NO 185
<211> LENGTH: 399
<212> TYPE: DNA
<213> ORGANISM: Artificial Sequence
<220> FEATURE:
<223> OTHER INFORMATION: WT379 beta chain variable domain - Codon
      Optimized

<400> SEQUENCE: 185
atgagcaacc aggtgctgtg ctgcgtggtg ctgtgtttcc tgggcgccaa cacagtggac       60
ggcggcatca cacagagccc caagtacctg ttccggaaag agggccagaa cgtgaccctg      120
agctgcgagc agaacctgaa ccacgacgcc atgtactggt acagacagga cccaggccag      180
ggcctgcggc tgatctacta cagccagatc gtgaacgact ccagaagggg cgacattgcc      240
gagggctaca cgctgtccag agagaagaaa gagtccttcc cactgaccgt gaccagcgcc      300
cagaagaacc ccaccgcctt ctacctgtgt gccagctctg gcagagccgg cgtgggcgag      360
ctgttttttg gcgagggcag caggctgacc gtgctggaa                             399
```

```
<210> SEQ ID NO 186
<211> LENGTH: 933
<212> TYPE: DNA
<213> ORGANISM: Artificial Sequence
<220> FEATURE:
<223> OTHER INFORMATION: WT379 beta chain WT

<400> SEQUENCE: 186
atgagcaacc aggtgctctg ctgtgtggtc ctttgtttcc tgggagcaaa caccgtggat       60
ggtggaatca ctcagtcccc aaagtacctg ttcagaaagg aaggacagaa tgtgaccctg      120
agttgtgaac agaatttgaa ccacgatgcc atgtactggt accgacagga cccagggcaa      180
gggctgagat tgatctacta ctcacagata gtaaatgact tcagaaagg agatatagct       240 gaagggtaca cgtctctcg ggagaagaag gaatcctttc ctctcactgt gacatcggcc       300
caaaagaacc cgacagcttt ctatctctgt gccagtagcg ggagggccgg ggttggggag      360
ctgttttttg gagaaggctc taggctgacc gtactggagg acctgaaaaa cgtgttccca      420
```

```
cccgaggtcg ctgtgtttga gccatcagaa gcagagatct cccacaccca aaaggccaca    480
ctggtgtgcc tggccacagg cttctacccc gaccacgtgg agctgagctg gtgggtgaat    540
gggaaggagg tgcacagtgg ggtcagcaca gacccgcagc ccctcaagga gcagcccgcc    600
ctcaatgact ccagatactg cctgagcagc cgcctgaggg tctcggccac cttctggcag    660 aaccccgca accacttccg ctgtcaagtc cagttctacg gctctcgga gaatgacgag    720 tggacccagg atagggccaa acctgtcacc cagatcgtca cgcccgaggc ctggggtaga    780
gcagactgtg gcttcacctc cgagtcttac cagcaagggg tcctgtctgc caccatcctc    840
tatgagatct gctagggaa ggccaccttg tatgccgtgc tggtcagtgc cctcgtgctg    900
atggccatgg tcaagagaaa ggattccaga ggc                                 933
```

<210> SEQ ID NO 187
<211> LENGTH: 933
<212> TYPE: DNA
<213> ORGANISM: Artificial Sequence
<220> FEATURE:
<223> OTHER INFORMATION: WT379 beta chain - Codon-Optimized, Cys
      Modified

<400> SEQUENCE: 187

```
atgagcaacc aggtgctgtg ctgcgtggtg ctgtgtttcc tgggcgccaa cacagtggac    60
ggcggcatca cacagagccc caagtacctg ttccggaaag agggccagaa cgtgaccctg    120
agctgcgagc agaacctgaa ccacgacgcc atgtactggt acagacagga cccaggccag    180
ggcctgcggc tgatctacta cagccagatc gtgaacgact ccagaagggg cgacattgcc    240
gagggctaca gcgtgtccag agagaagaaa gagtccttcc cactgaccgt gaccagcgcc    300
cagaagaacc ccaccgcctt ctacctgtgt gccagctctg gcagagccgg cgtgggcgag    360
ctgttttttg gcgagggcag caggctgacc gtgctggaag atctgaagaa cgtgttcccc    420
ccagaggtgg ccgtgttcga gcctagcgag gccgagatca gccacaccca gaaagccacc    480
ctcgtgtgcc tggccaccgg ctttttaccccc gaccacgtgg aactgtcttg gtgggtcaac    540
ggcaaagagg tgcacagcgg cgtctgcacc gaccccagc ccctgaaaga gcagcccgcc    600
ctgaacgaca gccggtactg tctgagcagc agactgagag tgtccgccac cttctggcag    660 aaccccgga accacttcag atgccaggtg cagttctacg gcctgagcga gaacgacgag    720
tggacccagg accgggccaa gcccgtgacc cagatcgtgt ctgctgaggc ctggggcaga    780
gccgattgcg gcttcaccag cgagagctac cagcagggcg tgctgagcgc caccatcctg    840
tacgagatcc tgctgggcaa ggccacccctg tacgccgtgc tggtgtccgc cctggtgctg    900
atggccatgg tcaagcggaa ggacagccgg ggc                                 933
```

<210> SEQ ID NO 188
<211> LENGTH: 1824
<212> TYPE: DNA
<213> ORGANISM: Artificial Sequence
<220> FEATURE:
<223> OTHER INFORMATION: WT379 beta-P2A-WT379 alpha Construct - WT

<400> SEQUENCE: 188

```
atgagcaacc aggtgctctg ctgtgtggtc ctttgtttcc tgggagcaaa caccgtggat    60
ggtggaatca ctcagtcccc aaagtacctg ttcagaaagg aaggacagaa tgtgaccctg    120
agttgtgaac agaatttgaa ccacgatgcc atgtactggt accgacagga cccagggcaa    180
gggctgagat tgatctacta ctcacagata gtaaatgact ttcagaaagg agatatagct    240
```

|  |  |  |  |  |
|---|---|---|---|---|
| gaagggtaca | gcgtctctcg | ggagaagaag | gaatcctttc | ctctcactgt gacatcggcc | 300 |
| caaaagaacc | cgacagcttt | ctatctctgt | gccagtagcg | ggagggccgg ggttggggag | 360 |
| ctgttttttg | gagaaggctc | taggctgacc | gtactggagg | acctgaaaaa cgtgttccca | 420 |
| cccgaggtcg | ctgtgtttga | gccatcagaa | gcagagatct | cccacaccca aaaggccaca | 480 |
| ctggtgtgcc | tggccacagg | cttctacccc | gaccacgtgg | agctgagctg gtgggtgaat | 540 |
| gggaaggagg | tgcacagtgg | ggtcagcaca | gacccgcagc | ccctcaagga gcagcccgcc | 600 |
| ctcaatgact | ccagatactg | cctgagcagc | cgcctgaggg | tctcggccac cttctggcag | 660 |
| aaccccgca | accacttccg | ctgtcaagtc | cagttctacg | gcctctcgga gaatgacgag | 720 |
| tggacccagg | atagggccaa | acctgtcacc | cagatcgtca | gcgccgaggc ctggggtaga | 780 |
| gcagactgtg | gcttcacctc | cgagtcttac | cagcaagggg | tcctgtctgc caccatcctc | 840 |
| tatgagatct | tgctagggaa | ggccaccttg | tatgccgtgc | tggtcagtgc cctcgtgctg | 900 |
| atggccatgg | tcaagagaaa | ggattccaga | ggcggttccg | gagccacgaa cttctctctg | 960 |
| ttaaagcaag | caggagacgt | ggaagaaaac | cccggtccca | tgaaatcctt gagagtttta | 1020 |
| ctagtgatcc | tgtggcttca | gttgagctgg | gtttggagcc | aacagaagga ggtggagcag | 1080 |
| aattctggac | ccctcagtgt | tccagaggga | gccattgcct | ctctcaactg cacttacagt | 1140 |
| gaccgaggtt | cccagtcctt | cttctggtac | agacaatatt | ctgggaaaag ccctgagttg | 1200 |
| ataatgttca | tatactccaa | tggtgacaaa | gaagatggaa | ggtttacagc acagctcaat | 1260 |
| aaagccagcc | agtatgtttc | tctgctcatc | agagactccc | agcccagtga ttcagccacc | 1320 |
| tacctctgtg | ccgtgggcgg | atctgggggt | taccagaaag | ttacctttgg aattggaaca | 1380 |
| aagctccaag | tcatcccaaa | tatccagaac | cctgaccctg | ccgtgtacca gctgagagac | 1440 |
| tctaaatcca | gtgacaagtc | tgtctgccta | ttcaccgatt | ttgattctca acaaatgtg | 1500 |
| tcacaaagta | aggattctga | tgtgtatatc | acagacaaaa | ctgtgctaga catgaggtct | 1560 |
| atggacttca | agagcaacag | tgctgtggcc | tggagcaaca | aatctgactt tgcatgtgca | 1620 |
| aacgccttca | caacagcat | tattccagaa | gacaccttct | cccccagccc agaaagttcc | 1680 |
| tgtgatgtca | gctggtcga | gaaaagcttt | gaaacagata | cgaacctaaa ctttcaaaac | 1740 |
| ctgtcagtga | ttgggttccg | aatcctcctc | ctgaaagtgg | ccgggtttaa tctgctcatg | 1800 |
| acgctgcggc | tgtggtccag | ctga |  |  | 1824 |

<210> SEQ ID NO 189
<211> LENGTH: 1824
<212> TYPE: DNA
<213> ORGANISM: Artificial Sequence
<220> FEATURE:
<223> OTHER INFORMATION: WT379 beta-P2A-WT379 alpha Construct -
      Codon-Optimized, Cys Modified

<400> SEQUENCE: 189

|  |  |  |  |  |
|---|---|---|---|---|
| atgagcaacc | aggtgctgtg | ctgcgtggtg | ctgtgtttcc | tgggcgccaa cacagtggac | 60 |
| ggcggcatca | cacagagccc | caagtacctg | ttccggaaag | agggccagaa cgtgaccctg | 120 |
| agctgcgagc | agaacctgaa | ccacgacgcc | atgtactggt | acagacagga cccaggccag | 180 |
| ggcctgcggc | tgatctacta | cagccagatc | gtgaacgact | ccagaagggg cgacattgcc | 240 |
| gagggctaca | gcgtgtccag | agagaagaaa | gagtccttcc | cactgaccgt gaccagcgcc | 300 |
| cagaagaacc | ccaccgcctt | ctacctgtgt | gccagctctg | gcagagccgg cgtgggcgag | 360 |
| ctgttttttg | gcgagggcag | caggctgacc | gtgctggaag | atctgaagaa cgtgttcccc | 420 |

```
ccagaggtgg ccgtgttcga gcctagcgag gccgagatca gccacaccca gaaagccacc      480
ctcgtgtgcc tggccaccgg cttttacccc gaccacgtgg aactgtcttg gtgggtcaac      540
ggcaaagagg tgcacagcgg cgtctgcacc gaccccagc ccctgaaaga gcagcccgcc       600
ctgaacgaca gccggtactg tctgagcagc agactgagag tgtccgccac cttctggcag      660
aaccccggga accacttcag atgccaggtg cagttctacg gcctgagcga gaacgacgag      720
tggacccagg accgggccaa gcccgtgacc cagatcgtgt ctgctgaggc ctggggcaga      780
gccgattgcg gcttcaccag cgagagctac cagcagggcg tgctgagcgc caccatcctg      840
tacgagatcc tgctgggcaa ggccacctg tacgccgtgc tggtgtccgc cctggtgctg       900
atggccatgg tcaagcggaa ggacagccgg ggcggttccg gagccacgaa cttctctctg      960
ttaaagcaag caggagacgt ggaagaaaac cccggtccca tgaagtccct gcgggtgctg      1020
ctcgtgatcc tgtggctgca gctgagctgg gtgtggtccc agcagaaaga ggtggaacag     1080
aacagcggcc ctctgagcgt gccagaaggc gctatcgcca gcctgaactg cacctacagc     1140
gacagaggca gccagagctt cttctggtac agacagtaca gcggcaagag ccccgagctg     1200
atcatgttca tctacagcaa cggcgacaaa gaggacggcc ggttcaccgc ccagctgaac     1260
aaggccagcc agtacgtgtc cctgctgatc agagacagcc agcccagcga cagcgccacc     1320
tatctgtgtg ccgtgggagg ctctggcggc taccagaaag tgaccttcgg catcggcacc     1380
aagctgcaag tgatccccaa catccagaac cccgaccccg cagtgtacca gctgcgggac     1440
agcaagagca gcgacaagag cgtgtgcctg ttcaccgact cgacagcca gaccaacgtg      1500 tcccagagca aggacagcga cgtgtacatc accgataagt gcgtgctgga catgcggagc     1560
atggacttca gagcaacag cgccgtggcc tggtccaaca gagcgactt cgcctgcgcc       1620 aacgccttca caacagcat tatccccgag gacacattct ccccaagccc cgagagcagc      1680
tgcgacgtga agctggtgga aaagagcttc gagacagaca ccaacctgaa cttccagaac    1740
ctcagcgtga tcggcttccg gatcctgctg ctgaaggtgg ccggcttcaa cctgctgatg     1800
accctgcggc tgtggtccag ctga                                            1824
```

<210> SEQ ID NO 190
<211> LENGTH: 405
<212> TYPE: DNA
<213> ORGANISM: Artificial Sequence
<220> FEATURE:
<223> OTHER INFORMATION: WT3710 alpha chain variable domain WT

<400> SEQUENCE: 190

```
atgatatcct tgagagtttt actggtgatc ctgtggcttc agttaagctg ggtttggagc       60
caacggaagg aggtggagca ggatcctgga cccttcaatg ttccagaggg agccactgtc     120
gctttcaact gtacttacag caacagtgct tctcagtctt tcttctggta cagacaggat     180
tgcaggaaag aacctaagtt gctgatgtcc gtatactcca gtggtaatga agatggaagg     240
tttacagcac agctcaatag agccagccag tatatttccc tgctcatcag agactccaag     300
ctcagtgatt cagccaccta cctctgtgtg gtgaaaccg accctgggc tgggagttac      360 caactcactt tcgggaaggg gaccaaactc tcggtcatac caaat                     405
```

<210> SEQ ID NO 191
<211> LENGTH: 405
<212> TYPE: DNA
<213> ORGANISM: Artificial Sequence
<220> FEATURE:
<223> OTHER INFORMATION: WT3710 alpha chain variable domain - Codon Optimized

<400> SEQUENCE: 191

| | | |
|---|---|---|
| atgatcagcc tgcgggtgct gctcgtgatc ctgtggctgc agctgagctg ggtgtggtcc | 60 |
| cagcggaaag aggtggaaca ggaccctggc cccttcaacg tgccagaggg cgccaccgtg | 120 |
| gccttcaact gcacctacag caacagcgcc agccagagct tcttctggta cagacaggac | 180 |
| tgccggaaag aacccaagct gctgatgagc gtgtacagca gcggcaacga ggacggcaga | 240 |
| ttcaccgccc agctgaacag agcctcccag tacatctccc tgctgatccg ggacagcaag | 300 |
| ctgagcgaca gcgccaccta cctgtgcgtc gtgaagcctg atcctggcgc cggaagctac | 360 |
| cagctgacct ttggcaaggg caccaagctg tccgtgatcc ccaac | 405 |

<210> SEQ ID NO 192
<211> LENGTH: 828
<212> TYPE: DNA
<213> ORGANISM: Artificial Sequence
<220> FEATURE:
<223> OTHER INFORMATION: WT3710 alpha chain WT

<400> SEQUENCE: 192

| | | |
|---|---|---|
| atgatatcct tgagagtttt actggtgatc ctgtggcttc agttaagctg ggtttggagc | 60 |
| caacggaagg aggtggagca ggatcctgga cccttcaatg ttccagaggg agccactgtc | 120 |
| gctttcaact gtacttacag caacagtgct tctcagtctt tcttctggta cagacaggat | 180 |
| tgcaggaaag aacctaagtt gctgatgtcc gtatactcca gtggtaatga agatggaagg | 240 |
| tttacagcac agctcaatag agccagccag tatatttccc tgctcatcag agactccaag | 300 |
| ctcagtgatt cagccaccta cctctgtgtg gtgaaacccg accctggggc tgggagttac | 360 |
| caactcactt tcgggaaggg gaccaaactc tcggtcatac aaatatcca gaaccctgac | 420 |
| cctgccgtgt accagctgag agactctaaa tccagtgaca gtctgtctg cctattcacc | 480 |
| gattttgatt ctcaaacaaa tgtgtcacaa gtaaggatt ctgatgtgta tatcacagac | 540 |
| aaaactgtgc tagacatgag gtctatggac ttcaagagca acagtgctgt ggcctggagc | 600 |
| aacaaatctg actttgcatg tgcaaacgcc ttcaacaaca gcattattcc agaagacacc | 660 |
| ttcttcccca gcccagaaag ttcctgtgat gtcaagctgg tcgagaaaag ctttgaaaca | 720 |
| gatacgaacc taaactttca aaacctgtca gtgattgggt tccgaatcct cctcctgaaa | 780 |
| gtggccgggt ttaatctgct catgacgctg cggctgtggt ccagctga | 828 |

<210> SEQ ID NO 193
<211> LENGTH: 828
<212> TYPE: DNA
<213> ORGANISM: Artificial Sequence
<220> FEATURE:
<223> OTHER INFORMATION: WT3710 alpha chain - Codon-Optimized, Cys Modified

<400> SEQUENCE: 193

| | | |
|---|---|---|
| atgatcagcc tgcgggtgct gctcgtgatc ctgtggctgc agctgagctg ggtgtggtcc | 60 |
| cagcggaaag aggtggaaca ggaccctggc cccttcaacg tgccagaggg cgccaccgtg | 120 |
| gccttcaact gcacctacag caacagcgcc agccagagct tcttctggta cagacaggac | 180 |
| tgccggaaag aacccaagct gctgatgagc gtgtacagca gcggcaacga ggacggcaga | 240 |
| ttcaccgccc agctgaacag agcctcccag tacatctccc tgctgatccg ggacagcaag | 300 |
| ctgagcgaca gcgccaccta cctgtgcgtc gtgaagcctg atcctggcgc cggaagctac | 360 |

```
cagctgacct tggcaaggg caccaagctg tccgtgatcc ccaacatcca gaaccccgac    420
cccgcagtgt accagctgcg ggacagcaag agcagcgaca agagcgtgtg cctgttcacc    480
gacttcgaca gccagaccaa cgtgtcccag agcaaggaca gcgacgtgta catcaccgat    540
aagtgcgtgc tggacatgcg gagcatggac ttcaagagca cagcgccgt ggcctggtcc    600 aacaagagcg acttcgcctg cgccaacgcc ttcaacaaca gcattatccc cgaggacaca    660
ttcttcccaa gccccgagag cagctgcgac gtgaagctgg tggaaaagag cttcgagaca    720
gacaccaacc tgaacttcca gaacctcagc gtgatcggct ccggatcct gctgctgaag    780 gtggccggct tcaacctgct gatgaccctg cggctgtggt ccagctga                828
```

<210> SEQ ID NO 194
<211> LENGTH: 402
<212> TYPE: DNA
<213> ORGANISM: Artificial Sequence
<220> FEATURE:
<223> OTHER INFORMATION: WT3710 beta chain variable domain WT

<400> SEQUENCE: 194

```
atgagcctcg ggctcctgtg ctgtgggggcc ttttctctcc tgtgggcagg tccagtgaat     60
gctggtgtca ctcagacccc aaaattccgg gtcctgaaga caggacagag catgacactg    120
ctgtgtgccc aggatatgaa ccatgaatac atgtactggt atcgacaaga cccaggcatg    180
gggctgaggc tgattcatta ctcagttggt gagggtacaa ctgccaaagg agaggtccct    240
gatggctaca atgtctccag attaaaaaaa cagaatttcc tgctggggtt ggagtcggct    300 gctcccctccc aaacatctgt gtacttctgt gccagcaggg gttatacag gttaaacaat    360 gagcagttct cgggccagg gacacggctc accgtgctag ag                       402
```

<210> SEQ ID NO 195
<211> LENGTH: 402
<212> TYPE: DNA
<213> ORGANISM: Artificial Sequence
<220> FEATURE:
<223> OTHER INFORMATION: WT3710 beta chain variable domain - Codon
      Optimized

<400> SEQUENCE: 195

```
atgtctctgg gcctgctgtg ctgtggcgcc ttctctctgc tgtgggccgg acctgtgaat     60
gccggcgtga cccagacccc caagttccgg gtgctgaaaa ccggcagag catgaccctg    120 ctgtgtgccc aggacatgaa ccacgagtac atgtattggt acagacagga ccccggcatg    180
ggcctgcggc tgatccacta ttctgtgggc gagggcacca ccgccaaggg cgaagtgcct    240
gatggctaca acgtgtcccg gctgaagaag cagaacttcc tgctgggcct ggaaagcgcc    300
gctcctagcc agaccagcgt gtacttctgt gccagccggg gctaccaccg gctgaacaac    360
gagcagttct cggccctgg cacccggctg accgtgctgg aa                       402
```

<210> SEQ ID NO 196
<211> LENGTH: 936
<212> TYPE: DNA
<213> ORGANISM: Artificial Sequence
<220> FEATURE:
<223> OTHER INFORMATION: WT3710 beta chain WT

<400> SEQUENCE: 196

```
atgagcctcg ggctcctgtg ctgtgggggcc ttttctctcc tgtgggcagg tccagtgaat     60
gctggtgtca ctcagacccc aaaattccgg gtcctgaaga caggacagag catgacactg    120
```

```
ctgtgtgccc aggatatgaa ccatgaatac atgtactggt atcgacaaga cccaggcatg      180
gggctgaggc tgattcatta ctcagttggt gagggtacaa ctgccaaagg agaggtccct      240
gatggctaca atgtctccag attaaaaaaa cagaatttcc tgctggggtt ggagtcggct      300
gctccctccc aaacatctgt gtacttctgt gccagcaggg gttatacacag gttaaacaat     360 gagcagttct tcgggccagg gacacggctc accgtgctag aggacctgaa aaacgtgttc      420
ccacccgagg tcgctgtgtt tgagccatca gaagcagaga tctcccacac ccaaaaggcc      480
acactggtgt gcctggccac aggcttctac cccgaccacg tggagctgag ctggtgggtg      540
aatgggaagg aggtgcacag tggggtcagc acagacccgc agcccctcaa ggagcagccc      600
gccctcaatg actccagata ctgcctgagc agccgcctga gggtctcggc caccttctgg      660
cagaaccccc gcaaccactt ccgctgtcaa gtccagttct acgggctctc ggagaatgac      720
gagtggaccc aggatagggc caaacctgtc acccagatcg tcagcgccga ggcctggggt      780
agagcagact gtggcttcac ctccgagtct taccagcaag gggtcctgtc tgccaccatc      840
ctctatgaga tcttgctagg gaaggccacc ttgtatgccg tgctggtcag tgccctcgtg      900
ctgatggcca tggtcaagag aaaggattcc agaggc                                936
```

<210> SEQ ID NO 197
<211> LENGTH: 936
<212> TYPE: DNA
<213> ORGANISM: Artificial Sequence
<220> FEATURE:
<223> OTHER INFORMATION: WT3710 beta chain - Codon-Optimized, Cys Modified

<400> SEQUENCE: 197

```
atgtctctgg gcctgctgtg ctgtggcgcc ttctctctgc tgtgggccgg acctgtgaat      60
gccggcgtga cccagacccc caagttccgg gtgctgaaaa ccggccagag catgaccctg      120
ctgtgtgccc aggacatgaa ccacgagtac atgtattggt acagacagga ccccggcatg      180
ggcctgcggc tgatccacta ttctgtgggc gagggcacca ccgccaaggg cgaagtgcct      240
gatggctaca cgtgtcccg gctgaagaag cagaacttcc tgctgggcct ggaaagcgcc      300
gctcctagcc agaccagcgt gtacttctgt gccagccggg gctaccaccg gctgaacaac      360
gagcagttct tcgggcctgg caccccggctg accgtgctgg aagatctgaa gaacgtgttc      420
cccccagagg tggccgtgtt cgagcctagc gaggccgaga tcagccacac ccagaaagcc      480
accctcgtgt gcctggccac cggcttttac cccgaccacg tggaactgtc ttggtgggtc      540
aacggcaaag aggtgcacag cggcgtctgc accgaccccc agcccctgaa agagcagccc      600
gccctgaacg acagccggta ctgtctgagc agcagactga gagtgtccgc caccttctgg      660
cagaaccccc ggaaccactt cagatgccag gtgcagttct acggcctgag cgagaacgac      720
gagtggaccc aggaccgggc caagcccgtg acccagatcg tgtctgctga ggcctggggc      780
agagccgatt gcggcttcac cagcgagagc taccagcagg gcgtgctgag cgccaccatc      840
ctgtacgaga tcctgctggg caaggccacc ctgtacgccg tgctggtgtc cgccctggtg      900
ctgatggcca tggtcaagcg gaaggacagc cggggc                                936
```

<210> SEQ ID NO 198
<211> LENGTH: 1830
<212> TYPE: DNA
<213> ORGANISM: Artificial Sequence
<220> FEATURE:
<223> OTHER INFORMATION: WT3710 beta-P2A-WT3710 alpha Construct - WT

<400> SEQUENCE: 198

```
atgagcctcg ggctcctgtg ctgtggggcc ttttctctcc tgtgggcagg tccagtgaat      60
gctggtgtca ctcagacccc aaaattccgg gtcctgaaga caggacagag catgacactg     120
ctgtgtgccc aggatatgaa ccatgaatac atgtactggt atcgacaaga cccaggcatg     180
gggctgaggc tgattcatta ctcagttggt gagggtacaa ctgccaaagg agaggtccct     240
gatggctaca atgtctccag attaaaaaaa cagaatttcc tgctggggtt ggagtcggct     300
gctccctccc aaacatctgt gtacttctgt gccagcaggg gttatcacag gttaaacaat     360
gagcagttct cgggccagg acacggctc accgtgctag aggacctgaa aaacgtgttc      420
ccacccgagg tcgctgtgtt tgagccatca gaagcagaga tctcccacac ccaaaaggcc     480
acactggtgt gcctggccac aggcttctac cccgaccacg tggagctgag ctggtgggtg     540
aatgggaagg aggtgcacag tggggtcagc acagacccgc agcccctcaa ggagcagccc     600
gccctcaatg actccagata ctgcctgagc agccgcctga gggtctcggc caccttctgg     660
cagaaccccc gcaaccactt ccgctgtcaa gtccagttct acgggctctc ggagaatgac     720
gagtggaccc aggatagggc caaacctgtc acccagatcg tcagcgccga ggcctggggt     780
agagcagact gtggcttcac ctccgagtct taccagcaag ggtcctgtc tgccaccatc     840
ctctatgaga tcttgctagg gaaggccacc ttgtatgccg tgctggtcag tgccctcgtg     900
ctgatggcca tggtcaagag aaaggattcc agaggcggtt ccggagccac gaacttctct    960
ctgttaaagc aagcaggaga cgtggaagaa accccggtc ccatgatatc cttgagagtt    1020
ttactggtga tcctgtggct tcagttaagc tgggtttgga gccaacggaa ggaggtggag    1080
caggatcctg gacccttcaa tgttccagag ggagccactg tcgctttcaa ctgtacttac    1140
agcaacagtg cttctcagtc tttcttctgg tacagacagg attgcaggaa agaacctaag    1200
ttgctgatgt ccgtatactc cagtggtaat gaagatggaa ggtttacagc acagctcaat    1260
agagccagcc agtatatttc cctgctcatc agagactcca agctcagtga ttcagccacc    1320
tacctctgtg tggtgaaacc cgaccctggg gctgggagtt accaactcac tttcgggaag    1380
gggaccaaac tctcggtcat accaaatatc cagaaccctg accctgccgt gtaccagctg    1440
agagactcta atccagtga caagtctgtc tgcctattca ccgattttga ttctcaaaca    1500
aatgtgtcac aaagtaagga ttctgatgtg tatatcacag acaaaactgt gctagacatg    1560
aggtctatgg acttcaagag caacagtgct gtggcctgga gcaacaaatc tgactttgca    1620
tgtgcaaacg ccttcaacaa cagcattatt ccagaagaca ccttcttccc cagcccagaa    1680
agttcctgtg atgtcaagct ggtcgagaaa agctttgaaa cagatacgaa cctaaacttt    1740
caaaacctgt cagtgattgg gttccgaatc ctcctcctga agtggccgg gtttaatctg    1800
ctcatgacgc tgcggctgtg gtccagctga                                     1830
```

<210> SEQ ID NO 199
<211> LENGTH: 1830
<212> TYPE: DNA
<213> ORGANISM: Artificial Sequence
<220> FEATURE:
<223> OTHER INFORMATION: WT3710 beta-P2A-WT3710 alpha Construct - Codon-Optimized, Cys Modified

<400> SEQUENCE: 199

```
atgtctctgg gctgctgtg ctgtggcgcc ttctctctgc tgtgggccgg acctgtgaat       60
gccggcgtga cccagacccc caagttccgg gtgctgaaaa ccggccagag catgaccctg     120
```

| | |
|---|---|
| ctgtgtgccc aggacatgaa ccacgagtac atgtattggt acagacagga ccccggcatg | 180 |
| ggcctgcggc tgatccacta ttctgtgggc gagggcacca ccgccaaggg cgaagtgcct | 240 |
| gatggctaca acgtgtcccg gctgaagaag cagaacttcc tgctgggcct ggaaagcgcc | 300 |
| gctcctagcc agaccagcgt gtacttctgt gccagccggg gctaccaccg gctgaacaac | 360 |
| gagcagttct tcggccctgg cacccggctg accgtgctgg aagatctgaa gaacgtgttc | 420 |
| cccccagagg tggccgtgtt cgagcctagc gaggccgaga tcagccacac ccagaaagcc | 480 |
| accctcgtgt gcctggccac cggcttttac cccgaccacg tggaactgtc ttggtgggtc | 540 |
| aacggcaaag aggtgcacag cggcgtctgc accgaccccc agcccctgaa agagcagccc | 600 |
| gccctgaacg acagccggta ctgtctgagc agcagactga gagtgtccgc caccttctgg | 660 |
| cagaaccccc ggaaccactt cagatgccag gtgcagttct acggcctgag cgagaacgac | 720 |
| gagtggaccc aggaccgggc caagcccgtg acccagatcg tgtctgctga ggcctggggc | 780 |
| agagccgatt gcggcttcac cagcgagagc taccagcagg gcgtgctgag cgccaccatc | 840 |
| ctgtacgaga tcctgctggg caaggccacc ctgtacgccg tgctggtgtc cgccctggtg | 900 |
| ctgatggcca tggtcaagcg aaggacagc cggggcggtt ccggagccac gaacttctct | 960 |
| ctgttaaagc aagcaggaga cgtggaagaa accccggtc ccatgatcag cctgcgggtg | 1020 |
| ctgctcgtga tcctgtggct gcagctgagc tgggtgtggt cccagcggaa agaggtggaa | 1080 |
| caggaccctg gcccccttcaa cgtgccagag gcgccaccg tggccttcaa ctgcacctac | 1140 |
| agcaacagcg ccagccagag cttcttctgg tacagacagg actgccggaa agaacccaag | 1200 |
| ctgctgatga gcgtgtacag cagcggcaac gaggacggca gattcaccgc ccagctgaac | 1260 |
| agagcctccc agtacatctc cctgctgatc cgggacagca gctgagcga cagcgccacc | 1320 |
| tacctgtgcg tcgtgaagcc tgatcctggc gccgaagct accagctgac ctttggcaag | 1380 |
| ggcaccaagc tgtccgtgat ccccaacatc cagaaccccg accccgcagt gtaccagctg | 1440 |
| cgggacagca gagcagcga caagagcgtg tgcctgttca ccgacttcga cagccagacc | 1500 |
| aacgtgtccc agagcaagga cagcgacgtg tacatcaccg ataagtgcgt gctggacatg | 1560 |
| cggagcatgg acttcaagag caacagcgcc gtggcctggt ccaacaagag cgacttcgcc | 1620 |
| tgcgccaacg ccttcaacaa cagcattatc cccgaggaca cattcttccc aagccccgag | 1680 |
| agcagctgcg acgtgaagct ggtggaaaag agcttcgaga cagacaccaa cctgaacttc | 1740 |
| cagaacctca gcgtgatcgg cttccggatc ctgctgctga aggtggccgg cttcaacctg | 1800 |
| ctgatgaccc tgcggctgtg gtccagctga | 1830 |

<210> SEQ ID NO 200
<211> LENGTH: 414
<212> TYPE: DNA
<213> ORGANISM: Artificial Sequence
<220> FEATURE:
<223> OTHER INFORMATION: WT371 alpha chain variable domain WT

<400> SEQUENCE: 200

| | |
|---|---|
| atgtcacttt ctagcctgct gaaggtggtc acagcttcac tgtggctagg acctggcatt | 60 |
| gcccagaaga taactcaaac ccaaccagga atgttcgtgc aggaaaagga ggctgtgact | 120 |
| ctggactgca catatgacac cagtgatcca agttatggtc tattctggta caagcagccc | 180 |
| agcagtgggg aaatgatttt tcttatttat caggggtctt atgaccagca aaatgcaaca | 240 |
| gaaggtcgct actcattgaa tttccagaag gcaagaaaat ccgccaacct tgtcatctcc | 300 |
| gcttcacaac tgggggactc agcaatgtac ttctgtgcaa tgagagctcg ggaagaaacc | 360 |

```
agtggctcta ggttgacctt tggggaagga acacagctca cagtgaatcc tgat         414
```

<210> SEQ ID NO 201
<211> LENGTH: 414
<212> TYPE: DNA
<213> ORGANISM: Artificial Sequence
<220> FEATURE:
<223> OTHER INFORMATION: WT371 alpha chain variable domain - Codon
      Optimized

<400> SEQUENCE: 201

```
atgagcctga gcagcctgct gaaagtcgtg accgccagcc tgtggctggg acctggaatc    60
gcccagaaga tcacccagac ccagcccggc atgttcgtgc aggaaaaaga agccgtgacc   120
ctggactgca cctacgacac cagcgaccct agctacggcc tgttctggta caagcagccc   180
agcagcggcg agatgatctt cctgatctac cagggcagct acgaccagca gaacgccacc   240
gagggccggt acagcctgaa cttccagaag gcccggaagt ccgccaacct cgtgatcagc   300
gctagccagc tgggcgacag cgccatgtac ttttgcgcca tgcgggccag agaggaaacc   360
agcggcagca gactgacctt cggcgagggc acacagctga ccgtgaaccc cgac         414
```

<210> SEQ ID NO 202
<211> LENGTH: 837
<212> TYPE: DNA
<213> ORGANISM: Artificial Sequence
<220> FEATURE:
<223> OTHER INFORMATION: WT371 alpha chain WT

<400> SEQUENCE: 202

```
atgtcacttt ctagcctgct gaaggtggtc acagcttcac tgtggctagg acctggcatt    60
gcccagaaga taactcaaac ccaaccagga atgttcgtgc aggaaaagga ggctgtgact   120
ctggactgca catatgacac cagtgatcca gttatggtc tattctggta caagcagccc   180
agcagtgggg aaatgatttt tcttatttat caggggtctt atgaccagca aaatgcaaca   240
gaaggtcgct actcattgaa tttccagaag gcaagaaaat ccgccaacct tgtcatctcc   300
gcttcacaac tgggggactc agcaatgtac ttctgtgcaa tgagagctcg ggaagaaacc   360
agtggctcta ggttgacctt tggggaagga acacagctca cagtgaatcc tgatatccag   420
aaccctgacc ctgccgtgta ccagctgaga gactctaaat ccagtgacaa gtctgtctgc   480
ctattcaccg attttgattc tcaaacaaat gtgtcacaaa gtaaggattc tgatgtgtat   540
atcacagaca aaactgtgct agacatgagg tctatggact tcaagagcaa cagtgctgtg   600
gcctggagca acaaatctga ctttgcatgt gcaaacgcct tcaacaacag cattattcca   660
gaagacacct tcttccccag cccagaaagt tcctgtgatg tcaagctggt cgagaaaagc   720
tttgaaacag atacgaacct aaactttcaa aacctgtcag tgattgggtt ccgaatcctc   780
ctcctgaaag tggccgggtt taatctgctc atgacgctgc ggctgtggtc cagctga      837
```

<210> SEQ ID NO 203
<211> LENGTH: 837
<212> TYPE: DNA
<213> ORGANISM: Artificial Sequence
<220> FEATURE:
<223> OTHER INFORMATION: WT371 alpha chain - Codon-Optimized, Cys
      Modified

<400> SEQUENCE: 203

```
atgagcctga gcagcctgct gaaagtcgtg accgccagcc tgtggctggg acctggaatc    60
```

```
gcccagaaga tcacccagac ccagcccggc atgttcgtgc aggaaaaaga agccgtgacc    120
ctggactgca cctacgacac cagcgaccct agctacggcc tgttctggta caagcagccc    180
agcagcggcg agatgatctt cctgatctac cagggcagct acgaccagca gaacgccacc    240
gagggccggt acagcctgaa cttccagaag gcccggaagt ccgccaacct cgtgatcagc    300
gctagccagc tgggcgacag cgccatgtac ttttgcgcca tgcgggccag agaggaaacc    360
agcggcagca gactgacctt cggcgagggc acacagctga ccgtgaaccc cgacatccag    420
aaccccgatc cgcagtgtac cagctgcggg acagcaagaa gcagcgacaa gagcgtgtgc    480
ctgttcaccg acttcgacag ccagaccaac gtgtcccaga gcaaggacag cgacgtgtac    540
atcaccgata agtgcgtgct ggacatgcgg agcatggact tcaagagcaa cagcgccgtg    600
gcctggtcca caagagcga cttcgcctgc gccaacgcct tcaacaacag cattatcccc    660
gaggacacat tcttcccaag ccccgagagc agctgcgacg tgaagctggt ggaaaagagc    720
ttcgagacag acaccaacct gaacttccag aacctcagcg tgatcggctt ccggatcctg    780
ctgctgaagg tggccggctt caacctgctg atgacccTgc ggctgtggtc cagctga       837
```

```
<210> SEQ ID NO 204
<211> LENGTH: 399
<212> TYPE: DNA
<213> ORGANISM: Artificial Sequence
<220> FEATURE:
<223> OTHER INFORMATION: WT371 beta chain variable domain WT

<400> SEQUENCE: 204
```

```
atgggctgca ggctcctctg ctgtgtggtc ttctgcctcc tccaagcagg tcccttggac     60
acagctgttt cccagactcc aaaatacctg gtcacacaga tgggaaacga caagtccatt    120
aaatgtgaac aaaatctggg ccatgatact atgtattggt ataaacagga ctctaagaaa    180
tttctgaaga taatgtttag ctacaataat aaggagctca ttataaatga aacagttcca    240
aatcgcttct cacctaaatc tccagacaaa gctcacttaa atcttcacat caattccctg    300
gagcttggtg actctgctgt gtatttctgt gccagcagcc aagatggccg gtcccggccc    360
cagcattttg gtgatgggac tcgactctcc atcctagag                           399
```

```
<210> SEQ ID NO 205
<211> LENGTH: 399
<212> TYPE: DNA
<213> ORGANISM: Artificial Sequence
<220> FEATURE:
<223> OTHER INFORMATION: WT371 beta chain variable domain - Codon
      Optimized

<400> SEQUENCE: 205
```

```
atgggctgca gactgctgtg ctgcgtggtg ttctgcctgc tgcaagccgg ccctctggat     60
accgccgtgt ctcagacccc caagtacctc gtgacccaga tgggcaacga caagagcatc    120
aagtgcgagc agaacctggg ccacgacacc atgtactggt acaagcagga cagcaagaaa    180
ttcctgaaga tcatgttcag ctacaacaac aaagagctga tcatcaacga cagtgtgccc    240
aaccggttca gccccaagag ccccgataag gcccacctga acctgcacat caacagcctg    300
gaactgggcg acagcgccgt gtacttctgt gccagcagcc aggacggcag aagcagacct    360
cagcactttg gcgacggcac ccggctgagc atcctggaa                           399
```

```
<210> SEQ ID NO 206
<211> LENGTH: 528
<212> TYPE: DNA
```

<213> ORGANISM: Artificial Sequence
<220> FEATURE:
<223> OTHER INFORMATION: WT371 beta chain constant domain WT

<400> SEQUENCE: 206

```
gacctgaaca aggtgttccc acccgaggtc gctgtgtttg agccatcaga agcagagatc      60
tcccacaccc aaaaggccac actggtgtgc ctggccacag gcttcttccc cgaccacgtg     120
gagctgagct ggtgggtgaa tgggaaggag gtgcacagtg gggtcagcac ggacccgcag     180
cccctcaagg agcagcccgc cctcaatgac tccagatact gcctgagcag ccgcctgagg     240
gtctcggcca ccttctggca gaaccccgc aaccacttcc gctgtcaagt ccagttctac      300
gggctctcgg agaatgacga gtggacccag gatagggcca aacccgtcac ccagatcgtc     360
agcgccgagg cctggggtag agcagactgt ggctttacct cggtgtccta ccagcaaggg     420
gtcctgtctg ccaccatcct ctatgagatc ctgctaggga aggccaccct gtatgctgtg     480
ctggtcagcg cccttgtgtt gatggccatg gtcaagagaa aggatttc                  528
```

<210> SEQ ID NO 207
<211> LENGTH: 528
<212> TYPE: DNA
<213> ORGANISM: Artificial Sequence
<220> FEATURE:
<223> OTHER INFORMATION: WT371 beta chain constant domain - Cys Modified

<400> SEQUENCE: 207

```
gacctgaaca aggtgttccc acccgaggtc gctgtgtttg agccatcaga agcagagatc      60
tcccacaccc aaaaggccac actggtgtgc ctggccacag gcttcttccc cgaccacgtg     120
gagctgagct ggtgggtgaa tgggaaggag gtgcacagtg gggtctgcac ggacccgcag     180
cccctcaagg agcagcccgc cctcaatgac tccagatact gcctgagcag ccgcctgagg     240
gtctcggcca ccttctggca gaaccccgc aaccacttcc gctgtcaagt ccagttctac      300
gggctctcgg agaatgacga gtggacccag gatagggcca aacccgtcac ccagatcgtc     360
agcgccgagg cctggggtag agcagactgt ggctttacct cggtgtccta ccagcaaggg     420
gtcctgtctg ccaccatcct ctatgagatc ctgctaggga aggccaccct gtatgctgtg     480
ctggtcagcg cccttgtgtt gatggccatg gtcaagagaa aggatttc                  528
```

<210> SEQ ID NO 208
<211> LENGTH: 528
<212> TYPE: DNA
<213> ORGANISM: Artificial Sequence
<220> FEATURE:
<223> OTHER INFORMATION: WT371 beta chain constant domain - Codon
    Optimized

<400> SEQUENCE: 208

```
gatctgaaca aggtgttccc cccagaggtg gccgtgttcg agccttctga ggccgagatc      60
tcccacaccc agaaagccac cctcgtgtgc ctggccaccg gctttttccc cgaccacgtg     120
gaactgtctt ggtgggtcaa cggcaaagag gtgcactccg gcgtgagcac cgatccccag     180
cctctgaaag aacagcccgc cctgaacgac agccggtact gcctgagcag cagactgaga     240
gtgtccgcca ccttctggca gaaccccgg aaccacttca tgccaggt gcagttctac        300
ggcctgagcg agaacgacga gtggacccag gacagagcca agcccgtgac acagatcgtg     360
tctgccgaag cctggggcag agccgattgc ggctttacct ccgtgtccta tcagcagggc     420
gtgctgagcg ccacaatcct gtacgagatc ctgctgggca aggccaccct gtacgccgtg     480
```

```
ctggtgtctg ccctggtgct gatggccatg gtcaagcgga aggacttc              528
```

<210> SEQ ID NO 209
<211> LENGTH: 528
<212> TYPE: DNA
<213> ORGANISM: Artificial Sequence
<220> FEATURE:
<223> OTHER INFORMATION: WT371 beta chain constant domain -
      Codon-Optimized, Cys Modified

<400> SEQUENCE: 209

```
gatctgaaca aggtgttccc cccagaggtg gccgtgttcg agccttctga ggccgagatc   60
tcccacaccc agaaagccac cctcgtgtgc ctggccaccg cttttttccc cgaccacgtg  120
gaactgtctt ggtgggtcaa cggcaaagag gtgcactccg gcgtgtgcac cgatccccag  180
cctctgaaag aacagcccgc cctgaacgac agccggtact gcctgagcag cagactgaga  240
gtgtccgcca ccttctggca gaaccccggg aaccacttca tgccaggt gcagttctac   300
ggcctgagcg agaacgacga gtggacccag gacagagcca agcccgtgac acagatcgtg  360
tctgccgaag cctggggcag agccgattgc ggctttacct ccgtgtccta tcagcagggc  420
gtgctgagcg ccacaatcct gtacgagatc ctgctgggca aggccaccct gtacgccgtg  480
ctggtgtctg ccctggtgct gatggccatg gtcaagcgga aggacttc              528
```

<210> SEQ ID NO 210
<211> LENGTH: 927
<212> TYPE: DNA
<213> ORGANISM: Artificial Sequence
<220> FEATURE:
<223> OTHER INFORMATION: WT371 beta chain WT

<400> SEQUENCE: 210

```
atgggctgca ggctcctctg ctgtgtggtc ttctgcctcc tccaagcagg tcccttggac   60
acagctgttt cccagactcc aaaatacctg gtcacacaga tgggaaacga caagtccatt  120
aaatgtgaac aaaatctggg ccatgatact atgtattggt ataaacagga ctctaagaaa  180
tttctgaaga taatgtttag ctacaataat aaggagctca ttataaatga acagttcca   240
aatcgcttct cacctaaatc tccagacaaa gctcacttaa tcttcacat caattccctg  300
gagcttggtg actctgctgt gtatttctgt gccagcagcc aagatggccg gtcccggccc  360
cagcattttg gtgatgggac tcgactctcc atcctagagg acctgaacaa ggtgttccca  420
cccgaggtcg ctgtgtttga gccatcagaa gcagagatct cccacaccca aaaggccaca  480
ctggtgtgcc tggccacagg cttcttcccc gaccacgtgg agctgagctg gtgggtgaat  540
gggaaggagg tgcacagtgg ggtcagcacg gacccgcagc cctcaagga gcagcccgcc  600
ctcaatgact ccagatactg cctgagcagc cgcctgaggg tctcggccac cttctggcag  660
aaccccgca ccacttccg ctgtcaagtc cagttctacg gctctcgga gaatgacgag    720
tggacccagg atagggccaa acccgtcacc cagatcgtca gcgccgaggc ctggggtaga  780
gcagactgtg gctttacctc ggtgtcctac cagcaagggg tcctgtctgc caccatcctc  840
tatgagatcc tgctagggaa ggccacccctg tatgctgtgc tggtcagcgc ccttgtgttg  900
atggccatgg tcaagagaaa ggatttc                                     927
```

<210> SEQ ID NO 211
<211> LENGTH: 927
<212> TYPE: DNA
<213> ORGANISM: Artificial Sequence
<220> FEATURE:

<223> OTHER INFORMATION: WT371 beta chain - Codon-Optimized, Cys
       Modified

<400> SEQUENCE: 211

```
atgggctgca gactgctgtg ctgcgtggtg ttctgcctgc tgcaagccgg ccctctggat      60
accgccgtgt ctcagacccc caagtacctc gtgacccaga tgggcaacga caagagcatc     120
aagtgcgagc agaacctggg ccacgacacc atgtactggt acaagcagga cagcaagaaa     180
ttcctgaaga tcatgttcag ctacaacaac aaagagctga tcatcaacga cagtgccc      240
aaccggttca gccccaagag ccccgataag gcccacctga acctgcacat caacagcctg     300
gaactgggcg acagcgccgt gtacttctgt gccagcagcc aggacggcag aagcagacct     360
cagcactttg gcgacggcac ccggctgagc atcctggaag atctgaacaa ggtgttcccc     420
ccagaggtgg ccgtgttcga gccttctgag gccgagatct cccacaccca gaaagccacc     480
ctcgtgtgcc tggccaccgg cttttttccc gaccacgtgg aactgtcttg gtgggtcaac     540
ggcaaagagg tgcactccgg cgtgtgcacc gatccccagc tctgaaaga acagcccgcc      600
ctgaacgaca gccggtactg cctgagcagc agactgagag tgtccgccac cttctggcag     660
aaccccgga ccacttcag atgccaggtc agttctacg gcctgagcga gaacgacgag        720
tggacccagg acagagccaa gcccgtgaca cagatcgtgt ctgccgaagc tggggcaga     780
gccgattgcg gctttacctc cgtgtcctat cagcagggcg tgctgagcgc acaatcctg      840
tacgagatcc tgctgggcaa ggccaccctg tacgccgtgc tggtgtctgc cctggtgctg     900
atggccatgg tcaagcggaa ggacttc                                          927
```

<210> SEQ ID NO 212
<211> LENGTH: 1830
<212> TYPE: DNA
<213> ORGANISM: Artificial Sequence
<220> FEATURE:
<223> OTHER INFORMATION: WT371 beta-P2A-WT371 alpha Construct - WT

<400> SEQUENCE: 212

```
atgggctgca ggctcctctg ctgtgtggtc ttctgcctcc tccaagcagg tcccttggac      60
acagctgttt cccagactcc aaaatacctg gtcacacaga tgggaaacga caagtccatt     120
aaatgtgaac aaaatctggg ccatgatact atgtattggt ataaacagga ctctaagaaa     180
tttctgaaga taatgtttag ctacaataat aaggagctca ttataaatga aacagttcca     240
aatcgcttct cacctaaatc tccagacaaa gctcacttaa atcttcacat caattccctg     300
gagcttggtg actctgctgt gtatttctgt gccagcagcc aagatggccg gtcccggccc     360
cagcattttg gtgatgggac tcgactctcc atcctagagg acctgaacaa ggtgttccca     420
cccgaggtcg ctgtgtttga gccatcagaa gcagagatct cccacaccca aaaggccaca     480
ctggtgtgcc tggccacagg cttcttcccc gaccacgtgg agctgagctg gtgggtgaat     540
gggaaggagg tgcacagtgg ggtcagcacg gacccgcagc ccctcaagga gcagcccgcc     600
ctcaatgact ccagatactg cctgagcagc cgcctgaggg tctcggccac cttctggcag     660
aaccccgca accacttccg ctgtcaagtc cagttctacg gctctcgga gaatgacgag       720
tggacccagg atagggccaa acccgtcacc cagatcgtca gcgccgaggc tggggtaga      780
gcagactgtg gctttacctc ggtgtcctac cagcaagggg tcctgtctgc caccatcctc     840
tatgagatcc tgctagggaa ggccaccctg tatgctgtgc tggtcagcgc ccttgtgttg     900
atggccatgg tcaagagaaa ggatttcggt tccggagcca cgaacttctc tctgttaaag     960
```

| | |
|---|---|
| caagcaggag acgtggaaga aaacccggt cccatgtcac tttctagcct gctgaaggtg | 1020 |
| gtcacagctt cactgtggct aggacctggc attgcccaga agataactca aacccaacca | 1080 |
| ggaatgttcg tgcaggaaaa ggaggctgtg actctggact gcacatatga caccagtgat | 1140 |
| ccaagttatg gtctattctg gtacaagcag cccagcagtg gggaaatgat tttcttatt | 1200 |
| tatcagggt cttatgacca gcaaaatgca acagaaggtc gctactcatt gaatttccag | 1260 |
| aaggcaagaa aatccgccaa ccttgtcatc tccgcttcac aactggggga ctcagcaatg | 1320 |
| tacttctgtg caatgagagc tcgggaagaa accagtggct ctaggttgac ctttggggaa | 1380 |
| ggaacacagc tcacagtgaa tcctgatatc cagaaccctg accctgccgt gtaccagctg | 1440 |
| agagactcta aatccagtga caagtctgtc tgcctattca ccgattttga ttctcaaaca | 1500 |
| aatgtgtcac aaagtaagga ttctgatgtg tatatcacag acaaaactgt gctagacatg | 1560 |
| aggtctatgg acttcaagag caacagtgct gtggcctgga gcaacaaatc tgactttgca | 1620 |
| tgtgcaaacg ccttcaacaa cagcattatt ccagaagaca ccttcttccc cagcccagaa | 1680 |
| agttcctgtg atgtcaagct ggtcgagaaa agctttgaaa cagatacgaa cctaaacttt | 1740 |
| caaaacctgt cagtgattgg gttccgaatc ctcctcctga agtggccgg gtttaatctg | 1800 |
| ctcatgacgc tgcggctgtg gtccagctga | 1830 |

<210> SEQ ID NO 213
<211> LENGTH: 1830
<212> TYPE: DNA
<213> ORGANISM: Artificial Sequence
<220> FEATURE:
<223> OTHER INFORMATION: WT371 beta-P2A-WT371 alpha Construct -
      Codon-Optimized, Cys Modified

<400> SEQUENCE: 213

| | |
|---|---|
| atgggctgca gactgctgtg ctgcgtggtg ttctgcctgc tgcaagccgg ccctctggat | 60 |
| accgccgtgt ctcagacccc caagtacctc gtgacccaga tgggcaacga caagagcatc | 120 |
| aagtgcgagc agaacctggg ccacgacacc atgtactggt acaagcagga cagcaagaaa | 180 |
| ttcctgaaga tcatgttcag ctacaacaac aaagagctga tcatcaacga cagtgccc | 240 |
| aaccggttca gccccaagag ccccgataag gcccacctga acctgcacat caacagcctg | 300 |
| gaactgggcg acagcgccgt gtacttctgt gccagcagcc aggacggcag aagcagacct | 360 |
| cagcactttg gcgacggcac ccggctgagc atcctggaag atctgaacaa ggtgttcccc | 420 |
| ccagaggtgg ccgtgttcga gccttctgag ccgagatct cccacaccca gaaagccacc | 480 |
| ctcgtgtgcc tggccaccgg cttttttccc gaccacgtgg aactgtcttg gtgggtcaac | 540 |
| ggcaaagagg tgcactccgg cgtgtgcacc gatcccagc tctgaaaga cagcccgcc | 600 |
| ctgaacgaca gccggtactg cctgagcagc agactgagag tgtccgccac cttctggcag | 660 |
| aaccccgga ccacttcag atgccaggtg cagttctacg gcctgagcga aacgacgag | 720 |
| tggacccagg acagagccaa gcccgtgaca cagatcgtgt ctgccgaagc tggggcaga | 780 |
| gccgattgcg gctttaccctc cgtgtcctat cagcagggcg tgctgagcgc acaatcctg | 840 |
| tacgagatcc tgctgggcaa ggccaccctg tacgccgtgc tggtgtctgc cctggtgctg | 900 |
| atggccatgg tcaagcggaa ggacttcggt tccggagcca cgaacttctc tctgttaaag | 960 |
| caagcaggag acgtggaaga aaaccccggt cccatgagcc tgagcagcct gctgaaagtc | 1020 |
| gtgaccgcca gctgtggct gggacctgga atcgcccaga agatcaccca gacccagccc | 1080 |
| ggcatgttcg tgcaggaaaa agaagccgtg accctggact gcacctacga caccagcgac | 1140 |

-continued

| | |
|---|---|
| cctagctacg gcctgttctg gtacaagcag cccagcagcg gcgagatgat cttcctgatc | 1200 |
| taccagggca gctacgacca gcagaacgcc accgagggcc ggtacagcct gaacttccag | 1260 |
| aaggcccgga agtccgccaa cctcgtgatc agcgctagcc agctgggcga cagcgccatg | 1320 |
| tacttttgcg ccatgcgggc cagagaggaa accagcggca gcagactgac cttcggcgag | 1380 |
| ggcacacagc tgaccgtgaa ccccgacatc cagaaccccg atcccgcagt gtaccagctg | 1440 |
| cgggacagca agagcagcga caagagcgtg tgcctgttca ccgacttcga cagccagacc | 1500 |
| aacgtgtccc agagcaagga cagcgacgtg tacatcaccg ataagtgcgt gctggacatg | 1560 |
| cggagcatgg acttcaagag caacagcgcc gtggcctggt ccaacaagag cgacttcgcc | 1620 |
| tgcgccaacg ccttcaacaa cagcattatc cccgaggaca cattcttccc aagccccgag | 1680 |
| agcagctgcg acgtgaagct ggtggaaaag agcttcgaga cagacaccaa cctgaacttc | 1740 |
| cagaacctca gcgtgatcgg cttccggatc ctgctgctga aggtggccgg cttcaacctg | 1800 |
| ctgatgaccc tgcggctgtg gtccagctga | 1830 |

<210> SEQ ID NO 214
<211> LENGTH: 399
<212> TYPE: DNA
<213> ORGANISM: Artificial Sequence
<220> FEATURE:
<223> OTHER INFORMATION: WT372 alpha chain variable domain WT

<400> SEQUENCE: 214

| | |
|---|---|
| atgaaatcct tgagagtttt actagtgatc ctgtggcttc agttgagctg ggtttggagc | 60 |
| caacagaagg aggtggagca gaattctgga cccctcagtg ttccagaggg agccattgcc | 120 |
| tctctcaact gcacttacag tgaccgaggt tcccagtcct tcttctggta cagacaatat | 180 |
| tctgggaaaa gccctgagtt gataatgttc atatactcca atggtgacaa agaagatgga | 240 |
| aggtttacag cacagctcaa taaagccagc cagtatgttt ctctgctcat cagagactcc | 300 |
| cagcccagtg attcagccac ctacctctgt gccgttccta cctcaggaac ctacaaatac | 360 |
| atctttggaa caggcaccag gctgaaggtt ttagcaaat | 399 |

<210> SEQ ID NO 215
<211> LENGTH: 399
<212> TYPE: DNA
<213> ORGANISM: Artificial Sequence
<220> FEATURE:
<223> OTHER INFORMATION: WT372 alpha chain variable domain - Codon
    Optimized

<400> SEQUENCE: 215

| | |
|---|---|
| atgaagtccc tgcgggtgct gctcgtgatc ctgtggctgc agctgagctg ggtgtggtcc | 60 |
| cagcagaaag aggtggaaca gaacagcggc cctctgagcg tgccagaagg cgctatcgcc | 120 |
| agcctgaact gcacctacag cgacagaggc agccagagct tcttctggta cagacagtac | 180 |
| agcggcaaga gccccgagct gatcatgttc atctacagca acggcgacaa agaggacggc | 240 |
| cggttcaccg cccagctgaa caaggccagc cagtacgtgt ccctgctgat cagagacagc | 300 |
| cagcccagcg acagcgccac ctatctgtgt gccgtgccta ccagcggcac ctacaagtac | 360 |
| atcttcggca ccggcacccg gctgaaggtg ctggccaac | 399 |

<210> SEQ ID NO 216
<211> LENGTH: 822
<212> TYPE: DNA
<213> ORGANISM: Artificial Sequence
<220> FEATURE:

<223> OTHER INFORMATION: WT372 alpha chain WT

<400> SEQUENCE: 216

| | |
|---|---|
| atgaaatcct tgagagtttt actagtgatc ctgtggcttc agttgagctg ggtttggagc | 60 |
| caacagaagg aggtggagca gaattctgga cccctcagtg ttccagaggg agccattgcc | 120 |
| tctctcaact gcacttacag tgaccgaggt tcccagtcct tcttctggta cagacaatat | 180 |
| tctgggaaaa gccctgagtt gataatgttc atatactcca atggtgacaa agaagatgga | 240 |
| aggtttacag cacagctcaa taaagccagc cagtatgttt ctctgctcat cagagactcc | 300 |
| cagcccagtg attcagccac ctacctctgt gccgttccta cctcaggaac ctacaaatac | 360 |
| atctttggaa caggcaccag gctgaaggtt ttagcaaata tccagaaccc tgaccctgcc | 420 |
| gtgtaccagc tgagagactc taaatccagt gacaagtctg tctgcctatt caccgatttt | 480 |
| gattctcaaa caaatgtgtc acaaagtaag gattctgatg tgtatatcac agacaaaact | 540 |
| gtgctagaca tgaggtctat ggacttcaag agcaacagtg ctgtggcctg gagcaacaaa | 600 |
| tctgactttg catgtgcaaa cgccttcaac aacagcatta ttccagaaga caccttcttc | 660 |
| cccagcccag aaagttcctg tgatgtcaag ctggtcgaga aaagctttga aacagatacg | 720 |
| aacctaaact ttcaaaacct gtcagtgatt gggttccgaa tcctcctcct gaaagtggcc | 780 |
| gggtttaatc tgctcatgac gctgcggctg tggtccagct ga | 822 |

<210> SEQ ID NO 217
<211> LENGTH: 822
<212> TYPE: DNA
<213> ORGANISM: Artificial Sequence
<220> FEATURE:
<223> OTHER INFORMATION: WT372 alpha chain - Codon-Optimized, Cys Modified

<400> SEQUENCE: 217

| | |
|---|---|
| atgaagtccc tgcgggtgct gctcgtgatc ctgtggctgc agctgagctg ggtgtggtcc | 60 |
| cagcagaaag aggtggaaca gaacagcggc cctctgagcg tgccagaagg cgctatcgcc | 120 |
| agcctgaact gcacctacag cgacagaggc agccagagct tcttctggta cagacagtac | 180 |
| agcggcaaga gccccgagct gatcatgttc atctacagca acggcgacaa agaggacggc | 240 |
| cggttcaccg cccagctgaa caaggccagc cagtacgtgt ccctgctgat cagagacagc | 300 |
| cagcccagcg acagcgccac ctatctgtgt gccgtgccta ccagcggcac ctacaagtac | 360 |
| atcttcggca ccggcacccg gctgaaggtg ctggccaaca tccagaaccc cgaccccgca | 420 |
| gtgtaccagc tgcgggacag caagagcagc gacaagagct gtgcctgtt caccgacttc | 480 |
| gacagccaga ccaacgtgtc ccagagcaag gacagcgacg tgtacatcac cgataagtgc | 540 |
| gtgctggaca tgcggagcat ggacttcaag agcaacagcg ccgtggcctg gtccaacaag | 600 |
| agcgacttcg cctgcgccaa cgccttcaac aacagcatta tccccgagga cacattcttc | 660 |
| ccaagccccg agagcagctg cgacgtgaag ctggtggaaa agagcttcga cacagacacc | 720 |
| aacctgaact tccagaacct cagcgtgatc ggcttccgga tcctgctgct gaaggtggcc | 780 |
| ggcttcaacc tgctgatgac cctgcggctg tggtccagct ga | 822 |

<210> SEQ ID NO 218
<211> LENGTH: 402
<212> TYPE: DNA
<213> ORGANISM: Artificial Sequence
<220> FEATURE:
<223> OTHER INFORMATION: WT372 beta chain variable domain WT

<400> SEQUENCE: 218

```
atgagcaacc aggtgctctg ctgtgtggtc ctttgtttcc tgggagcaaa caccgtggat    60
ggtggaatca ctcagtcccc aaagtacctg ttcagaaagg aaggacagaa tgtgaccctg   120
agttgtgaac agaatttgaa ccacgatgcc atgtactggt accgacagga cccagggcaa   180
gggctgagat tgatctacta ctcacagata gtaaatgact ttcagaaagg agatatagct   240
gaagggtaca gcgtctctcg ggagaagaag gaatcctttc ctctcactgt gacatcggcc   300
caaaagaacc cgacagcttt ctatctctgt gccagtagta tcaggattc aagcaatcag   360
ccccagcatt ttggtgatgg gactcgactc tccatcctag ag                      402
```

<210> SEQ ID NO 219
<211> LENGTH: 402
<212> TYPE: DNA
<213> ORGANISM: Artificial Sequence
<220> FEATURE:
<223> OTHER INFORMATION: WT372 beta chain variable domain - Codon Optimized

<400> SEQUENCE: 219

```
atgagcaacc aggtgctgtg ctgcgtggtg ctgtgtttcc tgggcgccaa cacagtggac    60
ggcggcatca cacagagccc caagtacctg ttccggaaag agggccagaa cgtgaccctg   120
agctgcgagc agaacctgaa ccacgacgcc atgtactggt acagacagga cccaggccag   180
ggcctgcggc tgatctacta cagccagatc gtgaacgact ccagaaggg cgacattgcc   240
gagggctaca gcgtgtccag agagaagaaa gagtccttcc cactgaccgt gaccagcgcc   300
cagaagaacc ccaccgcctt ctacctgtgc gccagcagca tccgggacag cagcaatcag   360
cctcagcact tcggcgacgg cacccggctg agcatcctgg aa                      402
```

<210> SEQ ID NO 220
<211> LENGTH: 930
<212> TYPE: DNA
<213> ORGANISM: Artificial Sequence
<220> FEATURE:
<223> OTHER INFORMATION: WT372 beta chain WT

<400> SEQUENCE: 220

```
atgagcaacc aggtgctctg ctgtgtggtc ctttgtttcc tgggagcaaa caccgtggat    60
ggtggaatca ctcagtcccc aaagtacctg ttcagaaagg aaggacagaa tgtgaccctg   120
agttgtgaac agaatttgaa ccacgatgcc atgtactggt accgacagga cccagggcaa   180
gggctgagat tgatctacta ctcacagata gtaaatgact ttcagaaagg agatatagct   240
gaagggtaca gcgtctctcg ggagaagaag gaatcctttc ctctcactgt gacatcggcc   300
caaaagaacc cgacagcttt ctatctctgt gccagtagta tcaggattc aagcaatcag   360
ccccagcatt ttggtgatgg gactcgactc tccatcctag aggacctgaa caaggtgttc   420
ccacccgagg tcgctgtgtt tgagccatca gaagcagaga tctcccacac ccaaaaggcc   480
acactggtgt gcctggccac aggcttcttc cccgaccacg tggagctgag ctggtgggtg   540
aatgggaagg aggtgcacag tggggtcagc acggacccgc agcccctcaa ggagcagccc   600
gccctcaatg actccagata ctgcctgagc agccgcctga gggtctcggc caccttctgg   660
cagaaccccc gcaaccactt ccgctgtcaa gtccagttct acgggctctc ggagaatgac   720
gagtggaccc aggataggc caaacccgtc acccagatcg tcagcgccga ggcctgggt   780
agagcagact gtggctttac ctcggtgtcc taccagcaag ggtcctgtc tgccaccatc   840
```

```
ctctatgaga tcctgctagg gaaggccacc ctgtatgctg tgctggtcag cgcccttgtg    900
ttgatggcca tggtcaagag aaaggatttc                                     930
```

<210> SEQ ID NO 221
<211> LENGTH: 930
<212> TYPE: DNA
<213> ORGANISM: Artificial Sequence
<220> FEATURE:
<223> OTHER INFORMATION: WT372 beta chain - Codon-Optimized, Cys
      Modified

<400> SEQUENCE: 221

```
atgagcaacc aggtgctgtg ctgcgtggtg ctgtgtttcc tgggcgccaa cacagtggac     60
ggcggcatca cacagagccc caagtacctg ttccggaaag agggccagaa cgtgaccctg    120
agctgcgagc agaacctgaa ccacgacgcc atgtactggt acagacagga cccaggccag    180
ggcctgcggc tgatctacta cagccagatc gtgaacgact ccagaaggg cgacattgcc    240 gagggctaca cgtgtccag agagaagaaa gagtccttcc cactgaccgt gaccagcgcc    300
cagaagaacc ccaccgcctt ctacctgtgc gccagcagca tccgggacag cagcaatcag    360
cctcagcact cggcgacgg cacccggctg agcatcctgg aagatctgaa caaggtgttc    420
cccccagagg tggccgtgtt cgagccttct gaggccgaga tctcccacac ccagaaagcc    480
accctcgtgt gcctggccac cggctttttc cccgaccacg tggaactgtc ttggtgggtc    540
aacggcaaag aggtgcactc cggcgtgtgc accgatcccc agcctctgaa agaacagccc    600
gccctgaacg acagccggta ctgcctgagc agcagactga gagtgtccgc caccttctgg    660
cagaaccccc ggaaccactt cagatgccag gtgcagttct acggcctgag cgagaacgac    720
gagtggaccc aggacagagc caagcccgtg acacagatcg tgtctgccga gcctggggc    780 agagccgatt gcggctttac ctccgtgtcc tatcagcagg gcgtgctgag cgccacaatc    840
ctgtacgaga tcctgctggg caaggccacc ctgtacgccg tgctggtgtc tgccctggtg    900
ctgatggcca tggtcaagcg gaaggacttc                                      930
```

<210> SEQ ID NO 222
<211> LENGTH: 1818
<212> TYPE: DNA
<213> ORGANISM: Artificial Sequence
<220> FEATURE:
<223> OTHER INFORMATION: WT372 beta-P2A-WT372 alpha Construct - WT

<400> SEQUENCE: 222

```
atgagcaacc aggtgctctg ctgtgtggtc ctttgtttcc tgggagcaaa caccgtggat     60
ggtggaatca ctcagtcccc aaagtacctg ttcagaaagg aaggacagaa tgtgaccctg    120
agttgtgaac agaatttgaa ccacgatgcc atgtactggt accgacagga cccagggcaa    180
gggctgagat tgatctacta ctcacagata gtaaatgact tcagaaagg agatatagct    240 gaagggtaca cgtctctcg ggagaagaag gaatccttc ctctcactgt gacatcggcc    300
caaaagaacc cgacagcttt ctatctctgt gccagtagta tcagggattc aagcaatcag    360
ccccagcatt ttggtgatgg gactcgactc tccatcctag aggacctgaa caaggtgttc    420
ccacccgagg tcgctgtgtt tgagccatca gaagcagaga tctcccacac ccaaaaggcc    480
acactggtgt gcctggccac aggcttcttc cccgaccacg tggagctgag ctggtgggtg    540
aatgggaagg aggtgcacag tggggtcagc acggacccgc agcccctcaa ggagcagccc    600
gccctcaatg actccagata ctgcctgagc agccgcctga gggtctcggc caccttctgg    660
```

| | |
|---|---|
| cagaaccccc gcaaccactt ccgctgtcaa gtccagttct acgggctctc ggagaatgac | 720 |
| gagtggaccc aggatagggc caaacccgtc acccagatcg tcagcgccga ggcctggggt | 780 |
| agagcagact gtggctttac ctcggtgtcc taccagcaag gggtcctgtc tgccaccatc | 840 |
| ctctatgaga tcctgctagg gaaggccacc ctgtatgctg tgctggtcag cgcccttgtg | 900 |
| ttgatggcca tggtcaagag aaaggatttc ggttccggag ccacgaactt ctctctgtta | 960 |
| aagcaagcag agacgtggga agaaaacccc ggtcccatga atccttgag agttttacta | 1020 |
| gtgatcctgt ggcttcagtt gagctgggtt tggagccaac agaaggaggt ggagcagaat | 1080 |
| tctggacccc tcagtgttcc agagggagcc attgcctctc tcaactgcac ttacagtgac | 1140 |
| cgaggttccc agtccttctt ctggtacaga caatattctg ggaaaagccc tgagttgata | 1200 |
| atgttcatat actccaatgg tgacaaagaa gatggaaggt ttacagcaca gctcaataaa | 1260 |
| gccagccagt atgtttctct gctcatcaga gactcccagc cagtgattc agccacctac | 1320 |
| ctctgtgccg ttcctacctc aggaacctac aaatacatct ttggaacagg caccaggctg | 1380 |
| aaggttttag caaatatcca gaaccctgac cctgccgtgt accagctgag agactctaaa | 1440 |
| tccagtgaca gtctgtctg cctattcacc gattttgatt ctcaaacaaa tgtgtcacaa | 1500 |
| agtaaggatt ctgatgtgta tatcacagac aaaactgtgc tagacatgag gtctatggac | 1560 |
| ttcaagagca acagtgctgt ggcctggagc aacaaatctg actttgcatg tgcaaacgcc | 1620 |
| ttcaacaaca gcattattcc agaagacacc ttcttcccca gcccagaaag ttcctgtgat | 1680 |
| gtcaagctgg tcgagaaaag ctttgaaaca gatacgaacc taaactttca aaacctgtca | 1740 |
| gtgattgggt tccgaatcct cctcctgaaa gtggccgggt taatctgct catgacgctg | 1800 |
| cggctgtggt ccagctga | 1818 |

<210> SEQ ID NO 223
<211> LENGTH: 1818
<212> TYPE: DNA
<213> ORGANISM: Artificial Sequence
<220> FEATURE:
<223> OTHER INFORMATION: WT372 beta-P2A-WT372 alpha Construct -
      Codon-Optimized, Cys Modified

<400> SEQUENCE: 223

| | |
|---|---|
| atgagcaacc aggtgctgtg ctgcgtggtg ctgtgtttcc tgggcgccaa cacagtggac | 60 |
| ggcggcatca cacagagccc caagtacctg ttccggaaag agggcagaa cgtgaccctg | 120 |
| agctgcgagc agaacctgaa ccacgacgcc atgtactggt acagacagga cccaggccag | 180 |
| ggcctgcggc tgatctacta cagccagatc gtgaacgact ccagaagggg cgacattgcc | 240 |
| gagggctaca gcgtgtccag agagaagaaa gagtccttcc cactgaccgt gaccagcgcc | 300 |
| cagaagaacc ccaccgcctt ctacctgtgc gccagcagca tcgggacag cagcaatcag | 360 |
| cctcagcact cggcgacgg caccggctg agcatcctgg aagatctgaa caaggtgttc | 420 |
| cccccagagg tggccgtgtt cgagccttct gaggccgaga tctcccacac ccagaaagcc | 480 |
| acctcgtgt gcctggccac cggcttttc cccgaccacg tggaactgtc ttggtgggtc | 540 |
| aacggcaaag aggtgcactc cggcgtgtgc accgatcccc agcctctgaa gaacagccc | 600 |
| gccctgaacg cagccggta ctgcctgagc agcagactga gagtgtccgc caccttctgg | 660 |
| cagaaccccc ggaaccactt cagatgccag gtgcagttct acggcctgag cgagaacgac | 720 |
| gagtggaccc aggacagagc caagcccgtg acacagatcg tgtctgccga gcctggggc | 780 |
| agagccgatt gcggctttac ctccgtgtcc tatcagcagg gcgtgctgag cgccacaatc | 840 |

| | |
|---|---:|
| ctgtacgaga tcctgctggg caaggccacc ctgtacgccg tgctggtgtc tgccctggtg | 900 |
| ctgatggcca tggtcaagcg gaaggacttc ggttccggag ccacgaactt ctctctgtta | 960 |
| aagcaagcag gagacgtgga agaaaacccc ggtcccatga agtccctgcg ggtgctgctc | 1020 |
| gtgatcctgt ggctgcagct gagctgggtg tggtcccagc agaaagaggt ggaacagaac | 1080 |
| agcggccctc tgagcgtgcc agaaggcgct atcgccagcc tgaactgcac ctacagcgac | 1140 |
| agaggcagcc agagcttctt ctggtacaga cagtacagcg gcaagagccc cgagctgatc | 1200 |
| atgttcatct acagcaacgg cgacaaagag gacggccggt tcaccgccca gctgaacaag | 1260 |
| gccagccagt acgtgtccct gctgatcaga gacagccagc ccagcgacag cgccacctat | 1320 |
| ctgtgtgccg tgcctaccag cggcacctac aagtacatct tcggcaccgg cacccggctg | 1380 |
| aaggtgctgg ccaacatcca gaaccccgac cccgcagtgt accagctgcg ggacagcaag | 1440 |
| agcagcgaca gagcgtgtg cctgttcacc gacttcgaca gccagaccaa cgtgtcccag | 1500 |
| agcaaggaca gcgacgtgta catcaccgat aagtgcgtgc tggacatgcg gagcatggac | 1560 |
| ttcaagagca acagcgccgt ggcctggtcc aacaagagcg acttcgcctg cgccaacgcc | 1620 |
| ttcaacaaca gcattatccc cgaggacaca ttcttcccaa gccccgagag cagctgcgac | 1680 |
| gtgaagctgg tggaaaagag cttcgagaca gacaccaacc tgaacttcca gaacctcagc | 1740 |
| gtgatcggct ccggatcct gctgctgaag gtggccggct tcaacctgct gatgaccctg | 1800 |
| cggctgtggt ccagctga | 1818 |

<210> SEQ ID NO 224
<211> LENGTH: 426
<212> TYPE: DNA
<213> ORGANISM: Artificial Sequence
<220> FEATURE:
<223> OTHER INFORMATION: WT373 alpha chain variable domain WT

<400> SEQUENCE: 224

| | |
|---|---:|
| atggccatgc tcctgggggc atcagtgctg attctgtggc ttcagccaga ctgggtaaac | 60 |
| agtcaacaga gaatgatga ccagcaagtt aagcaaaatt caccatccct gagcgtccag | 120 |
| gaaggaagaa tttctattct gaactgtgac tatactaaca gcatgtttga ttatttccta | 180 |
| tggtacaaaa ataccctgc tgaaggtcct acattcctga tatctataag ttccattaag | 240 |
| gataaaaatg aagatggaag attcactgtc ttcttaaaca aaagtgccaa gcacctctct | 300 |
| ctgcacattg tgccctccca gcctggagac tctgcagtgt acttctgtgc agcaggggct | 360 |
| cggggtggta ctagctatgg aaagctgaca tttggacaag ggaccatctt gactgtccat | 420 |
| ccaaat | 426 |

<210> SEQ ID NO 225
<211> LENGTH: 426
<212> TYPE: DNA
<213> ORGANISM: Artificial Sequence
<220> FEATURE:
<223> OTHER INFORMATION: WT373 alpha chain variable domain - Codon Optimized

<400> SEQUENCE: 225

| | |
|---|---:|
| atggctatgc tgctgggcgc ctctgtgctg atcctgtggc tgcagcccga ctgggtcaac | 60 |
| agccagcaga gaacgacga ccagcaagtg aagcagaaca gccccagcct gagcgtgcag | 120 |
| gaaggccgga tcagcatcct gaactgcgac tacaccaact ctatgttcga ctacttcctg | 180 |
| tggtacaaga gtaccccgc cgagggcccc accttcctga tctccatcag cagcatcaag | 240 |

```
gacaagaacg aggacggccg gttcaccgtg tttctgaaca agagcgccaa gcacctgagc    300
ctgcacatcg tgcctagcca gcctggcgat agcgccgtgt acttttgtgc cgctggcgct    360
agaggcggca ccagctatgg caagctgacc tttggccagg gcaccatcct gaccgtgcac    420
cccaac                                                               426
```

<210> SEQ ID NO 226
<211> LENGTH: 849
<212> TYPE: DNA
<213> ORGANISM: Artificial Sequence
<220> FEATURE:
<223> OTHER INFORMATION: WT373 alpha chain WT

<400> SEQUENCE: 226

```
atggccatgc tcctgggggc atcagtgctg attctgtggc ttcagccaga ctgggtaaac     60
agtcaacaga agaatgatga ccagcaagtt aagcaaaatt caccatccct gagcgtccag    120
gaaggaagaa tttctattct gaactgtgac tatactaaca gcatgtttga ttatttccta    180
tggtacaaaa ataccctgc tgaaggtcct acattcctga tatctataag ttccattaag    240
gataaaaatg aagatggaag attcactgtc ttcttaaaca aaagtgccaa gcacctctct    300
ctgcacattg tgccctccca gcctggagac tctgcagtgt acttctgtgc agcaggggct    360
cggggtggta ctagctatgg aaagctgaca tttggacaag ggaccatctt gactgtccat    420
ccaaatatcc agaaccctga ccctgccgtg taccagctga gagactctaa atccagtgac    480
aagtctgtct gcctattcac cgattttgat tctcaaacaa atgtgtcaca aagtaaggat    540
tctgatgtgt atatcacaga caaaactgtg ctagacatga ggtctatgga cttcaagagc    600
aacagtgctg tggcctggag caacaaatct gactttgcat gtgcaaacgc cttcaacaac    660
agcattattc cagaagacac cttcttcccc agcccagaaa gttcctgtga tgtcaagctg    720
gtcgagaaaa gctttgaaac agatacgaac ctaaactttc aaaacctgtc agtgattggg    780
ttccgaatcc tcctcctgaa agtggccggg tttaatctgc tcatgacgct gcggctgtgg    840
tccagctga                                                            849
```

<210> SEQ ID NO 227
<211> LENGTH: 849
<212> TYPE: DNA
<213> ORGANISM: Artificial Sequence
<220> FEATURE:
<223> OTHER INFORMATION: WT373 alpha chain - Codon-Optimized, Cys
     Modified

<400> SEQUENCE: 227

```
atggctatgc tgctgggcgc ctctgtgctg atcctgtggc tgcagcccga ctgggtcaac     60
agccagcaga gaacgacga ccagcaagtg aagcagaaca gccccagcct gagcgtgcag    120
gaaggccgga tcagcatcct gaactgcgac tacaccaact ctatgttcga ctacttcctg    180
tggtacaaga agtaccccgc cgagggccc accttcctga tctccatcag cagcatcaag    240
gacaagaacg aggacggccg gttcaccgtg tttctgaaca agagcgccaa gcacctgagc    300
ctgcacatcg tgcctagcca gcctggcgat agcgccgtgt acttttgtgc cgctggcgct    360
agaggcggca ccagctatgg caagctgacc tttggccagg gcaccatcct gaccgtgcac    420
cccaacatcc agaaccccga ccctgcagtg taccagctgc gggacagcaa gagcagcgac    480
aagagcgtgt gcctgttcac cgacttcgac agccagacca acgtgtccca gagcaaggac    540
agcgacgtgt acatcaccga taagtgcgtg ctggacatgc ggagcatgga cttcaagagc    600
```

```
aacagcgccg tggcctggtc aacaagagc gacttcgcct gcgccaacgc cttcaacaac    660
agcattatcc ccgaggacac attcttccca gcccccgaga gcagctgcga cgtgaagctg    720
gtggaaaaga gcttcgagac agacaccaac ctgaacttcc agaacctcag cgtgatcggc    780
ttccggatcc tgctgctgaa ggtggccggc ttcaacctgc tgatgaccct gcggctgtgg    840
tccagctga                                                           849

<210> SEQ ID NO 228
<211> LENGTH: 405
<212> TYPE: DNA
<213> ORGANISM: Artificial Sequence
<220> FEATURE:
<223> OTHER INFORMATION: WT373 beta chain variable domain WT

<400> SEQUENCE: 228
atgagcaacc aggtgctctg ctgtgtggtc ctttgtttcc tgggagcaaa caccgtggat     60
ggtggaatca ctcagtcccc aaagtacctg ttcagaaagg aaggacagaa tgtgaccctg    120
agttgtgaac agaatttgaa ccacgatgcc atgtactggt accgacagga cccagggcaa    180
gggctgagat tgatctacta ctcacagata gtaaatgact tcagaaagg agatatagct     240 gaagggtaca gcgtctctcg ggagaagaag gaatcctttc ctctcactgt gacatcggcc    300
caaaagaacc cgacagcttt ctatctctgt gccagtagtg ctcaggggc gtatggcaat     360 cagccccagc attttggtga tgggactcga ctctccatcc tagag                    405

<210> SEQ ID NO 229
<211> LENGTH: 405
<212> TYPE: DNA
<213> ORGANISM: Artificial Sequence
<220> FEATURE:
<223> OTHER INFORMATION: WT373 beta chain variable domain - Codon
      Optimized

<400> SEQUENCE: 229
atgagcaacc aggtgctgtg ctgcgtggtg ctgtgtttcc tgggcgccaa cacagtggac     60
ggcggcatca cacagagccc caagtacctg ttccggaaag agggccagaa cgtgaccctg    120
agctgcgagc agaacctgaa ccacgacgcc atgtactggt acagacagga cccaggccag    180
ggcctgcggc tgatctacta cagccagatc gtgaacgact ccagaaaggg cgacattgcc    240
gagggctaca gcgtgtccag agagaagaaa gagtccttcc cactgaccgt gaccagcgcc    300
cagaagaacc ccaccgcctt ctacctgtgt gccagctctg cccagggcgc ctacggaaat    360
cagcctcagc actttggcga cggcacccgg ctgagcatcc tggaa                    405

<210> SEQ ID NO 230
<211> LENGTH: 933
<212> TYPE: DNA
<213> ORGANISM: Artificial Sequence
<220> FEATURE:
<223> OTHER INFORMATION: WT373 beta chain WT

<400> SEQUENCE: 230
atgagcaacc aggtgctctg ctgtgtggtc ctttgtttcc tgggagcaaa caccgtggat     60
ggtggaatca ctcagtcccc aaagtacctg ttcagaaagg aaggacagaa tgtgaccctg    120
agttgtgaac agaatttgaa ccacgatgcc atgtactggt accgacagga cccagggcaa    180
gggctgagat tgatctacta ctcacagata gtaaatgact tcagaaagg agatatagct     240 gaagggtaca gcgtctctcg ggagaagaag gaatcctttc ctctcactgt gacatcggcc    300
```

```
caaaagaacc cgacagcttt ctatctctgt gccagtagtg ctcaggggggc gtatggcaat    360 cagccccagc attttggtga tgggactcga ctctccatcc tagaggacct gaacaaggtg    420
ttcccacccg aggtcgctgt gtttgagcca tcagaagcag agatctccca cacccaaaag    480
gccacactgg tgtgcctggc cacaggcttc ttccccgacc acgtgagctg agctggtgg    540 gtgaatggga aggaggtgca cagtggggtc agcacggacc cgcagcccct caaggagcag    600
cccgccctca atgactccag atactgcctg agcagccgcc tgagggtctc ggccaccttc    660
tggcagaacc ccgcaacca cttccgctgt caagtccagt tctacgggct ctcggagaat    720
gacgagtgga cccaggatag ggccaaaccc gtcacccaga tcgtcagcgc cgaggcctgg    780
ggtagagcag actgtggctt tacctcggtg tcctaccagc aagggggtcct gtctgccacc    840 atcctctatg agatcctgct agggaaggcc accctgtatg ctgtgctggt cagcgccctt    900
gtgttgatgg ccatggtcaa gagaaaggat ttc                                 933

<210> SEQ ID NO 231
<211> LENGTH: 933
<212> TYPE: DNA
<213> ORGANISM: Artificial Sequence
<220> FEATURE:
<223> OTHER INFORMATION: WT373 beta chain - Codon-Optimized, Cys
      Modified

<400> SEQUENCE: 231
atgagcaacc aggtgctgtg ctgcgtggtg ctgtgttttcc tgggcgccaa cacagtggac     60
ggcggcatca cacagagccc caagtacctg ttccggaaag agggccagaa cgtgaccctg    120
agctgcgagc agaacctgaa ccacgacgcc atgtactggt acagacagga cccaggccag    180
ggcctgcggc tgatctacta cagccagatc gtgaacgact ccagaaaggg cgacattgcc    240
gagggctaca gcgtgtccag agagaagaaa gagtccttcc cactgaccgt gaccagcgcc    300
cagaagaacc ccaccgcctt ctacctgtgt gccagctctg cccagggcgc ctacggaaat    360
cagcctcagc actttggcga cggcacccgg ctgagcatcc tggaagatct gaacaaggtg    420
ttccccccag aggtggccgt gttcgagcct tctgaggccg agatctccca cacccagaaa    480 gccacccctcg tgtgcctggc caccggcttt ttccccgacc acgtggaact gtcttggtgg    540
gtcaacggca agaggtgcac ctccggcgtg tgcaccgatc ccagcctct gaaagaacag    600 cccgccctga cgacagccg gtactgcctg agcagcagac tgagagtgtc cgccaccttc    660
tggcagaacc ccggaacca cttcagatgc caggtgcagt tctacggcct gagcgagaac    720
gacgagtgga cccaggacag agccaagccc gtgacacaga tcgtgtctgc cgaagcctgg    780
ggcagagccg attgcggctt tacctccgtg tcctatcagc agggcgtgct gagcgccaca    840
atcctgtacg agatcctgct gggcaaggcc accctgtacg ccgtgctggt gtctgccctg    900
gtgctgatgg ccatggtcaa gcggaaggac ttc                                 933

<210> SEQ ID NO 232
<211> LENGTH: 1848
<212> TYPE: DNA
<213> ORGANISM: Artificial Sequence
<220> FEATURE:
<223> OTHER INFORMATION: WT373 beta-P2A-WT373 alpha Construct - WT

<400> SEQUENCE: 232
atgagcaacc aggtgctctg ctgtgtggtc ctttgtttcc tgggagcaaa caccgtggat     60
ggtggaatca ctcagtcccc aaagtacctg ttcagaaagg aaggacagaa tgtgaccctg    120
```

| | | |
|---|---|---|
| agttgtgaac agaatttgaa ccacgatgcc atgtactggt accgacagga cccagggcaa | 180 | |
| gggctgagat tgatctacta ctcacagata gtaaatgact ttcagaaagg agatatagct | 240 | |
| gaagggtaca gcgtctctcg ggagaagaag gaatcctttc ctctcactgt gacatcggcc | 300 | |
| caaaagaacc cgacagcttt ctatctctgt gccagtagtg ctcaggggc gtatggcaat | 360 | |
| cagccccagc attttggtga tgggactcga ctctccatcc tagaggacct gaacaaggtg | 420 | |
| ttcccacccg aggtcgctgt gtttgagcca tcagaagcag agatctccca cacccaaaag | 480 | |
| gccacactgg tgtgcctggc cacaggcttc ttccccgacc acgtggagct gagctggtgg | 540 | |
| gtgaatggga aggaggtgca cagtggggtc agcacggacc cgcagcccct caaggagcag | 600 | |
| cccgccctca tgactccag atactgcctg agcagccgcc tgagggtctc ggccaccttc | 660 | |
| tggcagaacc cccgcaacca cttccgctgt caagtccagt tctacgggct ctcggagaat | 720 | |
| gacgagtgga cccaggatag gccaaaccc gtcacccaga tcgtcagcgc cgaggcctgg | 780 | |
| ggtagagcag actgtggctt tacctcggtg tcctaccagc aagggtcct gtctgccacc | 840 | |
| atcctctatg agatcctgct agggaaggcc accctgtatg ctgtgctggt cagcgccctt | 900 | |
| gtgttgatgg ccatggtcaa gagaaaggat ttcggttccg gagccacgaa cttctctctg | 960 | |
| ttaaagcaag caggagacgt ggaagaaaac cccggtccca tggccatgct cctgggggca | 1020 | |
| tcagtgctga ttctgtggct tcagccagac tgggtaaaca gtcaacagaa gaatgatgac | 1080 | |
| cagcaagtta gcaaaattc accatccctg agcgtccagg aaggaagaat ttctattctg | 1140 | |
| aactgtgact atactaacag catgtttgat tatttcctat ggtacaaaaa atacccttgct | 1200 | |
| gaaggtccta cattcctgat atctataagt tccattaagg ataaaaatga agatggaaga | 1260 | |
| ttcactgtct tcttaaacaa aagtgccaag cacctctctc tgcacattgt gccctcccag | 1320 | |
| cctggagact ctgcagtgta cttctgtgca gcagggctc ggggtggtac tagctatgga | 1380 | |
| aagctgacat ttggacaagg gaccatcttg actgtccatc caaatatcca gaaccctgac | 1440 | |
| cctgccgtgt accagctgag agactctaaa tccagtgaca gtctgtctg cctattcacc | 1500 | |
| gattttgatt ctcaaacaaa tgtgtcacaa agtaaggatt ctgatgtgta tatcacagac | 1560 | |
| aaaactgtgc tagacatgag gtctatggac ttcaagagca cagtgctgt ggcctggagc | 1620 | |
| aacaaatctg actttgcatg tgcaaacgcc ttcaacaaca gcattattcc agaagacacc | 1680 | |
| ttcttcccca gcccagaaag ttcctgtgat gtcaagctgg tcgagaaaag ctttgaaaca | 1740 | |
| gatacgaacc taaactttca aaacctgtca gtgattgggt tccgaatcct cctcctgaaa | 1800 | |
| gtggccgggt taatctgct catgacgctg cggctgtggt ccagctga | 1848 | |

<210> SEQ ID NO 233
<211> LENGTH: 1848
<212> TYPE: DNA
<213> ORGANISM: Artificial Sequence
<220> FEATURE:
<223> OTHER INFORMATION: WT373 beta-P2A-WT373 alpha Construct -
      Codon-Optimized, Cys Modified

<400> SEQUENCE: 233

| | | |
|---|---|---|
| atgagcaacc aggtgctgtg ctgcgtggtg ctgtgtttcc tgggcgccaa cacagtggac | 60 | |
| ggcggcatca cacagagccc caagtacctg ttccggaaag agggccagaa cgtgaccctg | 120 | |
| agctgcgagc agaacctgaa ccacgacgcc atgtactggt acagacagga cccaggccag | 180 | |
| ggcctgcggc tgatctacta cagccagatc gtgaacgact ccagaagggg cgacattgcc | 240 | |
| gagggctaca gcgtgtccag agagaagaaa gagtccttcc cactgaccgt gaccagcgcc | 300 | |

```
cagaagaacc ccaccgcctt ctacctgtgt gccagctctg cccagggcgc ctacggaaat        360
cagcctcagc actttggcga cggcacccgg ctgagcatcc tggaagatct gaacaaggtg        420
ttccccccag aggtggccgt gttcgagcct tctgaggccg agatctccca cacccagaaa        480
gccaccctcg tgtgcctggc caccggcttt tcccccgacc acgtggaact gtcttggtgg        540
gtcaacggca agaggtgca ctccggcgtg tgcaccgatc cccagcctct gaaagaacag        600
cccgccctga cgacagccg gtactgcctg agcagcagac tgagagtgtc cgccaccttc        660
tggcagaacc cccggaacca cttcagatgc caggtgcagt tctacggcct gagcgagaac        720
gacgagtgga cccaggacag agccaagccc gtgacacaga tcgtgtctgc cgaagcctgg        780
ggcagagccg attgcggctt tacctccgtg tcctatcagc agggcgtgct gagcgccaca        840
atcctgtacg agatcctgct gggcaaggcc accctgtacg ccgtgctggt gtctgccctg        900
gtgctgatgg ccatggtcaa gcggaaggac ttcggttccg gagccacgaa cttctctctg        960
ttaaagcaag caggagacgt ggaagaaaac cccggtccca tggctatgct gctgggcgcc       1020
tctgtgctga tcctgtggct gcagcccgac tgggtcaaca gccagcagaa gaacgacgac       1080
cagcaagtga agcagaacag ccccagcctg agcgtgcagg aaggccggat cagcatcctg       1140
aactgcgact acaccaactc tatgttcgac tacttcctgt ggtacaagaa gtaccccgcc       1200
gagggcccca ccttcctgat ctccatcagc agcatcaagg acaagaacga ggacggccgg       1260
ttcaccgtgt tctgaacaa gagcgccaag cacctgagcc tgcacatcgt gcctagccag       1320
cctggcgata gcgccgtgta cttttgtgcc gctggcgcta gaggcggcac cagctatggc       1380
aagctgacct ttggcaggg caccatcctg accgtgcacc caacatcca gaaccccgac       1440 cctgcagtgt accagctgcg ggacagcaag agcagcgaca gagcgtgtg cctgttcacc       1500 gacttcgaca ccagaccaa cgtgtcccag agcaaggaca cgacgtgta catcaccgat       1560 aagtgcgtgc tggacatgcg gagcatggac ttcaagagca acagcgccgt ggcctggtcc       1620
aacaagagcg acttcgcctg cgccaacgcc ttcaacaaca gcattatccc cgaggacaca       1680
ttcttcccaa gccccgagag cagctgcgac gtgaagctgg tggaaaagag cttcgagaca       1740
gacaccaacc tgaacttcca gaaccctcagc gtgatcggct ccggatcct gctgctgaag       1800 gtggccggct tcaacctgct gatgaccctg cggctgtggt ccagctga                   1848
```

<210> SEQ ID NO 234
<211> LENGTH: 387
<212> TYPE: DNA
<213> ORGANISM: Artificial Sequence
<220> FEATURE:
<223> OTHER INFORMATION: WT376 alpha chain variable domain WT

<400> SEQUENCE: 234

```
atgctactca tcacatcaat gttggtctta tggatgcaat tgtcacaggt gaatggacaa         60
caggtaatgc aaattcctca gtaccagcat gtacaagaag gagaggactt caccacgtac        120
tgcaattcct caactacttt aagcaatata cagtggtata gcaaaggcc tggtggacat        180 cccgtttttt tgatacagtt agtgaagagt ggagaagtga agaagcagaa aagactgaca        240
tttcagtttg gagaagcaaa aaagaacagc tccctgcaca tcacagccac ccagactaca        300
gatgtaggaa cctacttctg tgcagggcgc acctcctacg acaaggtgat atttgggcca        360
gggacaagct tatcagtcat tccaaat                                             387
```

<210> SEQ ID NO 235
<211> LENGTH: 387

```
<212> TYPE: DNA
<213> ORGANISM: Artificial Sequence
<220> FEATURE:
<223> OTHER INFORMATION: WT376 alpha chain variable domain - Codon
      Optimized

<400> SEQUENCE: 235
atgctgctga tcacctccat gctggtgctg tggatgcagc tgagccaagt gaacggccag      60
caagtgatgc agatccccca gtaccagcac gtgcaggaag gcgaggactt caccacctac     120
tgcaacagca gcaccaccct gagcaacatc cagtggtaca gcagcggcc tggcggccac      180 cccgtgtttc tgatccagct cgtgaagtcc ggcgaagtga agaagcagaa gcggctgacc     240
ttccagttcg gcgaggccaa gaagaacagc agcctgcaca tcaccgccac ccagaccacc     300
gacgtgggca cctactttg cgccggcaga accagctacg acaaagtgat cttcggccct      360
ggcaccagcc tgtccgtgat ccccaat                                          387

<210> SEQ ID NO 236
<211> LENGTH: 810
<212> TYPE: DNA
<213> ORGANISM: Artificial Sequence
<220> FEATURE:
<223> OTHER INFORMATION: WT376 alpha chain WT

<400> SEQUENCE: 236
atgctactca tcacatcaat gttggtctta tggatgcaat tgtcacaggt gaatggacaa      60
caggtaatgc aaattcctca gtaccagcat gtacaagaag gagaggactt caccacgtac     120
tgcaattcct caactacttt aagcaatata cagtggtata gcaaaggcc tggtggacat      180 cccgtttttt tgatacagtt agtgaagagt ggagaagtga agaagcagaa aagactgaca     240
tttcagtttg gagaagcaaa aaagaacagc tccctgcaca tcacagccac ccagactaca     300
gatgtaggaa cctacttctg tgcagggcgc acctcctacg acaaggtgat atttgggcca      360
gggacaagct atcagtcat ccaaatatc cagaaccctg accctgccgt gtaccagctg       420
agagactcta atccagtga caagtctgtc tgcctattca ccgattttga ttctcaaaca      480
aatgtgtcac aaagtaagga ttctgatgtg tatatcacag acaaaactgt gctagacatg     540
aggtctatgg acttcaagag caacagtgct gtggcctgga gcaacaaatc tgactttgca     600
tgtgcaaacg ccttcaacaa cagcattatt ccagaagaca ccttcttccc cagcccagaa     660
agttcctgtg atgtcaagct ggtcgagaaa agctttgaaa cagatacgaa cctaaacttt      720
caaaacctgt cagtgattgg gttccgaatc ctcctcctga agtggccgg gtttaatctg     780 ctcatgacgc tgcggctgtg gtccagctga                                      810

<210> SEQ ID NO 237
<211> LENGTH: 810
<212> TYPE: DNA
<213> ORGANISM: Artificial Sequence
<220> FEATURE:
<223> OTHER INFORMATION: WT376 alpha chain - Codon-Optimized, Cys
      Modified

<400> SEQUENCE: 237
atgctgctga tcacctccat gctggtgctg tggatgcagc tgagccaagt gaacggccag      60
caagtgatgc agatccccca gtaccagcac gtgcaggaag gcgaggactt caccacctac     120
tgcaacagca gcaccaccct gagcaacatc cagtggtaca gcagcggcc tggcggccac      180 cccgtgtttc tgatccagct cgtgaagtcc ggcgaagtga agaagcagaa gcggctgacc     240
```

| | |
|---|---|
| ttccagttcg gcgaggccaa gaagaacagc agcctgcaca tcaccgccac ccagaccacc | 300 |
| gacgtgggca cctactttg cgccggcaga accagctacg acaaagtgat cttcggccct | 360 |
| ggcaccagcc tgtccgtgat ccccaatatc cagaaccccg accccgcagt gtaccagctg | 420 |
| cgggacagca gagcagcga caagagcgtg tgcctgttca ccgacttcga cagccagacc | 480 |
| aacgtgtccc agagcaagga cagcgacgtg tacatcaccg ataagtgcgt gctggacatg | 540 |
| cggagcatgg acttcaagag caacagcgcc gtggcctggt ccaacaagag cgacttcgcc | 600 |
| tgcgccaacg ccttcaacaa cagcattatc cccgaggaca cattcttccc aagccccgag | 660 |
| agcagctgcg acgtgaagct ggtggaaaag agcttcgaga cagacaccaa cctgaacttc | 720 |
| cagaacctca gcgtgatcgg cttccggatc ctgctgctga aggtggccgg cttcaacctg | 780 |
| ctgatgaccc tgcggctgtg gtccagctga | 810 |

<210> SEQ ID NO 238
<211> LENGTH: 399
<212> TYPE: DNA
<213> ORGANISM: Artificial Sequence
<220> FEATURE:
<223> OTHER INFORMATION: WT376 beta chain variable domain WT

<400> SEQUENCE: 238

| | |
|---|---|
| atggcctccc tgctcttctt ctgtggggcc ttttatctcc tgggaacagg gtccatggat | 60 |
| gctgatgtta cccagacccc aaggaatagg atcacaaaga caggaaagag gattatgctg | 120 |
| gaatgttctc agactaaggg tcatgataga atgtactggt atcgacaaga cccaggactg | 180 |
| ggcctacggt tgatctatta ctcctttgat gtcaaagata taaacaaagg agagatctct | 240 |
| gatggataca gtgtctctcg acaggcacag gctaaattct ccctgtccct agagtctgcc | 300 |
| atccccaacc agacagctct ttacttctgt gccaccagtg cagggacggt tgaaacacc | 360 |
| atatattttg gagagggaag ttggctcact gttgtagag | 399 |

<210> SEQ ID NO 239
<211> LENGTH: 399
<212> TYPE: DNA
<213> ORGANISM: Artificial Sequence
<220> FEATURE:
<223> OTHER INFORMATION: WT376 beta chain variable domain - Codon
    Optimized

<400> SEQUENCE: 239

| | |
|---|---|
| atggccagcc tgctgttctt ctgcggcgcc ttctacctgc tgggcaccgg ctctatggac | 60 |
| gccgatgtga cccagacccc ccggaacaga atcaccaaga ccggcaagcg gatcatgctg | 120 |
| gaatgcagcc agaccaaggg ccacgaccgg atgtactggt acagacagga ccctggcctg | 180 |
| ggcctgcggc tgatctacta cagcttcgac gtgaaggaca tcaacaaggg cgagatcagc | 240 |
| gacggctaca gcgtgtccag acaggctcag gccaagttca gcctgtccct ggaaagcgcc | 300 |
| atccccaacc agaccgccct gtacttctgt gccacaagcg ccggcaccgt gggcaacacc | 360 |
| atctactttg gcgagggcag ctggctgacc gtggtggaa | 399 |

<210> SEQ ID NO 240
<211> LENGTH: 927
<212> TYPE: DNA
<213> ORGANISM: Artificial Sequence
<220> FEATURE:
<223> OTHER INFORMATION: WT376 beta chain WT

<400> SEQUENCE: 240

-continued

| | |
|---|---|
| atggcctccc tgctcttctt ctgtggggcc ttttatctcc tgggaacagg gtccatggat | 60 |
| gctgatgtta cccagacccc aaggaatagg atcacaaaga caggaaagag gattatgctg | 120 |
| gaatgttctc agactaaggg tcatgataga atgtactggt atcgacaaga cccaggactg | 180 |
| ggcctacggt tgatctatta ctcctttgat gtcaaagata taaacaaagg agagatctct | 240 |
| gatggataca gtgtctctcg acaggcacag gctaaattct ccctgtccct agagtctgcc | 300 |
| atccccaacc agacagctct ttacttctgt gccaccagtg cagggacggt tggaaacacc | 360 |
| atatattttg gagagggaag ttggctcact gttgtagagg acctgaacaa ggtgttccca | 420 |
| cccgaggtcg ctgtgtttga gccatcagaa gcagagatct cccacaccca aaaggccaca | 480 |
| ctggtgtgcc tggccacagg cttcttcccc gaccacgtgg agctgagctg gtgggtgaat | 540 |
| gggaaggagg tgcacagtgg ggtcagcacg gacccgcagc ccctcaagga gcagcccgcc | 600 |
| ctcaatgact ccagatactg cctgagcagc cgcctgaggg tctcggccac cttctggcag | 660 |
| aaccccgca accacttccg ctgtcaagtc cagttctacg ggctctcgga gaatgacgag | 720 |
| tggacccagg atagggccaa acccgtcacc cagatcgtca gcgccgaggc ctggggtaga | 780 |
| gcagactgtg gctttacctc ggtgtcctac cagcaagggg tcctgtctgc caccatcctc | 840 |
| tatgagatcc tgctagggaa ggccaccctg tatgctgtgc tggtcagcgc ccttgtgttg | 900 |
| atggccatgg tcaagagaaa ggatttc | 927 |

<210> SEQ ID NO 241
<211> LENGTH: 927
<212> TYPE: DNA
<213> ORGANISM: Artificial Sequence
<220> FEATURE:
<223> OTHER INFORMATION: WT376 beta chain - Codon-Optimized, Cys Modified

<400> SEQUENCE: 241

| | |
|---|---|
| atggccagcc tgctgttctt ctgcggcgcc ttctacctgc tgggcaccgg ctctatggac | 60 |
| gccgatgtga cccagacccc ccggaacaga atcaccaaga ccggcaagcg gatcatgctg | 120 |
| gaatgcagcc agaccaaggg ccacgaccgg atgtactggt acagacagga ccctggcctg | 180 |
| ggcctgcggc tgatctacta cagcttcgac gtgaaggaca tcaacaaggg cgagatcagc | 240 |
| gacggctaca gcgtgtccag acaggctcag gccaagttca gcctgtccct ggaaagcgcc | 300 |
| atccccaacc agaccgccct gtacttctgt gccacaagcg ccggcaccgt gggcaacacc | 360 |
| atctactttg gcgagggcag ctggctgacc gtggtggaag atctgaacaa ggtgttcccc | 420 |
| ccagaggtgg ccgtgttcga gccttctgag gccgagatct cccacaccca gaaagccacc | 480 |
| ctcgtgtgcc tggccaccgg cttttttccc gaccacgtgg aactgtcttg gtgggtcaac | 540 |
| ggcaaagagg tgcactccgg cgtgtgcacc gatccccagc ctctgaaaga acagcccgcc | 600 |
| ctgaacgaca gccggtactg cctgagcagc agactgagag tgtccgccac cttctggcag | 660 |
| aaccccggaa ccacttcag atgccaggtg cagttctacg gcctgagcga gaacgacgag | 720 |
| tggacccagg acagagccaa gcccgtgaca cagatcgtgt ctgccgaagc tggggcaga | 780 |
| gccgattgcg gctttacctc cgtgtcctat cagcagggcg tgctgagcgc cacaatcctg | 840 |
| tacgagatcc tgctgggcaa ggccaccctg tacgccgtgc tggtgtctgc cctggtgctg | 900 |
| atggccatgg tcaagcggaa ggacttc | 927 |

<210> SEQ ID NO 242
<211> LENGTH: 1803
<212> TYPE: DNA

<213> ORGANISM: Artificial Sequence
<220> FEATURE:
<223> OTHER INFORMATION: WT376 beta-P2A-WT376 alpha Construct - WT

<400> SEQUENCE: 242

```
atggcctccc tgctcttctt ctgtggggcc ttttatctcc tgggaacagg gtccatggat      60
gctgatgtta cccagacccc aaggaatagg atcacaaaga caggaaagag gattatgctg     120
gaatgttctc agactaaggg tcatgataga atgtactggt atcgacaaga cccaggactg     180
ggcctacggt tgatctatta ctcctttgat gtcaaagata taaacaaagg agagatctct     240
gatggataca gtgtctctcg acaggcacag gctaaattct ccctgtccct agagtctgcc     300
atccccaacc agacagctct ttacttctgt gccaccagtg cagggacggt tggaaacacc     360
atatattttg gagagggaag ttggctcact gttgtagagg acctgaacaa ggtgttccca     420
cccgaggtcg ctgtgtttga gccatcagaa gcagagatct cccacaccca aaaggccaca     480
ctggtgtgcc tggccacagg cttcttcccc gaccacgtgg agctgagctg gtgggtgaat     540
gggaaggagg tgcacagtgg ggtcagcacg gacccgcagc ccctcaagga gcagcccgcc     600
ctcaatgact ccagatactg cctgagcagc cgcctgaggg tctcggccac cttctggcag     660
aaccccgca accacttccg ctgtcaagtc cagttctacg gctctcgga gaatgacgag      720
tggacccagg atagggccaa acccgtcacc cagatcgtca gcgccgaggc ctggggtaga     780
gcagactgtg gctttacctc ggtgtcctac agcaagggg tcctgtctgc caccatcctc     840
tatgagatcc tgctagggaa ggccacccty tatgctgtgc tggtcagcgc ccttgtgttg     900
```

| | |
|---|---:|
| atggccagcc tgctgttctt ctgcggcgcc ttctacctgc tgggcaccgg ctctatggac | 60 |
| gccgatgtga cccagacccc ccggaacaga atcaccaaga ccggcaagcg gatcatgctg | 120 |
| gaatgcagcc agaccaaggg ccacgaccgg atgtactggt acagacagga ccctggcctg | 180 |
| ggcctgcggc tgatctacta cagcttcgac gtgaaggaca tcaacaaggg cgagatcagc | 240 |
| gacggctaca gcgtgtccag acaggctcag gccaagttca gcctgtccct ggaaagcgcc | 300 |
| atccccaacc agaccgccct gtacttctgt gccacaagcg ccggcaccgt gggcaacacc | 360 |
| atctactttg gcgagggcag ctggctgacc gtggtggaag atctgaacaa ggtgttcccc | 420 |
| ccagaggtgg ccgtgttcga gccttctgag gccgagatct cccacaccca gaaagccacc | 480 |
| ctcgtgtgcc tggccaccgg ctttttcccc gaccacgtgg aactgtcttg gtgggtcaac | 540 |
| ggcaaagagg tgcactccgg cgtgtgcacc gatccccagc tctgaaaga cagcccgcc | 600 |
| ctgaacgaca gccggtactg cctgagcagc agactgagag tgtccgccac cttctggcag | 660 |
| aaccccgga accacttcag atgccaggtg cagttctacg gcctgagcga aacgacgag | 720 |
| tggacccagg acagagccaa gcccgtgaca cagatcgtgt ctgccgaagc tggggcaga | 780 |
| gccgattgcg gctttacctc cgtgtcctat cagcagggcg tgctgagcgc cacaatcctg | 840 |
| tacgagatcc tgctgggcaa ggccaccctg tacgccgtgc tggtgtctgc cctggtgctg | 900 |
| atggccatgg tcaagcggaa ggacttcggt tccggagcca cgaacttctc tctgttaaag | 960 |
| caagcaggag acgtggaaga aaccccggt cccatgctgc tgatcacctc catgctggtg | 1020 |
| ctgtggatgc agctgagcca agtgaacggc cagcaagtga tgcagatccc ccagtaccag | 1080 |
| cacgtgcagg aaggcgagga cttcaccacc tactgcaaca gcagcaccac cctgagcaac | 1140 |
| atccagtggt acaagcagcg gcctggcggc cacccgtgt ttctgatcca gctcgtgaag | 1200 |
| tccggcgaag tgaagaagca gaagcggctg accttccagt tcggcgaggc caagaagaac | 1260 |
| agcagcctgc acatcaccgc cacccagacc accgacgtgg gcacctactt tgcgccggc | 1320 |
| agaaccagct acgacaaagt gatcttcggc cctggcacca gctgtccgt gatccccaat | 1380 |
| atccagaacc ccgaccccgc agtgtaccag ctgcgggaca gcaagagcag cgacaagagc | 1440 |
| gtgtgcctgt tcaccgactt cgacagccag accaacgtgt cccagagcaa ggacagcgac | 1500 |
| gtgtacatca ccgataagtg cgtgctggac atgcggagca tggacttcaa gagcaacagc | 1560 |
| gccgtggcct ggtccaacaa gagcgacttc gcctgcgcca acgccttcaa caacagcatt | 1620 |
| atccccgagg acacattctt cccaagcccc gagagcagct gcgacgtgaa gctggtggaa | 1680 |
| aagagcttcg agacagacac caacctgaac ttccagaacc tcagcgtgat cggcttccgg | 1740 |
| atcctgctgc tgaaggtggc cggcttcaac ctgctgatga ccctgcggct gtggtccagc | 1800 |
| tga | 1803 |

<210> SEQ ID NO 244
<211> LENGTH: 399
<212> TYPE: DNA
<213> ORGANISM: Artificial Sequence
<220> FEATURE:
<223> OTHER INFORMATION: WT377 alpha chain variable domain WT

<400> SEQUENCE: 244

| | |
|---|---:|
| atgtcacttt ctagcctgct gaaggtggtc acagcttcac tgtggctagg acctggcatt | 60 |
| gcccagaaga taactcaaac ccaaccagga atgttcgtgc aggaaaagga ggctgtgact | 120 |
| ctggactgca catatgacac cagtgatcca agttatggtc tattctgtta caagcagccc | 180 |
| agcagtgggg aaatgatttt tcttatttat caggggtctt atgaccagca aaatgcaaca | 240 | gaaggtcgct actcattgaa tttccagaag gcaagaaaat ccgccaacct tgtcatctcc     300 gcttcacaac tgggggactc agcaatgtac ttctgtgcaa tatcgggaaa cacacctctt     360 gtctttggaa agggcacaag actttctgtg attgcaaat                             399

<210> SEQ ID NO 245
<211> LENGTH: 399
<212> TYPE: DNA
<213> ORGANISM: Artificial Sequence
<220> FEATURE:
<223> OTHER INFORMATION: WT377 alpha chain variable domain - Codon
      Optimized

<400> SEQUENCE: 245
atgagcctga gcagcctgct gaaagtcgtg accgccagcc tgtggctggg acctggaatc      60
gcccagaaga tcacccagac ccagcccggc atgttcgtgc aggaaaaaga agccgtgacc     120
ctggactgca cctacgacac cagcgaccct agctacggcc tgttctggta caagcagccc     180
agcagcggcg agatgatctt cctgatctac cagggcagct acgaccagca gaacgccacc     240
gagggccggt acagcctgaa cttccagaag gcccggaagt ccgccaacct cgtgatcagc     300
gctagccagc tgggcgacag cgccatgtac ttttgcgcca tcagcggcaa cacccccctg     360
gtgtttggca agggcacccg gctgagcgtg atcgccaac                             399

<210> SEQ ID NO 246
<211> LENGTH: 822
<212> TYPE: DNA
<213> ORGANISM: Artificial Sequence
<220> FEATURE:
<223> OTHER INFORMATION: WT377 alpha chain WT

<400> SEQUENCE: 246
atgtcacttt ctagcctgct gaaggtggtc acagcttcac tgtggctagg acctggcatt      60
gcccagaaga taactcaaac ccaaccagga atgttcgtgc aggaaaagga ggctgtgact     120
ctggactgca catatgacac cagtgatcca gttatggtc tattctggta caagcagccc      180
agcagtgggg aaatgatttt tcttatttat caggggtctt atgaccagca aaatgcaaca     240
gaaggtcgct actcattgaa tttccagaag gcaagaaaat ccgccaacct tgtcatctcc     300
gcttcacaac tgggggactc agcaatgtac ttctgtgcaa tatcgggaaa cacacctctt     360
gtctttggaa agggcacaag actttctgtg attgcaaata tccagaaccc tgaccctgcc     420
gtgtaccagc tgagagactc taaatccagt gacaagtctg tctgcctatt caccgatttt     480
gattctcaaa caaatgtgtc acaaagtaag gattctgatg tgtatatcac agacaaaact     540
gtgctagaca tgaggtctat ggacttcaag agcaacagtg ctgtggcctg agcaacaaa     600 tctgactttg catgtgcaaa cgccttcaac aacagcatta ttccagaaga cacttcttc     660 cccagcccag aaagttcctg tgatgtcaag ctggtcgaga aaagctttga acagatacg     720 aacctaaact ttcaaaacct gtcagtgatt gggttccgaa tcctcctcct gaaagtggcc     780
gggtttaatc tgctcatgac gctgcggctg tggtccagct ga                        822

<210> SEQ ID NO 247
<211> LENGTH: 822
<212> TYPE: DNA
<213> ORGANISM: Artificial Sequence
<220> FEATURE:
<223> OTHER INFORMATION: WT377 alpha chain - Codon-Optimized, Cys
      Modified

<400> SEQUENCE: 247

```
atgagcctga gcagcctgct gaaagtcgtg accgccagcc tgtggctggg acctggaatc    60
gcccagaaga tcacccagac ccagcccggc atgttcgtgc aggaaaaaga agccgtgacc   120
ctggactgca cctacgacac cagcgaccct agctacggcc tgttctggta caagcagccc   180
agcagcggcg agatgatctt cctgatctac cagggcagct acgaccagca gaacgccacc   240
gagggccggt acagcctgaa cttccagaag gcccggaagt ccgccaacct cgtgatcagc   300
gctagccagc tgggcgacag cgccatgtac ttttgcgcca tcagcggcaa cacccccctg   360
gtgtttggca agggcacccg gctgagcgtg atcgccaaca tccagaaccc cgaccccgca   420
gtgtaccagc tgcgggacag caagagcagc gacaagagcg tgtgcctgtt caccgacttc   480
gacagccaga ccaacgtgtc ccagagcaag gacagcgacg tgtacatcac cgataagtgc   540
gtgctggaca tgcggagcat ggacttcaag agcaacagcg ccgtggcctg gtccaacaag   600
agcgacttcg cctgcgccaa cgccttcaac aacagcatta tccccgagga cacattcttc   660
ccaagccccg agagcagctg cgacgtgaag ctggtggaaa agagcttcga cagacacacc   720
aacctgaact tccagaacct cagcgtgatc ggcttccgga tcctgctgct gaaggtggcc   780
ggcttcaacc tgctgatgac cctgcggctg tggtccagct ga                      822
```

<210> SEQ ID NO 248
<211> LENGTH: 429
<212> TYPE: DNA
<213> ORGANISM: Artificial Sequence
<220> FEATURE:
<223> OTHER INFORMATION: WT377 beta chain variable domain WT

<400> SEQUENCE: 248

```
atgcttagtc ctgacctgcc tgactctgcc tggaacacca ggctcctctg ccatgtcatg    60
cttttgtctcc tgggagcagt ttcagtggct gctggagtca tccagtcccc aagacatctg   120
atcaaagaaa agagggaaac agccactctg aaatgctatc ctatccctag acacgacact   180
gtctactggt accagcaggg tccaggtcag gacccccagt tcctcatttc gtttttatgaa   240
aagatgcaga gcgataaagg aagcatccct gatcgattct cagctcaaca gttcagtgac   300
tatcattctg aactgaacat gagctccttg gagctggggg actcagccct gtacttctgt   360
gccagcagct tgcgaggggg cctcgaaaaa ctgttttttg gcagtggaac ccagctctct   420
gtcttggag                                                            429
```

<210> SEQ ID NO 249
<211> LENGTH: 429
<212> TYPE: DNA
<213> ORGANISM: Artificial Sequence
<220> FEATURE:
<223> OTHER INFORMATION: WT377 beta chain variable domain - Codon
      Optimized

<400> SEQUENCE: 249

```
atgctgagcc ccgatctgcc tgacagcgcc tggaacacca gactgctgtg ccacgtgatg    60
ctgtgcctgc tgggagccgt gtctgtggct gctggcgtga tccagagccc cagacacctg   120
atcaaagaga gagagagac agccaccctg aagtgctacc catcccag gcacgacacc   180
gtgtactggt atcagcaggg cccaggccag gacccccagt tcctgatcag cttctacgag   240
aagatgcaga gcgacaaggg cagcatcccc gacagattca gcgcccagca gttcagcgac   300
taccacagcg agctgaacat gagcagcctg gaactgggcg acagcgccct gtacttctgt   360
```

```
gccagctctc tgagaggcgg cctggaaaag ctgttcttcg gcagcggcac ccagctgagc    420
gtgctggaa                                                            429
```

<210> SEQ ID NO 250
<211> LENGTH: 957
<212> TYPE: DNA
<213> ORGANISM: Artificial Sequence
<220> FEATURE:
<223> OTHER INFORMATION: WT377 beta chain WT

<400> SEQUENCE: 250

```
atgcttagtc ctgacctgcc tgactctgcc tggaacacca ggctcctctg ccatgtcatg     60
ctttgtctcc tgggagcagt ttcagtggct gctggagtca tccagtcccc aagacatctg    120
atcaaagaaa agagggaaac agccactctg aaatgctatc ctatccctag acacgacact    180
gtctactggt accagcaggg tccaggtcag acccccagt tcctcatttc gttttatgaa     240
aagatgcaga gcgataaagg aagcatccct gatcgattct cagctcaaca gttcagtgac    300
tatcattctg aactgaacat gagctccttg gagctggggg actcagccct gtacttctgt    360
gccagcagct tgcgaggggg cctcgaaaaa ctgttttttg cagtggaac ccagctctct     420 gtcttggagg acctgaacaa ggtgttccca cccgaggtcg ctgtgtttga gccatcagaa    480
gcagagatct cccacaccca aaaggccaca ctggtgtgcc tggccacagg cttcttcccc    540
gaccacgtgg agctgagctg gtgggtgaat ggaaggagg tgcacagtgg ggtcagcacg     600
gacccgcagc cctcaagga gcagcccgcc ctcaatgact ccagatactg cctgagcagc    660
cgcctgaggg tctcggccac cttctggcag aaccccccgca accacttccg ctgtcaagtc   720
cagttctacg gctctcgga gaatgacgag tggacccagg ataggccaa acccgtcacc     780 cagatcgtca gcgccgaggc ctggggtaga gcagactgtg gctttacctc ggtgtcctac   840
cagcaagggg tcctgtctgc caccatcctc tatgagatcc tgctagggaa ggccacctg    900 tatgctgtgc tggtcagcgc ccttgtgttg atggccatgg tcaagagaaa ggatttc      957
```

<210> SEQ ID NO 251
<211> LENGTH: 957
<212> TYPE: DNA
<213> ORGANISM: Artificial Sequence
<220> FEATURE:
<223> OTHER INFORMATION: WT377 beta chain - Codon-Optimized, Cys
      Modified

<400> SEQUENCE: 251

```
atgctgagcc ccgatctgcc tgacagcgcc tggaacacca gactgctgtg ccacgtgatg     60
ctgtgcctgc tgggagccgt gtctgtggct gctggcgtga tccagagccc cagacacctg    120
atcaaagaga agagagagac agccaccctg aagtgctacc ccatcccag gcacgacacc     180 gtgtactggt atcagcaggg cccaggccag gacccccagt tcctgatcag cttctacgag    240
aagatgcaga gcgacaaggg cagcatcccc gacagattca gcgcccagca gttcagcgac    300
taccacagcg agctgaacat gagcagcctg gaactgggcg acagcgccct gtacttctgt    360
gccagctctc tgagaggcgg cctggaaaag ctgttcttcg gcagcggcac ccagctgagc    420
gtgctggaag atctgaacaa ggtgttcccc cagaggtgg ccgtgttcga gccttctgag    480
gccgagatct cccacaccca gaaagccacc ctcgtgtgcc tggccaccgg cttttttccc    540
gaccacgtgg aactgtcttg gtgggtcaac ggcaaagagg tgcactccgg cgtgtgcacc    600 gatcccagc ctctgaaaga acagcccgcc ctgaacgaca gccggtactg cctgagcagc    660
```

| | |
|---|---|
| agactgagag tgtccgccac cttctggcag aaccccggga accacttcag atgccaggtg | 720 |
| cagttctacg gcctgagcga gaacgacgag tggacccagg acagagccaa gcccgtgaca | 780 |
| cagatcgtgt ctgccgaagc ctggggcaga gccgattgcg gctttacctc cgtgtcctat | 840 |
| cagcagggcg tgctgagcgc cacaatcctg tacgagatcc tgctgggcaa ggccaccctg | 900 |
| tacgccgtgc tggtgtctgc cctggtgctg atggccatgg tcaagcggaa ggacttc | 957 |

<210> SEQ ID NO 252
<211> LENGTH: 1845
<212> TYPE: DNA
<213> ORGANISM: Artificial Sequence
<220> FEATURE:
<223> OTHER INFORMATION: WT377 beta-P2A-WT377 alpha Construct - WT

<400> SEQUENCE: 252

| | |
|---|---|
| atgcttagtc ctgacctgcc tgactctgcc tggaacacca ggctcctctg ccatgtcatg | 60 |
| ctttgtctcc tgggagcagt ttcagtggct gctggagtca tccagtcccc aagacatctg | 120 |
| atcaaagaaa agagggaaac agccactctg aaatgctatc ctatccctag acacgacact | 180 |
| gtctactggt accagcaggg tccaggtcag gacccccagt tcctcatttc gttttatgaa | 240 |
| aagatgcaga gcgataaagg aagcatccct gatcgattct cagctcaaca gttcagtgac | 300 |
| tatcattctg aactgaacat gagctccttg gagctggggg actcagccct gtacttctgt | 360 |
| gccagcagct tgcgaggggg cctcgaaaaa ctgtttttg cagtggaac ccagctctct | 420 |
| gtcttggagg acctgaacaa ggtgttccca cccgaggtcg ctgtgtttga gccatcagaa | 480 |
| gcagagatct cccacaccca aaaggccaca ctggtgtgcc tggccacagg cttcttcccc | 540 |
| gaccacgtgg agctgagctg gtgggtgaat gggaaggagg tgcacagtgg ggtcagcacg | 600 |
| gacccgcagc ccctcaagga gcagcccgcc tcaatgact ccagatactg cctgagcagc | 660 |
| cgcctgaggg tctcggccac cttctggcag aaccccgca accacttccg ctgtcaagtc | 720 |
| cagttctacg gcctctcgga gaatgacgag tggacccagg atagggccaa cccgtcacc | 780 |
| cagatcgtca gcgccgaggc ctgggggtaga gcagactgtg gctttacctc ggtgtcctac | 840 |
| cagcaagggg tcctgtctgc caccatcctc tatgagatcc tgctaggaa ggccaccctg | 900 |
| tatgctgtgc tggtcagcgc ccttgtgttg atggccatgg tcaagagaaa ggatttcggt | 960 |
| tccggagcca cgaacttctc tctgttaaag caagcaggag acgtggaaga aaaccccggt | 1020 |
| cccatgtcac tttctagcct gctgaaggtg gtcacagctt cactgtggct aggacctggc | 1080 |
| attgcccaga gataactca aacccaacca ggaatgttcg tgcaggaaaa ggaggctgtg | 1140 |
| actctggact gcacatatga caccagtgat ccaagttatg gtctattctg gtacaagcag | 1200 |
| cccagcagtg gggaaatgat ttttcttatt tatcagggt cttatgacca gcaaaatgca | 1260 |
| acagaaggtc gctactcatt gaatttccag aaggcaagaa aatccgccaa ccttgtcatc | 1320 |
| tccgcttcac aactggggga ctcagcaatg tacttctgtg caatatcggg aaacacacct | 1380 |
| cttgtctttg gaagggcac aagactttct gtgattgcaa atatccagaa ccctgacccct | 1440 |
| gccgtgtacc agctgagaga ctctaaatcc agtgacaagt ctgtctgcct attcaccgat | 1500 |
| tttgattctc aaacaaatgt gtcacaaagt aaggattctg atgtgtatat cacagacaaa | 1560 |
| actgtgctag acatgaggtc tatggacttc aagagcaaca gtgctgtggc ctggagcaac | 1620 |
| aaatctgact ttgcatgtgc aaacgccttc aacaacagca ttattccaga agacaccttc | 1680 |
| ttccccagcc cagaaagttc ctgtgatgtc aagctggtcg agaaaagctt tgaaacagat | 1740 |
| acgaacctaa actttcaaaa cctgtcagtg attgggttcc gaatcctcct cctgaaagtg | 1800 |

```
gccgggttta atctgctcat gacgctgcgg ctgtggtcca gctga          1845
```

<210> SEQ ID NO 253
<211> LENGTH: 1845
<212> TYPE: DNA
<213> ORGANISM: Artificial Sequence
<220> FEATURE:
<223> OTHER INFORMATION: WT377 beta-P2A-WT377 alpha Construct -
      Codon-Optimized, Cys Modified

<400> SEQUENCE: 253

```
atgctgagcc ccgatctgcc tgacagcgcc tggaacacca gactgctgtg ccacgtgatg     60
ctgtgcctgc tgggagccgt gtctgtggct gctggcgtga tccagagccc cagacacctg   120
atcaaagaga gagagagac agccacccctg aagtgctacc ccatccccag gcacgacacc   180
gtgtactggt atcagcaggg cccaggccag gaccccagt tcctgatcag cttctacgag   240
aagatgcaga gcgacaaggg cagcatcccc gacagattca gcgcccagca gttcagcgac   300
taccacagcg agctgaacat gagcagcctg gaactgggcg acagcgccct gtacttctgt   360
gccagctctc tgagaggcgg cctggaaaag ctgttcttcg gcagcggcac ccagctgagc   420
gtgctggaag atctgaacaa ggtgttcccc ccagaggtgg ccgtgttcga gccttctgag   480
gccgagatct cccacacccca gaaagccacc ctcgtgtgcc tggccaccgg cttttttcccc   540
gaccacgtga actgtcttg gtgggtcaac ggcaaagagg tgcactccgg cgtgtgcacc   600
gatccccagc ctctgaaaga cagcccgcc ctgaacgaca ccggtactg cctgagcagc   660
agactgagag tgtccgccac cttctggcag aaccccccgga accacttcag atgccaggtg   720
cagttctacg gcctgagcga gaacgacgag tggacccagg acagagccaa gcccgtgaca   780
cagatcgtgt ctgccgaagc ctggggcaga gccgattgcg gctttacctc cgtgtcctat   840
cagcagggcg tgctgagcgc cacaatcctg tacgagatcc tgctgggcaa ggccacccctg   900
tacgccgtgc tggtgtctgc cctggtgctg atggccatgg tcaagcggaa ggacttcggt   960
tccggagcca cgaacttctc tctgttaaag caagcaggag acgtggaaga aaaccccggt  1020
cccatgagcc tgagcagcct gctgaaagtc gtgaccgcca gcctgtggct gggacctgga  1080
atcgcccaga agatcaccca gacccagccc ggcatgttcg tgcaggaaaa agaagccgtg  1140
accctggact gcacctacga caccagcgac cctagctacg gcctgttctg gtacaagcag  1200
cccagcagcg gcgagatgat cttcctgatc taccagggca gctacgacca gcagaacgcc  1260
accgagggcc ggtacagcct gaacttccag aaggcccgga gtccgccaa cctcgtgatc  1320
agcgctagcc agctgggcga cagcgccatg tacttttgcg ccatcagcgg caacacccc  1380
ctggtgtttg caagggcac ccggctgagc gtgatcgcca acatccagaa ccccgacccc  1440
gcagtgtacc agctgcggga cagcaagagc agcgacaaga gcgtgtgcct gttcaccgac  1500
ttcgacagcc agaccaacgt gtcccagagc aaggacagcg acgtgtacat caccgataag  1560
tgcgtgctgg acatgcggag catggacttc aagagcaaca gcgccgtggc ctggtccaac  1620
aagagcgact tcgcctgcgc caacgccttc aacaacagca ttatccccga ggacacattc  1680
ttcccaagcc ccgagagcag ctgcgacgtg aagctggtgg aaaagagctt cgagacagac  1740
accaacctga acttccagaa cctcagcgtg atcggcttcc ggatcctgct gctgaaggtg  1800
gccggcttca acctgctgat gaccctgcgc ctgtggtcca gctga                 1845
```

<210> SEQ ID NO 254
<211> LENGTH: 66

```
<212> TYPE: DNA
<213> ORGANISM: Artificial Sequence
<220> FEATURE:
<223> OTHER INFORMATION: Porcine teschovirus-1 2A (P2A) peptide

<400> SEQUENCE: 254
ggaagcggag ctactaactt cagcctgctg aagcaggctg agacgtgga ggagaaccct    60 ggacct                                                              66

<210> SEQ ID NO 255
<211> LENGTH: 66
<212> TYPE: DNA
<213> ORGANISM: Artificial Sequence
<220> FEATURE:
<223> OTHER INFORMATION: Porcine teschovirus-1 2A (P2A) peptide - Codon
      Optimized

<400> SEQUENCE: 255
ggttccggag ccacgaactt ctctctgtta aagcaagcag agacgtgga agaaaacccc    60 ggtccc                                                              66

<210> SEQ ID NO 256
<211> LENGTH: 63
<212> TYPE: DNA
<213> ORGANISM: Artificial Sequence
<220> FEATURE:
<223> OTHER INFORMATION: Thoseaasigna virus 2A (T2A) peptide

<400> SEQUENCE: 256
ggaagcggag agggcagagg aagtctgcta acatgcggtg acgtcgagga gaatcctgga    60
cct                                                                 63

<210> SEQ ID NO 257
<211> LENGTH: 69
<212> TYPE: DNA
<213> ORGANISM: Artificial Sequence
<220> FEATURE:
<223> OTHER INFORMATION: Equine rhinitis A virus (ERAV) 2A (E2A) peptide

<400> SEQUENCE: 257
ggaagcggac agtgtactaa ttatgctctc ttgaaattgg ctggagatgt tgagagcaac    60
cctggacct                                                           69

<210> SEQ ID NO 258
<211> LENGTH: 75
<212> TYPE: DNA
<213> ORGANISM: Artificial Sequence
<220> FEATURE:
<223> OTHER INFORMATION: Foot-and-Mouth disease virus 2A (F2A) peptide

<400> SEQUENCE: 258
ggaagcggag tgaaacagac tttgaatttt gaccttctca gttggcggg agacgtggag    60 tccaaccctg gacct                                                    75
```

HIGH AFFINITY T CELL RECEPTORS AND USES THEREOF

STATEMENT OF GOVERNMENT INTEREST

This invention was made with government support under CA018029 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056_439USPC_SEQUENCE_LISTING. The text file is 366 KB, was created on June 18, 2018, and is being submitted electronically via EFS-Web.

BACKGROUND

Adoptive transfer of tumor-specific T-cells is an appealing strategy to eliminate existing tumors and requires the establishment of a robust population of antigen-specific T cells in vivo to eliminate existing tumor and prevent recurrences (Stromnes et al., *Immunol. Rev.* 257:145, 2014). Although transfer of tumor-specific CD8$^+$ cytotoxic T lymphocytes (CTLs) is safe and can mediate direct anti-tumor activity in select patients (Chapuis et al., *Cancer Res.* 72:LB-136, 2012; Chapuis et al., *Sci. Transl. Med.* 5:174ra127, 2013; Chapuis et al., *Proc. Nat'l. Acad. Sci. U.S.A.* 109:4592, 2012),[2-4] the variability in the avidity of the CTLs isolated from each patient or donor limits the anti-tumor efficacy in clinical trials (Chapuis et al., 2013). Since TCR affinity is an important determinant of CTL avidity (Zoete et al., *Frontiers Immunol.* 4:268, 2013), strategies have been developed to redirect the antigen specificity of donor or patient T cells using high affinity TCRα/β genes isolated from a well-characterized T cell clone specific for a tumor-specific antigen (Stromnes et al., *Immunol. Rev.* 257:145, 2014; Robbins et al., *J. Clin. Oncol.* 29:917, 2011). Such high affinity self/tumor-reactive T cells are rare since T cells that express self/tumor-reactive TCRs are subject to central and peripheral tolerance (Stone and Kranz, *Frontiers Immunol.* 4:244, 2013), with relative TCR affinities varying widely between donors. Therefore, many matched donors must be screened to identify a sufficiently high-affinity tumor-specific T cell clone from which a TCRα/β gene therapy construct can be generated. For example, isolation of a naturally elicited Wilms' Tumor antigen 1 (WT1)-specific TCR with high functional avidity for a single HLA-allele required screening of hundreds of WT-specific T cell lines representing thousands of individual T cell clones from the peripheral repertoires of greater than 75 normal donors, a very time and labor intensive process (Chapuis et al., 2013; Schmitt et al., *Hum. Gene Ther.* 20:1240, 2009; Ho et al., *J. Immunol. Methods* 310:40, 2006).

There is a clear need for alternative highly antigen-specific TCR immunotherapies directed against various cancers, such as leukemia and tumors. Presently disclosed embodiments address these needs and provide other related advantages.

BRIEF SUMMARY

The present disclosure provides, according to certain aspects, a binding protein (e.g., an immunoglobulin superfamily binding protein, TCR or the like) having (a) a T cell receptor (TCR) α-chain variable ($V_\alpha$) domain having a CDR3 amino acid sequence shown in any one of SEQ ID NOS.:93-102, and a TCR β-chain variable ($V_\beta$) domain; or (b) a $V_\alpha$ domain of (a) and a $V_\beta$ domain having a CDR3 amino acid sequence shown in any one of SEQ ID NOS.: 105-114; wherein the binding protein is capable of specifically binding to a WT-1 peptide:HLA complex on a cell surface, optionally independent of CD8 or in the absence of CD8.

In other aspects, the present disclosure provides a binding protein (e.g., an immunoglobulin superfamily binding protein, TCR or the like) having (a) a T cell receptor (TCR) α-chain variable ($V_\alpha$) domain having a CDR3 amino acid sequence shown in SEQ ID NO.:91 or 92, and a TCR β-chain variable ($V_\beta$) domain; or (b) a $V_\alpha$ domain of (a) and a $V_\beta$ domain having a CDR3 amino acid sequence shown in SEQ ID NO.:103 or 104; wherein the binding protein is capable of specifically binding to a mesothelin peptide:HLA complex on a cell surface independent, or in the absence of, CD8.

In further aspects there are provided methods for treating a hyperproliferative disorder, comprising administering to a human subject in need thereof a composition comprising any of the aforementioned binding proteins specific for human Wilms tumor protein 1 (WT-1) or mesothelin. In yet another aspect there is provided an adoptive immunotherapy method for treating a condition characterized by WT-1 or mesothelin overexpression in cells of a subject having a hyperproliferative disorder, comprising administering to the subject an effective amount of a engineered host cell expressing any of the aforementioned binding proteins.

In certain embodiments the methods provided are for treating a hyperproliferative disorder that is a hematological malignancy or a solid cancer. For example, the hematological malignancy to be treated may be acute lymphoblastic leukemia (ALL), acute myeloid leukemia (AML), chronic myelogenous leukemia (CIVIL), chronic eosinophilic leukemia (CEL), myelodysplastic syndrome (MDS), non-Hodgkin's lymphoma (NHL), or multiple myeloma (MM). Exemplary solid cancer to be treated may be biliary cancer, bladder cancer, bone and soft tissue carcinoma, brain tumor, breast cancer, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, gynecological tumor, head and neck squamous cell carcinoma, hepatic cancer, lung cancer, mesothelioma, malignant melanoma, osteosarcoma, ovarian cancer, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, testicular germ-cell tumor, urothelial cancer, uterine sarcoma, or uterine cancer.

These and other aspects and embodiments of the herein described invention will be evident upon reference to the following detailed description and attached drawings. All of the U.S. patents, U.S. patent application publications, U.S. patent applications, foreign patents, foreign patent applications, and non-patent publications referred to in this specification and/or listed in the Application Data Sheet are incorporated herein by reference in their entirety, as if each was incorporated individually. Aspects and embodiments of the invention can be modified, if necessary, to employ concepts of the various patents, applications and publications to provide yet further embodiments.

DETAILED DESCRIPTION

Figure 1:
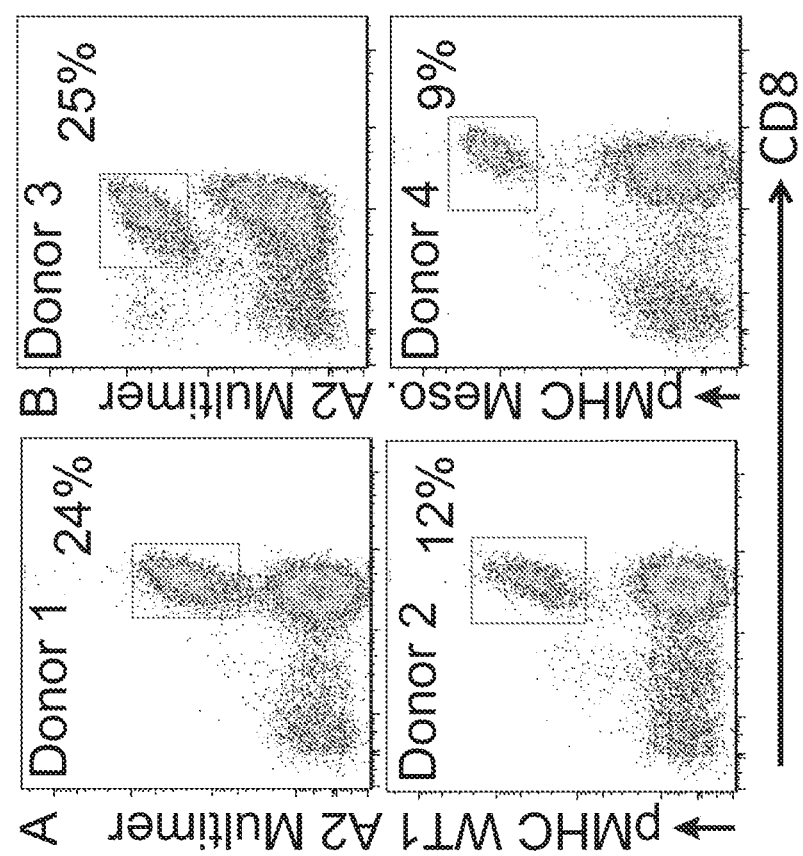
FIG. 1 shows the frequency of (A) WT-1$^{37-45}$- and (B) Mesothelin$^{20-28}$-specific (y-axis) CD8$^+$ T cells (x-axis) obtained from PBMCs of different normal HLA A*0201$^+$ donors after 3-rounds of ex vivo stimulation with peptide-pulsed dendritic cells and a cytokine cocktail. Saturating concentrations of pMHC were used for each line to identify all antigen-specific cells.

In one aspect, the present disclosure provides T cell receptors (TCRs) having high affinity for WT-1 or mesothelin peptide antigens associated with a major histocompatibility complex (MHC) (e.g., human leukocyte antigen, HLA) for use in, for example, adoptive immunotherapy to treat cancer.

By way of background, most tumor targets for T cell-based immunotherapies are self-antigens since tumors arise from previously normal tissue. For example, such tumor-associated antigens (TAAs) may be expressed at high levels in a cancer cell, but may not be expressed or may be minimally expressed in other cells. During T cell development in the thymus, T cells that bind weakly to self-antigens are allowed to survive in the thymus, and can undergo further development and maturation, while T cells that bind strongly to self-antigens are eliminated by the immune system since such cells would mount an undesirable autoimmune response. Hence, T cells are sorted by their relative ability to bind to antigens to prepare the immune system to respond against a foreign invader (i.e., recognition of non-self-antigen) while at the same time preventing an autoimmune response (i.e., recognition of self-antigen). This tolerance mechanism limits naturally occurring T cells that can recognize tumor (self) antigens with high affinity and, therefore, eliminates the T cells that would effectively eliminate tumor cells. Consequently, isolating T cells having high affinity TCRs specific for tumor antigens is difficult because most such cells are essentially eliminated by the immune system.

An advantage of the instant disclosure is to provide a high affinity TCRs specific for WT-1 or mesothelin peptides, wherein a cell expressing such a TCR is capable of binding to a WT-1:HLA complex independent of CD8, or capable of binding to a mesothelin:HLA complex independent of CD8. In addition, such TCRs may optionally be capable of more efficiently associating with a CD3 protein as compared to endogenous TCRs.

In certain embodiments, a high affinity TCR specific for a WT-1 peptide comprises a T cell receptor (TCR) α-chain having an amino acid sequence as set forth in any one of SEQ ID NOS.:20, 27, 34, 41, 48, 55, 64, 71, 78 and 85, and a TCR β-chain variable (V$_β$) domain as set forth in any one of SEQ ID NOS.:23, 30, 37, 44, 51, 60, 67, 74, 81 and 88. In certain embodiments, such high affinity TCRs are capable of binding to a VLDFAPPGA (SEQ ID NO.:117):HLA complex with a K$_d$ less than or equal to about 10$^{-8}$ M, or wherein the high affinity TCR dissociates from a VLDFAPPGA (SEQ ID NO.:117):HLA complex at a reduced k$_{off}$ rate as compared to a TCR composed of an α-chain of SEQ ID NO.:48 or 49 and a β-chain of SEQ ID NO.:51 or 52.

In other embodiments, an enhanced affinity TCR specific for a mesothelin peptide comprises a T cell receptor (TCR) α-chain having an amino acid sequence as set forth in SEQ ID NO.:4 or 13, and a TCR β-chain variable (V$_β$) domain as set forth in SEQ ID NO.:9 or 16. In certain embodiments, such high affinity TCRs are capable of binding to a SLL-FLLFSL (SEQ ID NO.:115):HLA complex with a K$_d$ less than or equal to about 10$^{-8}$ M, or to a VLPLTVAEV (SEQ ID NO.:116):HLA complex with a K$_d$ less than or equal to about 10$^{-8}$ M.

A method was developed to quickly and simultaneously screen and rank T cell clonotypes (based on affinity) from a large cohort of HLA matched donors in a short time (about 6-8 weeks). This method includes enriching for cells with high-affinity TCRs by using limiting concentrations of antigen-specific pMHC multimers. The TCRβ repertoire and frequency analysis, coupled with a bioinformatics, was used to accurately identify TCR α-chain and β-chain pairs. These methods allow for a quick comparison of the TCR affinity of thousands of clones from multiple donors as opposed to cloning individual TCRs.

The compositions and methods described herein will in certain embodiments have therapeutic utility for the treatment of diseases and conditions associated with WT-1 or mesothelin overexpression (e.g., detectable WT-1 or mesothelin expression at a level that is greater in magnitude, in a statistically significant manner, than the level of WT-1 or mesothelin expression that is detectable in a normal or disease-free cell). Such diseases include various forms of hyperproliferative disorders, such as hematological malignancies and solid cancers. Non-limiting examples of these and related uses are described herein and include in vitro, ex vivo and in vivo stimulation of WT-1 or mesothelin antigen-specific T cell responses, such as by the use of recombinant T cells expressing an enhanced affinity TCR specific for a WT-1 peptide (e.g., VLDFAPPGA, SEQ ID NO.:117) or a mesothelin peptide (e.g., SLLFLLFSL, SEQ ID NO.:115; or VLPLTVAEV, SEQ ID NO.:116).

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means ±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure.

The term "consisting essentially of" limits the scope of a claim to the specified materials or steps, or to those that do not materially affect the basic characteristics of a claimed invention. For example, a protein domain, region, or module (e.g., a binding domain, hinge region, linker module) or a protein (which may have one or more domains, regions, or modules) "consists essentially of" a particular amino acid sequence when the amino acid sequence of a domain, region, module, or protein includes extensions, deletions, mutations, or a combination thereof (e.g., amino acids at the amino- or carboxy-terminus or between domains) that, in combination, contribute to at most 20% (e.g., at most 15%, 10%, 8%, 6%, 5%, 4%, 3%, 2% or 1%) of the length of a domain, region, module, or protein and do not substantially affect (i.e., do not reduce the activity by more than 50%, such as no more than 40%, 30%, 25%, 20%, 15%, 10%, 5%, or 1%) the activity of the domain(s), region(s), module(s), or protein (e.g., the target binding affinity of a binding protein).

As used herein, an "immune system cell" means any cell of the immune system that originates from a hematopoietic stem cell in the bone marrow, which gives rise to two major lineages, a myeloid progenitor cell (which give rise to myeloid cells such as monocytes, macrophages, dendritic cells, meagakaryocytes and granulocytes) and a lymphoid progenitor cell (which give rise to lymphoid cells such as T cells, B cells and natural killer (NK) cells). Exemplary immune system cells include a CD4+ T cell, a CD8+ T cell, a CD4− CD8− double negative T cell, a γδ T cell, a regulatory T cell, a natural killer cell, and a dendritic cell. Macrophages and dendritic cells may be referred to as "antigen presenting cells" or "APCs," which are specialized cells that can activate T cells when a major histocompatibility complex (MHC) receptor on the surface of the APC complexed with a peptide interacts with a TCR on the surface of a T cell.

"Major histocompatibility complex" (MHC) refers to glycoproteins that deliver peptide antigens to a cell surface. MHC class I molecules are heterodimers having a membrane spanning a chain (with three a domains) and a non-covalently associated β2 microglobulin. MHC class II molecules are composed of two transmembrane glycoproteins, α and β, both of which span the membrane. Each chain has two domains. MHC class I molecules deliver peptides originating in the cytosol to the cell surface, where a peptide:MHC complex is recognized by $CD8^+$ T cells. MHC class II molecules deliver peptides originating in the vesicular system to the cell surface, where they are recognized by $CD4^+$ T cells. Human MHC is referred to as human leukocyte antigen (HLA).

A "T cell" is an immune system cell that matures in the thymus and produces T cell receptors (TCRs). T cells can be naïve (not exposed to antigen; increased expression of CD62L, CCR7, CD28, CD3, CD127, and CD45RA, and decreased expression of CD45RO as compared to $T_{CM}$), memory T cells ($T_M$) (antigen-experienced and long-lived), and effector cells (antigen-experienced, cytotoxic). $T_M$ can be further divided into subsets of central memory T cells ($T_{CM}$, increased expression of CD62L, CCR7, CD28, CD127, CD45RO, and CD95, and decreased expression of CD54RA as compared to naïve T cells) and effector memory T cells ($T_{EM}$, decreased expression of CD62L, CCR7, CD28, CD45RA, and increased expression of CD127 as compared to naïve T cells or $T_{CM}$). Effector T cells ($T_E$) refers to antigen-experienced CD8+ cytotoxic T lymphocytes that have decreased expression of CD62L, CCR7, CD28, and are positive for granzyme and perforin as compared to $T_{CM}$. Other exemplary T cells include regulatory T cells, such as CD4+ CD25+ (Foxp3+) regulatory T cells and Treg17 cells, as well as Tr1, Th3, CD8+CD28−, and Qa-1 restricted T cells.

"T cell receptor" (TCR) refers to an immunoglobulin superfamily member (having a variable binding domain, a constant domain, a transmembrane region, and a short cytoplasmic tail; see, e.g., Janeway et al., *Immunobiology: The Immune System in Health and Disease*, $3^{rd}$ Ed., Current Biology Publications, p. 4:33, 1997) capable of specifically binding to an antigen peptide bound to a MHC receptor. A TCR can be found on the surface of a cell or in soluble form and generally is comprised of a heterodimer having α and β chains (also known as TCRα and TCRβ, respectively), or γ and δ chains (also known as TCRγ and TCRδ, respectively). Like immunoglobulins, the extracellular portion of TCR chains (e.g., α-chain, β-chain) contain two immunoglobulin domains, a variable domain (e.g., α-chain variable domain or $V_\alpha$, β-chain variable domain or $V_\beta$; typically amino acids 1 to 116 based on Kabat numbering Kabat et al., "Sequences of Proteins of Immunological Interest, US Dept. Health and Human Services, Public Health Service National Institutes of Health, 1991, $5^{th}$ ed.) at the N-terminus, and one constant domain (e.g., α-chain constant domain or $C_\alpha$, typically amino acids 117 to 259 based on Kabat, β-chain constant domain or $C_\beta$, typically amino acids 117 to 295 based on Kabat) adjacent to the cell membrane. Also like immunoglobulins, the variable domains contain complementary determining regions (CDRs) separated by framework regions (FRs) (see, e.g., Jores et al., *Proc. Nat'l Acad. Sci. U.S.A.* 87:9138, 1990; Chothia et al., *EMBO J.* 7:3745, 1988; see also Lefranc et al., *Dev. Comp. Immunol.* 27:55, 2003). In certain embodiments, a TCR is found on the surface of T cells (or T lymphocytes) and associates with the CD3 complex. The source of a TCR as used in the present disclosure may be from various animal species, such as a human, mouse, rat, rabbit or other mammal.

"CD3" is known in the art as a multi-protein complex of six chains (see, Abbas and Lichtman, 2003; Janeway et al., p 172 and 178, 1999). In mammals, the complex comprises a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. Without wishing to be bound by theory, it is believed the ITAMs are important for the signaling capacity of a TCR complex. CD3 as used in the present disclosure may be from various animal species, including human, mouse, rat, or other mammals.

As used herein, "TCR complex" refers to a complex formed by the association of CD3 with TCR. For example, a TCR complex can be composed of a CD3γ chain, a CD3δ chain, two CD3ε chains, a homodimer of CD3ζ chains, a TCRα chain, and a TCRβ chain. Alternatively, a TCR complex can be composed of a CD3γ chain, a CD3δ chain, two CD3ε chains, a homodimer of CD3ζ chains, a TCRγ chain, and a TCR chain.

A "component of a TCR complex," as used herein, refers to a TCR chain (i.e., TCRα, TCRβ, TCRγ or TCRδ), a CD3 chain (i.e., CD3γ, CD3δ, CD3ε or CD3ζ), or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains).

A "binding domain" (also referred to as a "binding region" or "binding moiety"), as used herein, refers to a molecule or portion thereof (e.g., peptide, oligopeptide, polypeptide, protein) that possesses the ability to specifically and non-covalently associate, unite, or combine with a target (e.g., WT-1, mesothelin, WT-1 peptide:MHC complex, mesothelin peptide:MHC complex). A binding domain includes any naturally occurring, synthetic, semi-synthetic, or recombinantly produced binding partner for a biological molecule, a molecular complex (i.e., complex comprising two or more biological molecules), or other target of interest. Exemplary binding domains include single chain immunoglobulin variable regions (e.g., scTCR, scFv), receptor ectodomains, ligands (e.g., cytokines, chemokines), or synthetic polypeptides selected for their specific ability to bind to a biological molecule, a molecular complex or other target of interest.

As used herein, "specifically binds" or "specific for" refers to an association or union of a binding protein (e.g., TCR receptor) or a binding domain (or fusion protein thereof) to a target molecule with an affinity or $K_a$ (i.e., an equilibrium association constant of a particular binding interaction with units of 1/M) equal to or greater than $10^5$ $M^{-1}$ (which equals the ratio of the on-rate [$k_{on}$] to the off-rate [$k_{off}$] for this association reaction), while not significantly associating or uniting with any other molecules or components in a sample. Binding proteins or binding domains (or fusion proteins thereof) may be classified as "high affinity" binding proteins or binding domains (or fusion proteins thereof) or as "low affinity" binding proteins or binding domains (or fusion proteins thereof). "High affinity" binding proteins or binding domains refer to those binding proteins or binding domains having a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. "Low affinity" binding proteins or binding domains refer to those binding proteins or binding domains having a $K_a$ of up to $10^7$ $M^{-1}$, up to $10^6$ $M^{-1}$, up to $10^5$ $M^{-1}$. Alternatively, affinity may be defined as an equilibrium dissociation constant ($K_d$) of a particular binding interaction with units of M (e.g., $10^{-5}$ M to $10^{-13}$ M).

In certain embodiments, a receptor or binding domain may have "enhanced affinity," which refers to selected or engineered receptors or binding domains with stronger binding to a target antigen than a wild type (or parent) binding domain. For example, enhanced affinity may be due to a $K_a$ (equilibrium association constant) for the target antigen that is higher than the wild type binding domain, due to a $K_d$ (dissociation constant) for the target antigen that is less than that of the wild type binding domain, due to an off-rate ($k_{off}$) for the target antigen that is less than that of the wild type binding domain, or a combination thereof. In certain embodiments, enhanced affinity TCRs may be codon optimized to enhance expression in a particular host cell, such as T cells (Scholten et al., *Clin. Immunol.* 119:135, 2006).

A variety of assays are known for identifying binding domains of the present disclosure that specifically bind a particular target, as well as determining binding domain or fusion protein affinities, such as Western blot, ELISA, analytical ultracentrifugation, spectroscopy and surface plasmon resonance (Biacore®) analysis (see, e.g., Scatchard et al., *Ann. N.Y. Acad. Sci.* 51:660, 1949; Wilson, *Science* 295:2103, 2002; Wolff et al., *Cancer Res.* 53:2560, 1993; and U.S. Pat. Nos. 5,283,173, 5,468,614, or the equivalent).

The term "WT-1-specific binding protein" refers to a protein or polypeptide that specifically binds to WT-1 or a peptide or fragment thereof. In some embodiments, a protein or polypeptide binds to WT-1 or a peptide thereof, such as a WT-1 peptide in complexed with an MEW or HLA molecule, e.g., on a cell surface, with at or at least about a particular affinity. In certain embodiments, a WT-1-specific binding protein binds a WT-1-derived peptide:HLA complex (or WT-1-derived peptide:MHC complex) with a $K_d$ of less than about $10^{-8}$ M, less than about $10^{-9}$M, less than about $10^{-10}$ M, less than about $10^{-11}$M, less than about $10^{-12}$M, or less than about $10^{-13}$ M, or with an affinity that is about the same as, at least about the same as, or is greater than at or about the affinity exhibited by an exemplary WT-1 specific binding protein provided herein, such as any of the WT-1-specific TCRs provided herein, for example, as measured by the same assay. In certain embodiments, a WT-1-specific binding protein comprises a WT-1-specific immunoglobulin superfamily binding protein or binding portion thereof.

The term "mesothelin-specific binding protein" refers to a protein or polypeptide that specifically binds to mesothelin or peptide or fragment thereof. In some embodiments, a protein or polypeptide binds to mesothelin or a peptide thereof, such as a mesothelin peptide in complexed with an MEW or HLA molecule, e.g., on a cell surface, with at or at least about a particular affinity. In certain embodiments, a mesothelin-specific binding protein binds a mesothelin-derived peptide:HLA complex (or mesothelin-derived peptide:MHC complex) with a $K_d$ of less than about $10^{-8}$ M, less than about $10^{-9}$ M, less than about $10^{-10}$ M, less than about $10^{-11}$ M, less than about $10^{-12}$ M, or less than about $10^{-13}$ M, or with an affinity that is about the same as, at least about the same as, or is greater than at or about the affinity exhibited by an exemplary mesothelin specific binding protein provided herein, such as any of the mesothelin-specific TCRs provided herein, for example, as measured by the same assay. In certain embodiments, a mesothelin-specific binding protein comprises a mesothelin-specific immunoglobulin superfamily binding protein or binding portion thereof.

Assays for assessing affinity or apparent affinity or relative affinity are known. In certain examples, apparent affinity for a TCR is measured by assessing binding to various concentrations of tetramers, for example, by flow cytometry using labeled tetramers. In some examples, apparent $K_D$ of a TCR is measured using 2-fold dilutions of labeled tetramers at a range of concentrations, followed by determination of binding curves by non-linear regression, apparent $K_D$ being determined as the concentration of ligand that yielded half-maximal binding.

The term "WT-1 binding domain" or "WT-1 binding fragment" refer to a domain or portion of a WT-1-specific binding protein responsible for the specific WT-1 binding. A WT-1-specific binding domain alone (i.e., without any other portion of a WT-1-specific binding protein) can be soluble and can bind to WT-1 with a $K_d$ of less than about $10^{-8}$ M, less than about $10^{-9}$ M, less than about $10^{-10}$ M, less than about $10^{-11}$ M, less than about $10^{-12}$ M, or less than about $10^{-13}$ M. Exemplary WT-1-specific binding domains include WT-1-specific scTCR (e.g., single chain αβTCR proteins such as Vα-L-Vβ, Vβ-L-Vα, Vα-Cα-L-Vα, or Vα-L-Vβ-Cβ, wherein Vα and Vβ are TCRα and β variable domains respectively, Cα and Cβ are TCRα and β constant domains, respectively, and L is a linker) and scFv fragments as described herein, which can be derived from an anti-WT-1 TCR or antibody.

The term "mesothelin binding domain" or "mesothelin binding fragment" refer to a domain or portion of a mesothelin-specific binding protein responsible for the specific mesothelin binding. A mesothelin-specific binding domain alone (i.e., without any other portion of a mesothelin-specific binding protein) can be soluble and can bind to mesothelin with a $K_d$ of less than about $10^{-8}$ M, less than about $10^{-9}$ M, less than about $10^{-10}$ M, less than about $10^{-11}$ M, less than about $10^{-12}$ M, or less than about $10^{-13}$ M. Exemplary mesothelin-specific binding domains include mesothelin-specific scTCR (e.g., single chain αβTCR proteins such as Vα-L-Vβ, Vβ-L-Vα, Vα-Cα-L-Vα, or Vα-L-Vβ-Cβ, wherein Vα and Vβ are TCRα and β variable domains respectively, Cα and Cβ are TCRα and β constant domains, respectively, and L is a linker) and scFv fragments as described herein, which can be derived from an anti-mesothelin TCR or antibody.

Principles of antigen processing by antigen presenting cells (APC) (such as dendritic cells, macrophages, lymphocytes or other cell types), and of antigen presentation by APC to T cells, including major histocompatibility complex (MHC)-restricted presentation between immunocompatible (e.g., sharing at least one allelic form of an MHC gene that is relevant for antigen presentation) APC and T cells, are well established (see, e.g., Murphy, Janeway's Immunobiology (8$^{th}$ Ed.) 2011 Garland Science, NY; chapters 6, 9 and 16). For example, processed antigen peptides originating in the cytosol (e.g., tumor antigen, intrcellular pathogen) are generally from about 7 amino acids to about 11 amino acids in length and will associate with class I MHC molecules, whereas peptides processed in the vesicular system (e.g., bacterial, viral) will vary in length from about 10 amino acids to about 25 amino acids and associate with class II MHC molecules.

"WT-1 antigen" or "WT-1 peptide antigen" refer to a naturally or synthetically produced portion of a WT-1 protein ranging in length from about 7 amino acids to about 15 amino acids, which can form a complex with a MHC (e.g., HLA) molecule and such a complex can bind with a TCR specific for a WT-1 peptide:MHC (e.g., HLA) complex. Since WT-1 is an internal host protein, WT-1 antigen peptides will be presented in the context of class I MHC. In particular embodiments, a WT-1 peptide is VLDFAPPGA (SEQ ID NO.:117), which is known to associate with human class I HLA (and, more specifically, associates with allele HLA-A*201).

"Mesothelin antigen" or "mesothelin peptide antigen" refer to a naturally or synthetically produced portion of a mesothelin protein ranging in length from about 7 amino acids to about 15 amino acids, which can form a complex with a MHC (e.g., HLA) molecule and such a complex can bind with a TCR specific for a mesothelin peptide:MHC (e.g., HLA) complex. Exemplary mesothelin peptides include mesothelin amino acids 20-28 that form peptide antigen SLLFLLFSL (SEQ ID NO.:115, also referred to as Meso$^{20-28}$) or mesothelin amino acids 530-538 that form peptide antigen VLPLTVAEV (SEQ ID NO.:116, also referred to as Meso$^{530-538}$), which are known to associate with human with allele HLA-A*201.

A "linker" refers to an amino acid sequence that connects two proteins, polypeptides, peptides, domains, regions, or motifs and may provide a spacer function compatible with interaction of the two sub-binding domains so that the resulting polypeptide retains a specific binding affinity (e.g., scTCR) to a target molecule or retains signaling activity (e.g., TCR complex). In certain embodiments, a linker is comprised of about two to about 35 amino acids, for instance, or about four to about 20 amino acids or about eight to about 15 amino acids or about 15 to about 25 amino acids.

"Junction amino acids" or "junction amino acid residues" refer to one or more (e.g., about 2-10) amino acid residues between two adjacent motifs, regions or domains of a polypeptide, such as between a binding domain and an adjacent constant domain or between a TCR chain and an adjacent self-cleaving peptide. Junction amino acids may result from the construct design of a fusion protein (e.g., amino acid residues resulting from the use of a restriction enzyme site during the construction of a nucleic acid molecule encoding a fusion protein).

An "altered domain" or "altered protein" refers to a motif, region, domain, peptide, polypeptide, or protein with a non-identical sequence identity to a wild type motif, region, domain, peptide, polypeptide, or protein (e.g., a wild type TCRα chain, TCRβ chain, TCRα constant domain, TCRβ constant domain) of at least 85% (e.g., 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%).

As used herein, "nucleic acid" or "nucleic acid molecule" refers to any of deoxyribonucleic acid (DNA), ribonucleic acid (RNA), oligonucleotides, fragments generated, for example, by the polymerase chain reaction (PCR) or by in vitro translation, and fragments generated by any of ligation, scission, endonuclease action, or exonuclease action. In certain embodiments, the nucleic acids of the present disclosure are produced by PCR. Nucleic acids may be composed of monomers that are naturally occurring nucleotides (such as deoxyribonucleotides and ribonucleotides), analogs of naturally occurring nucleotides (e.g., α-enantiomeric forms of naturally-occurring nucleotides), or a combination of both. Modified nucleotides can have modifications in or replacement of sugar moieties, or pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. Nucleic acid molecules can be either single stranded or double stranded.

The term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such nucleic acid could be part of a vector and/or such nucleic acid or polypeptide could be part of a composition (e.g., a cell lysate), and still be isolated in that such vector or composition is not part of the natural environment for the nucleic acid or polypeptide. The term "gene" means the segment of DNA involved in producing a polypeptide chain; it includes regions preceding and following the coding region "leader and trailer" as well as intervening sequences (introns) between individual coding segments (exons).

As used herein, the term "recombinant" refers to a cell, microorganism, nucleic acid molecule, or vector that has been genetically engineered by human intervention—that is, modified by introduction of an exogenous or heterologous nucleic acid molecule, or refers to a cell or microorganism that has been altered such that expression of an endogenous nucleic acid molecule or gene is controlled, deregulated or constitutive. Human generated genetic alterations may include, for example, modifications that introduce nucleic acid molecules (which may include an expression control element, such as a promoter) that encode one or more proteins or enzymes, or other nucleic acid molecule additions, deletions, substitutions, or other functional disruption of or addition to a cell's genetic material. Exemplary modifications include those in coding regions or functional fragments thereof of heterologous or homologous polypeptides from a reference or parent molecule.

As used herein, "mutation" refers to a change in the sequence of a nucleic acid molecule or polypeptide molecule as compared to a reference or wild-type nucleic acid molecule or polypeptide molecule, respectively. A mutation can result in several different types of change in sequence, including substitution, insertion or deletion of nucleotide(s) or amino acid(s). In certain embodiments, a mutation is a substitution of one or three codons or amino acids, a deletion of one to about 5 codons or amino acids, or a combination thereof.

A "conservative substitution" is recognized in the art as a substitution of one amino acid for another amino acid that has similar properties. Exemplary conservative substitutions are well known in the art (see, e.g., WO 97/09433 at page 10; Lehninger, Biochemistry, $2^{nd}$ Edition; Worth Publishers, Inc. NY, NY, pp. 71-'7'7, 1975; Lewin, Genes IV, Oxford University Press, NY and Cell Press, Cambridge, Mass., p. 8, 1990).

The term "construct" refers to any polynucleotide that contains a recombinant nucleic acid molecule. A construct may be present in a vector (e.g., a bacterial vector, a viral vector) or may be integrated into a genome. A "vector" is a nucleic acid molecule that is capable of transporting another nucleic acid molecule. Vectors may be, for example, plasmids, cosmids, viruses, a RNA vector or a linear or circular DNA or RNA molecule that may include chromosomal, non-chromosomal, semi-synthetic or synthetic nucleic acid molecules. Exemplary vectors are those capable of autonomous replication (episomal vector) or expression of nucleic acid molecules to which they are linked (expression vectors).

Viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields et al., Eds., Lippincott-Raven Publishers, Philadelphia, 1996).

"Lentiviral vector," as used herein, means HIV-based lentiviral vectors for gene delivery, which can be integrative or non-integrative, have relatively large packaging capacity, and can transduce a range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration into the DNA of infected cells.

The term "operably-linked" refers to the association of two or more nucleic acid molecules on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). "Unlinked" means that the associated genetic elements are not closely associated with one another and the function of one does not affect the other.

As used herein, "expression vector" refers to a DNA construct containing a nucleic acid molecule that is operably-linked to a suitable control sequence capable of effecting the expression of the nucleic acid molecule in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, a virus, or simply a potential genomic insert. Once transformed into a suitable host, the vector may replicate and function independently of the host genome, or may, in some instances, integrate into the genome itself. In the present specification, "plasmid," "expression plasmid," "virus" and "vector" are often used interchangeably.

The term "expression", as used herein, refers to the process by which a polypeptide is produced based on the encoding sequence of a nucleic acid molecule, such as a gene. The process may include transcription, post-transcriptional control, post-transcriptional modification, translation, post-translational control, post-translational modification, or any combination thereof.

The term "introduced" in the context of inserting a nucleic acid molecule into a cell, means "transfection", or "transformation" or "transduction" and includes reference to the incorporation of a nucleic acid molecule into a eukaryotic or prokaryotic cell wherein the nucleic acid molecule may be incorporated into the genome of a cell (e.g., chromosome, plasmid, plastid, or mitochondrial DNA), converted into an autonomous replicon, or transiently expressed (e.g., transfected mRNA).

As used herein, "heterologous" or "exogenous" nucleic acid molecule, construct or sequence refers to a nucleic acid molecule or portion of a nucleic acid molecule that is not native to a host cell, but may be homologous to a nucleic acid molecule or portion of a nucleic acid molecule from the host cell. The source of the heterologous or exogenous nucleic acid molecule, construct or sequence may be from a different genus or species. In certain embodiments, a heterologous or exogenous nucleic acid molecule is added (i.e., not endogenous or native) to a host cell or host genome by, for example, conjugation, transformation, transfection, electroporation, or the like, wherein the added molecule may integrate into the host genome or exist as extra-chromosomal genetic material (e.g., as a plasmid or other form of self-replicating vector), and may be present in multiple copies. In addition, "heterologous" refers to a non-native enzyme, protein or other activity encoded by an exogenous nucleic acid molecule introduced into the host cell, even if the host cell encodes a homologous protein or activity.

As described herein, more than one heterologous or exogenous nucleic acid molecule can be introduced into a host cell as separate nucleic acid molecules, as a plurality of individually controlled genes, as a polycistronic nucleic acid molecule, as a single nucleic acid molecule encoding a fusion protein, or any combination thereof. For example, as disclosed herein, a host cell can be modified to express two or more heterologous or exogenous nucleic acid molecules encoding desired TCR specific for a WT-1 antigen peptide (e.g., TCRα and TCRβ). When two or more exogenous nucleic acid molecules are introduced into a host cell, it is understood that the two or more exogenous nucleic acid molecules can be introduced as a single nucleic acid molecule (e.g., on a single vector), on separate vectors, integrated into the host chromosome at a single site or multiple sites, or any combination thereof. The number of referenced heterologous nucleic acid molecules or protein activities refers to the number of encoding nucleic acid molecules or the number of protein activities, not the number of separate nucleic acid molecules introduced into a host cell.

As used herein, the term "endogenous" or "native" refers to a gene, protein, or activity that is normally present in a host cell. Moreover, a gene, protein or activity that is mutated, overexpressed, shuffled, duplicated or otherwise altered as compared to a parent gene, protein or activity is still considered to be endogenous or native to that particular host cell. For example, an endogenous control sequence from a first gene (e.g., promoter, translational attenuation sequences) may be used to alter or regulate expression of a second native gene or nucleic acid molecule, wherein the expression or regulation of the second native gene or nucleic acid molecule differs from normal expression or regulation in a parent cell.

The term "homologous" or "homolog" refers to a molecule or activity found in or derived from a host cell, species or strain. For example, a heterologous or exogenous nucleic acid molecule may be homologous to a native host cell gene, and may optionally have an altered expression level, a different sequence, an altered activity, or any combination thereof.

"Sequence identity," as used herein, refers to the percentage of amino acid residues in one sequence that are identical with the amino acid residues in another reference polypeptide sequence after aligning the sequences and introducing gaps, if necessary, to achieve the maximum percent sequence identity, and not considering any conservative substitutions as part of the sequence identity. The percentage sequence identity values can be generated using the NCBI BLAST2.0 software as defined by Altschul et al. (1997) "Gapped BLAST and PSI-BLAST: a new generation of protein database search programs", Nucleic Acids Res. 25:3389-3402, with the parameters set to default values.

As used herein, a "hematopoietic progenitor cell" is a cell that can be derived from hematopoietic stem cells or fetal tissue and is capable of further differentiation into mature cells types (e.g., immune system cells). Exemplary hematopoietic progenitor cells include those with a $CD24^{Lo}$ $Lin^-$ $CD117^+$ phenotype or those found in the thymus (referred to as progenitor thymocytes).

As used herein, the term "host" refers to a cell (e.g., T cell) or microorganism targeted for genetic modification with a heterologous or exogenous nucleic acid molecule to produce a polypeptide of interest (e.g., high or enhanced affinity anti-WT-1 TCR). In certain embodiments, a host cell may optionally already possess or be modified to include other genetic modifications that confer desired properties related or unrelated to biosynthesis of the heterologous or exogenous protein (e.g., inclusion of a detectable marker; deleted, altered or truncated endogenous TCR; increased co-stimulatory factor expression). In some embodiments, host cells are genetically modified to express a protein or fusion protein that modulates immune signaling in a host cell to, for example, promote survival and/or expansion advantage to the modified cell (e.g., see immunomodulatory fusion proteins of WO 2016/141357, which are herein incorporated by reference in their entirety). In other embodiments, host cells are genetically modified to knock-down or minimize immunosuppressive signals in a cell (e.g., a checkpoint inhibitor), which modification may be made using, for example, a CRISPR/Cas system (see, e.g., US 2014/0068797, U.S. Pat. No. 8,697,359; WO 2015/071474). In certain embodiments, a host cell is a human hematopoietic progenitor cell transduced with a heterologous or exogenous nucleic acid molecule encoding a TCRα chain specific for a WT-1 antigen peptide.

As used herein, "hyperproliferative disorder" refers to excessive growth or proliferation as compared to a normal or undiseased cell. Exemplary hyperproliferative disorders include tumors, cancers, neoplastic tissue, carcinoma, sarcoma, malignant cells, pre-malignant cells, as well as non-neoplastic or non-malignant hyperproliferative disorders (e.g., adenoma, fibroma, lipoma, leiomyoma, hemangioma, fibrosis, restenosis, as well as autoimmune diseases such as rheumatoid arthritis, osteoarthritis, psoriasis, inflammatory bowel disease, or the like).

Binding Proteins Specific for WT-1 and Mesothelin Antigen Peptides

Several peptides of the mesothelin and WT-1 proteins are known to be tumor-associated antigen peptides that are HLA A*0201-restricted antigens. The mesothelin and WT-1 proteins are attractive targets for clinical development due to (a) their immune characteristics (Cheever et al., *Clin. Cancer Res.* 15:5323, 2009), and (b) their expression in many aggressive tumor-types having associated poor-prognoses.

Mesothelin is a cell-surface glycoprotein uniformly expressed in near 100% of pancreatic and bile duct cancers (Argani et al., *Clin. Cancer Res.* 7:3862, 2001; Hassan et al., *American J. Clin. Pathol.* 124:838, 2005), 70% of ovarian epithelial tumors, 67% of triple negative breast cancers (TNBCs) (Tchou et al., *Breast Cancer Res. Treat.* 133:799, 2012), and 50% of lung cancers (Ren et al., *J. Biol. Chem.* 286:11960, 2011). Mesothelin contributes to the malignant phenotype and invasiveness (Hung et al., *Immunol. Rev.* 222:43, 2008), and both WT1 and mesothelin are immunogenic with sufficiently limited expression in normal adult tissues to be safely targeted by CTL (Armstrong et al., *Mech. Dev.* 40:85, 1993; Chang and Pastan, *Proc. Nat'l. Acad. Sci. U.S.A.* 93:136, 1996).

In certain aspects, the instant disclosure provides a binding protein (e.g., an immunoglobulin superfamily binding protein or portion thereof), comprising (a) a T cell receptor (TCR) α-chain variable ($V_\alpha$) domain having a CDR3 amino acid sequence shown in SEQ ID NO.:91 or 92, and a TCR β-chain variable ($V_\beta$) domain; or (b) a $V_\alpha$ domain of (a) and a $V_\beta$ domain having a CDR3 amino acid sequence shown in SEQ ID NO.:103 or 104. Such a binding protein is capable of binding with a high affinity to a mesothelin-derived peptide:human leukocyte antigen (HLA) complex on a cell surface. For example, binding proteins of this disclosure can bind to an antigen:HLA complex independent of CD8 or in the absence of CD8. In particular embodiments, the binding protein binds to a SLLFLLFSL (SEQ ID NO.:115):human leukocyte antigen (HLA) complex or to a VLPLTVAEV (SEQ ID NO.:116):HLA complex with a $K_d$ less than or equal to about $10^{-8}$ M.

In certain embodiments, a binding protein specific for a mesothelin peptide:HLA complex has a $V_\alpha$ domain that comprises or consists of an amino acid sequence as set forth in SEQ ID NO.:1 or 12, a $V_\beta$ domain that comprises or consists of an amino acid sequence as set forth in SEQ ID NO.:6 or 15, or any combination thereof.

In further embodiments, a binding protein specific for a mesothelin peptide:HLA complex comprises a T cell receptor (TCR) α-chain having an amino acid sequence as set forth in SEQ ID NO.:4 or 13, and a TCR β-chain variable ($V_\beta$) domain as set forth in SEQ ID NO.:9 or 16. In particular embodiments, a mesothelin specific binding protein includes: (a) a TCR α-chain comprising or consisting of an amino acid sequence as set forth in SEQ ID NO.:4, and a TCR β-chain comprising or consisting of an amino acid sequence as set forth in SEQ ID NO.:9; (b) a TCR α-chain comprising or consisting of an amino acid sequence as set forth in SEQ ID NO.:4, and a TCR β-chain comprising or consisting of an amino acid sequence as set forth in SEQ ID NO.:16; (c) a TCR α-chain comprising or consisting of an amino acid sequence as set forth in SEQ ID NO.:13, and a TCR β-chain comprising or consisting of an amino acid sequence as set forth in SEQ ID NO.:9; or (d) a TCR α-chain comprising or consisting of an amino acid sequence as set forth in SEQ ID NO.:13, and a TCR β-chain comprising or consisting of an amino acid sequence as set forth in SEQ ID NO.:16.

WT-1 is involved in the regulation of gene expression that promotes proliferation and oncogenicity (Oji et al., *Jpn. J. Cancer Res.* 90:194, 1999), is overexpressed in most high-risk leukemia (Menssen et al., *Leukemia* 9:1060, 1995), up to 80% of NSCLCs (Oji et al., *Int. J. Cancer* 100:297, 2002), 100% of mesotheliomas (Tsuta et al., *App. Immunohistochem. Mol. Morphol.* 17:126, 2009), and ≥80% of gynecological malignancies (Coosemans and Van Gool, *Expert Rev. Clin. Immunol.* 10:705, 2014).

In further aspects, the instant disclosure provides a WT-1 specific binding protein (e.g., an immunoglobulin superfamily binding protein or portion thereof), comprising (a) a T cell receptor (TCR) α-chain variable ($V_\alpha$) domain having a CDR3 amino acid sequence shown in any one of SEQ ID NOS.:93-102, and a TCR β-chain variable ($V_\beta$) domain; or (b) a $V_\alpha$ domain of (a) and a $V_\beta$ domain having a CDR3 amino acid sequence shown in any one of SEQ ID NOS.: 105-114. Such a binding protein is capable of binding with a high affinity to a WT-1 peptide:human leukocyte antigen (HLA) complex on a cell surface. For example, binding proteins of this disclosure can bind to an antigen:HLA complex independent of CD8 or in the absence of CD8. In particular embodiments, the binding protein binds to a VLDFAPPGA (SEQ ID NO.:117):human leukocyte antigen (HLA) complex with a $K_d$ less than or equal to about $10^{-8}$ M.

In certain embodiments, a binding protein specific for a WT-1 peptide:HLA complex has a $V_\alpha$ domain that comprises or consists of an amino acid sequence as set forth in any one of SEQ ID NOS.:19, 26, 33, 40, 47, 54, 63, 70, 77 and 84, has a $V_\beta$ domain comprises or consists of an amino acid sequence as set forth in any one of SEQ ID NOS.:22, 29, 36, 43, 50, 57, 66, 73, 80 and 87, or any combination thereof. In particular embodiments, the $V_\alpha$ domain comprises or consists of an amino acid sequence as set forth in any one of SEQ ID NOS.:19, 26, 33 and 40, the $V_\beta$ domain comprises or consists of an amino acid sequence as set forth in any one of SEQ ID NOS.:22, 29, 36, 43 and 50, or any combination thereof. In further particular embodiments, the $V_\alpha$ domain comprises or consists of an amino acid sequence as set forth in any one of SEQ ID NOS.: 54, 63, 70, 77, and 84, the $V_\beta$ domain comprises or consists of an amino acid sequence as set forth in any one of SEQ ID NOS.: 57, 66, 73, 80, and 87, or any combination thereof.

In further embodiments, a WT-1 specific binding protein includes: (a) a TCR α-chain comprising or consisting of an amino acid sequence as set forth in SEQ ID NO.:20, and a TCR β-chain comprising or consisting of an amino acid sequence as set forth in SEQ ID NO.:23; (b) a TCR α-chain comprising or consisting of an amino acid sequence as set forth in SEQ ID NO.:27, and a TCR β-chain comprising or consisting of an amino acid sequence as set forth in SEQ ID NO.:30; (c) a TCR α-chain comprising or consisting of an amino acid sequence as set forth in SEQ ID NO.:34, and a TCR β-chain comprising or consisting of an amino acid sequence as set forth in SEQ ID NO.:37; (d) a TCR α-chain comprising or consisting of an amino acid sequence as set forth in SEQ ID NO.:41, and a TCR β-chain comprising or consisting of an amino acid sequence as set forth in SEQ ID NO.:44; (e) a TCR α-chain comprising or consisting of an amino acid sequence as set forth in SEQ ID NO.:48, and a TCR β-chain comprising or consisting of an amino acid sequence as set forth in SEQ ID NO.:51; (f) a TCR α-chain comprising or consisting of an amino acid sequence as set forth in SEQ ID NO.:55, and a TCR β-chain comprising or consisting of an amino acid sequence as set forth in SEQ ID NO.:60; (g) a TCR α-chain comprising or consisting of an amino acid sequence as set forth in SEQ ID NO.:64, and a TCR β-chain comprising or consisting of an amino acid sequence as set forth in SEQ ID NO.:67; (h) a TCR α-chain comprising or consisting of an amino acid sequence as set forth in SEQ ID NO.:71, and a TCR β-chain comprising or consisting of an amino acid sequence as set forth in SEQ ID NO.:74; (i) a TCR α-chain comprising or consisting of an amino acid sequence as set forth in SEQ ID NO.:78, and a TCR β-chain comprising or consisting of an amino acid sequence as set forth in SEQ ID NO.:81; or (j) a TCR α-chain comprising or consisting of an amino acid sequence as set forth in SEQ ID NO.:85, and a TCR β-chain comprising or consisting of an amino acid sequence as set forth in SEQ ID NO.:88.

In certain embodiments, a binding protein (e.g., an immunoglobulin superfamily binding protein or portion thereof) or high affinity recombinant T cell receptor (TCR) specific for mesothelin or WT-1 as described herein includes variant polypeptide species that have one or more amino acid substitutions, insertions, or deletions in the amino acid sequence relative to the sequences of SEQ ID NOS.:1-18 or SEQ ID NOS.:19-90, respectively, as presented herein, provided that the binding protein retains or substantially retains its specific binding function.

Conservative substitutions of amino acids are well known and may occur naturally or may be introduced when the binding protein or TCR is recombinantly produced. Amino acid substitutions, deletions, and additions may be introduced into a protein using mutagenesis methods known in the art (see, e.g., Sambrook et al., *Molecular Cloning: A Laboratory Manual*, 3d ed., Cold Spring Harbor Laboratory Press, NY, 2001). Oligonucleotide-directed site-specific (or segment specific) mutagenesis procedures may be employed to provide an altered polynucleotide that has particular codons altered according to the substitution, deletion, or insertion desired. Alternatively, random or saturation mutagenesis techniques, such as alanine scanning mutagenesis, error prone polymerase chain reaction mutagenesis, and oligonucleotide-directed mutagenesis may be used to prepare immunogen polypeptide variants (see, e.g., Sambrook et al., supra).

A variety of criteria known to persons skilled in the art indicate whether an amino acid that is substituted at a particular position in a peptide or polypeptide is conservative (or similar). For example, a similar amino acid or a conservative amino acid substitution is one in which an amino acid residue is replaced with an amino acid residue having a similar side chain. Similar amino acids may be included in the following categories: amino acids with basic side chains (e.g., lysine, arginine, histidine); amino acids with acidic side chains (e.g., aspartic acid, glutamic acid); amino acids with uncharged polar side chains (e.g., glycine, asparagine, glutamine, serine, threonine, tyrosine, cysteine, histidine); amino acids with nonpolar side chains (e.g., alanine, valine, leucine, isoleucine, proline, phenylalanine, methionine, tryptophan); amino acids with beta-branched side chains (e.g., threonine, valine, isoleucine), and amino acids with aromatic side chains (e.g., tyrosine, phenylalanine, tryptophan). Proline, which is considered more difficult to classify, shares properties with amino acids that have aliphatic side chains (e.g., leucine, valine, isoleucine, and alanine). In certain circumstances, substitution of glutamine for glutamic acid or asparagine for aspartic acid may be considered a similar substitution in that glutamine and asparagine are amide derivatives of glutamic acid and aspartic acid, respectively. As understood in the art "similarity" between two polypeptides is determined by comparing the amino acid sequence and conserved amino acid substitutes thereto of the polypeptide to the sequence of a second polypeptide (e.g., using GENEWORKS, Align, the BLAST algorithm, or other algorithms described herein and practiced in the art).

Species (or variants) of a particular binding protein or high affinity engineered T cell receptors (TCRs) specific for mesothelin or WT-1 may include a protein that has at least 85%, 90%, 95%, or 99% amino acid sequence identity to any of the exemplary amino acid sequences disclosed herein (e.g., SEQ ID NOS:1-90), provided that (a) at least three or four of the CDRs have no mutations, (b) the CDRs that do have mutations have only up to two amino acid substitutions, up to a contiguous five amino acid deletion, or a combination thereof, and (c) the binding protein retains its ability to bind to a peptide antigen:HLA complex (e.g., SLLFLLFSL (SEQ ID NO.:115):HLA complex; VLPLTVAEV (SEQ ID NO.:116):HLA complex; VLDFAPPGA (SEQ ID NO.:117):HLA complex) with a $K_d$ less than or equal to about $10^{-8}$ M.

In certain embodiments, the present disclosure provides a binding protein, comprising (a) a T cell receptor (TCR) α-chain variable ($V_\alpha$) domain having at least 90% sequence identity to an amino acid sequence as set forth in SEQ ID NO.:1 or 12, and a TCR β-chain variable ($V_\beta$) domain; or (b) a $V_\alpha$ domain, and a $V_\beta$ domain having at least 90% sequence identity to an amino acid sequence as set forth in SEQ ID NO.:6 or 15; or (c) a $V_\alpha$ domain of (a) and a $V_\beta$ domain of (b); wherein the binding protein is capable of specifically binding to a mesothelin peptide:HLA cell surface complex independent, or in the absence, of CD8, such as a SLLFLLFSL (SEQ ID NO.:115):HLA complex or a VLPLTVAEV (SEQ ID NO.:116):HLA complex.

In further embodiments, the present disclosure provides a binding protein, comprising (a) a T cell receptor (TCR) α-chain variable ($V_\alpha$) domain having at least 90% sequence identity to an amino acid sequence as set forth in any one of SEQ ID NOS.:19, 26, 33, 40, 47, 54, 63, 70, 77 and 84, and a TCR β-chain variable ($V_\beta$) domain; or (b) a $V_\alpha$ domain, and a $V_\beta$ domain having at least 90% sequence identity to an amino acid sequence as set forth in any one of SEQ ID NOS.:22, 29, 36, 43, 50, 57, 66, 73, 80 and 87; or (c) a $V_\alpha$ domain of (a) and a $V_\beta$ domain of (b); wherein the binding protein is capable of specifically binding to a WT-1 peptide:HLA cell surface complex independent, or in the absence, of CD8, such as a VLDFAPPGA (SEQ ID NO.:117):HLA complex.

In any of the aforementioned embodiments, the present disclosure provides a high affinity engineered T cell receptor (TCR), comprising an α-chain and a β-chain, wherein the TCR binds to a mesothelin:HLA-A*201 complex or a WT-1:HLA-A*201 complex on a cell surface independent or in the absence of CD8. In certain embodiments, a $V_\beta$ chain comprises or is derived from a TRBV3, TRBV5, TRBV6, TRBV7, TRBV11, TRBV19, or TRBV24 allele. In further embodiments, a $V_\alpha$ chain comprises or is derived from a TRAV3, TRAV12, TRAV14, TRAV25, TRAV29, TRAV39, or TRAV40 allele. In particular embodiments, a binding protein comprises (a) a $V_\beta$ chain comprises or is derived from a TRBV19 allele and a $V_\alpha$ chain comprises or is derived from a TRAV12 allele; (b) a $V_\beta$ chain comprises or is derived from a TRBV24 allele and a $V_\alpha$ chain comprises or is derived from a TRAV25 allele; (c) a $V_\beta$ chain comprises or is derived from a TRBV13 allele and a $V_\alpha$ chain comprises or is derived from a TRAV14 allele; (d) a $V_\beta$ chain comprises or is derived from a TRBV19 allele and a $V_\alpha$ chain comprises or is derived from a TRAV29 allele; (e) a $V_\beta$ chain comprises or is derived from a TRBV11 allele and a $V_\alpha$ chain comprises or is derived from a TRAV29 allele; (f) a $V_\beta$ chain comprises or is derived from a TRBV5 allele and a $V_\alpha$ chain comprises or is derived from a TRAV39 allele; or (g) a $V_\beta$ chain comprises or is derived from a TRBV5 allele and a $V_\alpha$ chain comprises or is derived from a TRAV40 allele.

In certain embodiments, any of the aforementioned mesothelin or WT-1 specific binding proteins are each a T cell receptor (TCR), a chimeric antigen receptor or an antigen-binding fragment of a TCR, any of which can be chimeric, humanized or human. In further embodiments, an antigen-binding fragment of the TCR comprises a single chain TCR (scTCR) or a chimeric antigen receptor (CAR). In certain embodiments, a mesothelin or WT-1 specific binding protein is a TCR.

In any of the aforementioned embodiments, the present disclosure provides a mesothelin or WT-1 specific binding protein wherein a $V_\alpha$ domain comprises or consists of an α-chain constant domain having an amino acid sequence as set forth in SEQ ID NO.:2 or 3, a $V_\beta$ domain comprises or consists of a β-chain constant domain having an amino acid sequence as set forth in SEQ ID NO.:7, 8, 58 or 59, or any combination thereof. In further embodiments, an α-chain constant domain has at least 90% sequence identity to an amino acid sequence as set forth in SEQ ID NO.:2 or 3, a β-chain constant domain has at least 90% sequence identity to an amino acid sequence as set forth in SEQ ID NO.:7, 8, 58 or 59, or any combination thereof.

In certain embodiments, there is provided a composition comprising a mesothelin- or WT-1-specific binding protein or high affinity recombinant TCR according to any one of the aforementioned embodiments and a pharmaceutically acceptable carrier, diluent, or excipient.

Methods useful for isolating and purifying recombinantly produced soluble TCR, by way of example, may include obtaining supernatants from suitable host cell/vector systems that secrete the recombinant soluble TCR into culture media and then concentrating the media using a commercially available filter. Following concentration, the concentrate may be applied to a single suitable purification matrix or to a series of suitable matrices, such as an affinity matrix or an ion exchange resin. One or more reverse phase HPLC steps may be employed to further purify a recombinant polypeptide. These purification methods may also be employed when isolating an immunogen from its natural environment. Methods for large scale production of one or more of the isolated/recombinant soluble TCR described herein include batch cell culture, which is monitored and controlled to maintain appropriate culture conditions. Purification of the soluble TCR may be performed according to methods described herein and known in the art and that comport with laws and guidelines of domestic and foreign regulatory agencies.

In certain embodiments, nucleic acid molecules encoding an immunoglobulin superfamily binding protein or high affinity TCR specific for mesothelin or WT-1 are used to transfect/transduce a host cell (e.g., T cells) for use in adoptive transfer therapy. Advances in TCR sequencing have been described (e.g., Robins et al., *Blood* 114:4099, 2009; Robins et al., *Sci. Translat. Med.* 2:47ra64, 2010; Robins et al., (September 10) *J. Imm. Meth.* Epub ahead of print, 2011; Warren et al., *Genome Res.* 21:790, 2011) and may be employed in the course of practicing the embodiments according to the present disclosure. Similarly, methods for transfecting/transducing T cells with desired nucleic acids have been described (e.g., U.S. Patent Application Pub. No. US 2004/0087025) as have adoptive transfer procedures using T-cells of desired antigen-specificity (e.g., Schmitt et al., *Hum. Gen.* 20:1240, 2009; Dossett et al., *Mol. Ther.* 17:742, 2009; Till et al., *Blood* 112:2261, 2008; Wang et al., *Hum. Gene Ther.* 18:712, 2007; Kuball et al., *Blood* 109:2331, 2007; US 2011/0243972; US 2011/0189141; Leen et al., *Ann. Rev. Immunol.* 25:243, 2007), such that adaptation of these methodologies to the presently disclosed embodiments is contemplated, based on the teachings herein, including those directed to high affinity TCRs specific for mesothelin or WT-1 peptide antigens complexed with an HLA receptor.

The mesothelin and WT-1-specific binding proteins or domains as described herein (e.g., SEQ ID NOS.:1-90, and variants thereof), may be functionally characterized according to any of a large number of art accepted methodologies for assaying T cell activity, including determination of T cell binding, activation or induction and also including determination of T cell responses that are antigen-specific. Examples include determination of T cell proliferation, T cell cytokine release, antigen-specific T cell stimulation, MHC restricted T cell stimulation, CTL activity (e.g., by detecting $^{51}$Cr release from pre-loaded target cells), changes in T cell phenotypic marker expression, and other measures of T-cell functions. Procedures for performing these and similar assays are may be found, for example, in Lefkovits (*Immunology Methods Manual: The Comprehensive Sourcebook of Techniques*, 1998). See, also, *Current Protocols in Immunology*; Weir, *Handbook of Experimental Immunology*, Blackwell Scientific, Boston, Mass. (1986); Mishell and Shigii (eds.) *Selected Methods in Cellular Immunology*, Freeman Publishing, San Francisco, Calif. (1979); Green and Reed, *Science* 281:1309 (1998) and references cited therein.

"MHC-peptide tetramer staining" refers to an assay used to detect antigen-specific T cells, which features a tetramer of MHC molecules, each comprising an identical peptide having an amino acid sequence that is cognate (e.g., identical or related to) at least one antigen (e.g., mesothelin, WT-1), wherein the complex is capable of binding T cell receptors specific for the cognate antigen. Each of the MHC molecules may be tagged with a biotin molecule. Biotinylated MHC/peptides are tetramerized by the addition of streptavidin, which can be fluorescently labeled. The tetramer may be detected by flow cytometry via the fluorescent label. In certain embodiments, an MHC-peptide tetramer assay is used to detect or select enhanced affinity TCRs of the instant disclosure.

Levels of cytokines may be determined according to methods described herein and practiced in the art, including for example, ELISA, ELISPOT, intracellular cytokine staining, and flow cytometry and combinations thereof (e.g., intracellular cytokine staining and flow cytometry). Immune cell proliferation and clonal expansion resulting from an antigen-specific elicitation or stimulation of an immune response may be determined by isolating lymphocytes, such as circulating lymphocytes in samples of peripheral blood cells or cells from lymph nodes, stimulating the cells with antigen, and measuring cytokine production, cell proliferation and/or cell viability, such as by incorporation of tritiated thymidine or non-radioactive assays, such as MTT assays and the like. The effect of an immunogen described herein on the balance between a Th1 immune response and a Th2 immune response may be examined, for example, by determining levels of Th1 cytokines, such as IFN-γ, IL-12, IL-2, and TNF-β, and Type 2 cytokines, such as IL-4, IL-5, IL-9, IL-10, and IL-13.

Polynucleotides Encoding Binding Proteins Specific for WT-1 or Mesothelin Antigen Peptides Isolated or recombinant nucleic acid molecules encoding binding protein (e.g., immunoglobulin superfamily binding protein) or high affinity recombinant T cell receptor (TCR) specific for mesothelin or WT-1 as described herein may be produced and prepared according to various methods and techniques of the molecular biology or polypeptide purification arts. Construction of an expression vector that is used for recombinantly producing a binding protein or high affinity engineered TCR specific for a mesothelin or a WT-1 peptide of interest can be accomplished by using any suitable molecular biology engineering techniques known in the art, including the use of restriction endonuclease digestion, ligation, transformation, plasmid purification, and DNA sequencing as described in, for example, Sambrook et al. (1989 and 2001 editions; *Molecular Cloning: A Laboratory Manual, Cold Spring Harbor Laboratory* Press, NY) and Ausubel et al. (Current Protocols in Molecular Biology, 2003). To obtain efficient transcription and translation, a polynucleotide in each recombinant expression construct includes at least one appropriate expression control sequence (also called a regulatory sequence), such as a leader sequence and particularly a promoter operably (i.e., operatively) linked to the nucleotide sequence encoding the immunogen.

Certain embodiments relate to nucleic acids that encode the polypeptides contemplated herein, for instance, binding proteins or high affinity engineered TCRs specific for mesothelin or WT-1. As one of skill in the art will recognize, a nucleic acid may refer to a single- or a double-stranded DNA, cDNA or RNA in any form, and may include a positive and a negative strand of the nucleic acid which complement each other, including anti-sense DNA, cDNA and RNA. Also included are siRNA, microRNA, RNA-DNA hybrids, ribozymes, and other various naturally occurring or synthetic forms of DNA or RNA.

In certain embodiments, provided herein are isolated polynucleotides that encode a binding protein or high affinity engineered TCR of this disclosure specific for a mesothelin peptide or a WT-1 peptide. In particular embodiments related to encoded WT-1 specific binding proteins, a polynucleotide encodes a $V_\alpha$ domain that comprises or consists of a nucleotide sequence as set forth in any one of SEQ ID NOS.:150, 151, 160, 161, 170, 171, 180, 181, 190, 191, 200, 201, 214, 215, 224, 225, 234, 235, 244 and 245, and a polynucleotide encodes a $V_\beta$ domain that comprises or consists of a nucleotide sequence as set forth in any one of SEQ ID NOS.:154, 155, 164, 165, 174, 175, 184, 185, 194, 195, 204, 205, 218, 219, 228, 229, 238, 239, 248 and 249. In further embodiments, a polynucleotide encodes a $V_\alpha$ domain that is at least about 80% identical to a nucleotide sequence as set forth in any one of SEQ ID NOS.:150, 151, 160, 161, 170, 171, 180, 181, 190, 191, 200, 201, 214, 215, 224, 225, 234, 235, 244 and 245, and a polynucleotide encodes a $V_\beta$ domain that is at least about 80% identical to a nucleotide sequence as set forth in any one of SEQ ID NOS.:154, 155, 164, 165, 174, 175, 184, 185, 194, 195, 204, 205, 218, 219, 228, 229, 238, 239, 248 and 249. In particular embodiments related to encoded mesothelin specific binding proteins, a polynucleotide encodes a $V_\alpha$ domain that comprises or consists of a nucleotide sequence as set forth in any one of SEQ ID NOS.:122, 123, 140 and 141, and a polynucleotide encodes a $V_\beta$ domain that comprises or consists of a nucleotide sequence as set forth in any one of SEQ ID NOS.:130, 131, 144 and 145. In further embodiments, a polynucleotide encodes a $V_\alpha$ domain that is at least about 80% identical to a nucleotide sequence as set forth in any one of SEQ ID NOS.:122, 123, 140 and 141, and a polynucleotide encodes a $V_\beta$ domain that is at least about 80% identical to a nucleotide sequence as set forth in any one of SEQ ID NOS.:130, 131, 144 and 145.

In further embodiments related to encoded WT-1 specific binding proteins, provided herein are isolated polynucleotides that encode a TCR α-chain comprising or consisting of a nucleotide sequence as set forth in any one of SEQ ID NOS.:152, 153, 162, 163, 172, 173, 182, 183, 192, 193, 202, 203, 216, 217, 226, 227, 236, 237, 246 and 247, and a polynucleotide encoding a TCR β-chain comprising or consisting of a nucleotide sequence as set forth in any one of SEQ ID NOS.:156, 157, 166, 167, 176, 177, 186, 187, 196, 197, 210, 211, 220, 221, 230, 231, 240, 241, 250 and 251. In still further embodiments, a polynucleotide encodes a TCR α-chain that is at least about 80% identical to a nucleotide sequence as set forth in any one of SEQ ID NOS.:152, 153, 162, 163, 172, 173, 182, 183, 192, 193, 202, 203, 216, 217, 226, 227, 236, 237, 246 and 247, and a polynucleotide encodes a TCR β-chain that is at least about 80% identical to a nucleotide sequence as set forth in any one of SEQ ID NOS.:156, 157, 166, 167, 176, 177, 186, 187, 196, 197, 210, 211, 220, 221, 230, 231, 240, 241, 250 and 251.

In further embodiments related to encoded mesothelin specific binding proteins, provided herein are isolated polynucleotides that encode a TCR α-chain comprising or consisting of a nucleotide sequence as set forth in any one of SEQ ID NOS.:128, 129, 142 and 143, and a polynucleotide encoding a TCR β-chain comprising or consisting of a nucleotide sequence as set forth in any one of SEQ ID NOS.:136, 137, 146 and 147. In still further embodiments, a polynucleotide encodes a TCR α-chain that is at least about 80% identical to a nucleotide sequence as set forth in any one of SEQ ID NOS.:128, 129, 142 and 143, and a polynucleotide encodes a TCR β-chain that is at least about 80% identical to a nucleotide sequence as set forth in any one of SEQ ID NOS.:136, 137, 146 and 147.

In any of the aforementioned embodiments, a polynucleotide encoding a binding protein of the instant disclosure is codon optimized for efficient expression in a target host cell.

Standard techniques may be used for recombinant (i.e., engineered) DNA, peptide and oligonucleotide synthesis, immunoassays and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well-known in the art and as described in various general and more specific references in microbiology, molecular biology, biochemistry, molecular genetics, cell biology, virology and immunology techniques that are cited and discussed throughout the present specification. See, e.g., Sambrook et al., *Molecular Cloning: A Laboratory Manual*, 3d ed., Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, N.Y.); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); *Next-Generation Genome Sequencing* (Janitz, 2008 Wiley-VCH);

*PCR Protocols* (*Methods in Molecular Biology*) (Park, Ed., 3rd Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir and C C Blackwell, eds., 1986); Roitt, *Essential Immunology*, 6th Edition, (Blackwell Scientific Publications, Oxford, 1988); *Embryonic Stem Cells: Methods and Protocols* (Methods in Molecular Biology) (Kurstad Turksen, Ed., 2002); *Embryonic Stem Cell Protocols: Volume I: Isolation and Characterization* (Methods in Molecular Biology) (Kurstad Turksen, Ed., 2006); *Embryonic Stem Cell Protocols: Volume II: Differentiation Models* (Methods in Molecular Biology) (Kurstad Turksen, Ed., 2006); *Human Embryonic Stem Cell Protocols* (Methods in Molecular Biology) (Kursad Turksen Ed., 2006); *Mesenchymal Stem Cells: Methods and Protocols* (Methods in Molecular Biology) (Darwin J. Prockop, Donald G. Phinney, and Bruce A. Bunnell Eds., 2008); *Hematopoietic Stem Cell Protocols* (Methods in Molecular Medicine) (Christopher A. Klug, and Craig T. Jordan Eds., 2001); *Hematopoietic Stem Cell Protocols* (Methods in Molecular Biology) (Kevin D. Bunting Ed., 2008) *Neural Stem Cells: Methods and Protocols* (Methods in Molecular Biology) (Leslie P. Weiner Ed., 2008).

Certain embodiments include nucleic acid molecules contained in a vector. One of skill in the art can readily ascertain suitable vectors for use with certain embodiments disclosed herein. An exemplary vector may comprise a nucleic acid molecule capable of transporting another nucleic acid molecule to which it has been linked, or which is capable of replication in a host organism. Some examples of vectors include plasmids, viral vectors, cosmids, and others. Some vectors may be capable of autonomous replication in a host cell into which they are introduced (e.g. bacterial vectors having a bacterial origin of replication and episomal mammalian vectors), whereas other vectors may be integrated into the genome of a host cell or promote integration of the polynucleotide insert upon introduction into the host cell and thereby replicate along with the host genome (e.g., lentiviral vector)). Additionally, some vectors are capable of directing the expression of genes to which they are operatively linked (these vectors may be referred to as "expression vectors"). According to related embodiments, it is further understood that, if one or more agents (e.g., polynucleotides encoding binding proteins or high affinity recombinant TCRs specific for mesothelin or WT-1, or variants thereof, as described herein) is co-administered to a subject, that each agent may reside in separate or the same vectors, and multiple vectors (each containing a different agent the same agent) may be introduced to a cell or cell population or administered to a subject.

In certain embodiments, the nucleic acid encoding binding proteins or high affinity recombinant TCRs specific for mesothelin or WT-1, may be operatively linked to certain elements of a vector. For example, polynucleotide sequences that are needed to effect the expression and processing of coding sequences to which they are ligated may be operatively linked. Expression control sequences may include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; and possibly sequences that enhance protein secretion. Expression control sequences may be operatively linked if they are contiguous with the gene of interest and expression control sequences that act in trans or at a distance to control the gene of interest. In certain embodiments, polynucleotides encoding binding proteins of the instant disclosure are contained in an expression vector that is a viral vector, such as a lentiviral vector or a γ-retroviral vector.

In particular embodiments, the recombinant expression vector is delivered to an appropriate cell, for example, a T cell or an antigen-presenting cell, i.e., a cell that displays a peptide/MHC complex on its cell surface (e.g., a dendritic cell) and lacks CD8. In certain embodiments, the host cell is a hematopoietic progenitor cell or a human immune system cell. For example, the immune system cell can be a CD4+ T cell, a CD8+ T cell, a CD4− CD8− double negative T cell, a γδ T cell, a natural killer cell, a dendritic cell, or any combination thereof. In certain embodiments, wherein a T cell is the host, the T cell can be naïve, a central memory T cell, an effector memory T cell, or any combination thereof. The recombinant expression vectors may therefore also include, for example, lymphoid tissue-specific transcriptional regulatory elements (TREs), such as a B lymphocyte, T lymphocyte, or dendritic cell specific TREs. Lymphoid tissue specific TREs are known in the art (see, e.g., Thompson et al., *Mol. Cell. Biol.* 12:1043, 1992); Todd et al., *J. Exp. Med.* 177:1663, 1993); Penix et al., *J. Exp. Med.* 178:1483, 1993).

In addition to vectors, certain embodiments relate to host cells that comprise the vectors that are presently disclosed. One of skill in the art readily understands that many suitable host cells are available in the art. A host cell may include any individual cell or cell culture which may receive a vector or the incorporation of nucleic acids and/or proteins, as well as any progeny cells. The term also encompasses progeny of the host cell, whether genetically or phenotypically the same or different. Suitable host cells may depend on the vector and may include mammalian cells, animal cells, human cells, simian cells, insect cells, yeast cells, and bacterial cells. These cells may be induced to incorporate the vector or other material by use of a viral vector, transformation via calcium phosphate precipitation, DEAE-dextran, electroporation, microinjection, or other methods. See, for example, Sambrook et al., *Molecular Cloning: A Laboratory Manual* 2d ed. (Cold Spring Harbor Laboratory, 1989).

Methods of Treatment

In certain aspects, the instant disclosure is directed to methods for treating a hyperproliferative disorder or a condition characterized by mesothelion or Wilms tumor protein 1 (WT-1) overexpression by administering to human subject in need thereof a composition comprising a binding protein or high affinity recombinant TCR specific for human mesothelin or WT-1 according to any the aforementioned binding proteins or TCRs.

The presence of a hyperproliferative disorder or malignant condition in a subject refers to the presence of dysplastic, cancerous and/or transformed cells in the subject, including, for example neoplastic, tumor, non-contact inhibited or oncogenically transformed cells, or the like (e.g., solid cancers; hematologic cancers including lymphomas and leukemias, such as acute myeloid leukemia, chronic myeloid leukemia, etc.), which are known in the art and for which criteria for diagnosis and classification are established (e.g., Hanahan and Weinberg, *Cell* 144:646, 2011; Hanahan and Weinberg, *Cell* 100:57, 2000; Cavallo et al., *Canc. Immunol. Immunother.* 60:319, 2011; Kyrigideis et al., *J. Carcinog.* 9:3, 2010). In certain embodiments, such cancer cells may be cells of acute myeloid leukemia, B-cell lymphoblastic leukemia, T-cell lymphoblastic leukemia, or myeloma, including cancer stem cells that are capable of initiating and serially transplanting any of these types of cancer (see, e.g., Park et al., *Molec. Therap.* 17:219, 2009).

In certain embodiments, there are provided methods for treating a hyperproliferative disorder, such as a hematological malignancy or a solid cancer. Exemplary hematological malignancies include acute lymphoblastic leukemia (ALL), acute myeloid leukemia (AML), chronic myelogenous leukemia (CIVIL), chronic eosinophilic leukemia (CEL), myelodysplastic syndrome (MDS), non-Hodgkin's lymphoma (NHL), or multiple myeloma (MM).

In further embodiments, there are provided methods for treating a hyperproliferative disorder, such as a solid cancer is selected from biliary cancer, bladder cancer, bone and soft tissue carcinoma, brain tumor, breast cancer, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, gynecological tumor, head and neck squamous cell carcinoma, hepatic cancer, lung cancer, mesothelioma, malignant melanoma, osteosarcoma, ovarian cancer, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, testicular germ-cell tumor, urothelial cancer, uterine sarcoma, or uterine cancer.

As understood by a person skilled in the medical art, the terms, "treat" and "treatment," refer to medical management of a disease, disorder, or condition of a subject (i.e., patient, host, who may be a human or non-human animal) (see, e.g., Stedman's Medical Dictionary). In general, an appropriate dose and treatment regimen provide one or more of a binding protein or high affinity recombinant TCR specific for human mesothelin or WT-1 (e.g., SEQ ID NOS:1-90, and variants thereof) or a host cell expressing the same, and optionally an adjunctive therapy (e.g., a cytokine such as IL-2, IL-15, IL-21 or any combination thereof), in an amount sufficient to provide therapeutic or prophylactic benefit. Therapeutic or prophylactic benefit resulting from therapeutic treatment or prophylactic or preventative methods include, for example an improved clinical outcome, wherein the object is to prevent or retard or otherwise reduce (e.g., decrease in a statistically significant manner relative to an untreated control) an undesired physiological change or disorder, or to prevent, retard or otherwise reduce the expansion or severity of such a disease or disorder. Beneficial or desired clinical results from treating a subject include abatement, lessening, or alleviation of symptoms that result from or are associated the disease or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; or overall survival.

"Treatment" can also mean prolonging survival when compared to expected survival if a subject were not receiving treatment. Subjects in need of the methods and compositions described herein include those who already have the disease or disorder, as well as subjects prone to have or at risk of developing the disease or disorder. Subjects in need of prophylactic treatment include subjects in whom the disease, condition, or disorder is to be prevented (i.e., decreasing the likelihood of occurrence or recurrence of the disease or disorder). The clinical benefit provided by the compositions (and preparations comprising the compositions) and methods described herein can be evaluated by design and execution of in vitro assays, preclinical studies, and clinical studies in subjects to whom administration of the compositions is intended to benefit, as described in the examples.

In another aspect, the instant disclosure is directed to methods for treating a hyperproliferative disorder or a condition characterized by mesothelion or Wilms tumor protein 1 (WT-1) overexpression by administering to human subject in need thereof a composition comprising a isolated polynucleotide encoding a binding protein or high affinity recombinant TCR specific for human mesothelin or WT-1 according to any the aforementioned encoded binding proteins or TCRs. In certain embodiments, the polynucleotide encoding a binding protein or TCR specific for human mesothelin or WT-1 is codon optimized for a host cell of interest. In further embodiments, any of the aforementioned polynucleotides are operably linked to an expression control sequence and is optionally contained in an expression vector, such as a viral vector. Exemplary viral vectors include lentiviral vectors and γ-retroviral vectors. In related embodiments, the vector is capable of delivering the polynucleotide to a host cell, such as a hematopoietic progenitor cell or an immune system cell (e.g., human hematopoietic progenitor cell or a human immune system cell). Exemplary immune system cells include a CD4+ T cell, a CD8+ T cell, a CD4− CD8− double negative T cell, a γδ T cell, a natural killer cell, a dendritic cell, or any combination thereof (e.g., human). In certain embodiments, the immune system cell is a T cell, such as a naïve T cell, a central memory T cell, an effector memory T cell, or any combination thereof, all of which are optionally human.

In still another aspect, the instant disclosure is directed to methods for treating a hyperproliferative disorder or a condition characterized by mesothelion or Wilms tumor protein 1 (WT-1) overexpression by administering to human subject in need thereof a host cell comprising a heterologous polynucleotide or an expression vector according to any of the aforementioned embodiments, wherein the engineered or recombinant host cell expresses on its cell surface a binding protein or TCR specific for human mesothelin or WT-1 encoded by the heterologous polynucleotide.

Cells expressing the binding protein or recombinant TCR (e.g., high affinity) specific for human mesothelin or WT-1 as described herein may be administered to a subject in a pharmaceutically or physiologically acceptable or suitable excipient or carrier. Pharmaceutically acceptable excipients are biologically compatible vehicles, e.g., physiological saline, which are described in greater detail herein, that are suitable for administration to a human or other non-human mammalian subject.

A therapeutically effective dose is an amount of host cells (expressing a binding protein or high affinity recombinant TCR specific for human mesothelin or WT-1) used in adoptive transfer that is capable of producing a clinically desirable result (i.e., a sufficient amount to induce or enhance a specific T cell immune response against cells overexpressing mesothelin or WT-1 (e.g., a cytotoxic T cell response) in a statistically significant manner) in a treated human or non-human mammal. As is well known in the medical arts, the dosage for any one patient depends upon many factors, including the patient's size, weight, body surface area, age, the particular therapy to be administered, sex, time and route of administration, general health, and other drugs being administered concurrently. Doses will vary, but a preferred dose for administration of a host cell comprising a recombinant expression vector as described herein is about $10^7$ cells/m$^2$, about $5\times10^7$ cells/m$^2$, about $10^8$ cells/m$^2$, about $5\times10^8$ cells/m$^2$, about $10^9$ cells/m$^2$, about $5\times10^9$ cells/m$^2$, about $10^{10}$ cells/m$^2$, about $5\times10^{10}$ cells/m$^2$, or about $10^{11}$ cells/m$^2$.

Pharmaceutical compositions may be administered in a manner appropriate to the disease or condition to be treated (or prevented) as determined by persons skilled in the medical art. An appropriate dose and a suitable duration and frequency of administration of the compositions will be determined by such factors as the health condition of the patient, size of the patient (i.e., weight, mass, or body area), the type and severity of the patient's disease, the particular form of the active ingredient, and the method of administration. In general, an appropriate dose and treatment regimen provide the composition(s) in an amount sufficient to provide therapeutic and/or prophylactic benefit (such as described herein, including an improved clinical outcome, such as more frequent complete or partial remissions, or longer disease-free and/or overall survival, or a lessening of symptom severity). For prophylactic use, a dose should be sufficient to prevent, delay the onset of, or diminish the severity of a disease associated with disease or disorder. Prophylactic benefit of the immunogenic compositions administered according to the methods described herein can be determined by performing pre-clinical (including in vitro and in vivo animal studies) and clinical studies and analyzing data obtained therefrom by appropriate statistical, biological, and clinical methods and techniques, all of which can readily be practiced by a person skilled in the art.

A condition associated with mesothelin or WT-1 overexpression includes any disorder or condition in which underactivity, over-activity or improper activity of a mesothelin or WT-1 cellular or molecular event is present, and typically results from unusually high (with statistical significance) levels of mesothelin or WT-1 expression in afflicted cells (e.g., leukemic cells), relative to normal cells. A subject having such a disorder or condition would benefit from treatment with a composition or method of the presently described embodiments. Some conditions associated with mesothelin or WT-1 overexpression thus may include acute as well as chronic disorders and diseases, such as those pathological conditions that predispose the subject to a particular disorder.

Some examples of conditions associated with mesothelin or WT-1 overexpression include hyperproliferative disorders, which refer to states of activated and/or proliferating cells (which may also be transcriptionally overactive) in a subject including tumors, neoplasms, cancer, malignancy, etc. In addition to activated or proliferating cells, the hyperproliferative disorder may also include an aberration or dysregulation of cell death processes, whether by necrosis or apoptosis. Such aberration of cell death processes may be associated with a variety of conditions, including cancer (including primary, secondary malignancies as well as metastasis), or other conditions.

According to certain embodiments, virtually any type of cancer that is characterized by mesothelin or WT-1 overexpression may be treated through the use of compositions and methods disclosed herein, including hematological cancers (e.g., leukemia including acute myeloid leukemia (AML), T or B cell lymphomas, myeloma, and others). Furthermore, "cancer" may refer to any accelerated proliferation of cells, including solid tumors, ascites tumors, blood or lymph or other malignancies; connective tissue malignancies; metastatic disease; minimal residual disease following transplantation of organs or stem cells; multi-drug resistant cancers, primary or secondary malignancies, angiogenesis related to malignancy, or other forms of cancer. Also contemplated within the presently disclosed embodiments are specific embodiments wherein only one of the above types of disease is included, or where specific conditions may be excluded regardless of whether or not they are characterized by mesothelin or WT-1 overexpression.

Certain methods of treatment or prevention contemplated herein include administering a host cell (which may be autologous, allogeneic or syngeneic) comprising a desired nucleic acid molecule as described herein that is stably integrated into the chromosome of the cell. For example, such a cellular composition may be generated ex vivo using autologous, allogeneic or syngeneic immune system cells (e.g., T cells, antigen-presenting cells, natural killer cells) in order to administer a desired, mesothelin-targeted or WT-1-targeted T-cell composition to a subject as an adoptive immunotherapy.

As used herein, administration of a composition or therapy refers to delivering the same to a subject, regardless of the route or mode of delivery. Administration may be effected continuously or intermittently, and parenterally. Administration may be for treating a subject already confirmed as having a recognized condition, disease or disease state, or for treating a subject susceptible to or at risk of developing such a condition, disease or disease state. Co-administration with an adjunctive therapy may include simultaneous and/or sequential delivery of multiple agents in any order and on any dosing schedule (e.g., mesothelin or WT-1 specific recombinant (i.e., engineered) host cells with one or more cytokines; immunosuppressive therapy such as calcineurin inhibitors, corticosteroids, microtubule inhibitors, low dose of a mycophenolic acid prodrug, or any combination thereof). For example, a therapy of this disclosure can be combined with specific inhibitors or modulators of immunosuppression components, such as inhibitors or modulators of immune checkpoint molecules (e.g., anti-PD-1, anti-PD-L1, or anti-CTLA-4 antibodies; see, e.g., Pardol, *Nature Rev. Cancer* 12:252, 2012; Chen and Mellman, *Immunity* 39:1, 2013).

In certain embodiments, a plurality of doses of a recombinant host cell as described herein is administered to the subject, which may be administered at intervals between administrations of about two to about four weeks. In further embodiments, a cytokine is administered sequentially, provided that the subject was administered the recombinant host cell at least three or four times before cytokine administration. In certain embodiments, the cytokine is administered subcutaneously (e.g., IL-2, IL-15, IL-21). In still further embodiments, the subject being treated is further receiving immunosuppressive therapy, such as an antibody specific for PD-1 (e.g., pidilizumab, nivolumab, or pembrolizumab), an antibody specific for PD-L1 (e.g., MDX-1105, BMS-936559, MEDI4736, NIPDL3280A, or MSB0010718C), an antibody specific for CTLA4 (e.g., tremelimumab or ipilimumab), calcineurin inhibitors, corticosteroids, microtubule inhibitors, low dose of a mycophenolic acid prodrug, or any combination thereof. In yet further embodiments, the subject being treated has received a non-myeloablative or a myeloablative hematopoietic cell transplant, wherein the treatment may be administered at least two to at least three months after the non-myeloablative hematopoietic cell transplant.

An effective amount of a therapeutic or pharmaceutical composition refers to an amount sufficient, at dosages and for periods of time needed, to achieve the desired clinical results or beneficial treatment, as described herein. An effective amount may be delivered in one or more administrations. If the administration is to a subject already known or confirmed to have a disease or disease-state, the term "therapeutic amount" may be used in reference to treatment, whereas "prophylactically effective amount" may be used to describe administrating an effective amount to a subject that is susceptible or at risk of developing a disease or disease-state (e.g., recurrence) as a preventative course.

The level of a CTL immune response may be determined by any one of numerous immunological methods described herein and routinely practiced in the art. The level of a CTL immune response may be determined prior to and following administration of any one of the herein described WT-1-specific binding proteins expressed by, for example, a T cell. Cytotoxicity assays for determining CTL activity may be performed using any one of several techniques and methods routinely practiced in the art (see, e.g., Henkart et al., "Cytotoxic T-Lymphocytes" in *Fundamental Immunology*, Paul (ed.) (2003 Lippincott Williams & Wilkins, Philadelphia, Pa.), pages 1127-50, and references cited therein).

Antigen-specific T cell responses are typically determined by comparisons of observed T cell responses according to any of the herein described T cell functional parameters (e.g., proliferation, cytokine release, CTL activity, altered cell surface marker phenotype, etc.) that may be made between T cells that are exposed to a cognate antigen in an appropriate context (e.g., the antigen used to prime or activate the T cells, when presented by immunocompatible antigen-presenting cells) and T cells from the same source population that are exposed instead to a structurally distinct or irrelevant control antigen. A response to the cognate antigen that is greater, with statistical significance, than the response to the control antigen signifies antigen-specificity.

A biological sample may be obtained from a subject for determining the presence and level of an immune response to a mesothelin- or WT-1-derived antigen peptide as described herein. A "biological sample" as used herein may be a blood sample (from which serum or plasma may be prepared), biopsy specimen, body fluids (e.g., lung lavage, ascites, mucosal washings, synovial fluid), bone marrow, lymph nodes, tissue explant, organ culture, or any other tissue or cell preparation from the subject or a biological source. Biological samples may also be obtained from the subject prior to receiving any immunogenic composition, which biological sample is useful as a control for establishing baseline (i.e., pre-immunization) data.

The pharmaceutical compositions described herein may be presented in unit-dose or multi-dose containers, such as sealed ampoules or vials. Such containers may be frozen to preserve the stability of the formulation until. In certain embodiments, a unit dose comprises a recombinant host cell as described herein at a dose of about $10^7$ cells/m$^2$ to about $10^{11}$ cells/m$^2$. The development of suitable dosing and treatment regimens for using the particular compositions described herein in a variety of treatment regimens, including e.g., parenteral or intravenous administration or formulation.

If the subject composition is administered parenterally, the composition may also include sterile aqueous or oleaginous solution or suspension. Suitable non-toxic parenterally acceptable diluents or solvents include water, Ringer's solution, isotonic salt solution, 1,3-butanediol, ethanol, propylene glycol or polythethylene glycols in mixtures with water. Aqueous solutions or suspensions may further comprise one or more buffering agents, such as sodium acetate, sodium citrate, sodium borate or sodium tartrate. Of course, any material used in preparing any dosage unit formulation should be pharmaceutically pure and substantially non-toxic in the amounts employed. In addition, the active compounds may be incorporated into sustained-release preparation and formulations. Dosage unit form, as used herein, refers to physically discrete units suited as unitary dosages for the subject to be treated; each unit may contain a predetermined quantity of recombinant cells or active compound calculated to produce the desired therapeutic effect in association with an appropriate pharmaceutical carrier.

In general, an appropriate dosage and treatment regimen provides the active molecules or cells in an amount sufficient to provide therapeutic or prophylactic benefit. Such a response can be monitored by establishing an improved clinical outcome (e.g., more frequent remissions, complete or partial, or longer disease-free survival) in treated subjects as compared to non-treated subjects. Increases in preexisting immune responses to a tumor protein generally correlate with an improved clinical outcome. Such immune responses may generally be evaluated using standard proliferation, cytotoxicity or cytokine assays, which are routine in the art and may be performed using samples obtained from a subject before and after treatment.

EXAMPLES

Example 1

Methods

Peptides

Antigen-specific T cell lines were generated specific for the WT1 peptide WT1$^{37-45}$ (VLDFAPPGA, SEQ ID NO.: 117), and two Mesothelin (Msln) peptides, Meso$^{20-28}$ (SLL-FLLFSL, SEQ ID NO.:115) and Meso$^{530-538}$ (VLPLTVAEV, SEQ ID NO.:116).

Lentiviral Constructs

TCR expression constructs include codon-optimized TCRα and TCRβ genes derived from CD8+ T cell clones that are HLA-A2-restricted and have a high affinity for the WT-1 peptide WT1$^{37-45}$ (VLDFAPPGA, SEQ ID NO.:117). The TCRα and TCRβ genes are linked by a P2A element from the porcine teschovirus (see, e.g., SEQ ID NO.:118) to ensure coordinated expression under the control of a murine stem cell virus (MSCV) U3 promoter. The constant domains of each TCRα and TCRβ chain have been modified to express complementary cysteine residues at positions 48 (Thr to Cys) and 57 (Ser to Cys), respectively, in order to promote inter-chain pairing of the TCR chains and to discourage mispairing of the introduced TCR with endogenous TCR chains.

The vector pRRLSIN-C4α-P2A-C4β contained the TCR expression construct ligated into the pRRLSIN-.cPPT.MSCV/GFP.WPRE lentiviral vector between the AscI and SalI restriction endonuclease sites, replacing GFP. The pRRLSIN.cPPT.MSCV/GFP.WPRE plasmid is a third-generation, self-inactivating lentiviral vector (see Yang et al., *J. Immunother.* 31:830, 2008).

Generation of T Cell Lines

T cell lines were generated as described by Ho et al., *Immunol. Methods* 310:40, 2006). Briefly, dendritic cells (DCs) were derived from a fraction of plastic adherent PBMCs after culture for two days (days −2 to 0) in media supplemented with GM-CSF and IL-4. On day −1, TNFα, IL-1β, IL-6 and PGE$_2$ were added. On day 0, DCs were harvested, washed and pulsed with peptide. CD8+ T cells were isolated from the PBMCs using anti-CD8 microbeads and stimulated with peptide-pulsed DCs in the presence of IL-21. Cells were re-stimulated twice, between days 10 and 14, with the plastic adherent fraction of irradiated autologous PBMCs as antigen presenting cells pulsed with the relevant peptide.

Relative Affinity by Tetramer Titration

T cell clones were stained with 2-fold serial dilutions of WT-1 tetramer and analyzed by flow cytometry. Statistical analysis was performed in Graphpad Prism. KD values were extrapolated using a non-linear regression algorithm to a saturation binding curve with the formula $Y=B_{max}*X/[K_D+X]$.

Example 2

Figure 2:
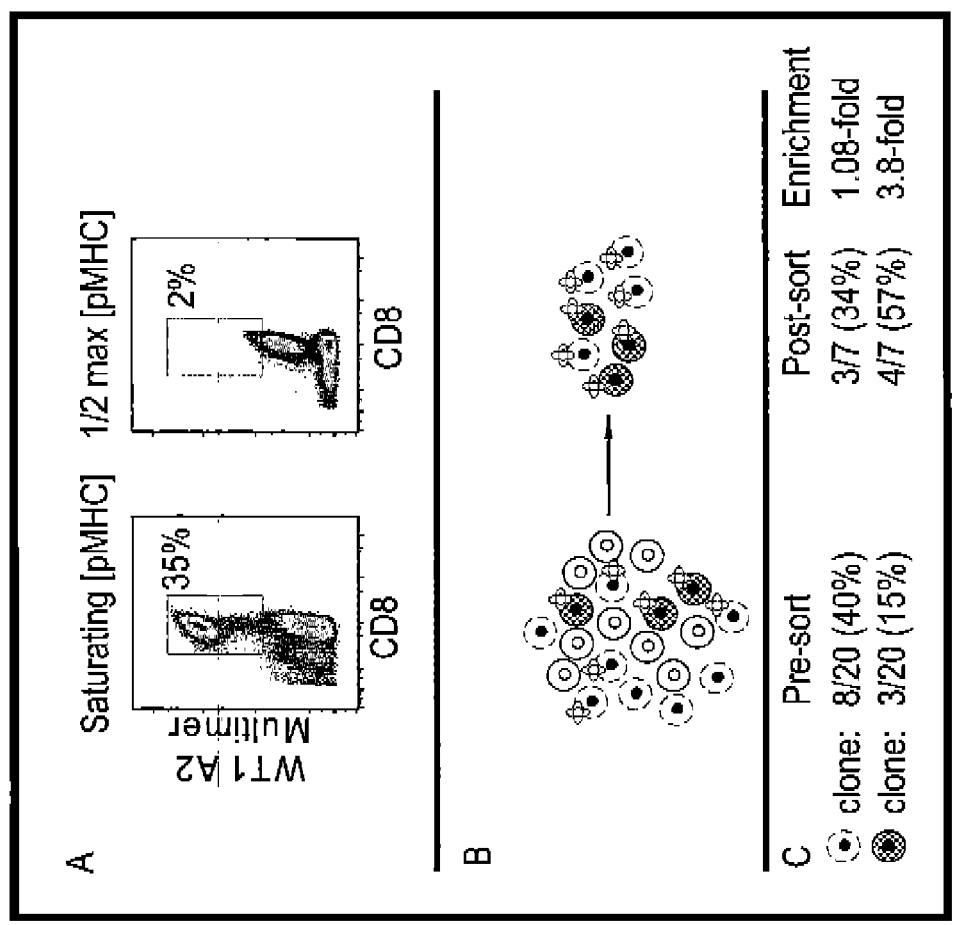
FIG. 2 includes (A) flow plots showing loss of mean fluorescence intensity (to achieve about half maximal binding) when 1% of the maximal concentration of WT-1$^{37-45}$ pMHC multimer was used; (B) a simplified schema of antigen-specific high-affinity (dashed-line) and lower-affinity (hatched) clones in the presence of limiting concentrations of pMHC and their respective selection after pMHC-based flow sorting; and (C) a calculation of enrichment fractions for illustrated dashed-line and hatched clones.

Identification and Cloning of High Affinity Wt-1-Specific and Mesothelin-Specific TCRs In order to identify high affinity HLA-A2-restricted WT-1$^{37-45}$-specific, Mesothelin$^{20-28}$-specific, and Mesothelin$^{530-538}$-specific T cell clones, T cell clones were generated from the peripheral repertoire of several donors. Briefly, CD8$^+$ cells were obtained from PBMCs of two HLA-A*0201$^+$ donors and simultaneously stimulated 2-3× with autologous dendritic cells (DCs) pulsed with growth factors and the following peptides: WT-1$^{37-45}$, Mesothelin$^{20-28}$, and Mesothelin$^{530-538}$ to obtain enriched multi-epitope polyclonal lines (FIG. 1). The polyclonal lines were combined, stained with peptide/MHC multimers (WT-1$^{37-45}$, Mesothelin$^{20-28}$ and Mesothelin$^{530-538}$ conjugated to APC) at 4° C. (to prevent endocytosis of the TCRs after pMHC ligation), and individually sorted. At equilibrium, and in the presence of limiting concentrations of pMHC multimer, determined as the concentration that yields ½ maximal multimer binding on a polyclonal antigen-specific CTL population (FIG. 2A), expanded cell clones that expressed a high affinity TCR (lower K$_D$) will have a higher probability of being bound to pMHC multimers than cells that express a low affinity TCR (higher K$_D$), and will therefore exhibit higher mean fluorescence intensity (MFI) (FIG. 2B). The intensity of the MHC multimer stain has been shown as a surrogate for CTL avidity (Yee et al., *J. Immunol.* 162:2227, 1999), only cells above the selected threshold MFI (i.e., top 2%) for multimer staining were selected through flow cytometric sorting. The highest affinity TCRs were preferentially enriched within this post-sort fraction, irrespective of whether the pre-sort frequencies were lower compared to other antigen-specific clones recognizing the same epitope (FIG. 2C).

To further characterize the WT-1$^{37-45}$-specific TCRs from these candidate T cell clones, codon-optimized expression constructs were generated for each TCRα and TCRβ chain pair. For each construct, the α and β chains were separated by a P2A element to promote coordinated expression of the TCRα and TCRβ chains (see, e.g., Szymczak et al., *Nat. Biotechnol.* 22:589, 2004; Dossett et al., *Mol. Ther.* 17:742, 2009). In addition, point mutations to create a second pair of cysteine residues in the external membrane-proximal regions of TCRα and TCRβ constant domains were introduced to promote preferential pairing of introduced TCR chains (Kuball et al., *Blood* 109:2331, 2007). Finally, these codon-optimized, cysteine-modified constructs were cloned into the lentiviral vector pRRLSIN.cPPT-MSCV.WPRE (see FIG. 3C).

Figure 3:
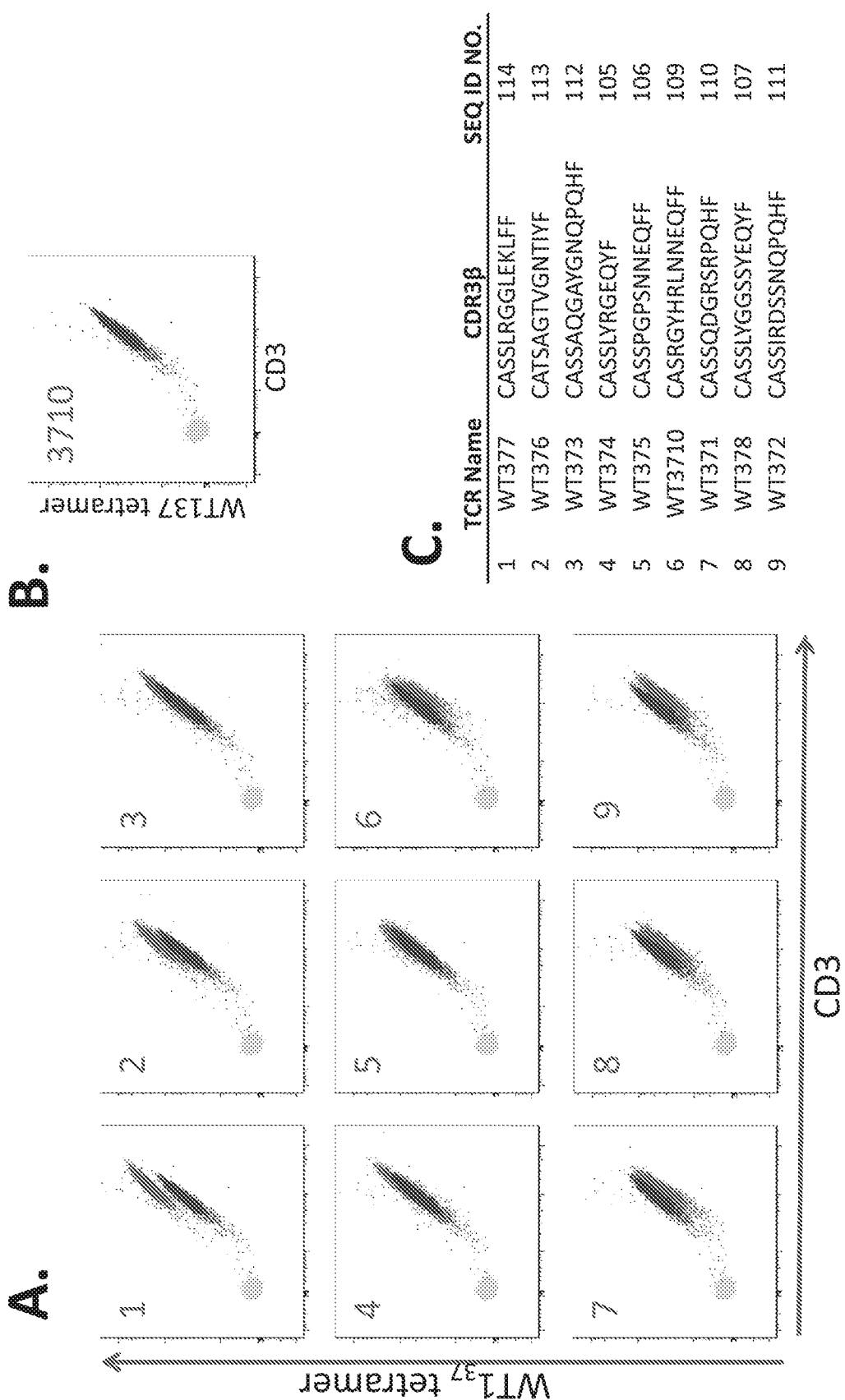
FIG. 3 shows the comparison of TCR surface expression for different WT1$^{37-45}$-specific TCR constructs. (A) Eight different codon-optimized, P2A-linked WT1$^{37-45}$-specific TCR constructs (light grey) were generated, transduced into a CD8$^-$ H9 T cell line, and (B) compared to the highest affinity WT1$^{37-45}$-specific TCR isolated from healthy donor peripheral blood mononuclear cells (PBMCs), referred to as WT3710 (dark grey). The light grey circular spot in the lower left quadrant of each plot is a negative control. (C) The various TCR β chain CDR3s of these different high affinity TCRs are provided.

Codon-optimized, P2A-linked WT1$^{37-45}$-specific, Mesothelin$^{20-28}$-specific, and Mesothelin$^{530-538}$-specific TCR constructs were separately generated, transduced into a CD8$^-$ H9 T cell line, and compared to the highest affinity WT1$^{37-45}$-specific TCR previously isolated from healthy donor peripheral blood mononuclear cells (PBMCs), referred to as WT3710 (FIGS. 3A and B). The various CDR3s from the β chain of these eight different high affinity TCRs are shown in FIG. 3C. The fact that these TCRs can efficiently bind tetramer independent of CD8 demonstrates the high affinity of these TCRs, since the affinity threshold for CD8-independent tetramer binding is estimated to be about 5 μM (Holler and Kranz, *Immunity* 18:255, 2003; Stone et al., *Immunol.* 126:165, 2009).

Figure 4:
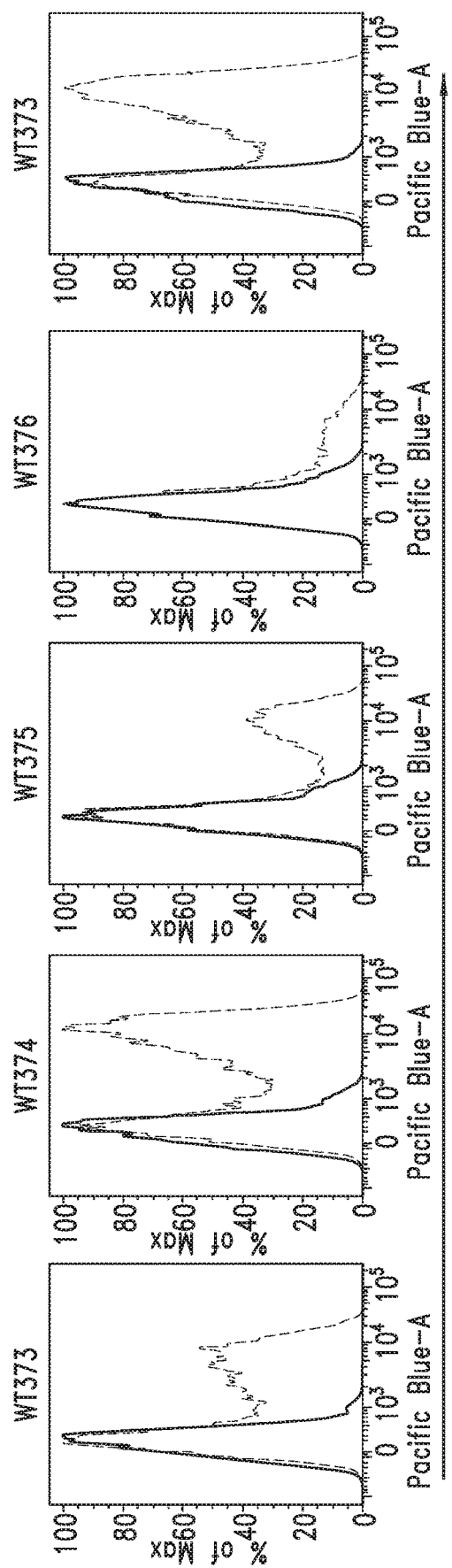
FIG. 4 shows TCR constructs that were transduced into PBMCs, expanded for 10 days and then re-stimulated with WT-1$^{37-45}$ peptide and examined for IFN-γ production by intracellular flow cytometry.

In addition, WT-1 specific TCR constructs were transduced into PBMCs, expanded for 10 days and then re-stimulated with WT-1$^{37-45}$ peptide and expanded a further 10 days. TCR transduced T cells were then mixed with T2 target cells pulsed with 10 mM peptide. After 5 hours of stimulation in the presence of GolgiStop™ (a protein transport inhibitor containing monensin, which results in increased accumulation of cytokines in the Golgi complex and enhances the detectability of cytokine-producing cells by flow cytometry). IFNγ production was measured by intracellular flow cytometry. FIG. 4 shows that these TCRs are functional since the TCR-transduced T cells incubated with the WT-1 peptide show production of IFN-γ (hatched line) as compared to controls (solid line, which are the same TCR-transduced T cells incubated without peptide).

These tumor-specific TCRs will be assessed for their ability to lyse T2 BLCL cells pulsed with the lowest concentrations of peptide (lowest comparative EC$_{50}$), and kill a range of tumor-expressing cell lines (such as the mesothelin-expressing lung cell line, NCL-H146, and the A2 OCI-AML3 WT1-expressing leukemia cell line) at the lowest effector to target ratio.

The various embodiments described herein can be combined to provide further embodiments. All of the patents, patent application publications, patent applications, and non-patent publications referred to in this specification and/or listed in the Application Data Sheet, including but not limited to U.S. Patent Application No. 62/387,546, are incorporated herein by reference in their entirety. In general, terms used in the following claims should not be construed as limited to specific embodiments disclosed herein, but should be construed to include all possible embodiments along with the full scope of equivalents to which such claims are entitled.

What is claimed is:

1. A binding protein, comprising:
   (a) a T cell receptor (TCR) α-chain variable ($V_\alpha$) domain having a CDR3 amino acid sequence shown in any one of SEQ ID NOS.:93-102, and a TCR β-chain variable ($V_\beta$) domain; or
   (b) a $V_\alpha$ domain of (a) and a $V_\beta$ domain having a CDR3 amino acid sequence shown in any one of SEQ ID NOS.:105-114;

wherein the binding protein is capable of specifically binding to a WT-1 peptide:HLA complex on a cell surface independent of CD8 or in the absence of CD8.

2. The binding protein according to claim 1, wherein the binding protein is capable of specifically binding to a VLDFAPPGA (SEQ ID NO.:117):human leukocyte antigen (HLA) complex with a $K_d$ less than or equal to about $10^{-8}$M.

3. The binding protein according to claim 1, wherein the binding protein comprises a $V_\alpha$ domain that is at least about 90% identical to an amino acid sequence as set forth in any one of SEQ ID NOS.:19, 26, 33, 40, 47, 54, 63, 70, 77 and 84, and comprises a $V_\beta$ domain that is at least about 90% identical to the amino acid sequence as set forth in any one of SEQ ID NOS.:22, 29, 36, 43, 50, 57, 66, 73, 80 and 87, provided that (a) at least three or four of the CDRs have no change in sequence, wherein the CDRs that do have sequence changes have only up to two amino acid substitutions, up to a contiguous five amino acid deletion, or a combination thereof, and (b) the binding protein remains capable of specifically binding to a WT-1 peptide:HLA cell surface complex independent, or in the absence, of CD8.

4. The binding protein according to claim 1, wherein the binding protein specifically binds to a VLDFAPPGA (SEQ ID NO.:117):HLA-A*201 complex.

5. The binding protein according to claim 1, wherein the $V_\alpha$ domain comprises or consists of an amino acid sequence as set forth in SEQ ID NO.:19, 26, 33, 40, 47, 54, 63, 70, 77, or 84; and/or the $V_\beta$ domain comprises or consists of an amino acid sequence as set forth in SEQ ID NO.:22, 29, 36, 43, 50, 57, 66, 73, 80, or 87.

6. The binding protein according to claim 1, wherein the binding protein comprises:
  (a) a TCR α-chain comprising or consisting of the amino acid sequence as set forth in SEQ ID NO.:20, and a TCR β-chain comprising or consisting of the amino acid sequence as set forth in SEQ ID NO.:23; or
  (b) a TCR α-chain comprising or consisting of the amino acid sequence as set forth in SEQ ID NO.:27, and the TCR β-chain comprising or consists of the amino acid sequence as set forth in SEQ ID NO:30; or
  (c) a TCR α-chain comprising or consisting of the amino acid sequence as set forth in SEQ ID NO:34, and the TCR β-chain comprising or consisting of the amino acid sequence as set forth in SEQ ID NO.:37; or
  (d) a TCR α-chain comprising or consisting of the amino acid sequence as set forth in SEQ ID NO.:41, and the TCR β-chain comprising or consisting of the amino acid sequence as set forth in SEQ ID NO.:44; or
  (e) a TCR α-chain comprising or consisting of the amino acid sequence as set forth in SEQ ID NO.:48, and the TCR β-chain comprising or consisting of the amino acid sequence as set forth in SEQ ID NO.:51; or
  (f) a TCR α-chain comprising or consisting of the amino acid sequence as set forth in SEQ ID NO.:55, and the TCR β-chain comprising or consisting of the amino acid sequence as set forth in SEQ ID NO.:60, or
  (g) a TCR α-chain comprising or consisting of the amino acid sequence as set forth in SEQ ID NO.:64, and the TCR β-chain comprising or consisting of the amino acid sequence as set forth in SEQ ID NO.:67; or
  (h) a TCR α-chain comprisng or consisting of the amino acid sequence as set forth in SEQ ID NO.:71, and the TCR β-chain comprising or consisting of the amino acid sequence as set forth in SEQ ID NO.:74; or
  (i) a TCR α-chain comprising or consisting of the amino acid sequence as set forth in SEQ ID NO.:78, and the TCR β-chain comprising or consisting of the amino acid sequence as set forth in SEQ ID NO.:81: or
  (j) a TCR α-chain comprising or consisting of the amino acid sequence as set forth in SEQ ID NO:85, and the TCR β-chain comprising or consisting of the amino acid sequence as set forth in SEQ ID NO.:88.

7. The binding protein according to claim 1, wherein the binding protein is a T cell receptor (TCR), an antigen-binding fragment of a TCR, or a chimeric antigen receptor.

8. A composition comprising a binding protein according to claim 1 and a pharmaceutically acceptable carrier, diluent, or excipient.

9. An isolated polynucleotide encoding a binding protein according to claim 1.

10. An expression vector, comprising a polynucleotide of claim 9 operably linked to an expression control sequence.

11. The expression vector according to claim 10, wherein the vector is capable of delivering the polynucleotide to a host cell, wherein the host cell is a hematopoietic progenitor cell or a human immune system cell.

12. A recombinant host cell, comprising a heterologous polynucleotide according to claim 9, wherein the recombinant host cell expresses on its cell surface a binding protein encoded by the heterologous polynucleotide.

13. The recombinant host cell according to claim 12, wherein the heterologous polynucleotide encodes a $V_\alpha$ domain comprising or consisting of a nucleotide sequence as set forth in any one of SEQ ID NOS.:150, 151, 160, 161, 170, 171, 180, 181, 190, 191 200, 201, 214, 215, 224, 225, 234, 235, 244 and 245; and/or encodes a $V_\beta$ domain comprising or consisting of a nucleotide sequence as set forth in any one SEQ ID NOS.:154, 155, 164, 165, 174, 175, 184, 185, 194, 204, 205, 218, 219, 228, 229, 238, 239, 248 and 249.

14. The recombinant host cell according to claim 12, wherein a polynucleotide encodes:
  (a) a TCR α-chain comprising or consisting of the nucleotide sequence as set forth in SEQ ID NO.:152 or 153, and-the a TCR β-chain encoding polynucleotide comprising or consisting of the nucleotide sequence as set forth in SEQ ID NO.:156 or 157; or
  (b) a TCR α-chain comprising or consisting of the nucleotide sequence as set forth in SEQ ID NO.:162 or 163, and the TCR β-chain encoding polynucleotide comprising or consisting of the nucleotide sequence as set forth in SEQ ID NO.:166 or 167; or
  (c) a TCR α-chain encoding polynucleotide comprising or consisting of the nucleotide sequence as set forth in SEQ ID NO.:172 or 173, and the TCR β-chain encoding polynucleotide comprising or consisting of the nucleotide sequence as set forth in SEQ NO.:176 or 177; or
  (d) a TCR α-chain encoding polynucleotide comprising or consisting of the nucleotide sequence as set forth in SEQ ID NO:182 or 183, and the TCR β-chain encoding polynucleotide comprising or consisting of the nucleotide sequence as set forth in SEQ ID NO.:186 or 187; or
  (e) a TCR α-chain encoding polynucleotide comprising or consisting of the nucleotide sequence as set forth in SEQ ID NO.:192 or 193, and the TCR β-chain encoding polynucleotide comprising or consisting of the nucleotide sequence as set forth in SEQ ID NO.:196 or 197; or
  (f) a TCR α-chain encoding polynucleotide comprising or consisting of the nucleotide sequence as set forth in SEQ ID NO.:202 or 203, and the TCR β-chain encoding polynucleotide comprising or consisting of the nucleotide sequence as set forth in SEQ ID NO:210 or 211; or
  (g) a TCR α-chain encoding polynucleotide comprising or consisting of the nucleotide sequence as set forth in SEQ ID NO.:216 or 217, and the TCR β-chain encoding polynucleotide comprising or consisting of the nucleotide sequence as set forth in SEQ ID NO:220 or 221; or (h) a TCR α-chain encoding polynucleotide comprising or consisting of the nucleotide sequence as set forth in SEQ ID NO.:226 or 227, and the TCR β-chain encoding polynucleotide comprising or consisting of the nucleotide sequence as set forth in SEQ ID NO.:230 or 231; or (i) a TCR α-chain encoding polynucleotide comprising or consisting of the nucleotide sequence as set forth in SEQ ID NO.:236 or 237 and the TCR β-chain encoding polynucleotide comprising or consisting of the nucleotide sequence as set forth in SEQ ID NO.:240 or 241; or (j) a TCR α-chain encoding polynucleotide comprising or consisting of the nucleotide sequence as set forth in SEQ ID NO.:246 or 247 and the TCR β-chain encoding polynucleotide comprising or consisting of the nucleotide sequence as set forth in SEQ ID NO.:250 or 251.

15. An adoptive immunotherapy method for treating a condition characterized by WT-1 overexpression in cells of a subject having a hyperproliferative disorder, comprising administering to the subject an effective amount of recombinant host cell according to any one of claim 12.

16. The method according to claim 15, wherein the host cell is a hematopoietic progenitor cell or a human immune system cell, optionally wherein the immune system cell is a CD4+T cell, a CD8+T cell, a CD4− CD8−double negative T cell, a γδ T cell, a natural killer cell, a dendritic cell, or any combination thereof.

17. A method for treating a hyperproliferative disorder, comprising administering to human subject in need thereof a composition comprising a binding protein specific for human Wilms tumor protein 1 (WT-1) according to claim 1.

* * * * *